US011116847B2

(12) United States Patent
Kolakowski et al.

(10) Patent No.: US 11,116,847 B2
(45) Date of Patent: Sep. 14, 2021

(54) METHYLENE CARBAMATE LINKERS FOR USE WITH TARGETED-DRUG CONJUGATES

(71) Applicant: Seagen Inc., Bothell, WA (US)

(72) Inventors: Robert Kolakowski, Kirkland, WA (US); Scott Jeffrey, Snohomish, WA (US); Patrick Burke, Seattle, WA (US)

(73) Assignee: Seagen Inc., Bothell, WA (US)

( * ) Notice: Subject to any disclaimer, the term of this patent is extended or adjusted under 35 U.S.C. 154(b) by 0 days.

(21) Appl. No.: 15/106,272

(22) PCT Filed: Dec. 19, 2014

(86) PCT No.: PCT/US2014/071593
§ 371 (c)(1),
(2) Date: Jun. 17, 2016

(87) PCT Pub. No.: WO2015/095755
PCT Pub. Date: Jun. 25, 2015

(65) Prior Publication Data
US 2016/0303254 A1 Oct. 20, 2016

Related U.S. Application Data

(60) Provisional application No. 61/918,539, filed on Dec. 19, 2013.

(30) Foreign Application Priority Data

Dec. 19, 2014 (TW) .................................. 103144705

(51) Int. Cl.
*A61K 47/68* (2017.01)
*A61K 47/60* (2017.01)

(52) U.S. Cl.
CPC .......... *A61K 47/6889* (2017.08); *A61K 47/60* (2017.08); *A61K 47/6803* (2017.08); *A61K 47/6863* (2017.08)

(58) Field of Classification Search
CPC ........................ A61K 47/6889; A61K 47/6803
See application file for complete search history.

(56) References Cited

U.S. PATENT DOCUMENTS

| | | | |
|---|---|---|---|
| 3,927,070 A | 12/1975 | Szabo | |
| 5,851,527 A | 12/1998 | Hansen | |
| 6,361,774 B1 | 3/2002 | Griffiths et al. | |
| 6,884,869 B2 | 4/2005 | Senter et al. | |
| 7,375,078 B2 | 5/2008 | Feng | |
| 7,754,681 B2 | 7/2010 | Feng | |
| 7,989,434 B2 | 8/2011 | Feng | |
| 8,039,273 B2 | 10/2011 | Jeffrey | |
| 8,455,622 B2 | 6/2013 | McDonagh et al. | |
| 8,568,728 B2 | 10/2013 | Jeffrey | |
| 8,680,315 B2 | 3/2014 | Santi | |
| 8,754,190 B2 | 6/2014 | Santi | |
| 9,061,074 B2 | 6/2015 | Carter et al. | |
| 9,242,013 B2 | 1/2016 | Howard et al. | |
| 9,295,731 B2 | 3/2016 | Nguyen | |
| 2008/0280937 A1 | 11/2008 | Leamon | |
| 2011/0152252 A1 | 6/2011 | Johannes et al. | |
| 2011/0263502 A1 | 10/2011 | Santi | |
| 2012/0027782 A1 | 2/2012 | Chin et al. | |
| 2013/0116407 A1 | 5/2013 | Ashley | |
| 2014/0086942 A1 | 3/2014 | Carter et al. | |
| 2014/0249319 A1 | 9/2014 | Nguyen | |
| 2014/0294851 A1 | 10/2014 | Nguyen | |
| 2014/0296476 A1 | 10/2014 | Santi | |

FOREIGN PATENT DOCUMENTS

| | | |
|---|---|---|
| EP | 0848957 A1 | 6/1998 |
| WO | 2001/0036003 A2 | 5/2001 |
| WO | 2003/026577 A2 | 4/2003 |
| WO | 2004/010957 A2 | 2/2004 |
| WO | WO2005/099768 A2 | 10/2005 |
| WO | WO2005/099768 A3 | 10/2005 |
| WO | 2007/011968 A2 | 1/2007 |
| WO | WO 2009/099741 | 8/2009 |
| WO | 2011/130616 A1 | 10/2011 |
| WO | 2013/053873 A1 | 4/2013 |
| WO | 2013/055990 A1 | 4/2013 |
| WO | 2013/055993 A1 | 4/2013 |
| WO | 2013/173337 A2 | 11/2013 |

(Continued)

OTHER PUBLICATIONS

Senter. Current Opinion in Chemical Biology, 2009, 13, 235-44 (Year: 2009).*
Henry. Tetrahedron Letters, 2007, 1791-94 (Year: 2007).*
Kirschke, Heidrun "Lysosomal Cysteine Peptidases and Malignant Tumours" Cellular Peptidases in Immune Functions and Diseases, 1997, 253-257, Plenum Press, New York.
Sperker, Bernhard et al "The Role of Beta-Glucuronidase in Drug Disposition and Drug Targeting in Humans" Clin. Pharmacokinet., Jul. 1997, 33(1): 18-31.
Dubowchik, G.M. et al "Pharmacology & Therapeutics" 1999, 83: 67-123.
Huang, Pearl S. et al "Drug-targeting Strategies in Cancer Therapy" Genetics & Development, 2001, 11:104-110.
Allen, Theresa M. "Ligand-Targeted Therapeutics in Anticancer Therapy" www.nature.com/reviews/cancer (2002) 2:750-765.
Papot, S. et al, "Design of Selectively Activated Anticancer Prodrugs: Elimination and Cyclization Strategies" Curr. Med. Chem.—Anti-Cancer Agents (2002) 2:155-185.

(Continued)

*Primary Examiner* — Noble E Jarrell
(74) *Attorney, Agent, or Firm* — Fish & Richardson P.C.

(57) ABSTRACT

The present invention provides Ligand-Drug Conjugates and Drug-Linker Compounds comprising a methylene carbamate unit. The invention provides inter alia, Ligand-Drug Conjugates, wherein the Ligand-Drug Conjugate is comprised of a Self-immolative Assembly Unit having a methylene carbamate unit for conjugation of a drug to a targeting ligand, methods of preparing and using them, and intermediates thereof. The Ligand-Drug Conjugates of the present invention are stable in circulation, yet capable of inflicting cell death once free drug is released from a Conjugate in the vicinity or within tumor cells.

53 Claims, 2 Drawing Sheets

(56) References Cited

FOREIGN PATENT DOCUMENTS

| WO | 2014/068443 A1 | 5/2014 |
|----|----------------|--------|
| WO | WO2016/141230 | 9/2016 |

OTHER PUBLICATIONS

Chen, Xi et al "Glucuronides in Anti-Cancer Therapy" Curr. Med. Chem.—Anti-Cancer Agents (2003) 3:139-150.
Sanderson, Russell J. et al "In vivo Drug-Linker Stability of an Anti-CD30 Dipeptide-Linked Auristatin Immunoconjugate" Clinical Cancer Research (2005) 11: 843-852.
Verheijen, Jeroen et al. "mTOR inhibitors in oncology" Annual Reports in Medicinal Chemistry (2008) 43; 189-202.
Jeffrey, Scott C. et al "Development and Properties of Beta-Glucuronide Linkers for Monoclonal Antibody-Drug Conjugates" Bioconjugate Chem. (2006) 17: 831-840.
Alley, Stephen C. et al "Contribution of Linker Stability to the Activities of Anticancer Immunoconjugates" Bioconjugate Chem. (2008) 19: 759-765.
Baldwin, Aaron D. et al "Tunable Degradation of Maleimide—Thiol Adducts in reducing Environments" Bioconjugate Chem. (2011) 22: 1946-1953.
De Graaf, Michelle et al "Beta-Glucuronidase-Mediated Drug Release" Current Pharmaceutical Design, (2002) 8: 1391-1403.
Lyon, Robert P. et al "Self-hydrolyzing Maleimides Improve the Stability and Pharmacological Properties of Antibody-drug Conjugates" Nature Biotechnology (2014) pp. 1-7.
Caufield, C.E. "Structure-activity relationships involving modifications to the macrolides FK-506 and rapamycin" Current Pharmaceutical Design (1995) 1: 145-160.
Lougerstay, Rachel M. et al. "Synthesis of self-immolative glucuronide spacers based on aminomethylcarbamate. Application to 5-fluorouracil prodrugs for antibody-directed enzyme prodrug therapy" J. Chem. Soc. Perkin 1 (1999) 1369-1375.
Luengo, Juan I. et al. "Structure-activity studies of rapamycin analogs: evidence that the C-7 methoxy group is part of the effector domain and positioned at the FKBP12-FRAP interface" Chemistry & Biology (1995) 2: 471-481.
Majumdar, Susruta, and Sloan, Kenneth B."N-Alkyl-N-alkyloxycarbonylaminomethyl (NANAOCAM) prodrugs of carboxylic acid containing drugs" Bioorganic & Medicinal Chemistry Letters (2007) 17: 1447-1450.
Porta, Camillo et al. "Targeting PI3K/Akt/mTOR signaling in cancer" Frontiers in Oncology (2014) 4, Article 64.
Sewell, Tonya, J. "Inhibition of Calcineurin by a Novel FK-506-binding Protein" Journal of Biological Chemistry (1994), 269: 21094-21102.
Tanaka, Hirokazu et al. "Structure of FK506: A novel immunosuppressant isolated from Streptomyces" Journal American Chemical Society (1987) 109: 5031-5033.
Burke et al. "Design, Synthesis, and Biological Evaluation of Antibody-Drug Conjugates Comprised of Potent Camptothecin Analogues," Bioconjugate Chem., 2009, 20(6): 1242-1250.
PCT International Preliminary Report on Patentability in Application No. PCT/US2014/0/1593, dated Jun. 21, 2016, 8 pages.
PCT International Search Report and Written Opinion in Application No. PCT/US2014/071593, dated May 1, 2015, 14 pages.
"PubChem. Compound Summary for: CID 44199991, Create Date.: Sep. 21, 2009. [Retrieved on Apr. 2015]. Retrieved from the Internet. URL: https.//pubchem.ncbi.nlm.nih.gov/compound/44199991 >".
Toki et al., "Protease-Mediated Fragmentation of p-Amidobenzyl Ethers: A New Strategy for the Activation of Anticancer Prodrugs." J. Org. Chem, 2002, 67:1866-1872.
Ganguly et al., "Protonation/deprotonation energetics of uracil, thymine, and cytosine in water from e.m.f./spectrophotometsic measurements," Canadian Journal of Chemistry, 1994, 72:1120-1126.
Jang et al., "First Principles Calculation of pKa Values for 5-Substituted Uracils," J. Phys. Chem. A., 2001, 105:274-280.
Nolting, "Linker Technologies for Anitbody-Drug Conjugates," Methods Mol Biol, 2013, 1045:71-100.
Privat et al., "A proposed mechanism for the mutagenicity of 5-formyluracil," Mutation Research, 1996, 354:151-156.
Santi et al., "Predictable and tunable half-life extension of therapeutic agents bv controlled chemical release from macromolecular conjugates," PNAS, Apr. 2012, 109(16):6211-6216.
Schneider et al., "β-Eliminative Releasable Linkers Adapted for Bioconjugation of Macromolecules to Phenols," Bioconjugate Chemistry, 2013, 24(12):1990-7.
Thomas et al., "Soft Alkyl Ether Prodrugs of a Model Phenolic Drug: The Effect of Incorporation of Ethyleneoxy Groups on Transdermal Delivery," Molecules, 2009, 14:4231-4245.

* cited by examiner

METHYLENE CARBAMATE LINKERS FOR USE WITH TARGETED-DRUG CONJUGATES

CROSS-REFERENCE TO RELATED APPLICATIONS

This non-provisional application claims priority under 35 U.S.C. § 119(e) to U.S. Appl. Ser. No. 61/918,539, filed on Dec. 19, 2013, which is incorporated herein by reference in its entirety.

BACKGROUND OF THE INVENTION

A great deal of interest has surrounded the use of monoclonal antibodies (mAbs) for the targeted delivery of cytotoxic agents to tumor cells. While a number of different drug classes have been evaluated for delivery via antibodies, only a few drug classes have proved sufficiently active as antibody drug conjugates, while having a suitable toxicity profile, to warrant clinical development. One such class is the auristatins, related to the natural product dolastatin 10. Representative auristatins include MMAE (N-methylvaline-valine-dolaisoleuine-dolaproine-norephedrine) and MMAF (N-methylvaline-valine-dolaisoleuine-dolaproine-phenylalanine).

The design of Antibody Drug Conjugates (ADCs), by attaching a cytotoxic agent to antibody, typically via a linker, involves consideration of a variety of factors, including the presence of a conjugation handle on the drug for attachment to the linker and linker technology for attaching the drug to an antibody in a conditionally stable manner. Certain drug classes thought to be lacking appropriate conjugation handles have been considered unsuitable for use as ADCs. Although it may be possible to modify such a drug to include a conjugation handle, such a modification can negatively interfere with the drug's activity profile.

Linkers comprising esters and carbonates have typically been used for conjugation of alcohol-containing drugs and result in ADCs having variable stability and drug release profiles. A non-optimal profile can result in reduced ADC potency, insufficient immunologic specificity of the conjugate and increased toxicity due to non-specific release of the drug from the conjugate. Although it has been shown that certain phenolic alcohols can be directly attached through ether linkages to the self-immolative Spacer Unit p-amidobenzyl alcohol, these linker strategies are unlikely to work for all alcohol-containing drugs, including many aliphatic alcohol-containing drugs (see, for example, Told, et al. J. Org. Chem. 2002, 67, 1866-1872). One reason for that may be due to the high pKa of aliphatic alcohol-containing drugs.

Therefore, a need exists for new linker technologies that can be used to attach drugs heretofore believed to be unsuitable for use as ADCs, and Ligand Drug Conjugates (LDCs) in general, including a need for more versatile methods for linking aromatic alcohol- and aliphatic alcohol-containing drugs to other targeting ligands in addition to antibodies. The present invention addresses those and other needs.

BRIEF SUMMARY OF THE INVENTION

The invention provides inter alia, Ligand-Drug Conjugates, wherein the Ligand-Drug Conjugate is comprised of a Self-immolative Assembly Unit having a methylene carbamate unit for conjugation of a drug to a targeting ligand, methods of preparing and using them, and intermediates thereof. The Ligand-Drug Conjugates of the present invention are stable in circulation, yet capable of inflicting cell death once free drug is released from a Conjugate in the vicinity or within tumor cells.

In one principle embodiment, a Ligand Drug Conjugate (LDC), or composition thereof, is comprised of a Ligand Unit, a Drug Unit and a Linker Unit that connects the Ligand Unit to the Drug Unit, wherein the Linker Unit is comprised of a Self-immolative Assembly Unit having a methylene carbamate unit and an activateable self-immolative moiety, wherein activation of the activateable self-immolative moiety results in release of free drug from the LDC from self-immolation, and wherein the methylene carbamate unit is covalently attached to the Drug Unit and the activateable self-immolative moiety, wherein the methylene carbamate unit covalently attached to the Drug Unit is represented by the structure of formula I:

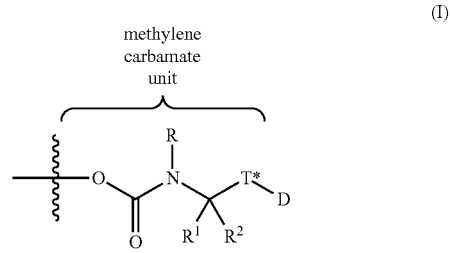

(I)

or a pharmaceutically acceptable salt thereof, wherein
the wavy line indicates covalent attachment of the methylene carbamate unit to an activateable self-immolative moiety (X);

D is a Drug Unit having a functional group (e.g., hydroxyl, thiol, amide or amine functional group) that has been incorporated into the methylene carbamate unit, T* is a heteroatom from said functional group (e.g., oxygen, sulfur, optionally substituted nitrogen) that becomes incorporated into the methylene carbamate unit;

X is an activateable self-immolative moiety;

R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or R and $R^1$ together with the nitrogen and carbon atoms to which they are attached comprise an azetidinyl, pyrrolodinyl, piperidinyl or homopiperidinyl moiety, and $R^2$ is hydrogen.

In some of those embodiments, a Ligand Drug Conjugate, or composition thereof, having the methylene carbamate unit of formula I is represented by the structure of formula II:

(II)

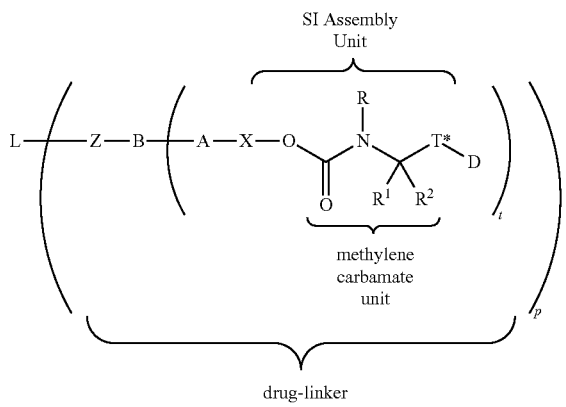

drug-linker or a pharmaceutically acceptable salt thereof; wherein
L is a Ligand Unit;
Z is a Stretcher Unit;
B is an optional Branching Unit and is present when t is greater than 1 and is absent when t is 1;
A is an optional Connector Unit;
X is an activateable self-immolative moiety;
the subscript t ranges from 1 to 4;
the subscript p is an integer (for an individual LDC) or a number (for a population of LDCs in a LDC composition) ranging from 1 to 16; and
and D, T*, R, $R^1$ and $R^2$ are as defined in formula I.

Other principle embodiments are Drug-Linker Compounds useful as intermediates for preparing Ligand-Drug Conjugates, wherein the Drug-Linker Compound is comprised of a Drug Unit and a Linker Unit, wherein the Linker Unit is comprised of a Stretcher Unit precursor (Z') capable of forming a covalent bond to a targeting ligand that provides for a Ligand Unit, a Self-immolative Assembly Unit having a methylene carbamate unit and an activateable self-immolative moiety, wherein activation of the activateable self-immolative moiety in a LDC in which the Drug-Linker Compound is incorporated results in release of free drug from the LDC by self-immolation, and wherein the methylene carbamate unit is covalently attached to the Drug Unit and the activateable self-immolative moiety.

In some of those embodiments the Drug-Linker Compound having the methylene carbamate unit of formula I has the structure of formula V:

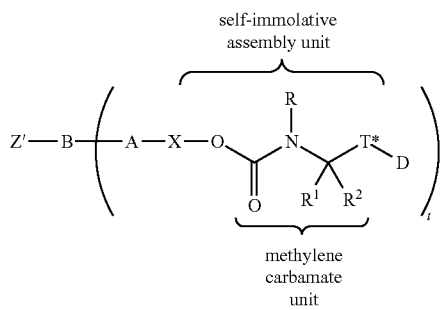

(V)

or a pharmaceutically acceptable salt thereof, wherein
Z' is a Stretcher Unit precursor to a Stretcher Unit (Z) and is comprised of a functional group that provides for covalent attachment of a Ligand Unit to Z;

and B, A, X, R, $R^1$, $R^2$, T*, D, and the subscript t are as defined for Formula (II).

DESCRIPTION OF THE INVENTION

General

Figure 1:
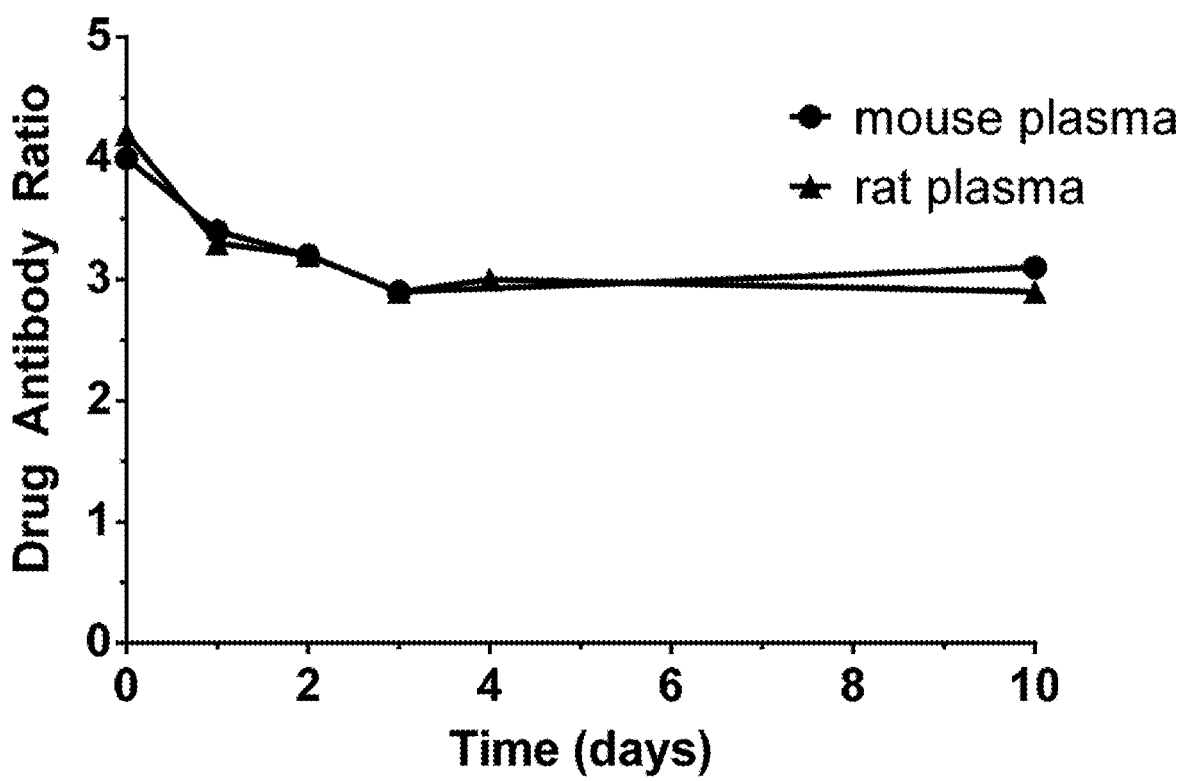
FIG. 1 demonstrates the stability ex vivo in rat and mouse plasma of an ADC composition having an average drug loading of 4 in which the ADCs of the composition are comprised of a methylene alkoxy carbamate unit (MAC unit) that incorporates the oxygen heteroatom from the hydroxyl functional group of Auristatin E.

The present invention is based, in part, on the discovery that attachment of a drug-linker moiety having a Self-Immolative Assembly Unit comprising a activeatable self-immolative moiety (X) and a methylene alkoxy (or aryloxy) carbamate unit (also referred to herein as a MAC unit) that incorporates the oxygen heteroatom from a hydroxyl functional group of a drug (e.g., a drug having an aromatic or aliphatic alcohol) to a Ligand Unit permits the synthesis of conditionally stable Ligand-Drug Conjugates (LDCs) via the drug's hydroxy functional group. The resultant LDCs and are able to liberate free drug on activation, which regenerates the hydroxyl functional group.

Other embodiments are based, in part, on the discovery that the MAC unit can be adapted to provide other methylene carbamate units for use with drugs having functional groups other than hydroxyl, including drugs containing thiol, amide or amine functional groups. Accordingly, exemplary Self-immolative Assembly Units provided herein comprise methylene carbamate units that are directly attached to heteroatoms from drug functional groups having varying leaving group abilities. In some aspects, the functional group is hydroxyl (including that of primary, secondary and tetiary aliphatic alcohols and aromatic alcohols), thiol (including alkylthiol and arylthiol), amide (including carboxamide, sulfonamide, and phosphoramide), or amine (including, primary aliphatic amines, secondary aliphatic amines and tertiary aliphatic amines that are cyclic or alicyclic, or primary or secondary aryl amines) from a drug so that the heteroatom attached to the methylene carbamate unit (T*) is an oxygen, sulfur or nitrogen heteroatom (optionally substituted, as for example, when the functional group is a secondary amide, a tertiary amine, a cyclic aliphatic amine or an N-substituted aryl amine) In those instances conditional activation of a Self-immolative Assembly Unit releases H-T*-D, or in the case of tertiary amines, T*-D. A MAC unit is one type of methylene carbamate unit, wherein the functional group heteroatom used for covalent attachment of a hydroxyl-containing drug is the oxygen atom from the drug's hydroxyl functional group.

In some embodiments, a methylene carbamate unit covalently attached to a Drug Unit in a Self-immolative Assembly Unit of an LDC or a Drug-Linker Compound has Formula I represented below:

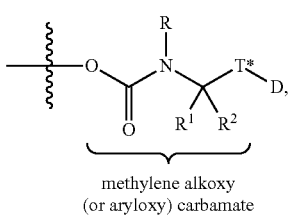

methylene alkoxy
(or aryloxy) carbamate wherein the wavy line indicates covalent attachment to an activateable self-immolative moiety (X) of the Self-immolative Assembly Unit; D is a Drug Unit having a functional group that has been incorporated into a drug-linker moiety of an LDC or a Drug-Linker Compound, T* is the oxygen, sulfur, or optionally substituted nitrogen heteroatom from said functional group that is incorporated into the methylene carbamate unit; R and $R^1$ and $R^2$ are independently hydrogen, optionally substituted $C_{1-6}$ alkyl, optionally substituted $C_{6-14}$ aryl or optionally substituted C-linked $C_{3-8}$ heteroaryl, or both R and R' together with the nitrogen and carbon atoms to which they are attached comprise an azetidinyl, pyrrolodinyl, piperidinyl or homopiperidinyl moiety (preferably a pyrrolodinyl or piperidinyl moiety) and $R^2$ is hydrogen.

Exemplary embodiments include those wherein $R^2$ is hydrogen as set forth in Formula (Ia)

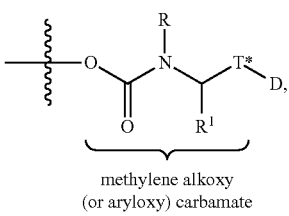

methylene alkoxy
(or aryloxy) carbamate and the wavy line, T*, D, R, and $R^1$ are as defined for Formula I. R and $R^1$ are preferably hydrogen, optionally substituted $C_{1-6}$ alkyl, or optionally substituted $C_{6-14}$ aryl (more preferably hydrogen, optionally substituted $C_{1-4}$ alkyl or optionally substituted phenyl, most preferably hydrogen or optionally substituted $C_{1-4}$ alkyl). In some embodiments of formula Ia, R and $R^1$ are hydrogen. In other embodiments of formula Ia, one of R and $R^1$ is a PEG Unit or a Basic Unit and the other is hydrogen or unsubstituted $C_{1-4}$ alkyl.

Exemplary embodiments include those wherein $R^1$ and $R^2$ together with the nitrogen and carbon atoms to which they are attached comprise a heterocyclo as set forth in Formula (Ib):

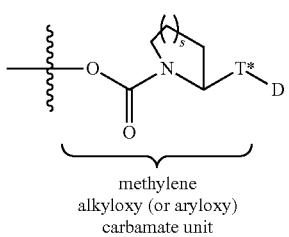

methylene
alkyloxy (or aryloxy)
carbamate unit wherein T*, and D and the wavy line are as defined for Formula I and s is 0, 1, 2 or 3 (preferably 0, 1, or 2; more preferably 1 or 2).

In some aspects, the methylene carbamate unit is a MAC unit. In such embodiments, D is a Drug Unit having a hydroxyl functional group and the MAC unit covalently attached to a Drug Unit in a Self-immolative Assembly Unit of an LDC or a Drug-Linker Compound has the Formula I' represented below:

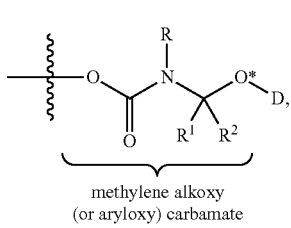

methylene alkoxy
(or aryloxy) carbamate wherein the wavy line, R, $R^1$, and $R^2$ are as defined for Formula I, D is a Drug Unit having a hydroxyl functional group that has been incorporated into a drug-linker moiety of an LDC or a Drug-Linker Compound, and O* is the oxygen heteroatom from said functional group that is incorporated into the methylene carbamate unit. In some embodiments of formula I' one of $R^1$ and $R^2$ is a Basic Unit and the other is hydrogen or unsubstituted $C_1$-$C_4$ alkyl. In other embodiments of formula I', one of $R^1$ and $R^2$ is a PEG Unit and the other is hydrogen or unsubstituted $C_1$-$C_4$ alkyl.

Exemplary embodiments include those wherein $R^2$ is hydrogen as set forth in Formula (Ia')

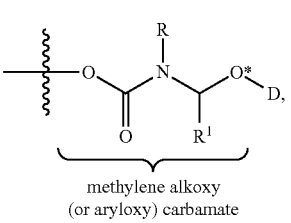

methylene alkoxy
(or aryloxy) carbamate wherein the wavy line, R, and $R^1$ are as defined for Formula I, D is a Drug Unit having a hydroxyl functional group that has been incorporated into a drug-linker moiety of an LDC or a Drug-Linker Compound, and O* is the oxygen heteroatom from said functional group that is incorporated into the methylene carbamate unit. R and $R^1$ are preferably independently selected hydrogen, optionally substituted $C_{1-6}$ alkyl, or optionally substituted $C_{6-14}$ aryl, (more preferably hydrogen, optionally substituted $C_{1-4}$ alkyl or optionally substituted phenyl, most preferably hydrogen or optionally substituted $C_{1-4}$ alkyl). In some embodiments of formula Ia', $R^1$ and $R^2$ are hydrogen. In other embodiments of formula Ia' one of R and R' is a PEG Unit or a Basic Unit and the other is hydrogen or unsubstituted $C_{1-4}$ alkyl.

Exemplary embodiments include those wherein $R^1$ and $R^2$ together with the nitrogen and carbon atoms to which they are attached comprise a heterocyclo as set forth in Formula (Ib')

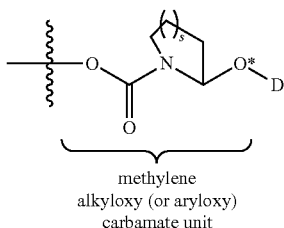

(Ib')

methylene
alkyloxy (or aryloxy)
carbamate unit wherein the wavy line is as defined for Formula I, D is a Drug Unit having a hydroxyl functional group that has been incorporated into a drug-linker moiety of an LDC or a Drug-Linker Compound, O* is the oxygen heteroatom from said functional group that is incorporated into the methylene carbamate unit, and the subscript s is 0, 1, 2, or 3 (preferably 0, 1, or 2; more preferably 1 or 2).

The MAC Unit is the terminus of a Self-immolative Assembly Unit. The main function of the Self-immolative Assembly Unit is to release free drug (e.g., H—O*-D) after a selective (i.e., conditional) activation event that initiates self-immolation of the self-immolative moiety within the Self-immolative Assembly Unit. The Self-immolative Assembly Unit is designed to have in addition to a MAC unit, a self-immolative Spacer Unit (Y), which is the self-immolative portion of the activeatable self-immolative moiety (X) and an Activation Unit (W) that is conditionally acted upon to initiate the self-immolation reaction sequence within the self-immolative Spacer Unit. Activation of self-immolation is by a cleavage event that leads to rapid fragmentation of Y to liberate free drug (e.g., free alcohol-containing drug). The drug incorporated into a LDC of the present invention can contain multiple functional groups, although attachment of the Drug Unit to the MAC Unit in those instances is through a heteroatom from only one of the functional groups. For example, in the case of alcohol-containing drugs, the drug may contain more than one alcohol moieties (i.e., more than one hydroxy functional group), although attachment of the Drug Unit to the MAC Unit in those instances is through the oxygen heteroatom from only one of the hydroxyl functional groups.

It will be understood for embodiments wherein the Drug Unit has an amine as the functional group whose nitrogen becomes part of a methylene carbamate unit that T* as N* represents the —NH— moiety from a primary amine-containing compound or an (hetero)aryl amine-containing drug comprising the moiety of -(hetero)arylene-NH$_2$ or -(hetero)arylene-NH— (i.e., a drug having a primary, secondary or cyclic aromatic amine functional group wherein (hetero)aryl or (hetero)arylene includes an optionally substituted phenyl or phenylene or a 5- or 6-membered heteroaryl or heteroarylene. Accordingly, T* as N* is referred to as an optionally substituted nitrogen. Likewise, when the Drug Unit has an amide as the functional group whose nitrogen becomes part of a methylene carbamate unit [so] that T* as N* represents the moiety —NH(C=O)— from a primary amide-containing drug (i.e., having the functional group of NH$_2$C(=O)—, a secondary amide (i.e., having the functional group of NH(R$^N$)C(=O)—, wherein RN includes alkyl, aryl, C-linked heteroaryl, alkyl(aryl)sulfonyl, and alkyl(aryl)phosphoryl, then T* as N* is also referred to as an optionally substituted nitrogen. For a secondary amine-containing free drug having that nitrogen within a hetero-carbocycle or hetereocarbocyclo, including an aromatic amine-containing drug wherein its aryl or arylene is substituted by —NH-alkylene- in which the alkylene moiety is bonded to the aryl or arylene thus forming a fused ring system, it will be further understood that T*-D represents that cyclic amine structure.

Definitions

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

The term "antibody" as used herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. The native form of an antibody is a tetramer and consists of two identical pairs of immunoglobulin chains, each pair having one light chain and one heavy chain. In each pair, the light and heavy chain variable regions (VL and VH) are together primarily responsible for binding to an antigen. The light chain and heavy chain variable domains consist of a framework region interrupted by three hypervariable regions, also called "complementarity determining regions" or "CDRs." The constant regions may be recognized by and interact with the immune system. (see, e.g., Janeway et al., 2001, *Immunol. Biology*, 5th Ed., Garland Publishing, New York). An antibody can be of any type (e.g., IgG, IgE, IgM, IgD, and IgA), class (e.g., IgG1, IgG2, IgG3, IgG4, IgA1 and IgA2) or subclass. The antibody can be derived from any suitable species. In some embodiments, the antibody is of human or murine origin. An antibody can be, for example, human, humanized or chimeric.

The term "monoclonal antibody" as used herein refers to an antibody obtained from a population of substantially homogeneous antibodies, i.e., the individual antibodies comprising the population are identical in sequence except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An "antibody fragment" comprises a portion of an intact antibody, comprising the antigen-binding or variable region thereof. Examples of antibody fragments include Fab, Fab', F(ab')2, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically bind to a target antigen (e.g., a cancer cell antigen, a viral antigen or a microbial antigen).

An "antigen" is an entity to which an antibody specifically binds.

The terms "specific binding" and "specifically binds" mean that the antibody or antibody derivative will bind, in a highly selective manner, with its corresponding epitope of a target antigen and not with the multitude of other antigens. Typically, the antibody or antibody derivative binds with an affinity of at least about $1\times10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen.

The term "inhibit" or "inhibition of" means to reduce by a measurable amount, or to prevent entirely.

The term "therapeutically effective amount" refers to an amount of a conjugate effective to treat a disease or disorder in a mammal. In the case of cancer, the therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

The term "substantial" or "substantially" refers to a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

The term "cytotoxic activity" refers to a cell-killing effect of a drug or Ligand-Drug Conjugate or an intracellular metabolite of a Ligand-Drug Conjugate. Cytotoxic activity may be expressed as the $IC_{50}$ value, which is the concentration (molar or mass) per unit volume at which half the cells survive.

The term "cytostatic activity" refers to an anti-proliferative effect of a drug or Ligand-Drug Conjugate or an intracellular metabolite of a Ligand-Drug Conjugate.

The term "cytotoxic agent" as used herein refers to a substance that has cytotoxic activity and causes destruction of cells. The term is intended to include chemotherapeutic agents, and toxins such as small molecule toxins or enzymatically active toxins of bacterial, fungal, plant or animal origin, including synthetic analogs and derivatives thereof.

The term "cytostatic agent" as used herein refers to a substance that inhibits a function of cells, including cell growth or multiplication. Cytostatic agents include inhibitors such as protein inhibitors, e.g., enzyme inhibitors. Cytostatic agents have cytostatic activity.

The terms "cancer" and "cancerous" refer to or describe the physiological condition or disorder in mammals that is typically characterized by unregulated cell growth. A "tumor" comprises one or more cancerous cells.

An "autoimmune disease" as used herein refers to a disease or disorder arising from and directed against an individual's own tissues or proteins.

"Patient" as used herein refers to a subject to whom is administered a Ligand-Drug Conjugate of the present invention. Patient includes, but are not limited to, a human, rat, mouse, guinea pig, non-human primate, pig, goat, cow, horse, dog, cat, bird and fowl. Typically, the patient is a rat, mouse, dog, human or non-human primate, more typically a human.

The terms "treat" or "treatment," unless otherwise indicated by context, refer to therapeutic treatment and prophylactic wherein the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder.

In the context of cancer, the term "treating" includes any or all of: killing tumor cells; inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of: inhibiting replication of cells associated with an autoimmune disease state including, but not limited to, cells that produce an autoimmune antibody, lessening the autoimmune-antibody burden and ameliorating one or more symptoms of an autoimmune disease.

The phrase "pharmaceutically acceptable salt," as used herein, refers to pharmaceutically acceptable organic or inorganic salts of a compound (e.g., a Drug, Drug-Linker, or a Ligand-Drug Conjugate). In some aspects, the compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

A Linker Unit is a bifunctional moiety that connects a Drug Unit to a Ligand Unit in a Ligand Drug Conjugate. The Linker Units of the present invention have several components (e.g., a Stretcher Unit having an optional Basic Unit, optional Branching Unit, optional Connector Unit, and Self-Immolative Assembly Unit).

"Basic Unit" as used herein is an organic moiety of a Stretcher Unit (Z), or Stretcher Unit precursor (Z'), comprised of a succinimide or maleimide system, respectively, or an instance of R, which is a substituent on the carbamate nitrogen of a methylene carbamate unit or an instance of $R^1$ or $R^2$, which are substituents of the methylene carbon of a methylene carbamate unit. When part of a Stretcher Unit, a Basic Unit is capable of catalyzing addition of a water molecule to one of the succinimide carbonyl-nitrogen bonds of Z and can be initiated under controlled conditions tolerable by the Ligand Unit, which is attached to that Stretcher Unit. For that purpose, the basic functional group of the Basic Unit (BU) and its relative position in Z with respect to its succinimide ring system is selected for its ability to hydrogen bond to a carbonyl group of that ring system to effectively increase its electrophilicity and hence its susceptibility to water attack. Alternatively, those variables are selected so that a water molecule, whose nucleophilicity is increased by hydrogen bonding to the basic functional group of BU, is directed to a carbonyl group of the succinimide ring system of Z. Typically, such a Basic Unit, acting through either mechanism, is comprised of 1-6 contiguous carbon atoms that connect its basic amino functional group to the remainder of the Stretcher Unit. For increasing the electrophilicity of a succinimide carbonyl in Z by hydrogen bonding, BU is required to have a primary or secondary amine functional group, whereas increasing water nucleophilicity in the manner described may be done with a primary, secondary or tertiary amine as the basic functional group of BU. In order that the basic amine functional group be in the required proximity to assist in the hydrolysis of the succinimide of Z by either mechanism, the amine-bearing carbon chain of BU is typically attached to an alpha carbon of an optionally substituted alkyl moiety that is boned to the maleimide nitrogen of the corresponding Stretcher Unit precursor Z'.

When part of a Stretcher Unit precursor, a basic amine functional group of a Basic Unit is typically protected as a salt form or with a suitable protecting group to avoid premature hydrolysis of the maleimide moiety or direct attach by nucleophillic nitrogen of the basic amine functional group onto a carbonyl of the maleimide moiety ring system. A suitable protecting group for that purpose is an acid-labile protecting group such an alkyloxycarbonyl group. When part of a methylene carbamate unit, the moiety in a Basic Unit connecting the carbamate nitrogen to the basic functional group (and/or the methylene carbon of a methylene carbamate unit to the basic functional group) which typically is a comprised of 2-6 contiguous carbon atoms, is chosen to have the required proximity to the T*-D moiety of the methylene carbamate unit having that Basic Unit to decrease the tendency of that moiety to be prematurely lost as H-T*-D due to spontaneous solvolysis. Exemplary, but non-limiting examples of Basic Units are $-(CH_2)_xNH_2$, $-(CH_2)_xNHR^{op}$, or $-(CH_2)_xN(R^{op})_2$, wherein x is an integer ranging from 1-4 and $R^{op}$ in these examples is $C_{1-6}$ alkyl.

"PEG Unit" as used herein is an organic moiety comprised of repeating ethylene-oxy subunits and may be polydisperse, monodisperse or discrete (i.e., having discrete number of ethylene-oxy subunits). Polydisperse PEGs are a heterogeneous mixture of sizes and molecular weights whereas monodisperse PEGs are typically purified from heterogeneous mixtures and are therefore provide a single chain length and molecular weight. Preferred PEG Units are discrete PEGs, compounds that are synthesized in step-wise fashion and not via a polymerization process. Discrete PEGs provide a single molecule with defined and specified chain length.

The PEG Unit provided herein comprises one or multiple polyethylene glycol chains, each comprised of one or more ethyleneoxy subunits, covalently attached to each other. The polyethylene glycol chains can be linked together, for example, in a linear, branched or star shaped configuration. Typically, at least one of the polyethylene glycol chains prior to incorporation into a Ligand Drug Conjugate is derivitized at one end with an alkyl moiety substituted with an electrophilic group for covalent attachment to the carbamate nitrogen of its methylene carbamate unit (i.e., represents an instance of R). In other instances a PEG Unit is an instance of $R^1$ or $R^2$, which are substituents of the methylene carbon of a methylene carbamate unit. Typically the terminal ethyleneoxy subunit in each polyethylene glycol chains not involved in covalent attachment to the carbamate nitrogen or methylene carbon of the methylene carbamate unit is modified with a PEG Capping Unit, typically an optionally substituted alkyl such as $-CH_3$, $CH_2CH_3$ or $CH_2CH_2CO_2H$. A preferred PEG Unit has a single polyethylene glycol chain with 8 to 24 $-CH_2CH_2O-$ subunits covalently attached in series and terminated at one end with a PEG Capping Unit.

Unless otherwise indicated, the term "alkyl" by itself or as part of another term refers to a substituted or unsubstituted straight chain or branched, saturated or unsaturated hydrocarbon having the indicated number of carbon atoms (e.g., "$-C_1-C_8$ alkyl" or "$-C_1-C_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "$-C_1-C_8$ alkyl" groups include, but are not limited to, -methyl, -ethyl, -n-propyl, -n-butyl, -n-pentyl, -n-hexyl, -n-heptyl and -n-octyl; while branched $-C_1-C_8$ alkyls include, but are not limited to, -isopropyl, -sec-butyl, -isobutyl, -tert-butyl, -isopentyl, and -2-methylbutyl; unsaturated $-C_2-C_8$ alkyls include, but are not limited to, -vinyl, -allyl, -1-butenyl, -2-butenyl, -isobutylenyl, -1 pentenyl, -2 pentenyl, -3 methyl-1-butenyl, -2 methyl-2-butenyl, -2,3 dimethyl-2-butenyl, -1-hexyl, 2-hexyl, -3-hexyl, -acetylenyl, -propynyl, -1 butynyl,-2 butynyl, -1 pentynyl, -2 pentynyl and -3 methyl 1 butynyl. Sometimes an alkyl group is unsubstituted. An alkyl group can be substituted with one or more groups. In other aspects, an alkyl group will be saturated.

Unless otherwise indicated, "alkylene," by itself of as part of another term, refers to a substituted or unsubstituted saturated, branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene ($-CH_2-$), 1,2-ethyl ($-CH_2CH_2-$), 1,3-propyl ($-CH_2CH_2CH_2-$), 1,4-butyl ($-CH_2CH_2CH_2CH_2-$), and the like. In preferred aspects, an alkylene is a branched or straight chain hydrocarbon (i.e., it is not a cyclic hydrocarbon).

Unless otherwise indicated, "aryl," by itself or as part of another term, means a substituted or unsubstituted monovalent carbocyclic aromatic hydrocarbon radical of the stated number of carbon atoms, typically 6-20 carbon atoms, derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. An exemplary aryl group is a phenyl group.

Unless otherwise indicated, an "arylene," by itself or as part of another term, is an aryl group as defined above which has two covalent bonds (i.e., it is divalent) and can be in the ortho, meta, or para orientations as shown in the following structures, with phenyl as the exemplary group:

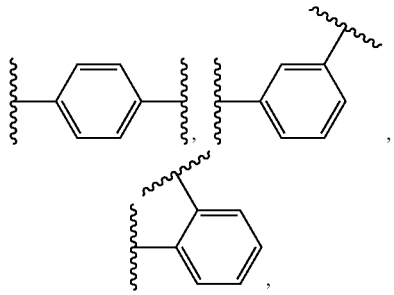

Unless otherwise indicated, a "$C_3$-$C_8$ heterocycle," by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Heterocycles in which all or the ring atoms are involved in aromaticity are referred to as heteroaryls and otherwise are referred to heterocarbocycles. Unless otherwise noted, the heterocycle is attached to its pendant group at any heteroatom or carbon atom that results in a stable structure. As such a heteroaryl may be bonded through an aromatic carbon of its aromatic ring system, referred to as a C-linked heteroaryl, or through a non-double-bonded N atom (i.e., not =N—) in its aromatic ring system, which is referred to as an N-linked heteroaryl. Thus, nitrogen-containing heterocycles may be C-linked or N-linked and include pyrrole moieties, such as pyrrol-1-yl (N-linked) and pyrrol-3-yl (C-linked), and imidazole moieties such as imidazol-1-yl and imidazol-3-yl (both N-linked), and imidazol-2-yl, imidazol-4-yl and imidazol-5-yl moieties (all of which are C-linked).

Unless otherwise indicated, a "$C_3$-$C_8$ heteroaryl," is an aromatic $C_3$-$C_8$ heterocycle in which the subscript denotes the total number of carbons of the cyclic ring system of the heterocycle or the total number of aromatic carbons of the aromatic ring system of the heteroaryl and does not implicate the size of the ring system or the presence or absence of ring fusion. Representative examples of a $C_3$-$C_8$ heterocycle include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl. When explicitly given, the size of the ring system of a heterocycle or heteroaryl is indicated by the total number of atoms in the ring. For example, designation as a 5- or 6-membered heteroaryl indicates the total number or aromatic atoms (i.e., 5 or 6) in the heteroaromatic ring system of the heteroaryl, but does not imply the number of aromatic heteroatoms or aromatic carbons in that ring system. Fused heteroaryls are explicitly stated or implied by context as such and are typically indicated by the number of aromatic atoms in each aromatic ring that are fused together to make up the fused heteroaromatic ring system. For example a 5,6-membered heteroaryl is an aromatic 5-membered ring fused to an aromatic 6-membered ring in which one or both of the rings have aromatic heteroatom(s) or where a heteroatom is shared between the two rings.

A heterocycle fused to an aryl or heteroaryl such that the heterocycle remains non-aromatic and is part of a larger structure through attachment with the non-aromatic portion of the fused ring system is an example of an optionally substituted heterocycle in which the heterocycle is substituted by ring fusion with the aryl or heteroaryl. Likewise, an aryl or heteroaryl fused to heterocycle or carbocycle that is part of a larger structure through attachment with the aromatic portion of the fused ring system is an example of an optionally substituted aryl or heterocycle in which the aryl or heterocycle is substituted by ring fusion with the heterocycle or carbocycle.

Unless otherwise indicated, "$C_3$-$C_8$ heterocyclo," by itself or as part of another term, refers to a $C_3$-$C_8$ heterocyclic defined above wherein one of the hydrogen atoms of the heterocycle is replaced with a bond (i.e., it is divalent). Unless otherwise indicated, a "$C_3$-$C_8$ heteroarylene," by itself or as part of another term, refers to a $C_3$-$C_8$ heteroaryl group defined above wherein one of the heteroaryl group's hydrogen atoms is replaced with a bond (i.e., it is divalent).

Unless otherwise indicated, a "$C_3$-$C_8$ carbocycle," by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Unless otherwise indicated, a "$C_3$-$C_8$ carbocyclo," by itself or as part of another term, refers to a $C_3$-$C_8$ carbocycle group defined above wherein another of the carbocycle groups' hydrogen atoms is replaced with a bond (i.e., it is divalent).

Unless otherwise indicated, the term "heteroalkyl," by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Typically a $C_1$ to $C_4$ heteroalkyl or heteroalkylene has 1 to 4 carbon atoms and 1 or 2 heteroatoms and a $C_1$ to $C_3$ heteroalkyl or heteroalkylene has 1 to 3 carbon atoms and 1 or 2 heteroatoms. In some aspects, a heteroalkyl or heteroalkylene is saturated.

Unless otherwise indicated, the term "heteroalkylene" by itself or in combination with another term means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

Unless otherwise indicated, "aminoalkyl" by itself or in combination with another term means a heteroalkyl wherein an alkyl moiety as defined herein is substituted with an amino, alkylamino, dialkylamino or cycloalkylamino group. Exemplary non-limiting aminoalkyls are —$CH_2NH_2$, —$CH_2CH_2NH_2$, —$CH_2CH_2NHCH_3$ and —$CH_2CH_2N(CH_3)_2$ and further includes branched species such as —CH($CH_3$)$NH_2$ and —C($CH_3$)$CH_2NH_2$ in the (R)- or (S)-configuration. Alternatively, an aminoalkyl is an alkyl moiety, group, or substituent as defined herein wherein a $sp^3$ carbon other than the radical carbon has been replaced with an amino or alkylamino moiety wherein its $sp^3$ nitrogen replaces the $sp^3$ carbon of the alkyl provided that at least one $sp^3$ carbon remains. When referring to an aminoalkyl moiety as a substituent to a larger structure or another moiety the aminoalkyl is covalently attached to the structure or moiety through the carbon radical of the alkyl moiety of the aminoalkyl.

Unless otherwise indicated "alkylamino" and "cycloalkylamino" by itself or in combination with another term means an alkyl or cycloalkyl radical, as described herein, wherein the radical carbon of the alkyl or cycloalkyl radical has been replaced with a nitrogen radical, provided that at least one $sp^3$ carbon remains. In those instances where the alkylamino is substituted at its nitrogen with another alkyl moiety the resulting substituted radical is sometimes referred to as a dialkylamino moiety, group or substituent wherein the alkyl moieties substituting nitrogen are independently selected. Exemplary and non-limiting amino, alkylamino and dialkylamino substituents, include those having the structure of —N($R^{op}$)$_2$, wherein $R^{op}$ in these examples are independently selected from hydrogen or $C_{1-6}$ alkyl, typically hydrogen or methyl, whereas in cycloalkyl amines, which are included in heterocycloalkyls, both $R^{op}$ together with the nitrogen to which they are attached define a heterocyclic ring. When both $R^{op}$ are hydrogen or alkyl, the moiety is sometimes described as a primary amino group and a tertiary amine group, respectively. When one $R^{op}$ is hydrogen and the other is alkyl, then the moiety is sometimes described as a secondary amino group. Primary and secondary alkylamino moieties are more reactive as nucleophiles towards carbonyl-containing electrophilic centers whereas tertiary amines are more basic.

"Substituted alkyl" and "substituted aryl" mean alkyl and aryl, respectively, in which one or more hydrogen atoms, typically one, are each independently replaced with a substituent. Typical substituents include, but are not limited to a Basic Unit a PEG Unit, —X, —$R^{op}$, —OH, —$OR^{op}$, —$SR^{op}$, —N($R^{op}$)$_2$, —N($R^{op}$)$_3$, =$NR^{op}$, —$CX_3$, —CN, —$NO_2$, —$NR^{op}C(=O)R^{op}$, —C(=O)$R^{op}$, —C(=O)N($R^{op}$)$_2$, —S(=O)$_2R^{op}$, —S(=O)$_2NR^{op}$, —S(=O)$R^{op}$, —OP(=O)(O$R^{op}$)$_2$, —P(=O)(O$R^{op}$)$_2$, —PO$_{-3}^{=}$, PO$_3H_2$, —C(=O)$R^{op}$, —C(=S)$R^{op}$, —CO$_2R^{op}$, —CO$_2^-$, —C(=S)O$R^{op}$, —C(=O)S$R^{op}$, —C(=S)S$R^{op}$, —C(=O)N($R^{op}$)$_2$, —C(=S)N($R^{op}$)$_2$, and —C(=NR)N($R^{op}$)$_2$, where each X is independently selected from the group consisting of a halogen: —F, —Cl, —Br, and —I; and wherein each $R^{op}$ is independently selected from the group consisting of —H, —$C_1$-$C_{20}$ alkyl, —$C_6$-$C_{20}$ aryl, —$C_3$-$C_{14}$ heterocycle, a protecting group, and a prodrug moiety.

More typically substituents are selected from the group consisting of a Basic, Unit a PEG Unit —X, —$R^{op}$, —OH, —$OR^{op}$, —$SR^{op}$, —N($R^{op}$)$_2$, —N($R^{op}$)$_3$, =$NR^{op}$, —$NR^{op}$C(=O)$R^{op}$, —C(=O)$R^{op}$, —C(=O)N($R^{op}$)$_2$, —S(=O)$_2R^{op}$, —S(=O)$_2NR^{op}$, —S(=O)$R^{op}$, —C(=O)$R^{op}$, —C(=S)$R^{op}$, —C(=O)N($R^{op}$)$_2$, —C(=S)N($R^{op}$)$_2$, and —C(=NR)N($R^{op}$)$_2$, wherein each X is independently selected from the group consisting of —F and —Cl, or are selected from the group consisting of a Basic, Unit a PEG Unit —X, —$R^{op}$, —OH, —$OR^{op}$, —N($R^{op}$)$_2$, —N($R^{op}$)$_3$, —$NR^{op}C(=O)R^{op}$, —C(=O)N($R^{op}$)$_2$, —S(=O)$_2R^{op}$, —S(=O)$_2NR^{op}$, —S(=O)$R^{op}$, —C(=O)$R^{op}$, —C(=O)N($R^{op}$)$_2$, —C(=NR)N($R^{op}$)$_2$, a protecting group, and a prodrug moiety wherein each X is —F; and wherein each $R^{op}$ is independently selected from the group consisting of hydrogen, —$C_1$-$C_{20}$ alkyl, —$C_6$-$C_{20}$ aryl, —$C_3$-$C_{14}$ heterocycle, a protecting group, and a prodrug moiety. In some aspects, an alkyl substituent is selected from the group consisting —N($R^{op}$)$_2$, —N($R^{op}$)$_3$ and —C(=NR)N($R^{op}$)$_2$, wherein $R^{op}$ is a defined above, which may provide for a Basic Unit as when $R^{op}$ is independently selected from the group consisting of hydrogen and —$C_1$-$C_{20}$ alkyl. In other aspects, alkyl is substituted with a series or ethyleneoxy moieties to define a PEG Unit. Alkylene, carbocycle, carbocyclo, arylene, heteroalkyl, heteroalkylene, heterocycle, heterocyclo, heteroaryl, and heteroarylene groups as described above may also be similarly substituted.

Protecting group" as used here means a moiety that prevents or reduces the ability of the atom or functional group to which it is linked from participating in unwanted reactions. Typical protecting groups for atoms or functional groups are given in Greene (1999), "Protective groups in organic synthesis, $3^{rd}$ ed.", Wiley Interscience. Protecting groups for heteroatoms such as oxygen, sulfur and nitrogen are sometime used to minimize or avoid unwanted their reactions with electrophilic compounds. Other times the protecting group is used to reduce or eliminate the nucleophilicity and/or basicity of the unprotected heteroatom. Non-limiting examples of protected oxygen are given by —$OR^{PR}$, wherein $R^{PR}$ is a protecting group for hydroxyl, wherein hydroxyl is typically protected as an ester (e.g. acetate, propionate or benzoate). Other protecting groups for hydroxyl avoid interfering with the nucleophilicity of organometallic reagents or other highly basic reagents, where hydroxyl is typically protected as an ether, including alkyl or heterocycloalkyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —$NHR^{PR}$ or —N($R^{PR}$)$_2$—, wherein least one of $R^{PR}$ is a nitrogen atom protecting group or both $R^{PR}$ together comprise a protecting group.

A protecting group is a suitable protecting when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. By way of example and not limitation, a suitable protecting group may include those previously described for protecting functional groups. A suitable protecting group is sometimes a protecting group used in peptide coupling reactions.

"Aromatic alcohol" by itself or part of a larger structure refers to an aromatic ring system substituted with the hydroxyl functional group —OH. Thus, aromatic alcohol refers to any aryl, heteroaryl, arylene and heteroarylene moiety as described herein having a hydroxyl functional group bonded to an aromatic carbon of its aromatic ring system. The aromatic alcohol may be part of a larger moiety as when its aromatic ring system is a substituent of this moiety, or may be embedded into the larger moiety by ring fusion, and may be optionally substituted with moieties as described herein including one or more other hydroxyl substitutents. A phenolic alcohol is an aromatic alcohol having a phenyl group as the aromatic ring.

"Aliphatic alcohol" by itself or part of a larger structure refers to a moiety having a non-aromatic carbon bonded to the hydroxyl functional group —OH. The hydroxy-bearing carbon may be unsubstituted (i.e., methyl alcohol) or may have one, two or three optionally substituted branched or unbranched alkyl substituents to define a primary alcohol, or a secondary or tertiary aliphatic alcohol within a linear or cyclic structure. When part of a larger structure, the alcohol may be a substituent of this structure by bonding through the hydroxy bearing carbon, through a carbon of an alkyl or other moiety as described herein to this hydroxyl-bearing carbon or through a substituent of this alkyl or other moiety. An aliphatic alcohol contemplates a non-aromatic cyclic structure (i.e., carbocycles and heterocarbocycles, optionally substituted) in which a hydroxy functional group is bonded to a non-aromatic carbon of its cyclic ring system.

"Arylalkyl" or "heteroarylalkyl" as used herein means a substituent, moiety or group where an aryl moiety is bonded to an alkyl moiety, i.e., aryl-alkyl-, where alkyl and aryl groups are as described above, e.g., $C_6H_5$—$CH_2$— or $C_6H_5$—$CH(CH_3)CH_2$—. An arylalkyl or heteroarylalkyl is associated with a larger structure or moiety through a $sp^a$ carbon of its alkyl moiety.

"Electron withdrawing group" as used herein means a functional group or electronegative atom that draws electron density away from an atom to which it is bonded either inductively and/or through resonance, whichever is more dominant (i.e., a functional group or atom may be electron withdrawing inductively but may overall be electron donating through resonance), and tends to stabilize anions or electron-rich moieties. The electron withdrawing effect is typically transmitted inductively, albeit in attenuated form, to other atoms attached to the bonded atom that has been made electron deficient by the electron withdrawing group (EWG), thus affecting the electrophilicity of a more remote reactive center. Exemplary electron withdrawing groups include, but are not limited to —C(=O), —CN, —$NO_2$, —$CX_3$, —X, —C(=O)$OR^{op}$, —C(=O)N($R^{op}$)$_2$, —C(=O) $R^{op}$, —C(=O)X, —S(=O)$_2R^{op}$, —S(=O)$_2OR^{op}$, —S(=O)$_2NHR^{op}$, —S(=O)$_2N(R^{op})_2$, —P(=O)(O$R^{op}$)$_2$, —P(=O)(CH$_3$)NH$R^{op}$, —NO, —N($R^{op}$)$_3\pm$, wherein X is —F, —Br, —$C_1$, or —I, and $R^{op}$ in some aspects is, at each occurrence, independently selected from the group consisting of hydrogen and $C_{1-6}$ alkyl, and certain 0-linked moieties as described herein such as acyloxy.

Exemplary EWGs can also include aryl groups (e.g., phenyl) depending on substitution and certain heteroaryl groups (e.g., pyridine). Thus, the term "electron withdrawing groups" also includes aryls or heteroaryls that are further substituted with electron withdrawing groups. Typically, electron withdrawing groups on aryls or heteroaryls are —C(=O), —CN, —$NO_2$, —$CX_3$, and —X, wherein X independently selected is halogen, typically —F or —Cl. Depending on their substituents, an alkyl moiety may also be an electron withdrawing group.

"Electron donating group" as used herein means a functional group or electropositive atom that increases electron density of an atom to which it is bonded either inductively and/or through resonance, whichever is more dominant (i.e., a functional group or atom may be electron donating through resonance but may overall be electron withdrawing inductively) and tends to stabilize cations or electron poor systems. The electron donating effect is typically transmitted through resonance to other atoms attached to the bonded atom that has been made electron rich by the electron donating group (EWG) thus affecting the nucleophilicity of a more remote reactive center. Exemplary electron donating groups include, but are not limited to amines and certain O-linked substituents as described herein such as —OH and ethers. Depending on their substituents, an aryl or heteroaryl moiety may also be an electron donating group. Unsubstituted alkyl moieties are typically electron donating.

"O-linked moiety" as used herein means a moiety that is attached to a larger structure or moiety directly through an oxygen atom of the O-linked moiety. An O-linked moiety may be a monovalent moiety, including moieties such as hydroxyl, i.e., —OH, acetoxy, i.e., —OC(=O)CH$_3$, acyloxy, i.e., —OC(=O)R, wherein R is hydrogen, or alkyl, cycloalkyl, alkenyl, alkynyl, aryl or heterocycle, optionally substituted, and aryloxy (Aryl-O—), phenoxy (Ph-O—) and heteroaryloxy (heteroaryl-O), optionally substituted, or silyloxy, i.e., $R_3SiO$—, wherein R independently are alkyl, aryl, or heteroaryl, optionally substituted, an ether, i.e., —OR, wherein R is as defined for silyloxy, and —$OR^{PR}$, wherein $R^{PR}$ is a protecting group as previously defined. A monovalent O-linked moiety may be electron donating or electron withdrawing depending on the electronegativity of the bonded oxygen heteroatom and the availability of its lone pair electrons. For example, —OH or an ether, when its oxygen atom is a substituent to a carbon atom, is an electron donating moiety, while an acyloxy similarly substituted is an electron withdrawing moiety. An O-linked moiety may also be divalent, i.e. =O or a ketal moiety, e.g., —X—(CH$_2$)$_n$—Y—, wherein X and Y independently are S and O and n is 2 to 3, to form a spiro ring system with the carbon to which X and Y are attached.

"Leaving group ability" relates to the ability of an alcohol-, thiol-, amine- or amide-containing compound corresponding to a Drug Unit in a Ligand Drug Conjugate to be released from the Conjugates a free drug subsequent to activation of a self-immolative event within the conjugate. That release can be variable without the benefit of a methylene carbamate unit to which its Drug Unit is attached (i.e., when the Drug Unit is directly attached to a self-immolative moiety and does not have an intervening methylene carbamate unit). Good leaving groups are usually weak bases and the more acidic the functional group that is expelled from such conjugates the weaker the conjugate base is. Thus, the leaving group ability of an alcohol-, thiol-, amine- or amide-containing free drug from a Drug Unit will be related to the pKa of the drug's functional group that is expelled from a conjugate in cases where [a] methylene carbamate unit (i.e., one in which a Drug Unit is directly attached to a self-immolative moiety) is not used. Thus, a lower pKa for that functional group will increase its leaving group ability.

Although other factors may contribute to release of free drug from conjugates not having the benefit of a methylene carbamate unit, generally a drug having a functional group with a lower pKa value will typically be a better leaving group than a drug attached via a functional group with a higher pKa value. Another consideration is that a functional group having too low of a pKa value may result in an unacceptable activity profile due to premature loss of the Drug Unit via spontaneous hydrolysis. For conjugates employing a methylene carbamate unit, a common functional group (i.e., a carbamic acid) having a pKa value that allows for efficient release of free drug, without suffering unacceptable loss of Drug Unit, is produced upon self-immolation.

"Succinimide moiety" as used herein refers to an organic moiety comprised of a succinimide ring system, which is present in one type of Stretcher Unit (Z) that is typically further comprised of an alkylene-containing moiety bonded to the imide nitrogen of that ring system. A succinimide moiety typically results from Michael addition of an sulfhydryl group of a Ligand Unit to the maleimide ring system of a Stretcher Unit precursor (Z). A succinimide moiety is therefore comprised of a thio-substituted succinimide ring system and when present in a LDC has its imide nitrogen substituted with the remainder of the Linker Unit of the LDC and is optionally substituted with substituent(s) that were present on the maleimide ring system of Z'.

"Acid-amide moiety" as used herein refers to succinic acid having an amide substituent that results from the thio-substituted succinimide ring system of a succinimide moiety having undergone breakage of one of its carbonyl-nitrogen bonds by hydrolysis. Hydrolysis resulting in a succinic acid-amide moiety provides a Linker Unit less likely to suffer premature loss of the Ligand Unit to which it is bonded through elimination of the antibody-thio substituent. Hydrolysis of the succinimide ring system of the thio-substituted succinimide moiety is expected to provide regiochemical isomers of acid-amide moieties that are due to differences in reactivity of the two carbonyl carbons of the succinimide ring system attributable at least in part to any substituent present in the maleimide ring system of the Stretcher Unit precursor and to the thio substituent introduced by the targeting ligand.

The term "Prodrug" as used herein refers to a less biologically active or inactive compound which is transformed within the body into a more biologically active compound via a chemical or biological process (i.e., a chemical reaction or an enzymatic biotransformation). Typically, a biologically active compound is rendered less biologically active (i.e., is converted to a prodrug) by chemically modifying the compound with a prodrug moiety. In some aspects the prodrug is a Type II prodrug, which are bioactivated outside cells, e.g., in digestive fluids, or in the body's circulation system, e.g., in blood. Exemplary prodrugs are esters and β-D-glucopyranosides.

EMBODIMENTS

A number of embodiments of the invention are described below, which are no meant to limit the invention in any way, and are followed by a more detailed discussion of the components that make up the conjugates. One of skill in the art will understand that each of the conjugates identified and any of the selected embodiments thereof is meant to include the full scope of each component and linker.

Ligand-Drug Conjugates

In one group of embodiments, provided herein are Ligand-Drug Conjugates (LDCs) and compositions thereof comprising populations of these LDCs (i.e., LDC compositions).

In one aspect, a Ligand-Drug Conjugate comprises a Ligand Unit, a Drug Unit, and a Linker Unit that connects the Ligand Unit to the Drug Unit, wherein the Linker Unit is comprised of a Self-immolative Assembly Unit through which the Ligand Unit is connected to the Drug Unit. The Drug Unit is directly attached to a methylene carbamate unit of the Self-immolative Assembly Unit, wherein the methylene carbamate unit covalently attached to a Drug Unit in the Ligand-Drug Conjugate has the structure of Formula I:

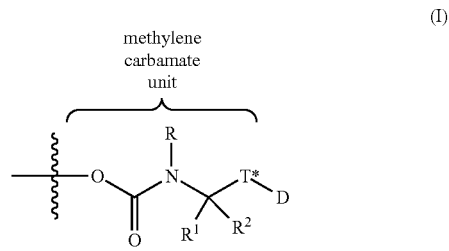

(I)

or a pharmaceutically acceptable salt thereof;

wherein

D is a Drug Unit having a functional group (e.g., hydroxyl, thiol, amide or amine functional group) that has been incorporated into the methylene carbamate unit;

T* is a heteroatom from said functional group (e.g., oxygen, sulfur, optionally substituted nitrogen) that becomes incorporated into the methylene carbamate unit;

R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl;

or both R and $R^1$ together with the nitrogen and carbon atoms to which they are attached comprise an azetidinyl, pyrrolodinyl, piperidinyl or homopiperidinyl moiety (preferably a pyrrolodinyl or piperidinyl moiety) and $R^2$ is hydrogen; and the wavy line indicates covalent attachment of the formula I structure to the remainder of the Self-Immolative Assembly Unit (i.e., attachment within the LDC), and wherein the Self-Immolative Assembly Unit releases free drug (i.e., D-T*H) following activation of the Self-Immolative Assembly Unit.

In some embodiments of formula I, one of R, $R^1$, $R^2$ is a Basic Unit or a PEG Unit and the others are as defined above. In some embodiments of formula I the released D-T*H has a pKa of between about 9 to about 36 for its T*H functional group. In other embodiments of formula SI the released D-T*H has a pKa of between about 12 to about 36 or between about 15 to about 36 for its T*H functional group.

Typically, the methylene carbamate unit is attached to an activateable self-immolative moiety, X, as represented by Formula (SI):

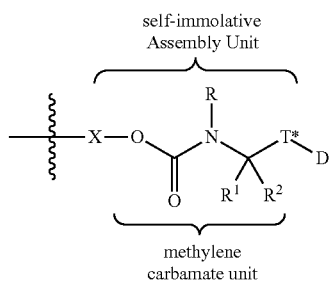

or a pharmaceutically acceptable salt thereof; wherein the wavy line indicates covalent attachment of the Formula SI structure within the LDC;

R, $R^1$, $R^2$, T* and D are as defined for formula I;

X is an activateable self-immolative moiety; and wherein the indicated Self-immolative Assembly Unit releases free drug (i.e., D-T*H) following activation of X.

In some embodiments of formula SI, one of R, R1, R2 is a Basic Unit or a PEG Unit and the others are as defined for formula I. In some embodiments of formula I the released D-T*H has a pKa of between about 9 to about 36 for its T*H functional group. In other embodiments of formula SI the released D-T*H has a pKa of between about 12 to about 36 or between about 15 to about 36 for its T*H functional group.

Exemplary embodiments include those wherein $R^2$ is hydrogen as set forth in Formula SIa:

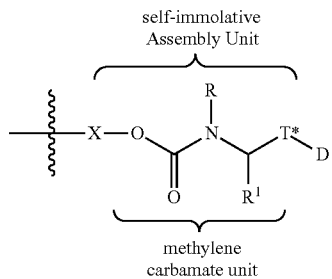

or a pharmaceutically acceptable salt thereof, wherein the wavy line, X, R, $R^1$, T* and D are as defined for formula SI. R and R' are preferably hydrogen, optionally substituted $C_{1-6}$ alkyl, or optionally substituted $C_{6-14}$ aryl, (more preferably hydrogen, optionally substituted $C_{1-4}$ alkyl or optionally substituted phenyl, most preferably hydrogen or optionally substituted $C_{1-4}$ alkyl).

In some preferred embodiments of formula SIa, R is unsubstituted $C_{1-4}$ alkyl. In other preferred embodiments one of R and $R^1$ is a Basic Unit or a PEG Unit and the other is hydrogen or unsubstituted $C_{1-4}$ alkyl. In other preferred embodiments R is hydrogen, a Basic Unit or a PEG Unit and $R^1$ is hydrogen Exemplary embodiments include those wherein $R^1$ and $R^2$ together with the nitrogen and carbon atoms to which they are attached comprise a heterocyclo as set forth in Formula (SIb):

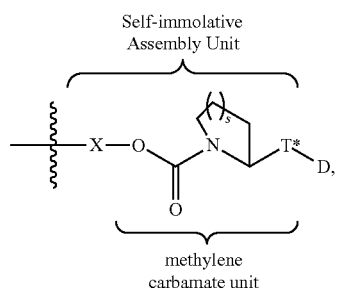

or a pharmaceutically acceptable salt thereof, wherein the wavy line, X, R, $R^2$, T* and D are as defined for formula SI, and the subscript s is 0, 1, 2, or 3. In some embodiments of formula SIb, the subscript s is 0, 1 or 2; preferably s is 1 or 2.

In some embodiments, the methylene carbamate unit is a MAC Unit. In those embodiments, D is a Drug Unit having a hydroxyl functional group that has been incorporated into the methylene carbamate unit. In such embodiments, the Self-Immolative Assembly Unit covalently attached to the Drug Unit is represented by Formula SI':

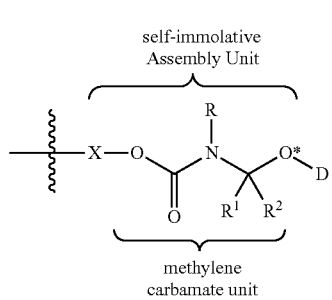

or a pharmaceutically acceptable salt thereof; wherein the wavy line, X, R, $R^1$, and $R^2$, are as defined for formula SI, D is a Drug Unit having a hydroxyl functional group prior to its incorporation into the indicated methylene carbamate unit and O* is the oxygen atom from said hydroxyl functional group; and wherein the indicated Self-immolative Assembly Unit releases free drug (i.e., D-O*H) following activation of X.

In some embodiments of formula SI' the released D-O*H has a pKa of between about 10 to about 19 for its hydroxyl functional group. In other embodiments of formula I the released D-O*H has a pKa of between about 12 to about 19 or between 15 to about 19 for its hydroxyl functional group.

Exemplary embodiments include those wherein $R^2$ is hydrogen as set forth in formula SIa':

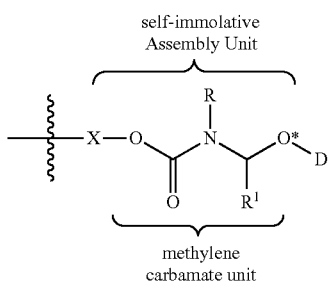

(SIa')

self-immolative Assembly Unit methylene carbamate unit wherein the wavy line, X, R, $R^1$, O* and D are as defined for formula SI'. R and R' are preferably hydrogen, optionally substituted $C_{1-6}$ alkyl, or optionally substituted $C_{6-14}$ aryl, (more preferably hydrogen, optionally substituted $C_{1-4}$ alkyl or optionally substituted phenyl, most preferably hydrogen or optionally substituted $C_{1-4}$ alkyl). In some embodiments of formula SIa', one of R and $R^1$ is a Basic Unit or a PEG Unit and the other is hydrogen or unsubstituted $C_{1-4}$ alkyl. In other embodiments R is hydrogen, a Basic Unit or a PEG Unit and $R^1$ is hydrogen.

Exemplary embodiments include those wherein $R^1$ and $R^2$ together with the nitrogen and carbon atoms to which they are attached comprise a heterocyclo as set forth in Formula (SIb'):

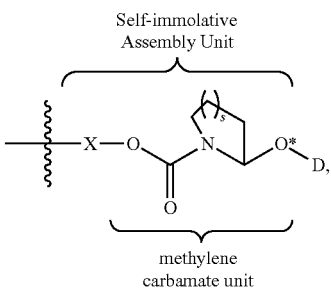

(SIb')

Self-immolative Assembly Unit methylene carbamate unit wherein the wavy line, X, $R^2$, O* and D are as defined for formula SI', and the subscript s is 0, 1, 2, or 3. Preferably the subscript s is 0, 1, or 2 (more preferably s is 1 or 2).

In one aspect, a Ligand-Drug Conjugate comprises a Ligand Unit, a Drug Unit and a Linker Unit that connects the Ligand Unit to the Drug Unit, wherein the Linker Unit is comprised of a Self-immolative Assembly Unit and a Stretcher Unit. The drug is incorporated into a drug-linker moiety of an LDC by incorporation of a hydroxyl, thiol, amine or amide functional group of the drug through the oxygen, sulfur or optionally substituted nitrogen heteroatom of that functional group to a methylene carbamate unit of the Self-immolative Assembly Unit. The Self-immolative Assembly unit is then connected to the Ligand Unit through the Stretcher Unit.

In some embodiments there can be from 1 to 4 Self-immolative Assembly Units within a drug-linker moiety for each site of attachment to a Ligand Unit (represented by the subscript t) and from 1 to 16 drug-linker moieties per Ligand Unit (represented by the subscript p). In those embodiments wherein there are two or more Self-immolative Assembly Units connected to each site of attachment on the Ligand Unit, a Branching Unit is present to allow for the required branching.

In some aspects, an additional Connector Unit (A) covalently attaches a Stretcher Unit (Z) or Branching Unit (B), depending on the presence or absence of B, to a Self-immolative Assembly Unit.

In some embodiments a Ligand-Drug Conjugate, or a composition thereof that is comprised of a population of these LDCs (i.e., a LDC composition), is represented by Formula II below:

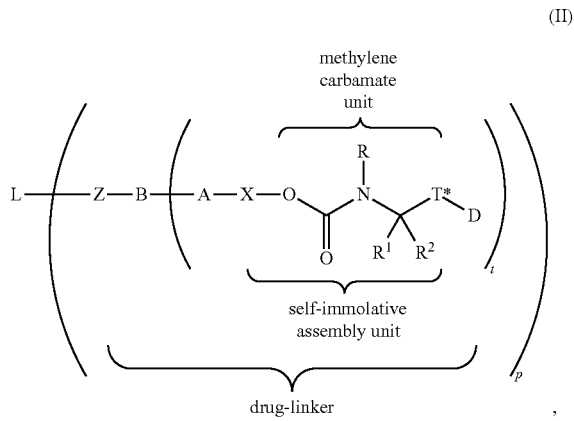

(II)

methylene carbamate unit self-immolative assembly unit drug-linker or a pharmaceutically acceptable salt; wherein D is a Drug Unit having a functional group (e.g., hydroxyl, thiol, amide or amine functional group) that has been incorporated into the methylene carbamate unit;

T* is a heteroatom from said functional group (e.g., oxygen, sulfur, optionally substituted nitrogen) that becomes incorporated into the methylene carbamate unit;

R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or R and $R^1$ together with the nitrogen and carbon atoms to which they are attached comprise an azetidinyl, pyrrolodinyl, piperidinyl or homopiperidinyl moiety and $R^2$ is hydrogen;

X is an activateable self-immolative moiety;

L is a Ligand Unit;

Z is a Stretcher Unit;

B is an optional Branching Unit that is present when t is 2, 3 or 4, and absent when t is 1;

A is an optional Connector Unit;

the subscript s is 1 or 2;

the subscript t ranges from 1 to 4; and the subscript p is an integer (for an individual LDC) or a number (for a population of LDCs) ranging from 1 to 16; and wherein the indicated Self-immolative Assembly Unit releases free drug (i.e., D-T*H) following activation of X.

In some embodiments of formula I the released D-T*H has a pKa of between about 9 to about 36 for its T*H functional group. In other embodiments of formula SI the released D-T*H has a pKa of between about 12 to about 36 or between about 15 to about 36 for its T*H functional group.

In some embodiments of formula II one of R, $R^1$ and $R^2$ is a Basic Unit or a PEG Unit and the others are as defined. In other embodiments of formula II, R is a Basic Unit or a PEG Unit and $R^1$ and $R^2$ are as defined.

Exemplary embodiments include those wherein $R^2$ is hydrogen as set forth in Formula IIa or $R^1$ and $R^2$ together with the nitrogen atom to which they are attached comprise an azetidinyl, pyrrolodinyl, piperidinyl or homopiperidinyl as set forth in Formula IIb:

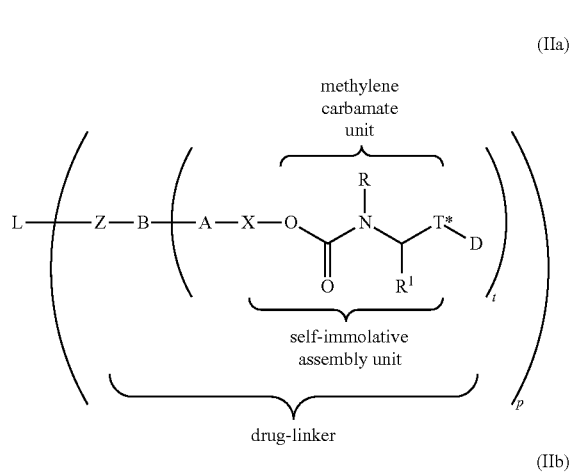

or a pharmaceutically acceptable salt thereof, wherein R, R$^1$, R$^2$, L, Z, B, X, A, T*, D, and the subscripts t and p are as defined for formula II, and the subscript s is 0, 1, 2, or 3.

In Formula IIa, R and R$^1$ are preferably hydrogen, optionally substituted C$_1$-C$_6$ alkyl or optionally substituted C$_{6-14}$ aryl (more preferably hydrogen, optionally substituted C$_1$-C$_4$ alkyl or optionally substituted phenyl, most preferably hydrogen or optionally substituted C$_1$-C$_4$ alkyl). In some preferred embodiments of formula IIa, R is a Basic Unit or a PEG Unit and R$^1$ is hydrogen or unsubstituted C$_1$-C$_4$ alkyl or R is hydrogen or unsubstituted C$_1$-C$_4$ alkyl and R$^2$ is a Basic Unit or a PEG Unit. In Formula IIb the subscript s is preferably 0, 1, or 2; more preferably s is 1 or 2.

Drugs to be used in the present invention include alcohol (e.g., aromatic and aliphatic hydroxyl)-containing drugs, thiol-containing drugs, amine (e.g., aliphatic and aryl amine)-containing drugs, amide (e.g., carboxamide)-containing drugs. Thus, attachment of a Drug Unit to the Self-immolative Assembly Unit can be, for example, from incorporation of drug via the oxygen heteroatom from the hydroxyl functional group from an alcohol-containing drug, the sulfur heteroatom from the thiol functional group of a thiol-containing drug, or the optionally substituted nitrogen heteroatom from the amine or amide functional group of an amine- or amide-containing drug. Such oxygen, sulfur or nitrogen heteroatoms are designated by T*. It will be understand that whereas incorporation of drug may be through an alcohol functionality (i.e., through the oxygen heteroatom of a hydroxyl functional group), the drug may have additional alcohol functionalities or thiol, amine or amide functionalities that are not so linked. Similarly, whereas incorporation of drug may be through its thiol, amine or amide functionalities, the drug may have additional alcohol, thiol, amine or amide functionalities that are not so linked.

The methylene carbamate unit in formulas II, IIa, and IIb can be a methylene alkoxy(aryloxy) carbamate unit (MAC Unit) as shown by Formulas II', IIa', and IIb' below

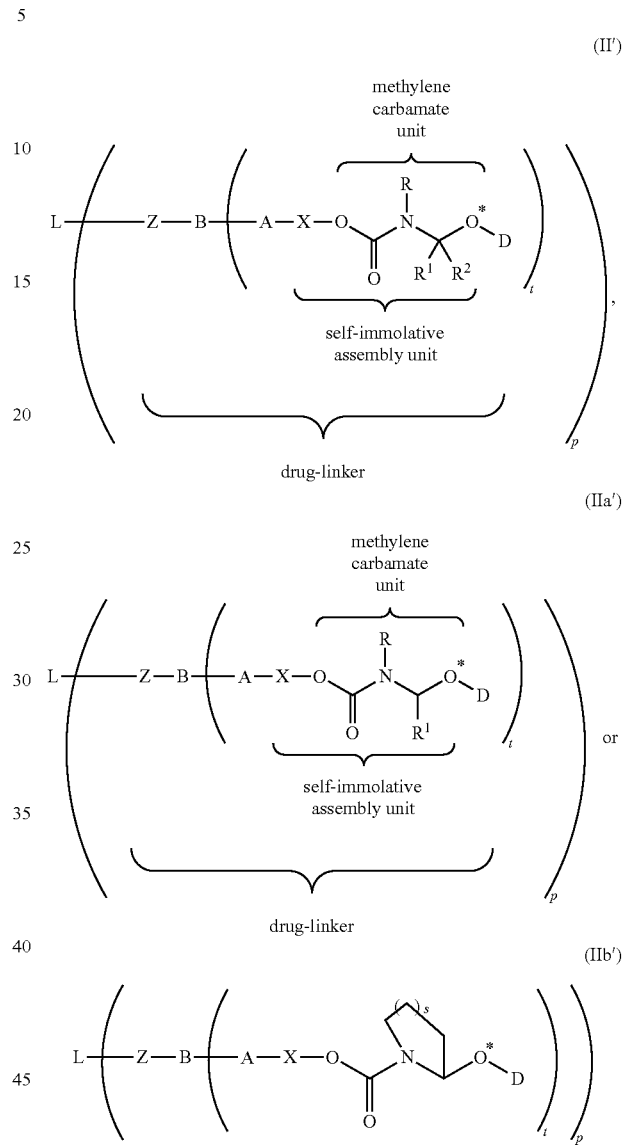

or a pharmaceutically acceptable salt; wherein

D is a Drug Unit having a hydroxyl functional group prior to its incorporation into the indicated methylene alkoxy (aryloxy) carbamate unit (MAC Unit), the oxygen heteroatom from which is designated by O*;

R is hydrogen, optionally substituted C$_1$-C$_6$ alkyl, optionally substituted C$_{6-14}$ aryl or optionally substituted C-linked C$_3$-C$_8$ heteroaryl;

R$^1$ and R$^2$ are independently hydrogen, optionally substituted C$_1$-C$_6$ alkyl, optionally substituted C$_{6-14}$ aryl or optionally substituted C-linked C$_3$-C$_8$ heteroaryl, or R and R$^1$ together with the nitrogen and carbon atoms to which they are attached comprise an azetidinyl, pyrrolodinyl, piperidinyl or homopiperidinyl moiety and R$^2$ is hydrogen;

X is an activateable self-immolative moiety;

L is a Ligand Unit;

Z is a Stretcher Unit;

B is an optional Branching Unit that is present when t is 2, 3 or 4, and absent when t is 1;

A is an optional Connector Unit;

the subscript s is 1 or 2;

the subscript t ranges from 1 to 4;

the subscript s is 0, 1, 2 or 3 and the subscript p is an integer (for an individual LDC) or a number (for a population of LDCs) ranging from 1 to 16; and wherein the indicated Self-immolative Assembly Unit releases free drug (i.e., D-O*H) following activation of X.

In some embodiments of formula II', IIa' or IIb', the released D-O*H has a pKa of between about 10 to about 19 for its hydroxyl functional group. In other embodiments of formula II', IIa' or IIb' the released D-O*H has a pKa of between about 12 to about 19 or between 15 to about 19 for its hydroxyl functional group.

In some embodiments of formula II' one of R, $R^1$ and $R^2$ is a Basic Unit or a PEG Unit and the others are as defined. In other preferred embodiments of formula II', R is a Basic Unit or a PEG Unit and $R^1$ and $R^2$ are as defined.

In some embodiments of Formula IIa', R and $R^1$ are hydrogen, optionally substituted $C_1$-$C_6$ alkyl or optionally substituted $C_{6-14}$ aryl (preferably hydrogen, optionally substituted $C_1$-$C_4$ alkyl or optionally substituted phenyl, more preferably hydrogen or optionally substituted $C_1$-$C_4$ alkyl). In some embodiments of Formula IIb', preferably the subscript s is 0, 1, or 2; more preferably 1 or 2.

In some preferred embodiments of formula IIa', R is a Basic Unit or a PEG Unit and R' is hydrogen or unsubstituted $C_1$-$C_4$ alkyl or R is hydrogen or unsubstituted $C_1$-$C_4$ alkyl and $R^1$ is a Basic Unit or a PEG Unit.

In other preferred embodiments of formula II' or formula IIa' R and R' together with the nitrogen and carbon atoms to which they are attached comprise a pyrrolodinyl or piperidinyl moiety.

The hydroxyl functional group referred to herein can be the hydroxyl functional group of an aromatic alcohol or an aliphatic alcohol. The aliphatic alcohol can be a primary, secondary or tertiary aliphatic alcohol. Preferably the alcohol is an aliphatic alcohol, more preferably a primary or secondary aliphatic alcohol.

A Self-Immolative Assembly Unit comprises, in addition to a methylene carbamate unit, an activateable self-immolative moiety. That activateable moiety is comprised of an Activation Unit and a self-immolative Spacer Unit. The Spacer Unit can comprise one or multiple self-immolative spacer subunits each capable of self-immolation (e.g., from 1 to 4). The Activation Unit initiates a self-immolative reaction sequence within the Spacer Unit or a subunit thereof that results in the release of free drug. Either the Activation Unit or the self-immolative Spacer Unit (A) can provide the site of covalent attachment to A, B or Z within a LDC or an Intermediate thereof depending on the presence or absence of A and/or B. In some embodiments the self-immolative moiety (X), of a Self-immolative Assembly Unit is represented as follows by formula i or ii

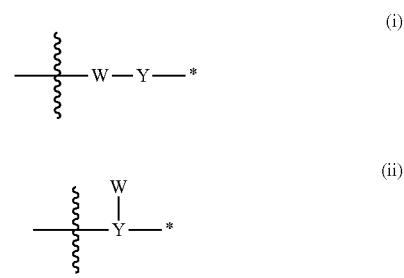

wherein

W is an Activation Unit; and

Y is a self-immolative Spacer Unit;

and the wavy line indicates the site of attachment to the remainder of the conjugate (i.e., to A, B or Z depending on the presence or absence of A and/or B) and the asterisk (*) indicates the site of attachment to the methylene carbamate linker.

In some aspects, a Ligand-Drug Conjugate (LDC), or a composition thereof that is comprised of a population of these LDCs (i.e., a LDC composition), is represented by formula III(i), III(ii), IIIa(i), IIIa(ii), IIIb(i), or IIIb(ii):

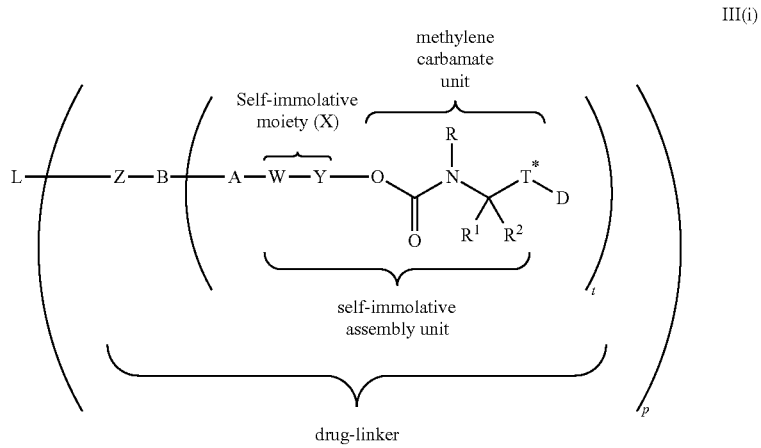

III(ii)
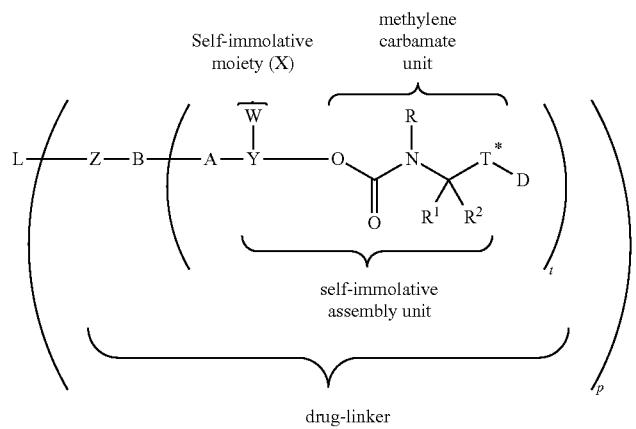
(IIIa(i))
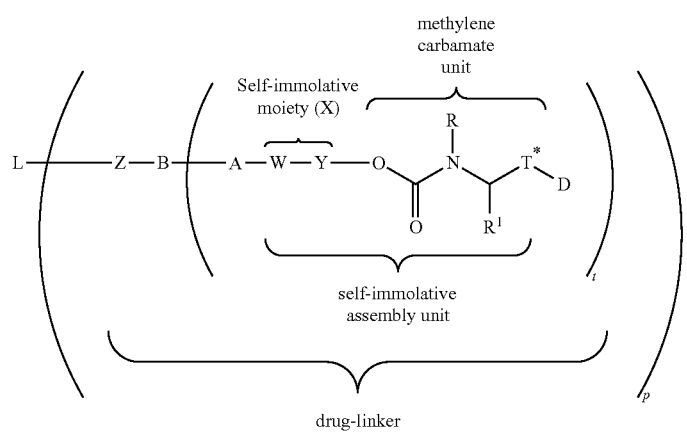
(IIIa(ii))
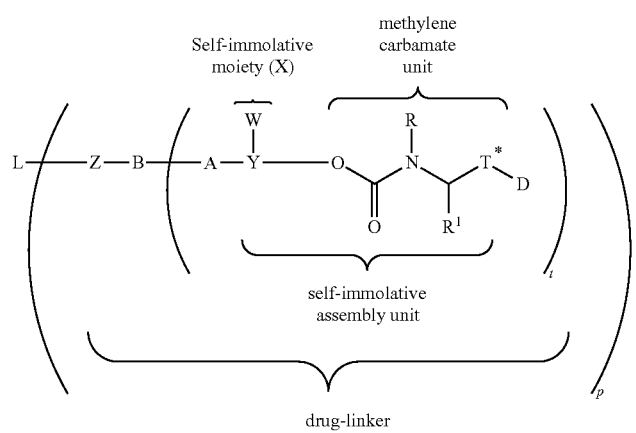

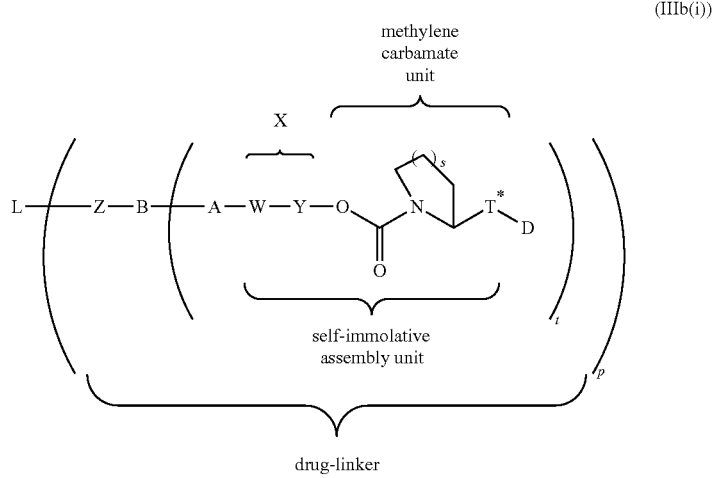

(IIIb(i))

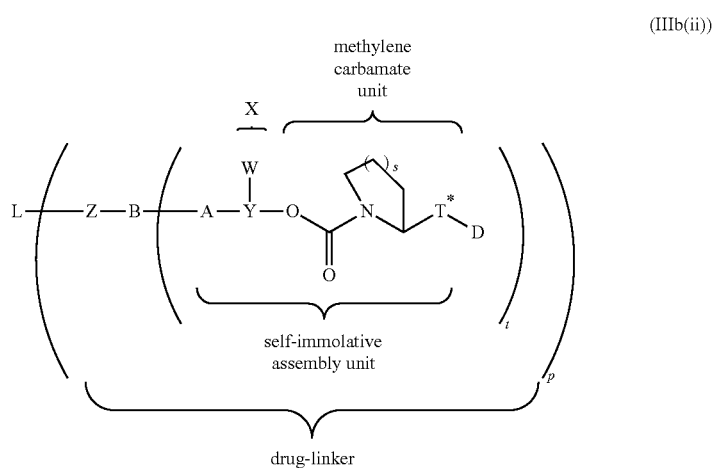

(IIIb(ii))

or a pharmaceutically acceptable salt thereof; wherein
W is an Activation Unit;
Y is a self-immolative Spacer Unit; and
L, Z, B, A, R, $R^1$, $R^2$, T*, D, and the subscripts t, s, and p are as defined for Formulas II, IIa and IIb.

In some embodiments of formula III(i), IIIa(i), IIIa(ii), IIIb(i) or IIIb(ii) the released D-T*H has a pKa of between about 9 to about 36 for its T*H functional group. In other embodiments of formula III(i), IIIa(i), IIIa(ii), IIIb(i) or IIIb(ii), the released D-TH has a pKa of between about 12 to about 36 or between about 15 to about 36 for its T*H functional group.

In some embodiments of formula III(i) or III(ii), one of R, $R^1$ and $R^2$ is a Basic Unit or a PEG Unit and the others are as defined. In other preferred embodiments of formula III(i) or III(ii), R is a Basic Unit or a PEG Unit and $R^1$ and $R^2$ are as defined. In other preferred embodiments of formula III(i) or III(ii), R and R' together with the nitrogen and carbon atoms to which they are attached comprise a pyrrolodinyl or piperidinyl moiety and $R^2$ is hydrogen.

In some embodiments of formula IIIa(i) and IIIa(ii), R and R' are hydrogen, optionally substituted $C_1$-$C_6$ alkyl or optionally substituted $C_{6-14}$ aryl (preferably hydrogen, optionally substituted $C_1$-$C_4$ alkyl or optionally substituted phenyl, more preferably hydrogen or optionally substituted $C_1$-$C_4$ alkyl). In some embodiments of formula IIIb(i) and IIIb(ii), preferably the subscript s is 0, 1, or 2, preferably 1 or 2.

In some preferred embodiments of formula IIIa(i) or IIIa(ii), R is a Basic Unit or a PEG Unit and $R^1$ is hydrogen or unsubstituted $C_1$-$C_4$ alkyl or R is hydrogen or unsubstituted $C_1$-$C_4$ alkyl and $R^2$ is a Basic Unit or a PEG Unit.

In other preferred embodiments of formula IIIa(i) or IIIa(ii), R and R' together with the nitrogen and carbon atoms to which they are attached comprise a pyrrolodinyl or piperidinyl moiety.

In other preferred embodiments of formula IIIa(i) or IIIa(ii), R is hydrogen or unsubstituted $C_1$-$C_4$ alkyl and $R^1$ is hydrogen. In other preferred embodiments of formula IIIa(i) or IIIa(ii) R is a Basic Unit or a PEG Unit and $R^1$ is hydrogen.

The methylene carbamate unit in formulas III (i), III (ii), IIIc (i), IIIc (ii), IIIb (i), or IIIb (ii) can be a methylene alkoxy(aryloxy) carbamate unit (MAC Unit) as shown by formula III(i)', III(ii)', IIIa(i)', IIIa(ii)', IIIb(i)', or IIIb(ii)' below:

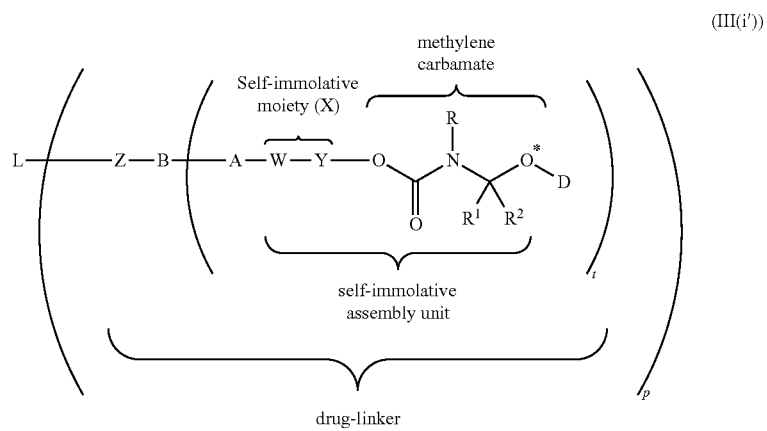
(III(i'))
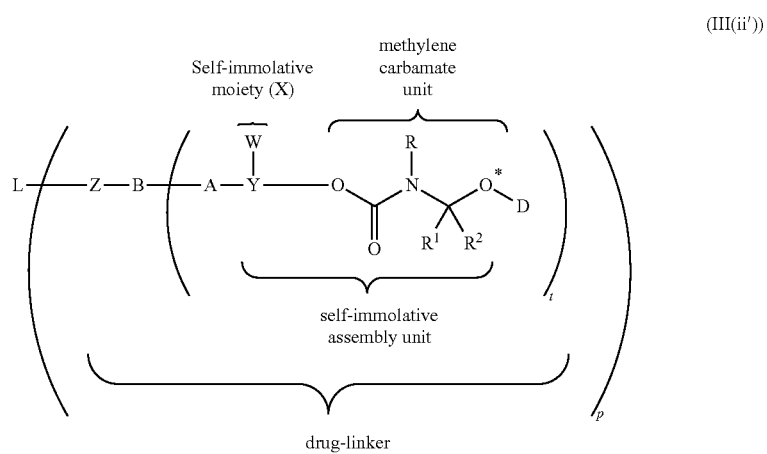
(III(ii'))
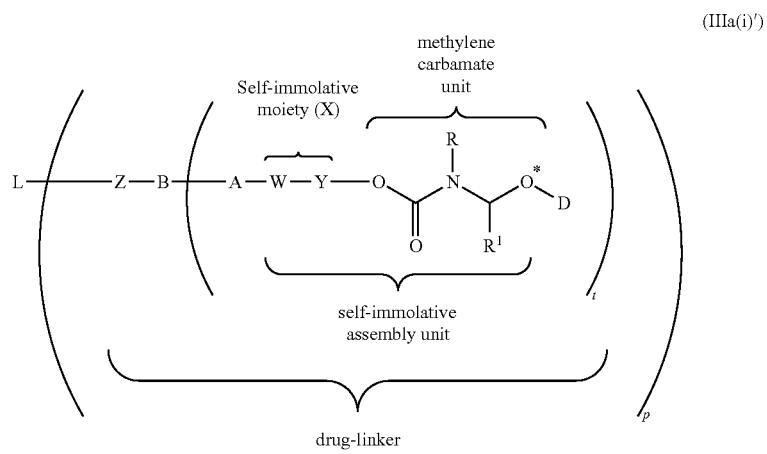
(IIIa(i)')

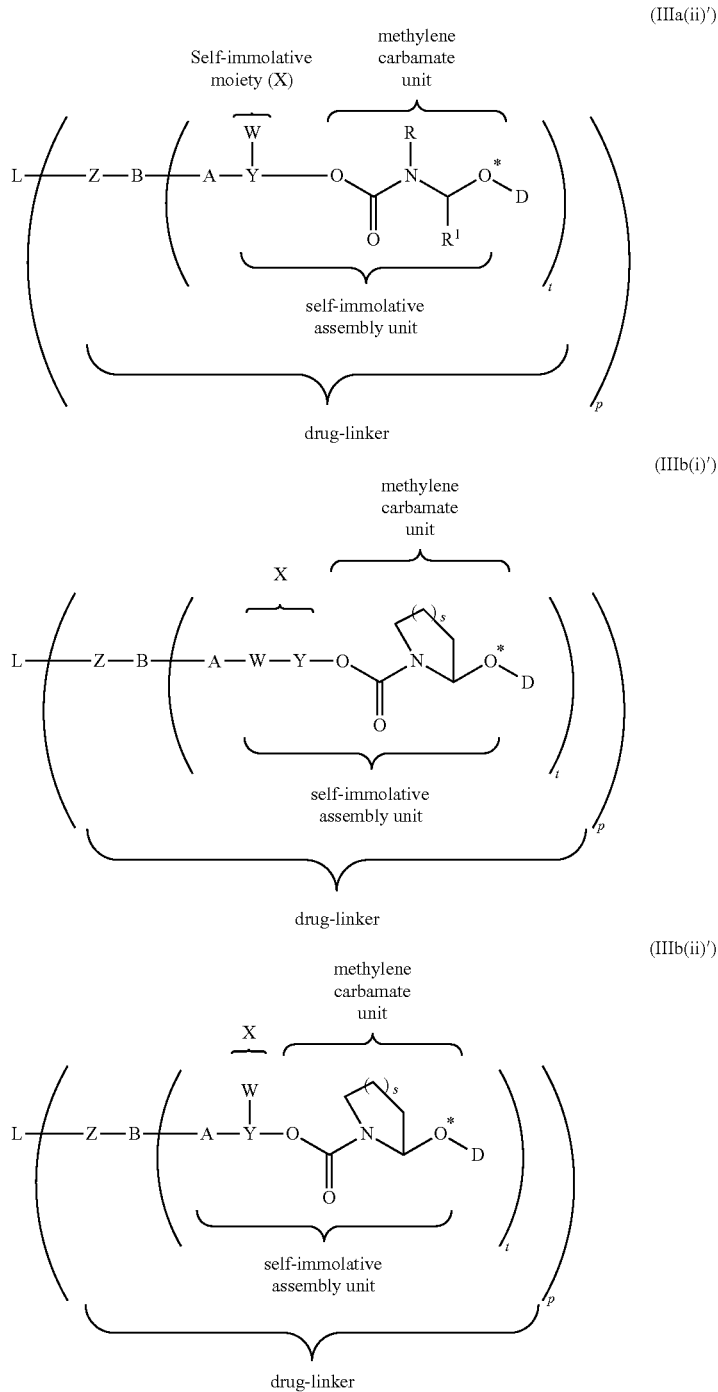

or a pharmaceutically acceptable salt thereof; wherein

D is a Drug Unit having a hydroxyl functional group prior to incorporation into the indicated methylene alkoxy(aryloxy) carbamate unit (MAC Unit), the oxygen heteroatom from which is designated by O*;

L, Z, B, A, Y, W, R, $R^1$, $R^2$, and the subscripts t, p, and s are as defined for formulas III(i), III(ii), IIIa(i), IIIa(ii), IIIb(i), or IIIb(ii).

In some embodiments of formula III(i)', III(ii)', IIIa(i)', IIIa(ii)', IIIb(i)', or IIIb(ii)', the released D-O*H has a pKa of between about 10 to about 19 for its hydroxyl functional group. In other embodiments of III(i)', III(ii)', IIIa(i)', IIIa(ii)', IIIb(i)', or IIIb(ii)', the released D-O*H has a pKa of between about 12 to about 19 or between 15 to about 19 for its hydroxyl functional group.

In some embodiments of formula III(i)' or III(ii)', one of R, $R^1$ and $R^2$ is a Basic Unit or a PEG Unit and the others are as defined. In other preferred embodiments of formula III(i)' or III(ii)', R is a Basic Unit or a PEG Unit and $R^1$ and $R^2$ are as defined.

In some embodiments of Formula IIIa(i)' and IIIa(ii) R and $R^1$ are hydrogen, optionally substituted $C_1$-$C_6$ alkyl or optionally substituted $C_{6-14}$ aryl (more preferably hydrogen, optionally substituted $C_1$-$C_4$ alkyl or optionally substituted phenyl, most preferably hydrogen or optionally substituted $C_1$-$C_4$ alkyl). In some embodiments of Formula IIIb(i)' and IIIb(ii)', $R^2$ is preferably hydrogen and the subscript s is 0, 1, or 2 (preferably 1 or 2).

In some preferred embodiments of formula IIIa(i)' or IIIa(ii)', R is a Basic Unit or a PEG Unit and $R^1$ is hydrogen or unsubstituted $C_1$-$C_4$ alkyl or R is hydrogen or unsubstituted $C_1$-$C_4$ alkyl and $R^2$ is a Basic Unit or a PEG Unit.

In other preferred embodiments of formula IIIa(i)' or IIIa(ii)', R and $R^1$ together with the nitrogen and carbon atoms to which they are attached define a pyrrolodinyl or piperidinyl moiety.

In other preferred embodiments of formula IIIa(i)' or IIIa(ii)', R is hydrogen or unsubstituted $C_1$-$C_4$ alkyl and R' is hydrogen. In other preferred embodiments of formula IIIa(i)' or IIIa(ii)' R is a Basic Unit or a PEG Unit and R' is hydrogen.

The hydroxyl functional group referred to herein can be the hydroxyl functional group of an aromatic alcohol or an aliphatic alcohol. The aliphatic alcohol can be a primary, secondary or tertiary aliphatic alcohol. Preferably the alcohol is an aliphatic alcohol, more preferably a primary or secondary aliphatic alcohol.

In some preferred Ligand Drug Conjugates having or comprised of formula I, SI, II, Ia, SIa, IIa, III(i), III(ii), IIIa(i), or IIIa(ii), $R^1$ is hydrogen.

In many of the embodiments described herein R can hydrogen, optionally substituted $C_1$-$C_6$ alkyl, including substituents defining a Basic Unit or a PEG Unit, optionally substituted $C_{6-14}$ aryl, or optionally substituted C-linked $C_3$-$C_8$ heteroaryl. R need not be substituted but when substituted, R is preferably substituted a so as to define a Basic Unit or a PEG Unit. Contemplated herein are those embodiments where R is an optionally substituted $C_{1-6}$ alkyl, more preferably an optionally substituted $C_{1-4}$ alkyl. The alkyl group can be unsubstituted or substituted. In some aspects when substituted, it is preferably substituted with a basic amino functional group to define a Basic Unit. In other aspects when substituted the alkyl group is preferably substituted with a series of ethylene-oxy groups to define a PEG Unit, Representative basic amino functional groups in a Basic Unit include amines and C-linked or N-linked nitrogen-containing 3, 4, 5, or 6 membered heterocycles that can be optionally substituted. The present inventors have surprisingly found that the addition of a basic functional group on an R alkyl substituent (i.e., R is a Basic Unit) can impart extra stability to the resultant LDCs.

In Ligand Drug Conjugates having or comprised of Formula I, Ia, SI, SIa, II, IIa, III(i), III(ii), IIIa(i), IIIa(ii), I', Ia', SI', SIa', II', IIa', III(i)', III(ii)', IIIa(i)', or IIIa(ii)', R can be hydrogen, optionally substituted $C_1$-$C_6$ alkyl, optionally substituted $C_{6-14}$ aryl, or optionally substituted C-linked $C_3$-$C_8$ heteroaryl. Also contemplated are those Ligand Drug Conjugates where R is as defined herein, but excludes optionally substituted $C_{6-14}$ aryl, excludes optionally substituted C-linked heteroaryl, or excludes optionally substituted $C_{6-14}$ aryl and optionally substituted C-linked heteroaryl. Also contemplated are those Ligand Drug Conjugates where R is as defined herein, but excludes optionally substituted phenyl. Also contemplated are those Ligand Drug Conjugates where R is as defined herein, but excludes electron withdrawing groups (i.e., R is hydrogen, optionally substituted $C_1$-$C_6$ alkyl, optionally substituted $C_{6-14}$ aryl, or optionally substituted C-linked $C_3$-$C_8$ heteroaryl, provided that R is not an electron withdrawing group). Also contemplated are those Ligand Drug Conjugates where R is as defined herein, but the optional substituent of R is not an electron withdrawing group. Also contemplated are those Ligand Drug Conjugates where R is not substituted. Also contemplated are those Ligand Drug Conjugates where R and $R^1$ together with the nitrogen and carbon atoms to which they are attached comprise a pyrrolodinyl or piperidinyl moiety. These Ligand Drug Conjugates wherein R is as defined in this paragraph can be included in combination with any of the various possibilities for the other substituent groups on the Ligand Drug Conjugates (e.g., L. Z, B, A, X, $R^1$, $R^2$, T*, D, and the subscripts s, p, and t).

In Ligand Drug Conjugates having or comprised of formula I, Ib, SI, SIb, II, IIb, III(i), III(ii), IIIb(i), IIIb(ii), I', Ib', SI', SIb', II', IIb', III(i)', III(ii)', IIIb(i)', and IIIb(ii)', $R^2$ can be hydrogen, optionally substituted $C_1$-$C_6$ alkyl, optionally substituted $C_{6-14}$ aryl, or optionally substituted C-linked $C_3$-$C_8$ heteroaryl. Also contemplated are those Ligand Drug Conjugates where $R^2$ is simply hydrogen. These Ligand Drug Conjugates wherein $R^2$ is simply hydrogen can be included in combination with any of the various possibilities for the other substituent groups on the Ligand Drug Conjugates (e.g., L. Z, B, A, X, R, $R^1$, T*, D, and the subscripts s, p, and t).

Ligand Drug Conjugates having formula II, IIa, IIb, II', IIa' IIb', III(i), IIIa(i), IIIa(ii), IIIb(i), IIIb(ii), III(i)', III(ii)', IIIa(i)', IIIa(ii)', IIIb(i)', or IIIb(ii)' include those wherein:

1) t ranges from 1 to 4, p is an integer or number ranging from 1 to 16, and there are from 1 to 36 Drug Units attached to each Ligand Unit,
2) t is 1 and the Branching Unit, B, is absent,
3) t is 2 to 4 and the Branching Unit, B, is present,
4) t is 2, and the Branching Unit, B, is present,
5) p is an integer or a number ranging from 1 to 12 or 2 to 12, and, in any one of the embodiments set forth in 1-4 of this paragraph, p is an integer or number ranging from 1 to 12 or 2 to 12,
6) p is an integer or number ranging from 1 to 10 or 2 to 10 and in any one of the embodiments set forth in 1-4 of this paragraph, p is an integer or number ranging from 1 to 10 or 2 to 10,
7) p is an integer or number ranging from 1 to 8 or 2 to 10, and in any one of the embodiments set forth in 1-4 of this paragraph, p is an integer or number ranging from 1 to 8 or 2 to 10, and LDCs having formula II, IIa, II', IIa', IIIa(i), IIIa(ii), III(i)', III(ii)', IIIa(i)', or IIIa(ii)', further include those wherein
8) R is hydrogen, optionally substituted $C_{1-6}$ alkyl, optionally substituted $C_{6-14}$ aryl, or optionally substituted C-linked $C_{3-8}$ heteroaryl and in any one of the embodiments set forth in 1-7 of this paragraph, R is hydrogen, optionally substituted $C_{1-6}$ alkyl, optionally substituted $C_{6-14}$ aryl, or optionally substituted C-linked $C_{3-8}$ heteroaryl
9) R is hydrogen, optionally substituted $C_{1-6}$ alkyl, or optionally substituted $C_{6-14}$ aryl, and in any one of the embodiments set forth in 1-7 of this paragraph, R is hydrogen, optionally substituted $C_{1-6}$ alkyl, or optionally substituted $C_{6-14}$ aryl,
10) R is hydrogen, methyl, ethyl or propyl, and in any one of the embodiments set forth in 1-7 of this paragraph, R is hydrogen, methyl, ethyl or propyl,
11) R is hydrogen, methyl, ethyl, propyl, isopropyl, butyl or isobutyl, and in any one of the embodiments set forth in 1-7 of this paragraph, R is hydrogen, methyl, ethyl, propyl, isopropyl, butyl or isobutyl, 12) R is hydrogen or methyl, and in any one of the embodiments set forth in 1-7 of this paragraph, R is hydrogen or methyl,
13) R is as defined herein but excludes electron-withdrawing groups and in any one of the embodiments set forth in 1-7 of this paragraph, R excludes electron-withdrawing groups,
14) R is as defined herein but the optional substituents that can be present on R exclude electron withdrawing groups, and in any one of the embodiments set forth in 1-7 of this paragraph, the optional substituents that can be present on R exclude electron-withdrawing groups,
15) R is $C_{1-4}$ alkyl or $C_{1-6}$ alkyl, optionally substituted with an amine, or C-linked or N-linked nitrogen-containing 3, 4, 5, or 6 membered heterocycle and in any one of the embodiments set forth in 1-7 of this paragraph, R is $C_{1-4}$ alkyl or $C_{1-6}$ alkyl optionally substituted with an amine, or C-linked or N-linked nitrogen-containing 3, 4, 5, or 6 membered heterocycle,
16) R is $C_{1-4}$ alkyl or $C_{1-6}$ alkyl, optionally substituted with —$N(R^{3a})(R^{4a})$ wherein $R^{3a}$ and $R^{4a}$ are independently selected from hydrogen, —$C_1$-$C_{20}$ alkyl, —$C_6$-$C_{14}$ aryl, or —$C_3$-$C_8$ heterocycle, preferably H or $C_{1-6}$ alkyl, more preferably hydrogen or methyl, and in any one of the embodiments set forth in 1-7 of this paragraph, R is $C_{1-4}$ alkyl or $C_{1-6}$ alkyl optionally substituted with —$N(R^{3a})(R^{4a})$ wherein $R^{3a}$ and $R^{4a}$ are independently selected from hydrogen, —$C_1$-$C_{20}$ alkyl, —$C_6$-$C_{14}$ aryl, or —$C_3$-$C_8$ heterocycle, preferably H or $C_{1-6}$ alkyl, more preferably hydrogen or methyl,
17) R is $C_{1-4}$ alkyl or $C_{1-6}$ alkyl, optionally substituted with a basic unit and in any one of the embodiments set forth in 1-7 of this paragraph, R is $C_{1-4}$ alkyl or $C_{1-6}$ alkyl optionally substituted with a basic unit,
18) R is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl), and in any one of the embodiments set forth in 1-7 of this paragraph, R is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl),
19) R is optionally substituted $C_1$-$C_4$ alkyl, wherein the optionally substituted $C_1$-$C_4$ alkyl is unsubstituted aminoalkyl (preferably unsubstituted dimethylaminoalkyl; more preferably dimethylaminoethyl), and in any one of the embodiments set forth in 1-7 of this paragraph, R is optionally substituted $C_1$-$C_4$ alkyl, wherein the optionally substituted $C_1$—$C_4$ alkyl is unsubstituted aminoalkyl (preferably unsubstituted dimethylaminoalkyl; more preferably dimethylaminoethyl),
20) The alkyl of R is saturated and in any one of the embodiments set forth in 1-17 of this paragraph, the alkyl of R is saturated,
21) R is —$CH_2CH_2N(R^{3a})(R^{4a})$ wherein $R^{3a}$ and $R^{4a}$ are independently selected from the group consisting of hydrogen and methyl, and in any one of the embodiments set forth in 1-7 of this paragraph, R is —$CH_2CH_2N(R^{3a})(R^{4a})$ wherein $R^{3a}$ and $R^{4a}$ are independently selected from the group consisting of hydrogen and methyl,
22) $R^1$ is hydrogen, methyl, ethyl or propyl, and in any one of the embodiments set forth in 1-21 of this paragraph, $R^1$ is hydrogen, methyl, ethyl or propyl,
23) $R^1$ is hydrogen or methyl, and in any one of the embodiments set forth in 1-21 of this paragraph, $R^1$ is hydrogen or methyl,
24) $R^1$ is hydrogen and in any one of the embodiments set forth in 1-21 of this paragraph, $R^1$ is hydrogen,
25) $R^1$ is $C_{1-4}$ alkyl or $C_{1-6}$ alkyl, optionally substituted with an amine, or C-linked or N-linked nitrogen-containing 3, 4, 5, or 6 membered heterocycle and in any one of the embodiments set forth in 1-21 of this paragraph, $R^1$ is $C_{1-4}$ alkyl or $C_{1-6}$ alkyl optionally substituted with an amine, or C-linked or N-linked nitrogen-containing 3, 4, 5, or 6 membered heterocycle,
26) $R^1$ is $C_{1-4}$ alkyl or $C_{1-6}$ alkyl, optionally substituted with —$N(R^{3a})(R^{4a})$ wherein $R^{3a}$ and $R^{4a}$ are independently selected from the group consisting of hydrogen, —$C_1$-$C_{20}$ alkyl, —$C_6$-$C_{14}$ aryl, and —$C_3$-$C_8$ heterocycle, preferably from the group consisting of H and $C_{1-6}$ alkyl, more preferably from the group consisting of hydrogen and methyl, and in any one of the embodiments set forth in 1-21 of this paragraph, $R^1$ is $C_{1-4}$ alkyl or $C_{1-6}$ alkyl optionally substituted with —$N(R^{3a})(R^{4a})$ wherein $R^{3a}$ and $R^{4a}$ are independently selected from the group consisting of hydrogen, —$C_1$-$C_{20}$ alkyl, —$C_6$-$C_{14}$ aryl and —$C_3$-$C_8$ heterocycle, preferably the group consisting of H and $C_{1-6}$ alkyl, more preferably the group consisting of hydrogen and methyl,
27) $R^1$ is $C_{1-4}$ alkyl or $C_{1-6}$ alkyl, optionally substituted with a Basic Unit and in any one of the embodiments set forth in 1-21 of this paragraph, $R^1$ is $C_{1-4}$ alkyl or $C_{1-6}$ alkyl optionally substituted with a Basic Unit,
28) $R^1$ is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl), and in any one of the embodiments set forth in 1-21 of this paragraph, $R^1$ is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl),
29) $R^1$ is optionally substituted $C_1$-$C_4$ alkyl, wherein the optionally substituted $C_1$-$C_4$ alkyl is unsubstituted aminoalkyl (preferably unsubstituted dimethylaminoalkyl; more preferably dimethylaminoethyl), and in any one of the embodiments set forth in 1-21 of this paragraph, $R^1$ is optionally substituted $C_1$-$C_4$ alkyl, wherein the optionally substituted $C_1$-$C_4$ alkyl is unsubstituted aminoalkyl (preferably unsubstituted dimethylaminoalkyl; more preferably dimethylaminoethyl),
30) The alkyl of $R^1$ is saturated and in any one of the embodiments set forth in 1-21 of this paragraph, the alkyl of $R^1$ is saturated,
31) $R^1$ is —$CH_2CH_2N(R^{3a})(R^{4a})$ wherein $R^{3a}$ and $R^{4a}$ are independently selected from hydrogen or methyl, and in any one of the embodiments set forth in 1-21 of this paragraph, $R^1$ is —$CH_2CH_2N(R^{3a})(R^{4a})$ wherein $R^{3a}$ and $R^{4a}$ are independently selected from the group consisting of hydrogen and methyl,
32) One of R and $R^1$ is a PEG Unit or a Basic Unit and the other is hydrogen or unsubstituted $C_{1-4}$ alkyl and in any one of the embodiments set forth in 1-7 of this paragraph, one of R and R' is a PEG Unit or a Basic Unit and the other is hydrogen or unsubstituted $C_{1-4}$ alkyl,
33) $R^2$ is hydrogen and in any one of the embodiments set forth in 1-32 of this paragraph, $R^2$ is hydrogen and LDCs having formula II, IIa, IIb, II', IIa' IIb', III(i), IIIa(i), IIIa(ii), IIIb(i), III(i)', III(i), IIIa(i)', IIIa(ii)', IIIb(i)', or IIIb(ii)', further include those wherein 34) A is present, and in any one of the embodiments set forth in 1-33 of this paragraph A is present,
35) A is absent, and in any one of the embodiments set forth in 1-33 of this paragraph, A is absent,
36) The Ligand Unit is an antibody, and in any one of the embodiments set forth in 1-35 of this paragraph, the Ligand Unit is an antibody,
37) W is comprised of 1 to no more than 12 amino acids, and in any one of the embodiments set forth in 1-36 of this paragraph, W is comprised of 1 to no more than 12 amino acid residues,
38) W is a sugar or a glycosidic-bonded carbohydrate, and in any one of the embodiments set forth in 1-36 of this paragraph W is a sugar or a glycosidic-bonded carbohydrate,
39) activation of the activateable self-immolative moiety (X) is by enzymatic cleavage within W or enzymatic cleavage of the peptidic bond between W and the self-immolative Spacer Unit (Y), and in any one of the embodiments set forth in 1-36 of this paragraph, activation of the activateable self-immolative moiety is by enzymatic cleavage within W or enzymatic cleavage of the peptidic bond between W and the self-immolative Spacer Unit (Y),
40) activation of the activateable self-immolative moiety is by a disulfide reduction (i.e., W is comprised of a reducible disulfide functional group involving a sulfur atom substituent of the self-immolative Spacer Unit), and in any one of the embodiments set forth in 1-36 of this paragraph wherein activation of the activateable self-immolative moiety is by a disulfide reduction (i.e., W is comprised of a reducible disulfide functional group involving a sulfur atom substituent of the self-immolative Spacer Unit),
41) the Activation Unit is a sugar or a glycosidic-bonded carbohydrate and attachment of the Ligand Unit within its LDC is through the self-immolative Spacer Unit (Y), and in any one of the embodiments set forth in 1-36 of this paragraph, the activation unit is a sugar or a glycosidic-bonded carbohydrate and attachment of the Ligand Unit within it LDC is through Y,
42) the Activation Unit is comprised of 1 to no more than 12 amino acid residues and attachment of the Ligand Unit is via the Activation Unit, and in any one of the embodiments set forth in 1-36 of this paragraph, wherein the activation unit is comprised of 1 to no more than 12 amino acid residues and attachment of the Ligand Unit is via the Activation Unit,
43) T* or O* is an oxygen heteroatom of a methylene carbamate unit covalently attached to a Drug Unit corresponding to the heteroatom from the functional group of an aliphatic alcohol-containing drug, and in any one of the embodiments set forth in 1-42 of this paragraph, T* or O* is an oxygen heteroatom of a methylene carbamate unit covalently attached to a Drug Unit corresponding to the heteroatom from the functional group of an aliphatic alcohol-containing drug,
44) T* or O* is an oxygen heteroatom of a methylene carbamate unit covalently attached to a Drug Unit corresponding to the heteroatom from the functional group of an aromatic alcohol-containing drug, and in any one of the embodiments set forth in 1-42 of this paragraph, T* or O* is an oxygen heteroatom of a methylene carbamate unit covalently attached to a Drug Unit corresponding to the heteroatom from the functional group of from an aromatic alcohol-containing drug,
45) T* or O* is an oxygen heteroatom of a methylene carbamate unit covalently attached to a Drug Unit corresponding to the heteroatom from the functional group of an aromatic alcohol-containing drug wherein the aromatic alcohol is not a phenolic alcohol, and in any one of the embodiments set forth in 1-42 of this paragraph, T* or O* is an oxygen heteroatom of a methylene carbamate unit covalently attached to a Drug Unit corresponding to the heteroatom from the functional group of an aromatic alcohol-containing drug, wherein the aromatic alcohol is not a phenolic alcohol,
46) D is a Drug Unit covalently attached to a methylene carbamate unit having an oxygen heteroatom as T* or O* corresponding to that of a hydroxyl functional group of a drug, wherein the hydroxyl functional group is an aromatic hydroxyl functional group, and R is optionally substituted saturated $C_1$-$C_6$ alkyl, and in any one of the embodiments set forth in 1-7 of this paragraph, D is a Drug Unit covalently attached to a methylene carbamate unit having oxygen heteroatom as T* or O* corresponding to that of a hydroxyl functional group of a drug, wherein the hydroxyl functional group is an aromatic hydroxyl functional group, and R is optionally substituted $C_1$-$C_6$ saturated alkyl,
47) D is a Drug Unit covalently attached to a methylene carbamate unit having an oxygen heteroatom as T* or O* corresponding to that of a hydroxyl functional group of a drug, wherein the hydroxyl functional group is an aromatic hydroxyl functional group, and R is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl), and in any one of the embodiments set forth in 1-7 of this paragraph, D is a Drug Unit covalently attached to a methylene carbamate unit having an oxygen heteroatom as T* or O* corresponding to that of a hydroxyl functional group of a drug, and R is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl),
48) D is a Drug Unit covalently attached to a methylene carbamate unit having an oxygen heteroatom as T* or O* corresponding to that of a hydroxyl functional group of a drug, wherein the hydroxyl functional group is an aliphatic hydroxyl functional group, and R is optionally substituted saturated $C_1$-$C_6$ alkyl, and in any one of the embodiments set forth in 1-7 of this paragraph, D is a Drug Unit covalently attached to a methylene carbamate unit having an oxygen heteroatom as T* or O* corresponding to that of a hydroxyl functional group, wherein the hydroxyl functional group is an aliphatic hydroxyl functional group of a drug, and R is optionally substituted saturated $C_1$-$C_6$ alkyl,
49) D is a Drug Unit covalently attached to a methylene carbamate unit having an oxygen heteroatom as T* or O* corresponding to that of a hydroxyl functional group, wherein the hydroxyl functional group is a aliphatic hydroxyl functional group of a drug, and R is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl), and in any one of the embodiments set forth in 1-7 of this paragraph, D is a Drug Unit covalently attached to a methylene carbamate unit having an oxygen heteroatom as T* or O* corresponding to that of a hydroxyl functional group of a drug, and R is optionally substituted $C_1$-$C_4$ alkyl, wherein the optionally substituted $C_1$-$C_4$ alkyl is an optionally substituted aminoalkyl (preferably dimethylaminoalkyl; more preferably dimethylaminoethyl), 50) T* is the oxygen heteroatom of a MAC Unit covalently attached to a Drug Unit corresponding to the heteroatom from a hydroxyl functional group of an aliphatic or aromatic alcohol-containing drug, and in any one of the embodiments set forth in 1-42 of this paragraph, T* is the oxygen heteroatom of MAC Unit covalently attached to a Drug Unit corresponding to the heteroatom from a hydroxyl functional group of an aliphatic or aromatic alcohol-containing drug, and wherein the self-immolative SI Assembly Unit comprised of the MAC Unit covalently attached to the Drug Unit is capable of releasing an aliphatic or aromatic alcohol-containing drug, 51) T* is the sulfur heteroatom of a methylene carbamate unit covalently attached to a Drug Unit corresponding to the heteroatom from a sulfhydryl functional group of a thiol-containing drug, and in any one of the embodiments set forth in 1-42 of this paragraph, T* is the sulfur heteroatom of a methylene carbamate unit covalently attached to a Drug Unit corresponding to the heteroatom from a sulfhydryl functional group of a thiol-containing drug, and wherein the self-immolative SI Assembly Unit comprised of the methylene carbamate unit covalently attached to the Drug Unit is capable of releasing a thiol-containing drug, 52) T* is the optionally substituted nitrogen heteroatom of a methylene carbamate unit covalently attached to a Drug Unit corresponding to the heteroatom of an amide or amine functional group of an amine- or carboxamide-containing drug, and in any one of the embodiments set forth in 1-42 of this paragraph, T* is the nitrogen heteroatom of a methylene carbamate unit covalently attached to a Drug Unit corresponding to the heteroatom from an amine or amide functional group of an amine- or carboxamide-containing drug, and wherein the self-immolative SI Assembly Unit comprised of the methylene carbamate unit covalently attached to the Drug Unit is capable of releasing and amide- or amine-containing drug 53) T* is the optionally substituted nitrogen heteroatom that covalently attaches a methylene carbamate unit to a Drug Unit and corresponds to the heteroatom of a primary or secondary amine functional group of a drug, and in any one of the embodiments set forth in 1-42 of this paragraph T* is the optionally substituted nitrogen heteroatom that covalently attaches a methylene carbamate unit to a Drug Unit and corresponds to the heteroatom of a primary or secondary amine functional group of a drug, and wherein the self-immolative SI Assembly Unit comprised of the methylene carbamate unit covalently attached to the Drug Unit is capable of releasing a primary or secondary amine-containing drug, 54) T* is the optionally substituted nitrogen heteroatom that covalently attaches a methylene carbamate unit to a Drug Unit and corresponds to the heteroatom of a primary or secondary amide functional group of a drug, and in any one of the embodiments set forth in 1-42 of this paragraph T*, is the optionally substituted nitrogen heteroatom that covalently attaches a methylene carbamate unit to a Drug Unit and corresponds to the heteroatom of a drug having a primary or secondary amide functional group prior, and wherein the SI Assembly Unit comprised of the methylene carbamate unit covalently attached to the Drug Unit is capable of releasing a primary or secondary (amide-containing free drug.

55) T* or O* is an oxygen heteroatom of a methylene carbamate unit covalently attached to a Drug Unit corresponding to the heteroatom from the functional group of the drug everolimus, tacrolimus or sirolimus.

Drug-Linker Compounds

In some aspects, when designing the Ligand-Drug Conjugates, it will be desirable to synthesize the full drug-linker prior to conjugation to a targeting ligand. In such embodiments, Drug-Linker Compounds act as Intermediate compounds. The Stretcher Unit in a Drug-Linker Compound is not yet covalently attached to the Ligand Unit and therefore has a functional group for conjugation to a targeting ligand (i.e., is a Stretcher Unit precursor, Z'). In one aspect, a Drug-Linker Compound comprises a Ligand Unit, a Drug Unit, and a Linker Unit comprising a Self-immolative Assembly Unit through which the Ligand Unit is connected to the Drug Unit. The Linker Unit comprises, in addition to the SI assembly Unit, a Stretcher Unit precursor (Z') comprising a functional group for conjugation to a Ligand Unit and capable of (directly or indirectly) connecting the Self-immolative Assembly Unit to the Ligand Unit. A Branching Unit is typically present in embodiments when it is desired that more than one drug is to be conjugated to each attachment site of the Ligand Unit. A Connector Unit is typically present when it is desirable to add more distance between the Stretcher Unit and the Self-immolative Assembly Unit. In one aspect, a Drug-Linker Compound has a methylene carbamate unit covalently attached to a Drug Unit with the structure of formula I, Ia, Ib, SI, SIa, SIb, I', Ia', Ib', SI', SIa', or SIb' as previously defined herein.

In one aspect, a Drug-Linker Compound is comprised of a Drug Unit and a Linker Unit, wherein that unit is comprised of an activateable self-immolative moiety (X) of a self-immolative Assembly Unit directly attached to a Stretcher Unit precursor (Z') or indirectly to Z' through attachment to intervening component(s) of the Drug-Linker Compound's Linker Unit (i.e., A and/or B), wherein Z' is comprised of a functional group capable of forming a covalent bond to a targeting ligand, and a Drug Unit that is directly attached to a methylene carbamate unit of the SI Assembly Unit. In some embodiments there are from 1 to 4 SI Assembly Units in each Linker Unit or Drug-Linker moiety at each site of attachment to the Ligand Unit. In embodiments wherein there are two or more SI Assembly Units in a Drug-Linker Compound's Linker Unit due to branching in the Linker Unit, a branching unit, B, (or its precursor B' when a Branching Unit becomes directly attached to the Ligand Unit), is present to allow for such branching. In those embodiments an exemplary Drug-Linker Compound is represented by formula V below:

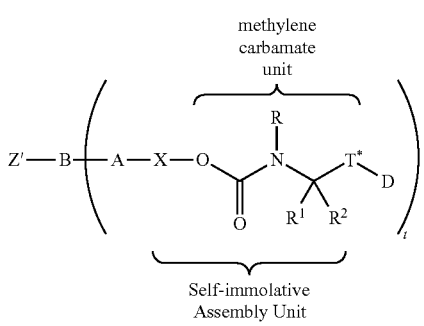

or a pharmaceutically acceptable salt thereof; wherein wherein

D is a Drug Unit having a hydroxyl, thiol, amine or amide functional group that has been incorporated into the indicated methylene carbamate unit;

T* is the oxygen, sulfur or optionally substituted nitrogen heteroatom from said functional group that becomes incorporated into the indicated methylene carbamate unit;

R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or both R and $R^1$ together with the nitrogen and carbon atoms to which they are attached comprise an azetidinyl, pyrrolodinyl, piperidinyl or homopiperidinyl moiety (preferably a pyrrolodinyl or piperidinyl moiety) and $R^2$ is hydrogen;

X is an activateable self-immolative moiety;

Z' is a Stretcher Unit precursor to a Stretcher Unit (Z) and is comprised of a functional group that provides for covalent attachment of a Ligand Unit to Z;

B is an optional Branching Unit that is present when t is 2, 3 or 4 and absent when t is 1;

A is an optional Connector Unit; and the subscript t ranges from 1 to 4.

In other embodiments the Self-immolative Assembly Unit of formula SI in the Drug-Linker Compound of Formula V is replaced with that of formula SIa or SIb to define Formulas Va and Vb Drug-Linker Compounds, respectively. Preferred combinations and subcombinations of R, R, $R^1$ and $R^2$ in formula V, Va or Vb are as given for formula II, IIa or IIb.

In some aspects, a Drug-Linker Compound has the structure of Formula V' as follows:

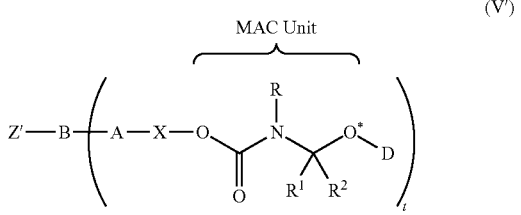

or a pharmaceutically acceptable salt thereof; wherein

D is a Drug Unit having a hydroxyl functional group prior to its incorporation into the indicated methylene alkoxy (aryloxy) carbamate unit (MAC Unit), the oxygen atom from which is designated by O*;

R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or both R and $R^1$ together with the nitrogen and carbon atoms to which they are attached comprise a azetidinyl, pyrrolodinyl, piperidinyl or homopiperidinyl moiety (preferably a pyrrolodinyl or piperidinyl moiety) and $R^2$ is hydrogen;

X is an activateable self-immolative moiety;

Z' is a Stretcher Unit precursor to a Stretcher Unit (Z) and is comprised of a functional group that provides for covalent attachment of a Ligand Unit to Z;

B is an optional Branching Unit that is present when t is from 2, 3 or 4 and absent when t is 1;

A is an optional Connector Unit; and the subscript t ranges from 1 to 4.

In other embodiments the Self-immolative Assembly Unit of formula SI' in the Drug-Linker Compound of formula V' is replaced with that of formula SIa' or SIb' to define formula Va' and Vb' Drug-Linker Compounds, respectively. Preferred combinations and subcombination of R, R, $R^1$ and $R^2$ in formula V', Va' or Vb' are as given for formula II', IIa' or IIb'.

The hydroxyl functional group referred to with respect to providing for a Drug Unit of a Drug-Linker Compound of formula V, Va' or Vb' is the hydroxyl functional group of an aromatic alcohol or an aliphatic alcohol. The aliphatic alcohol can be a primary, secondary or tertiary aliphatic alcohol. Preferably, the alcohol is an aliphatic alcohol, more preferably, a primary or secondary aliphatic alcohol.

The Self-immolative Assembly Unit is comprised of an activateable self-immolative moiety (X) and a methylene carbamate unit. In some embodiments that activateable moiety is comprised of an Activation Unit (W) and a self-immolative Spacer Unit (Y). The Activation Unit initiates a self-immolative reaction sequence within the Spacer Unit, which results in the release of free drug from the Drug Linker Compound. Either the Activation Unit or the self-immolative Spacer Unit can form the site of covalent attachment to the remainder of the Drug-Linker Compound (i.e., to A, B, or Z' depending on the presence or absence of A and/or B). In some embodiments a Drug-Linker Compound is comprised of a Self-immolative Assembly Unit attached to a Drug Unit and is represented by formula VI(i) or VI(ii):

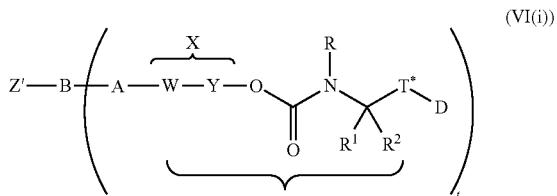

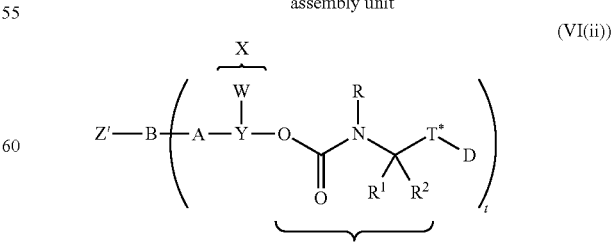

or a pharmaceutically acceptable salt thereof; wherein
A is an optional Connector Unit;
W is an Activation Unit;
Y is a Self-Immolative Spacer Unit;
Z' is a Stretcher Unit precursor to a Stretcher Unit (Z) and is comprised of a functional group that provides for covalent attachment of a Ligand Unit to Z;
B is an optional Branching Unit that is present when t is 2, 3 or 4, and absent when t is 1;
R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl or both R and $R^1$ together with the nitrogen and carbon atoms to which they are attached comprise a azetidinyl, pyrrolodinyl, piperidinyl or homopiperidinyl moiety (preferably a pyrrolodinyl or piperidinyl moiety) and $R^2$ is hydrogen;
D is a Drug Unit having a hydroxyl, thiol, amine or amide functional group prior to its incorporation into the indicated methylene alkoxy carbamate unit;
T* is the oxygen, sulfur or optionally substituted nitrogen heteroatom from said functional group that becomes incorporated into the indicated methylene carbamate unit; and the subscript t ranges from 1 to 4.

Formulas VI (i) and VI (ii) have the methylene carbamate unit from formula Ia. In other embodiments of Drug-Linker Compound that methylene carbamate unit structure is replaced by that of formula Ia to define Drug Linker Compounds of formula VI(a)(i) and VIa(ii), respectively. In other embodiments of Drug-Linker Compound that methylene carbamate unit structure is replaced by that of formula Ib to define Drug Linker Compounds of formula VI(b)(i) and VIb(ii), respectively. Preferred combinations and subcombination of R, R, $R^1$ and $R^2$ in formula VI(i), VI(ii), VIa(i), VIa(ii), VIb(i) or VIb(ii) are as given for formula III(i), III(ii), IIIa(i), IIIa(ii), IIIb(i) or IIIb(ii).

In some embodiments a Drug-Linker Compound is comprised of a Self-immolative Assembly Unit attached to Drug Unit and is represented by Formula VI (i)' or VI (ii)':

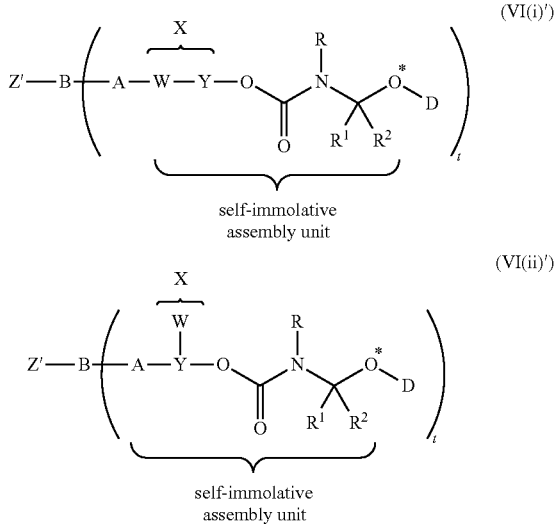

self-immolative
assembly unit self-immolative
assembly unit or a pharmaceutically acceptable salt thereof; wherein
A is an optional Connector Unit;
W is an Activation Unit;
Y is a Self-Immolative Spacer Unit;

Z' is a precursor to a Stretcher Unit (Z) and is comprised of a functional group that provides for covalent attachment of a Ligand Unit to Z;
B is an optional Branching Unit that is present when t is from 2 to 4 and absent when t is 1;
R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or both R and $R^1$ together with the nitrogen and carbon atoms to which they are attached comprise an azetidinyl, pyrrolodinyl, piperidinyl or homopiperidinyl moiety (preferably a pyrrolodinyl or piperidinyl moiety) and $R^2$ is hydrogen;
D is a Drug Unit having a hydroxyl functional group prior to its incorporation into the indicated methylene alkoxy carbamate unit;
T* is the oxygen heteroatom from said functional group that becomes incorporated into the indicated methylene alkoxy(aryloxy) carbamate unit (MAC Unit); and
the subscript t is an integer ranging from 1 to 4.

Formula VI (i)' and VI (ii)' have a MAC structure of formula I'.

As indicated, Drug-Linker Compounds can act as Intermediate compounds for the LDCs of the present invention. Accordingly, any of the embodiments set forth for the LDCs are applicable as well for the Drug-Linker Compounds of the present invention. In other words, any of the definitions for B, A, X, R, $R^1$, $R^2$, T*, D, O*, and the subscripts s and t and combinations thereof are applicable and contemplated for the Drug-Linker Compounds of the present invention.

Component Groups
Ligand Units:
In some embodiments of the invention, a Ligand Unit is present, as for example in a Ligand Drug Conjugate. The Ligand unit (L-) is a targeting agent that specifically binds to a target moiety. In one group of embodiments, the Ligand Unit specifically and selectively binds to a cell component (a Cell Binding Agent) or to other target molecules of interest. The Ligand Unit acts to target and present the Drug Unit of a Ligand Drug Conjugate to the particular target cell population with which the Ligand Unit interacts due to the presence of its targeted component or molecule and allows for subsequent release of free drug within (i.e., intracellularly) or within the vicinity of the target cells (i.e., extracellularly). Ligands include, but are not limited to, proteins, polypeptides and peptides. Suitable Ligand units include, for example, antibodies, e.g., full-length antibodies and antigen binding fragments thereof, interferons, lymphokines, hormones, growth factors and colony-stimulating factors, vitamins, nutrient-transport molecules (such as, but not limited to, transferrin), or any other cell binding molecule or substance. In some embodiments the Ligand Unit is from an antibody or a non-antibody protein targeting agent.

In one group of embodiments a Ligand Unit is bonded to a Stretcher unit (Z). In some of those embodiments the Ligand Unit is bonded to Z of the Linker Unit via a heteroatom of the Ligand Unit. Heteroatoms that may be present on a Ligand Unit for that bonding include sulfur (in one embodiment, from a sulfhydryl group of a targeting ligand), oxygen (in one embodiment, from a carboxyl or hydroxyl group of a targeting ligand) and nitrogen, optionally substituted (in one embodiment, from a primary or secondary amine functional group of a targeting ligand or in another embodiment from an optionally substituted amide nitrogen). Those heteroatoms can be present on the targeting ligand in the ligand's natural state, for example in a naturally-occurring antibody, or can be introduced into the targeting ligand via chemical modification or biological engineering.

In one embodiment, a Ligand Unit has a sulfhydryl functional group so that the Ligand Unit is bonded to the Linker Unit via the sulfur atom of the sulfhydryl functional group.

In another embodiment, a Ligand Unit has one or more lysine residues that are capable of reacting with activated esters (such esters include, but are not limited to, N-hydroxysuccinimide, pentafluorophenyl, and p-nitrophenyl esters) of a Stretcher Unit precursor of a Drug-Linker Compound intermediate and thus provides an amide bond consisting of the nitrogen atom of the Ligand Unit and the C=O group of the Linker Unit's Stretcher Unit.

In yet another aspect, a Ligand Unit has one or more lysine residues capable of chemical modification to introduce one or more sulfhydryl groups. In those embodiments the Ligand Unit is bonded to the Linker Unit via the sulfhydryl functional group's sulfur atom. The reagents that can be used to modify lysines in that manner include, but are not limited to, N-succinimidyl S-acetylthioacetate (SATA) and 2-Iminothiolane hydrochloride (Traut's Reagent).

In another embodiment, a Ligand Unit one or more carbohydrate groups capable of modification to provide one or more sulfhydryl functional groups. The chemically modified Ligand Unit in a Ligand Drug Conjugate is bonded to a Linker Unit component (e.g., a Stretcher Unit) via the sulfur atom of the sulfhydryl functional group.

In yet another embodiment, the Ligand Unit has one or more carbohydrate groups that are capable of being oxidized to provide an aldehyde (—CHO) functional group (see, e.g., Laguzza, et al., 1989, *J. Med. Chem.* 32(3):548-55). In that embodiment, the corresponding aldehyde interacts with a reactive site on a Stretcher Unit precursor to form a bond between the Stretcher Unit and the Ligand Unit. Reactive sites on a Stretcher Unit precursor that capable of interacting with a reactive carbonyl-containing functional group on a targeting ligand include, but are not limited to, hydrazine and hydroxylamine Other protocols for the modification of proteins for the attachment of Linker Units or Drug-Linker Compounds are described in Coligan et al., *Current Protocols in Protein Science*, vol. 2, John Wiley & Sons (2002) (incorporated herein by reference).

In some aspects, a Ligand Unit is capable of forming a bond by interacting with a reactive functional group on a Stretcher Unit precursor (Z') to form a covalent bond between the Stretcher Unit (Z) and the Ligand Unit corresponding to the targeting ligand. The functional group of Z' having that capability for interacting with a targeting ligand will depend on the nature of the Ligand Unit. In some embodiments, the reactive group is a maleimide that is present on a Stretcher Unit prior to its attachment to form a Ligand Unit. (i.e., a maleimide moiety of a Stretcher Unit precursor). Covalent attachment of a Ligand Unit to a Stretcher Unit is accomplished through a sulfhydryl functional group of a Ligand Unit interacting with the maleimide functional group of Z' to form a thio-substituted succinimide. The sulfhydryl functional group can be present on the Ligand Unit in the Ligand's natural state, for example, in a naturally-occurring residue, or can be introduced into the Ligand via chemical modification or by biological engineering.

In still another embodiment, the Ligand Unit is from an antibody and the sulfhydryl group is generated by reduction of an interchain disulfide of the antibody. Accordingly, in some embodiments, the Linker Unit is conjugated to a cysteine residue from reduced interchain disulfide(s).

In yet another embodiment, the Ligand Unit is from an antibody and the sulfhydryl functional group is chemically introduced into the antibody, for example, by introduction of a cysteine residue. Accordingly, in some embodiments, the Linker Unit is conjugated to a Drug Unit through an introduced cysteine residue of a Ligand Unit.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker moiety to a Ligand Unit can affect the ability of the conjugated drug-linker moiety to undergo an elimination reaction to cause premature release of free drug and for the drug linker moiety to be transferred from the Ligand of an LDC to an alternative reactive thiol present in the milieu of the LDC, such as, for example, a reactive thiol in albumin, free cysteine, or glutathione present in plasma. Sites for conjugation on a targeting ligand include, for example, a reduced interchain disulfide as well as select cysteine residue at engineered sites. In some embodiments conjugation methods to form Ligand-Drug Conjugates as described herein use thiol residues at genetically engineered sites that are less susceptible to the elimination reaction (e.g., positions 239 according to the EU index as set forth in Kabat) in comparison to conjugation methods that use thiol residues from a reduced disulfide bond. In other embodiments conjugation methods to form Ligand-Drug Conjugates as described herein use thiol residues at sites that are more susceptible to the elimination reaction (e.g. resulting from interchain disulfide reduction).

When a Ligand Drug Conjugate is comprised of a non-immunoreactive protein, polypeptide, or peptide, its Ligand Unit, instead of being from antibody, is from a non-immunoreactive protein, polypeptide, or peptide which includes, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Particularly preferred Ligand Units are from antibodies. In fact, in any of the embodiments described herein, the Ligand Unit can be from an antibody. Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies may be made by any of numerous techniques known in the art (e.g., Teng et al., 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immunospecifically binds to target cells. To determine which CDR sequences bind the antigen, synthetic peptides containing the CDR sequences can be used in binding assays with the antigen by any binding assay method known in the art (e.g., the BIA core assay) (See, e.g., Kabat et al., 1991, *Sequences of Proteins of Immunological Interest*, Fifth Edition, National Institute of Health, Bethesda, Md.; Kabat E et al., 1980, *J. Immunology* 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, Science 240:1041-1043; Liu et al., 1987, *Proc. Natl. Acad. Sci. USA* 84:3439-3443; Liu et al., 1987, *J. Immunol.* 139:3521-3526; Sun et al., 1987, *Proc. Natl. Acad. Sci. USA* 84:214-218; Nishimura et al., 1987, *Cancer. Res.* 47:999-1005; Wood et al., 1985, *Nature* 314:446-449; and Shaw et al., 1988, *J. Natl. Cancer Inst.* 80:1553-1559; Morrison, 1985, *Science* 229:1202-1207; Oi et al., 1986, *BioTechniques* 4:214; U.S. Pat. No. 5,225,539; Jones et al., 1986, *Nature* 321:552-525; Verhoeyan et al., 1988, *Science* 239:1534; and Beidler et al., 1988, *J. Immunol.* 141:4053-4060; each of which is incorporated herein by reference in its entirety.

Completely human antibodies in some instances (e.g., when immunogenicity to a non-human or chimeric antibody may occur) are more desirable and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivitization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies immunospecific for a cancer cell antigen can be obtained commercially or produced by any method known to one of skill in the art such as, recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, a known antibody for the treatment of cancer can be used.

In another specific embodiment, antibodies for the treatment of an autoimmune disease are used in accordance with the compositions and methods of the invention.

In certain embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In some aspects, the antibody that is incorporated into a Ligand Drug Conjugate will specifically bind CD19, CD20, CD30, CD33, CD70, NTBA, alpha-v-beta-6, Liv-1 or Lewis Y antigen.

Drug Units (D):

The Drug Unit (D) can be from any cytotoxic, cytostatic or immunosuppressive drug (also referred to herein as a cytotoxic, cytostatic or immunosuppressive agent), that has a hydroxyl, thiol, amine or amide functional group whose oxygen, sulfur or optionally substituted nitrogen heteroatom is capable of incorporation into a methylene carbamate unit, and is capable of being released from the methylene carbamate unit as the functional group of a free drug. In some aspects, that functional group provides the only site on a drug available for attachment to that Linker Unit component. The resulting drug-linker moiety is one that can release active free drug from an LDC having that moiety at the site targeted by its Ligand Unit in order to exert a cytotoxic, cytostatic or immunosuppressive effect.

"Free drug" refers to drug, as it exists once released from the drug-linker moiety. The free drug differs from the conjugated drug in that the functional group of the drug for attachment to the self-immolative assembly unit is no longer associated with components of the Ligand-Drug Conjugate (other than a previously shared heteroatom). For example, the free hydroxyl functional group of an alcohol-containing drug can be represented as D-O*H, whereas in the conjugated form the oxygen heteroatom designated by O* is incorporated into the methylene carbamate unit of a Self-immolative Assembly Unit. Upon activation of the self-immolative moiety and release of free drug, the covalent bond to O* is replaced by a hydrogen atom so that the oxygen heteroatom designated by O* is present on the free drug as —O—H. In another example, O* is from a free hydroxyl functional group of a precursor to alcohol-containing drug, which is represented as D'-O*H. After O* from that precursor is incorporation into a methylene carbamate unit of a Self-immolative Assembly Unit D'-O*— that moiety in the Self-immolative Assembly Unit is subsequently converted to D-O*—.

Useful classes of cytotoxic or immunosuppressive agents having a hydroxyl, sulfhydryl, amine or amide functional group, or can be modified to have such functional groups without incurring unacceptable loss of biological activity, that are suitable for attachment to a methylene carbamate unit include, for example, antitubulin agents, DNA minor groove binders, DNA replication inhibitors, alkylating agents, antibiotics, antifolates, antimetabolites, chemotherapy sensitizers, topoisomerase inhibitors, vinca alkaloids, or the like. Examples of particularly useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids, taxanes, benzodiazepines or benzodiazepine containing drugs (e.g., pyrrolo[1,4]-benzodiazepines (PBDs), indolinobenzodiazepines, and oxazolidinobenzodiazepines) and vinca alkaloids.

In some embodiments, the Drug unit is from an antitubulin agent. Examples of anti-tubulin agents include, but are not limited to, taxanes, vinca alkaloids maytansine and maytansinoids, dolastatins and auristatins.

In certain embodiments, the cytotoxic agent is from maytansine or a maytansinoid.

In some embodiments, the Drug unit is from an auristatin, with those having a hydroxyl functional group whose heteroatom is incorporation into a MAC Unit preferred. Exemplary preferred auristatins include compounds having one of the following structures:

erocycle); $R^{17}$ independently are hydrogen, —OH, $C_1$-$C_8$ alkyl, $C_3$-$C_8$ cycloalkyl and O—($C_1$-$C_8$ alkyl); $R^{18}$ is hydrogen or $C_1$-$C_8$ alkyl; $R^{19}$ is —C($R^{19A}$)$_2$—C($R^{19A}$)$_2$—aryl, —C($R^{19A}$)$_2$—C($R^{19A}$)$_2$—($C_3$-$C_8$ heterocycle) or —C($R^{19A}$)$_2$—C($R^{19A}$)$_2$—($C_3$-$C_8$ cycloalkyl), wherein each $R^{19A}$ independently is hydrogen, $C_1$-$C_8$ alkyl, —OH or —O—$C_1$-$C_8$ alkyl, provided that at least one $R^{19A}$ is —OH; $R^{20}$ is hydroxylalkyl, including —CH(CH$_3$)—OH; Z is O, S, NH, and $X^1$ is $C_1$-$C_{10}$ alkylene.

The syntheses and structures of auristatins having an hydroxyl functional group whose oxygen heteroatom capable of being incorporated into a MAC unit are described in U.S. Patent Application Publication Nos. 2003-0083263, 2005-0238649 2005-0009751, 2009-0111756, and 2011-0020343; International Patent Publication No. WO 04/010957, International Patent Publication No. WO 02/088172, and U.S. Pat. Nos. 7,659,241 and 8,343,928; each of which is incorporated by reference in its entirety and for all purposes. Exemplary alcohol-containing auristatins released from LDCs of the present invention bind tubulin and exert a cytotoxic or cytostatic effect on the desired cells (i.e., target cells) as a result of that binding.

More preferred auristatins having a hydroxyl functional group whose heteroatom is incorporation into a MAC Unit is monomethyl auristatin E and auristatin T.

In some embodiments, the Drug Unit is from a benzodiazepine (including benzodiazepine-containing drugs (e.g., pyrrolo[1,4]benzodiazepines (PBDs), indolinobenzodiazepines, and oxazolidinobenzodiazepines) having or modified to have a hydroxyl, amine, amide or thiol functional group suitable for incorporation into a Drug Unit covalently attached to a methylene carbamate unit through a heteroatom of that functional group.

In other aspects, the drug unit is an immunophilin of the FKBP class (as described in Wiederrecht and Etzhorn "Immunophilins" *Perspec. Drug Discov. Des.* (1994) 2(1): 57-84), referred herein as a FKBP immunophilin, having a

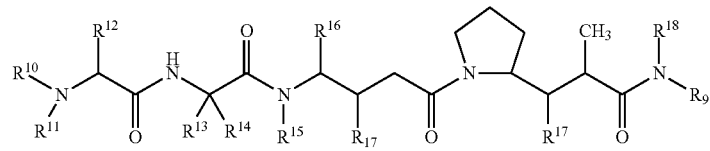

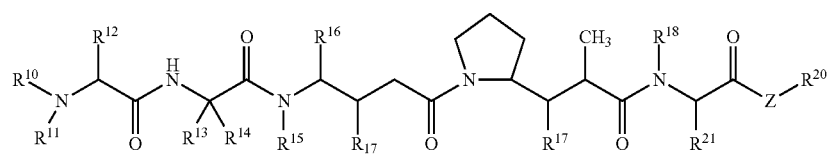

wherein $R^{10}$ and $R^{11}$ are independently hydrogen or $C_1$-$C_8$ alkyl; $R^{12}$ is hydrogen, $C_1$-$C_8$ alkyl, $C_3$-$C_8$ cycloalkyl, aryl, —$X^1$-aryl, —$X^1$—($C_3$-$C_8$ cycloalkyl), $C_3$-$C_8$ heterocycle or —$X^1$—($C_3$-$C_8$ heterocycle); $R^{13}$ is hydrogen, $C_1$-$C_8$ alkyl, $C_3$-$C_8$ cycloalkyl, aryl, —$X^1$-aryl, —$X^1$—($C_3$-$C_8$ cycloalkyl), $C_3$-$C_8$ heterocycle and —$X^1$—($C_3$-$C_8$ heterocycle); $R^{14}$ is hydrogen or methyl, or $R^{13}$ and $R^{14}$ taken together with the carbon to which they are attached comprise a $C_3$-$C_8$ cycloalkyl; $R^{15}$ is hydrogen or $C_1$-$C_8$ alkyl; $R^{16}$ is hydrogen, $C_1$-$C_8$ alkyl, $C_3$-$C_8$ cycloalkyl, aryl, —$X^1$-aryl, —$X^1$—($C_3$-$C_8$ cycloalkyl), $C_3$-$C_8$ heterocycle and —$X^1$—($C_3$-$C_8$ hethydroxyl functional group suitable for incorporation into a Drug Unit covalently attached to a MAC unit through the oxygen heteroatom of that functional group.

In one group of embodiments the immunophilin suitable for incorporation into a Drug Unit covalent attachment to a MAC unit binds to FKBP-12 as the free drug to inhibit effector function of calcineurin required for T-cell proliferation. In one embodiment, the FKBP immunophilin that is capable of incorporation into a MAC unit and as the free drug binds to FKBP-12 to inhibit effector function of calcineurin has the general structure of formula VIIa

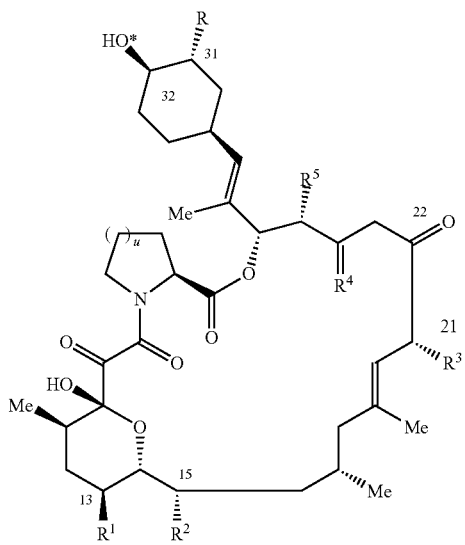

(VIIa)

wherein u is 0 or 1 to define a prolinyl or pipecolic acid moiety, wherein R, $R^1$ and $R^2$ independently are —OH, an optionally substituted $C_1$-$C_6$ ether or an optionally substituted $C_1$-$C_6$ ester (preferably R, $R^1$ and $R^2$ are —OMe); $R^3$ is optionally substituted $C_1$-$C_4$ alkyl (preferably methyl, ethyl, —CH$_2$CH=CH$_2$, —CH$_2$CH$_2$CH$_2$CH$_3$; $R^4$ is oxo (i.e., =O), or —OH or $C_1$-$C_6$ ester in the α- or β-configuration (preferably =O or α-OH); and $R^5$ is hydrogen or optionally substituted $C_1$-$C_4$ alkyl (preferably hydrogen or methyl).

In preferred embodiments of formula VIIa, u is 2; R, $R^1$ and $R^2$ are —OMe; $R^3$ is ethyl; $R^4$ is α-OH; and $R^5$ is methyl, or u is 2; R, $R^1$ and $R^2$ are —OMe; $R^3$ is methyl; $R^4$ is α-OH; and $R^5$ is methyl, or u is 1; R, $R^1$ and $R^2$ are —OMe; $R^3$ is —CH$_2$CH=CH$_2$; $R^4$ is α-OH; and $R^5$ is methyl, or u is 2; R, $R^1$ and $R^2$ are —OMe; $R^3$ is ethyl, $R^4$ is α-OH; and $R^5$ is hydrogen, or u is 1; R, $R^1$ and $R^2$ are —OMe; $R^3$ is ethyl, $R^4$ is α-OH; and $R^5$ is methyl, or u is 2; R, $R^1$ and $R^2$ are —OMe, $R^3$ is —CH$_2$CH=CH$_2$; $R^4$ is α-OH; and $R^5$ is methyl, or u is 2; R is —OMe; R' is —OH; $R^2$ is methyl, $R^3$ is —CH$_2$CH=CH$_2$; $R^4$ is α-OH; and $R^5$ is methyl.

In other embodiments the moiety A in formula VIIa of

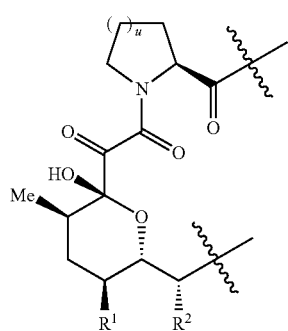

(A)

is replaced by the moiety B

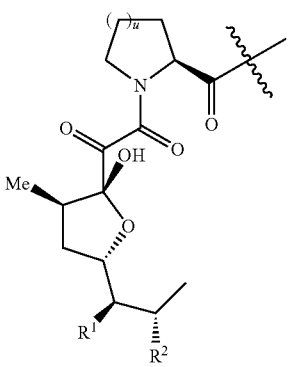

(B)

to define FKBP immunophilins of formula VIIb, wherein the wavy line indicate covalent attachment to the remainder of the macrolide; u, R, $R^1$, $R^2$, $R^3$, $R^4$ and $R^5$ are as defined formula VIIa. In preferred embodiments of formula VIIb, u is 2, R is —OMe; R' is —OH; $R^2$ is —OMe; $R^3$ is methyl, ethyl or —CH$_2$CH=CH$_2$; $R^4$ is α-OH; and $R^5$ is hydrogen or methyl.

In other embodiments the moiety A in formula VIIa is replaced by the moiety of C or D

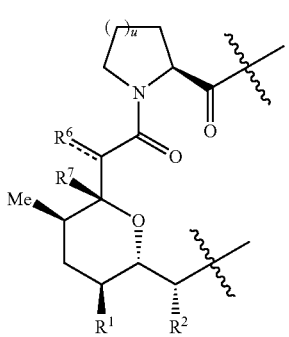

(C)

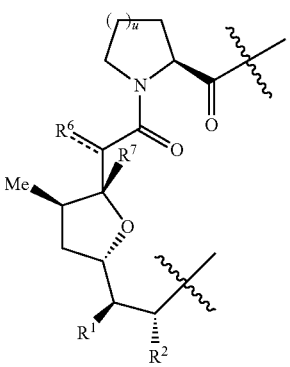

(D)

to define FKBP immunophilins of formula VIIc or VIId, respectively, wherein $R^6$ is hydrogen, oxo (i.e., =O), —OH in the α- or β-configuration, epoxide (i.e., —CH$_2$O—), =N(R$^{6'}$) or =C(R$^{6'}$)$_2$; $R^7$ is —OH or —N(R$^{6'}$)$_2$; and u, R, $R^1$, $R^2$, $R^3$, $R^4$ and $R^5$ are as defined formula VIIa, wherein in each occurrence R$^{6'}$ is independently selected from the group consisting of hydrogen and optionally substituted $C_1$-$C_4$ alkyl.

In other embodiments the moiety A in formula VIIa is replaced by moiety E or F

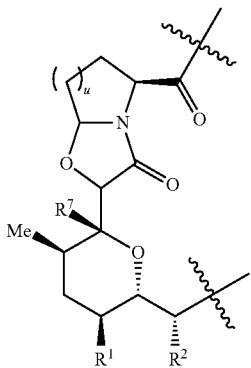
(E)

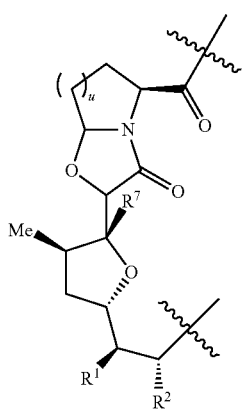
(F)

to define FKBP immunophilins of formula VIIe or VIIf, respectively, wherein u, R, $R^1$, $R^2$, $R^3$, $R^4$ and $R^5$ are as defined in Formula VIa and $R^7$ is as defined in formula VIc/VId. Preferably in formula VIIe, R, $R^1$ and $R^2$ are —OMe; $R^3$ is methyl, ethyl or —CH$_2$CH=CH$_2$; $R^4$ is α-OH; $R^5$ is hydrogen or methyl; and $R^7$ is —OH, and preferably in formula VIIf, u is 2, R is —OMe, $R^1$ is —OH; $R^2$ is —OMe; $R^3$ is methyl, ethyl or —CH$_2$CH=CH$_2$; $R^4$ is α-OH; $R^5$ is hydrogen or methyl; and $R^7$ is —OH.

In other embodiments the moiety of formula A in formula VIa is replace by moiety G, H or J

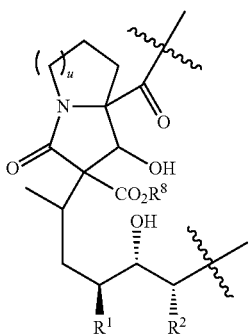
(G)

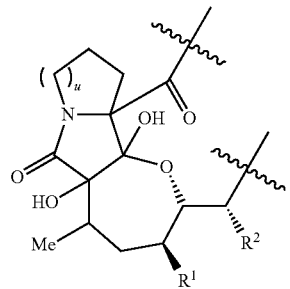
(H)

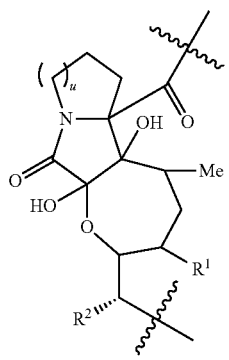
(J)

to define FKBP immunophilins of formula VIIg, VIIh and VIIj, respectively, wherein IV, $R^2$, $R^3$, $R^4$, $R^5$ and $R^6$ are as defined in formula VIIa; and $R^8$ is hydrogen or optionally substituted $C_1$-$C_6$ alkyl. Preferably in those formulae u is 2; R, $R^1$ and $R^2$ are —OMe; $R^3$ is methyl, ethyl or —CH$_2$CH=CH$_2$; $R^4$ is α-OH; $R^5$ is hydrogen or methyl; and $R^8$ is methyl or ethyl.

In other embodiments the moiety A in formula VIIa is replaced by moiety K

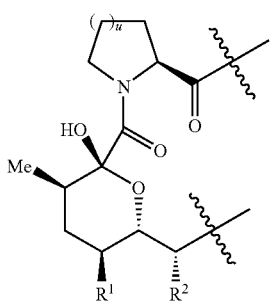
(K)

to define FKBP immunophilins of formula VIIk, wherein u, R, $R^1$, $R^2$, $R^3$, $R^4$ and $R^5$ are as defined formula VIIa.

In other embodiments the moiety A' in formula VIIa, VIIb, VIIc, VIId, VIIe, VIIf, VIIg, VIIh, VIIj or VIIk is replaced by the moiety,

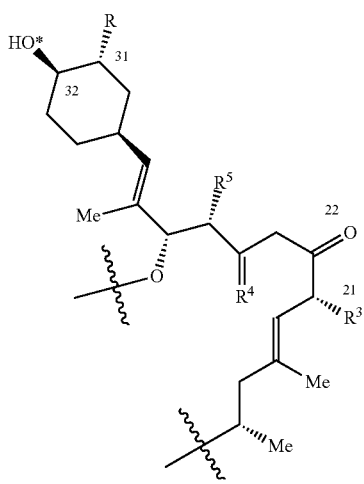

(A')

is replaced by the moiety M

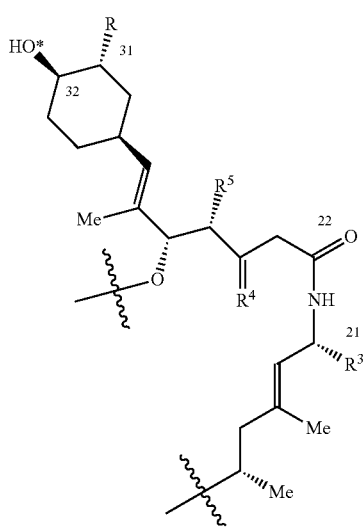

(M)

to define FKBP immunophilins of formula VIIm(i), VIIm(ii), VIIm(iii), VIIm(iv), VIIm(v), VIIm(vi), VIIm(vii), VIIm(viii), VIIm(ix) and VIIm(x), respectively, wherein the variable groups are as defined in their corresponding parent structure. A preferred A' replacement with moiety M is for formula VIa defining FKBP immunophilins of formula VIIm(i), wherein R, $R^1$ and $R^2$ are —OMe; $R^3$ is methyl, ethyl or —CH$_2$CH=CH$_2$; $R^4$ is α-OH; and $R^5$ is hydrogen or methyl.

In other embodiments the moiety A' in formula VIIa, VIIb, VIIc, VIId, VIIe, VIIf, VIIg, VIIh, VIIj, or VIIk is replace by the moiety N

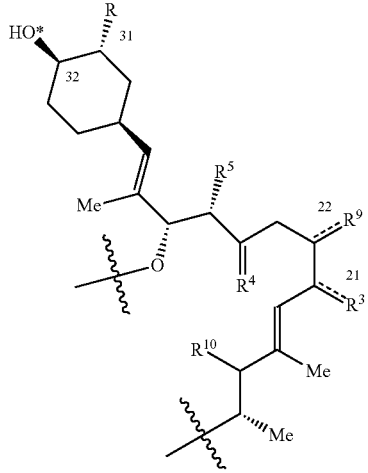

(N)

to define FKBP immunophilins of formula VIIn(i), VIIn(ii), VIIn(iii), VIIn(iv), VIIn(v), VIIn(vi), VIIn(vii), VIIn(viii), VIIn(ix) and VIIn(x), wherein $R^3$ is $R^{3A}$, $R^{3B}$ (i.e., C-21 is bonded to $R^{3A}$ and $R^{3B}$), wherein $R^{3A}$ in the α-configuration is optionally substituted $C_1$-$C_6$ alkyl (preferably methyl, ethyl, —CH$_2$CH=CH$_2$, —CH$_2$CH$_2$CH$_2$CH$_3$) and $R^{3B}$ in the β-configuration is hydrogen or —OH, or $R^{3A}$ in the α-configuration is —OH and $R^{3B}$ in the β-configuration is optionally substituted $C_1$-$C_6$ alkyl (preferably methyl, ethyl, —CH$_2$CH=CH$_2$, —CH$_2$CH$_2$CH$_2$CH$_3$); $R^9$ is oxo or —OH in the α- or β-configuration; and $R^{10}$ is hydrogen or fluoro in the α- or β-configuration, provided that when $R^{3B}$ is hydrogen and $R^9$ is oxo, then $R^{10}$ is not hydrogen; and the remaining variable groups are as defined in their corresponding parent structure.

A preferred A' replacement with moiety N is for formula VIa defining FKBP immunophilins of formula VIIn(i), wherein R, $R^1$ and $R^2$ are —OMe; $R^{3A}$ is methyl or ethyl and $R^{3B}$ is hydrogen; $R^4$ is α-OH; $R^5$ is hydrogen or methyl; $R^9$ is oxo; and $R^{10}$ is fluoro in the α- or β-configuration or R, $R^1$ and $R^2$ are —OMe; $R^{3A}$ is methyl or ethyl and $R^{3B}$ is —OH or $R^{3A}$ is —OH and $R^{3B}$ is methyl or ethyl; $R^4$ is α-OH; $R^5$ is hydrogen or methyl; $R^9$ is oxo; and $R^{10}$ is hydrogen or —OH in the α- or β-configuration.

In other embodiments the moiety A' in formula VIIa, VIIb, VIIc, VIId, VIIe, VIIg, VIIh, VIIj, or VIIk is replaced by the moiety 0

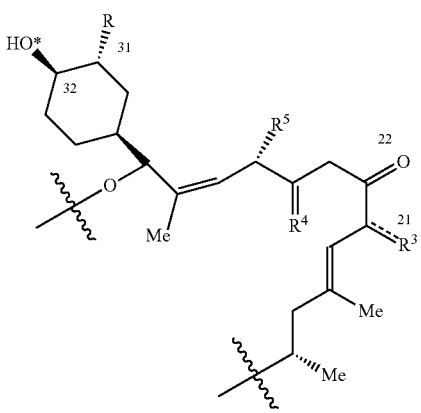

(O)

to define FKBP immunophilins of formula VIIo(i), VIIo(ii), VIIo(iii), VIIo(iv), VIIo(v), VIIo(vi), VIIo(vii), VIIo(viii), VIIo(ix) and VIIo(x), respectively, wherein R, $R^3$, $R^4$ and $R^5$ are as defined for the VIIn-immunophilins and the remaining variable groups are as defined in their corresponding parent structure.

A preferred A' replacement with moiety 0 is for formula VIa defining FKBP immunophilins of formula VIIo(i), wherein R, $R^1$ and $R^2$ are —OMe; $R^{3A}$ in the α-configuration is optionally substituted $C_1$-$C_6$ alkyl (preferably methyl, ethyl, —$CH_2CH=CH_2$, —$CH_2CH_2CH_2CH_3$); $R^{3B}$ in the β-configuration is hydrogen; $R^4$ is α-OH; $R^5$ is hydrogen or methyl.

In more preferred embodiments of formula VIIa, u is 2; R, $R^1$ and $R^2$ are —OMe, $R^3$ is —$CH_2CH=CH_2$; $R^4$ is α-OH; and $R^5$ is methyl, or u is 2; R is —OMe; $R^1$ is —OH; $R^2$ is methyl, $R^3$ is —$CH_2CH=CH_2$; $R^4$ is α-OH; and $R^5$ is methyl. In more preferred embodiments of formula VIIb, u is 2; R is —OMe; $R^1$ is —OH; $R^2$ is methyl, $R^3$ is —$CH_2CH=CH_2$; $R^4$ is α-OH; and $R^5$ is methyl. In more preferred embodiments of formula VIIc, u is 2; R, $R^1$ and $R^2$ are —OMe, $R^3$ is —$CH_2CH=CH_2$; $R^4$ is α-OH; $R^5$ is methyl; $R^6$ is hydrogen, =$CH_2$, or —OH in the α- or β-configuration (preferably —OH); and $R^7$ is —OH. In more preferred embodiments of formula VIId, u is 2; R is —OMe; $R^1$ is —OH; $R^2$ is methyl, $R^3$ is —$CH_2CH=CH_2$; $R^4$ is α-OH; $R^5$ is methyl; $R^6$ is hydrogen, =$CH_2$, or —OH in the α- or β-configuration (preferably —OH); and $R^7$ is —OH. In more preferred embodiments of formula VIIe, R, $R^1$ and $R^2$ are —OMe; $R^3$ is —$CH_2CH=CH_2$; $R^4$ is α-OH; $R^5$ is methyl; and $R^7$ is —OH. In more preferred embodiments of formula VIIf, u is 2, R is —OMe, $R^1$ is —OH; $R^2$ is —OMe; $R^3$ is —$CH_2CH=CH_2$; $R^4$ is α-OH; $R^5$ is methyl; and $R^7$ is —OH.

In more preferred embodiments of VIIg, VIIh or VIIj, R, $R^1$ and $R^2$ are —OMe; $R^3$ is —$CH_2CH=CH_2$; $R^4$ is α-OH; $R^5$ is methyl; and $R^8$ is methyl. In more preferred embodiments of formula VIIk or formula VIIm(i), u is 2; R, $R^1$ and $R^2$ are —OMe, $R^3$ is —$CH_2CH=CH_2$; $R^4$ is α-OH. In more preferred embodiments of formula VIIn(i), R, $R^1$ and $R^2$ are —OMe; $R^3$ is ethyl; $R^4$ is α-OH; $R^5$ is methyl; $R^9$ is oxo; and $R^{19}$ is —OH in the α- or β-configuration. In more preferred embodiments of formula VIIn(i), R, $R^1$ and $R^2$ are —OMe; $R^{3A}$ in the α-configuration is —$CH_2CH=CH_2$, —$CH_2CH_2CH_2CH_3$); $R^{3B}$ in the β-configuration is hydrogen; $R^4$ is α-OH; and $R^5$ is methyl.

In other more preferred embodiments the Drug Unit in any one of formula I, I', Ia, Ia', II, II', IIIa(i), IIIa(ii), IIIb(i), IIIb(ii), Va, Vb, Va', Vb', VIa, VIb, VIa', VIb', VIa(i), VIa(ii), VIb(i), and VIb(ii) is from the FKBP immunophilin of formula VIIa, VIIb, VIIc, VIId, VIIe, VIIf, VIIg, VIIh, VIIj, VIIm(i), VIIm(ii), VIIm(iii), VIIm(iv), VIIm(v), VIIm(vi), VIIm(vii), VIIm(viii), VIIm(ix), VIIm(x), VIIn(i), VIIn(ii), VIIn(iii), VIIn(iv), VIIn(v), VIIn(vi), VIIn(vii), VIIn(viii), VIIn(ix) VIIn(x), VIIo(i), VIIo(ii), VIIo(iii), VIIo(iv), VIIo(v), VIIo(vi), VIIo(vii), VIIo(viii), VIIo(ix) and VIIo(x), wherein the oxygen heteroatom from the hydroxyl functional group at position C-32 in any one of these FKBP immunophilins is represented by O* or T* in formula I, I', Ia, Ia', II, II', IIIa(i), IIIa(ii), IIIb(i), IIIb(ii), Va, Vb, Va', Vb', VIa, VIb, VIa', VIb', VIa(i), VIa(ii), VIb(i), and VIb(ii).

In particularly preferred embodiments the Drug Unit in any one of formula I, I', Ia, Ia', II, II', IIIa(i), IIIa(ii), IIIb(i), IIIb(ii), Va, Vb, Va', Vb', VIa, VIb, VIa', VIb', VIa(i), VIa(ii), VIb(i), and VIb(ii) is from the FKBP immunophilin tacrolimus (FK-506), the structure for which is the following:

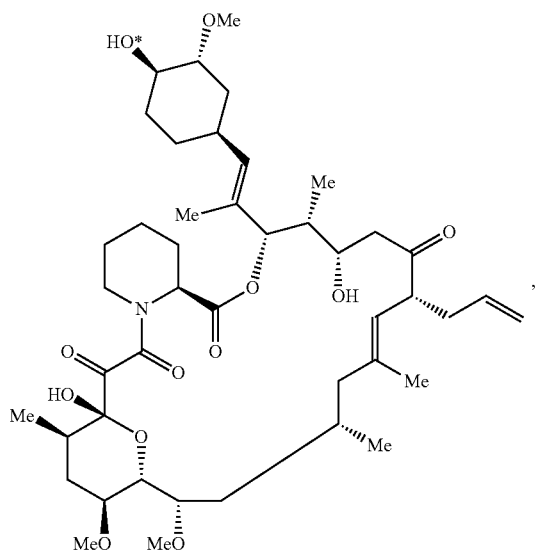

wherein the indicated O* is the O* or T* heteroatom that is incorporated into a methylene carbamate unit in any one of these formulae, or is from another macrolide inhibitor of calcineurin effector function having a hydroxyl functional group whose oxygen heteroatom is capable of incorporation into a MAC unit or is from another macrolide inhibitor of calcineurin effector function having a hydroxyl functional group whose oxygen heteroatom is capable of incorporation into a MAC unit. The hydroxyl functional group heteroatom incorporated into a MAC unit is indicated by O* for tacrolimus.

In another group of embodiments the immunophilin suitable for incorporation into a Drug Unit covalent attachment to a MAC unit binds to FKBP-12 as the free drug to inhibit effector function of mammalian target of rapamycin (mTOR) required for increased protein synthesis to support cancer cell proliferation and survival.

In one embodiment the FKBP immunophilin that is capable of incorporation into a MAC unit and as the free drug binds to FKBP-12 to inhibit effector function of mTOR has the general structure of formula VIIaa (VIIaa)

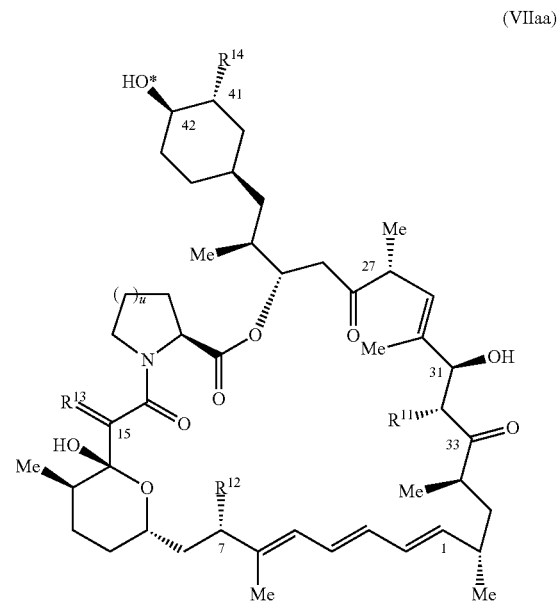

wherein u is 1 or 2 to define a prolinyl or pipecolic acid moiety; $R^{14}$ and $R^{12}$ independently are, —OH, an optionally substituted $C_1$-$C_6$ ether or an optionally substituted $C_1$-$C_6$ ester (preferably —OH or an optionally substituted $C_1$-$C_6$ ether; more preferably —OH or —OCH$_3$); $R^{11}$ is hydrogen, —OH, an optionally substituted $C_1$-$C_6$ ether or an optionally substituted $C_1$-$C_6$ ester (preferably hydrogen, —OH or an optionally substituted $C_1$-$C_6$ ether; more preferably hydrogen, —OH or —OCH$_3$); and $R^{13}$ is O (i.e., defines =O at C15) or CH$_2$ (i.e., defines =CH$_2$ at C15).

In other embodiments the moiety AA in formula VIIaa of

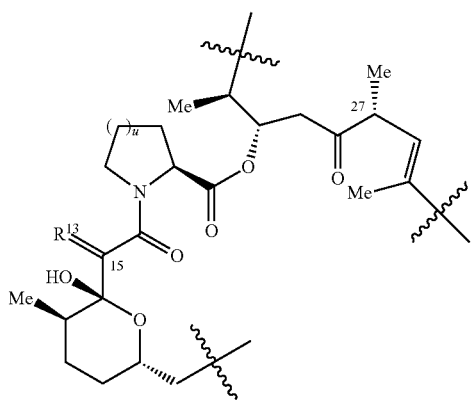

(AA)

is replaced with the moiety of formula BB

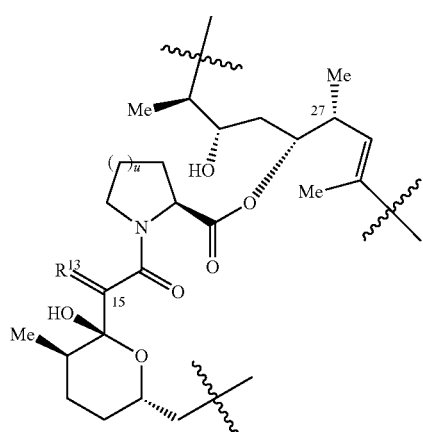

(BB)

to define FKBP immunophilins of formula VIIbb, wherein u, R, $R^{11}$, $R^{12}$ and $R^{13}$ are as defined for formula VIIaa. In preferred embodiments of formula VIIaa, u is 2; R and $R^{12}$ independently are, —OH or an optionally substituted $C_1$-$C_6$ ether (more preferably —OH or —OCH$_3$); $R^{11}$ is hydrogen, —OH or an optionally substituted $C_1$-$C_6$ ether (more preferably hydrogen, —OH or —OCH$_3$); and $R^{13}$ is O (i.e., defines =O at C-15) or CH$_2$ (i.e., defines =CH$_2$ at C-15) (more preferably $R^{13}$ is O).

In other embodiments the moiety AA is replaced by the moiety of formula CC

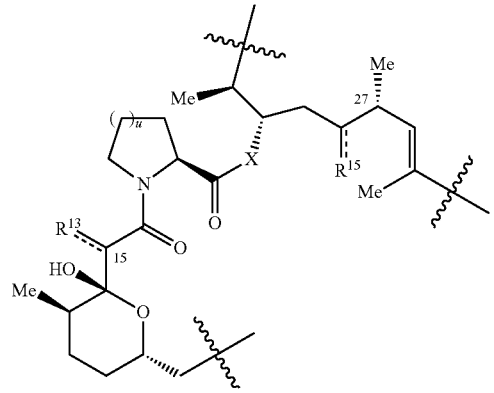

(CC)

to define FKBP immunophilins of formula VIIcc, wherein u is 1 or 2; X is O or —OCH$_2$CH$_2$S—; $R^{13}$ is O, NOR$^{13'}$ (i.e., defines an oxime at C15) or NHNHR$^{13'}$ (i.e., defines a hydrazone at C15), wherein $R^{13'}$ is independently selected from the group consisting of hydrogen and optionally substituted $C_1$-$C_4$ alkyl; $R^{13}$ is $R^{13A}$, $R^{13B}$ (i.e., C-15 is bonded to $R^{13A}$ and $R^{13B}$), wherein $R^{13A}$ in the α-configuration is hydrogen and $R^{13B}$ in the β-configuration is —OH or $R^{13A}$ in the α-configuration is —OH and $R^{13B}$ in the β-configuration is hydrogen; $R^{15}$ is O or $R^{15}$ is $R^{15A}$, $R^{15B}$ (i.e., C-15 is bonded to $R^{15A}$ and $R^{15B}$), wherein $R^{15A}$ in the α-configuration is hydrogen and $R^{15B}$ in the β-configuration is —OH or $R^{15A}$ in the α-configuration is —OH and $R^{15B}$ in the β-configuration is hydrogen.

In other embodiments the moiety AA' in formula VIIaa, VIIbb or VIIcc of

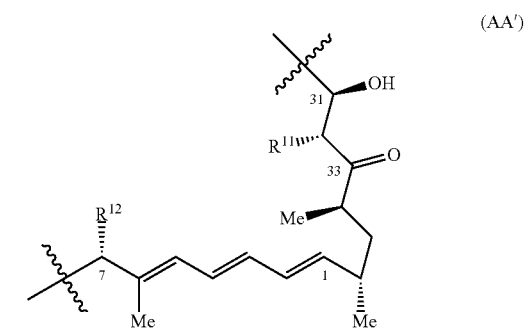

(AA')

is replaced by the moiety of formula DD

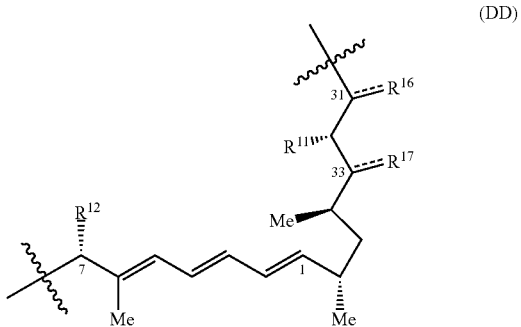

(DD)

to defined FKBP immunophilins of formula VIIdd(i), VIIdd (ii) and VIIdd(iii), respectively, wherein $R^{11}$ and $R^{12}$ are as defined in formula VIIaa, $R^{16}$ is O (i.e., to define =O at C-31) or $R^{16}$ is $R^{16A}$, $R^{16B}$ (i.e., C-31 is bonded to $R^{16A}$ and $R^{16B}$), wherein $R^{16A}$ in the α-configuration is hydrogen and $R^{16B}$ in the β-configuration is —OH or $R^{16A}$ in the α-configuration is —OH and $R^{16B}$ in the β-configuration is hydrogen; $R^{17}$ is O (i.e., to define =O at C-33) or $R^{17}$ is $R^{17A}$, $R^{17B}$ (i.e., C-33 is bonded to $R^{17A}$ and $R^{17B}$), wherein $R^{17A}$ in the α-configuration is hydrogen and $R^{17B}$ in the β-configuration is —OH, an optionally substituted $C_1$-$C_6$ ether (preferably –$OR^{17B'}$) or an optionally substituted O-linked carbamate (preferably —O(C=O)NHR$^{17B'}$) or $R^{17A}$ in the α-configuration is —OH, an optionally substituted $C_1$-$C_6$ ether (preferably —$OR^{17A'}$) or an optionally substituted O-linked carbamate (preferably —O(C=O)NHR$^{17B'}$) and $R^{17B}$ in the β-configuration is hydrogen, wherein $R^{17A'}$ and $R^{17B'}$ are independently hydrogen or $C_1$-$C_4$ alkyl (preferably hydrogen, methyl or ethyl), or $R^{16}$ and $R^{17}$ are N (to define =N at C-31 and C-32) and together with the C-32 and C-32 carbon to which they are attached define a pyrazole heterocyclo; and the remaining variable groups are as defined in their corresponding parent structure.

In other embodiments the moiety AA' in formula VIIaa, VIIbb or VIIcc is replaced by the moiety of formula EE, FF or GG

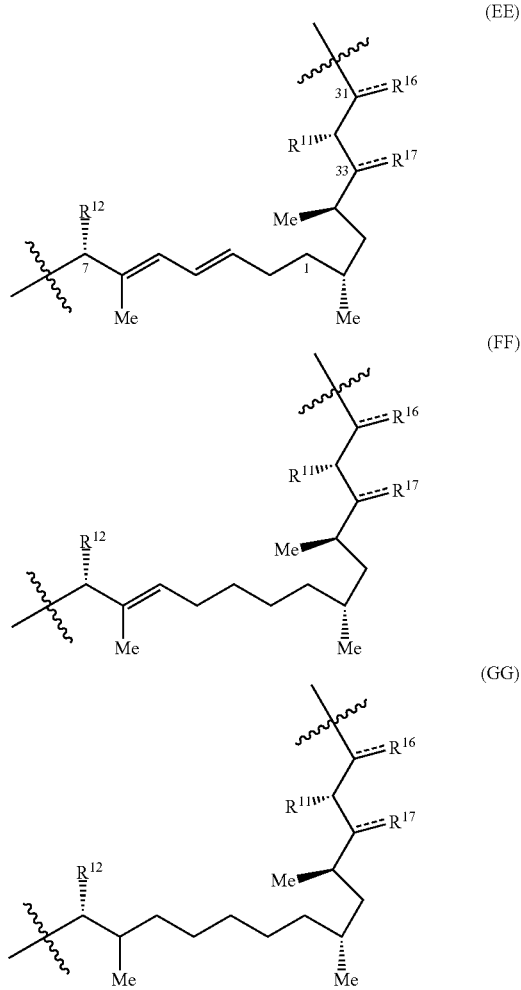

to define from formula EE, FKBP immunophilins of formula VIIee(i), VIIee(ii) and VIIee(iii), respectively, from formula FF, FKBP immunophilins of formula VIIff(i), VIIff(ii) and VIIff(iii), respectively or from formula GG, FKBP immunophilins of formula VIIff(i), VIIff(ii) and VIIff(iii), wherein $R^{11}$ and $R^{12}$ are as defined in formula VIIaa; $R^{16}$ and $R^{17}$ are as defined in formula DD and the remaining variable groups are as defined by their respective parent structure.

In other embodiments the moiety AA' in formula VIIaa, VIIbb or VIIcc is replaced by the moiety of formula HH or JJ

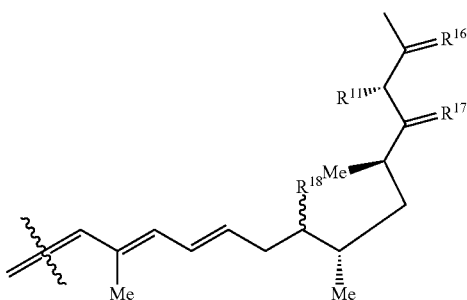

to define from formula HH, FKBP immunophilins of formula VIIhh(i), VIIhh (ii) and VIIhh(iii), respectively, or from formula JJ, FKBP immunophilins of formula VIIjj(i), VIIff(ii) and VIIff(iii), respectively.

In particularly preferred embodiments the Drug Unit in any one of formula I, I', Ia, Ia', II, II', IIIa(i), IIIa(ii), IIIb(i), IIIb(ii), Va, Vb, Va', Vb', VIa, VIb, VIa', VIb', VIa(i), VIa(ii), VIb(i), and VIb(ii) is from the FKBP immunophilin, everolimus, sirolimus (rapamycin) or other macrolide inhibitor of mammalian target of rapamycin (mTOR) effector function having a hydroxyl functional group whose oxygen heteroatom is capable of incorporation into a MAC unit. The hydroxyl functional group heteroatom incorporated into a MAC unit is indicated by O* for tacrolimus, everolimus and sirolimus in the following structures.

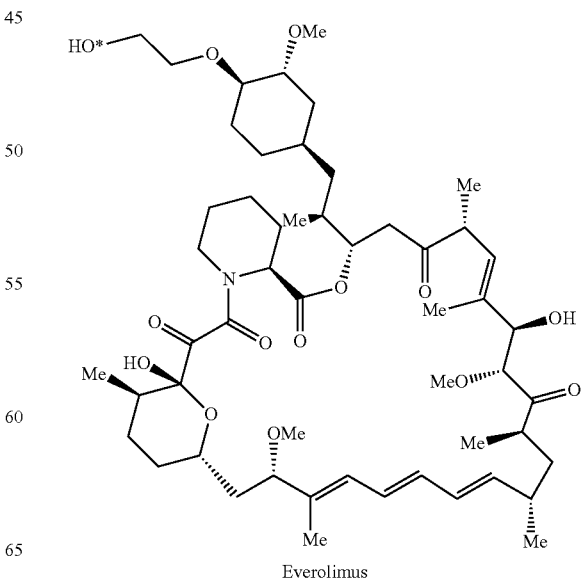

Everolimus

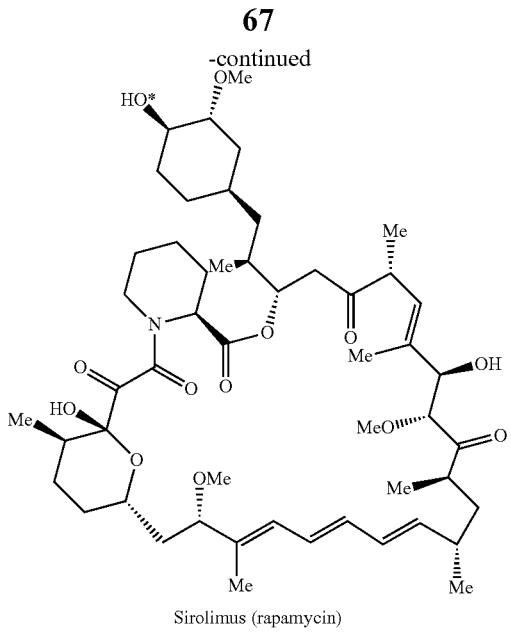

Sirolimus (rapamycin)

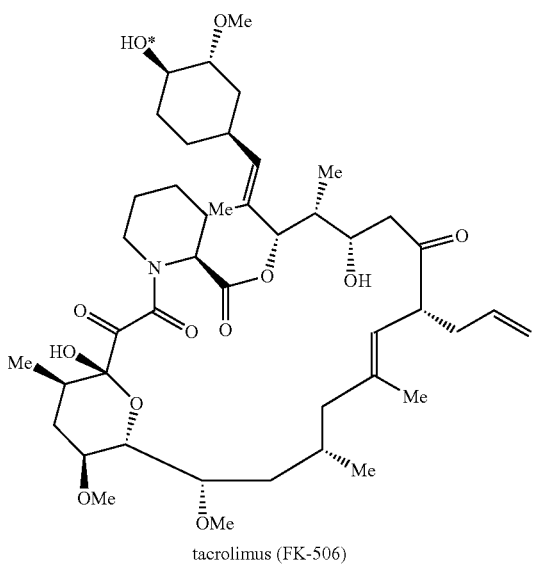

tacrolimus (FK-506)

In other embodiments a Drug Unit of an ADC or a Drug-Linker Compound represents a tetrahydroquinoline-containing drug that is incorporated into a methylene carbamate unit through its amine functional group (i.e., its aniline amino) In any one of the embodiments disclosed herein of formula I, Ia, II, IIIa(i), IIIa(ii), IIIb(i), IIIb(ii), Va, Vb, VIa, VIb, VIa(i), VIa(ii), VIb(i), and VIb(ii), T* represents the cyclic amine (i.e. the aniline) nitrogen corresponding to the tetrahydroquinoline-containing free drug and accordingly is encompassed by T* as an optionally substituted nitrogen. In those embodiments PARP inhibitors whose structures are comprised of a tetrahydroquinoline moiety having an aniline nitrogen capable of incorporation into a methylene carbamate unit are preferred. In one such embodiment the PARP inhibitor has the following structure:

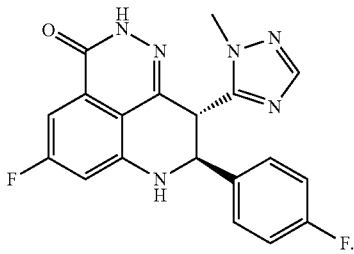 [SMILES: Cn1ncnc1[C@H]1c2n[nH]c(=O)c3cc(F)cc(c23)N[C@@H]1c1ccc(F)cc1]

In some aspects, a Drug Unit is an alcohol-containing drug wherein the hydroxyl functional group of the alcohol is incorporated into the methylene carbamate unit of a Self-immolative Assembly Unit via the oxygen atom of that functional group. In some such aspects, the alcohol of the drug is an aliphatic alcohol (e.g., a primary, secondary or tertiary alcohol). In other such aspects, the drug is an aromatic alcohol. In other embodiments, the drug comprises an amine (e.g., a primary or secondary aliphatic or aromatic amine) functional group that becomes incorporated into the methylene carbamate unit of a Self-immolative Assembly Unit via the optionally substituted nitrogen heteroatom of the amine. In other embodiments, the drug is thiol-containing drug and incorporation into the methylene carbamate unit of a Self-immolative Assembly Unit is via the sulfur atom of the sulfhydryl functional group of the thiol-containing drug. In other aspects, the drug comprises an amide functional group and incorporation into the methylene carbamate unit of a Self-immolative Assembly Unit is via an optionally substituted nitrogen heteroatom of the amide, (e.g., a carboxamide).

There are a number of different assays that can be used for determining whether a Ligand-Drug Conjugate exerts a cytostatic or cytotoxic effect on a cell line. In one example for determining whether a Ligand-Drug Conjugate exerts a cytostatic or cytotoxic effect on a cell line, a thymidine incorporation assay is used. For example, cells at a density of 5,000 cells/well of a 96-well plated is cultured for a 72-hour period and exposed to 0.5 µCi of $^3$H-thymidine during the final 8 hours of the 72-hour period, and the incorporation of $^3$H-thymidine into cells of the culture is measured in the presence and absence of Ligand-Drug Conjugate. The Ligand-Drug Conjugate has a cytostatic or cytotoxic effect on the cell line if the cells of the culture have reduced $^3$H-thymidine incorporation compared to cells of the same cell line cultured under the same conditions but not contacted with the Ligand-Drug Conjugate.

In another example, for determining whether a Ligand-Drug Conjugate exerts a cytostatic or cytotoxic effect on a cell line, cell viability is measured by determining in a cell the uptake of a dye such as neutral red, trypan blue, or ALAMAR™ blue (see, e.g., Page et al., 1993, Intl. J. of Oncology 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytotoxicity (Skehan et al., 1990, J. Nat'l Cancer Inst. 82:1107-12). Preferred Ligand-Drug Conjugates include those with an $IC_{50}$ value (defined as the mAb concentration that gives 50% cell kill) of less than 1000 ng/ml, preferably less than 500 ng/ml, more preferably less than 100 ng/ml, even most preferably less than 50 or even less than 10 ng/ml on the cell line.

General procedures for linking a drug to a linker moiety to provide a Linker Drug Compound and conjugating such compounds to a ligand moiety to provide a Linker Drug Conjugate are known in the art and can be used in combination with the methods described herein. See, for example, U.S. Pat. Nos. 8,163,888, 7,659,241, 7,498,298, U.S. Publication No. US20110256157 and International Application Nos. WO2011023883, and WO2005112919.

Stretcher Unit (Z) or (Z'):

A Stretcher Unit (Z) is a component of an LDC or a Drug-Linker Compound or other Intermediate that acts to connect the Ligand Unit to the Self-immolative Assembly Unit. In that regard a Stretcher Unit, prior to attachment to a Ligand Unit (i.e. a Stretcher Unit precursor, Z'), has a functional group that can form a bond with a functional group of a targeting ligand. In aspects when there is branching within the Linker Unit, attachment to the Self-immolative Assembly Unit is through a Branching Unit, B (optionally through an intervening Connector Unit, A). In aspects where it is desirable to provide more distance between the Self-immolative Assembly Unit and the Stretcher Unit, attachment of the Self-immolative Assembly Unit to B or Z, depending on the presence of absence of B, can be through a Connector Unit (A).

In some aspects, a Stretcher Unit precursor (Z') has an electrophilic group that is capable of interacting with a reactive nucleophillic group present on a Ligand Unit (e.g., an antibody) to provide a covalent bond between a Ligand Unit and the Stretcher Unit of a Linker Unit. Nucleophillic groups on an antibody having that capability include but are not limited to, sulfhydryl, hydroxyl and amino functional groups. The heteroatom of the nucleophillic group of an antibody is reactive to an electrophilic group on a Stretcher Unit precursor and provides a covalent bond between the Ligand Unit and Stretcher Unit of a Linker Unit or Drug-Linker moiety. Useful electrophilic groups for that purpose include, but are not limited to, maleimide, haloacetamide groups, and NHS esters. The electrophilic group provides a convenient site for antibody attachment to form a LDC or Ligand-Linker intermediate.

In another embodiment, a Stretcher Unit precursor has a reactive site which has a nucleophillic group that is reactive to an electrophilic group present on a Ligand Unit (e.g., an antibody). Useful electrophilic groups on an antibody for that purpose include, but are not limited to, aldehyde and ketone carbonyl groups. The heteroatom of a nucleophillic group of a Stretcher Unit precursor can react with an electrophilic group on an antibody and form a covalent bond to the antibody. Useful nucleophillic groups on a Stretcher Unit precursor for that purpose include, but are not limited to, hydrazide, hydroxylamine, amino, hydrazine, thiosemicarbazone, hydrazine carboxylate, and arylhydrazide. The electrophilic group on an antibody provides a convenient site for antibody attachment to form a LDC or Ligand-Linker intermediate.

In some embodiments, a sulfur atom of a Ligand Unit is bound to a succinimide ring system of a Stretcher Unit formed by reaction of a thiol functional group of a targeting ligand with a maleimide moiety of the corresponding Stretcher Unit precursor. In other embodiments a thiol functional group of a Ligand Unit reacts with an alpha haloacetamide moiety to provide a sulfur-bonded Stretcher Unit by nucleophillic displacement of its halogen substituent.

Representative Stretcher Units of those embodiments include those within the square brackets of Formulas Xa and Xb:

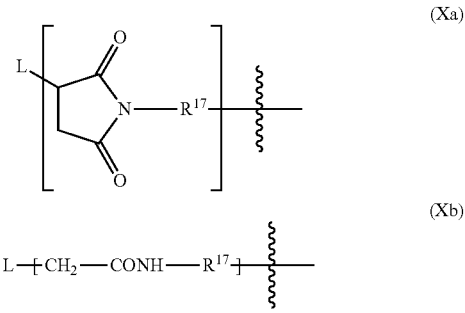

wherein the wavy line indicates attachment to the Branching Unit (B) or Connector Unit (A) if B is absent or Self-Immolative Assembly Unit (X), if A and B are absent and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$ alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$ alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, $C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In some aspects, the $R^{17}$ group of formula Xa is optionally substituted by a Basic Unit (BU) such as an aminoalkyl moiety, e.g. —$(CH_2)_xNH_2$, —$(CH_2)_xNHR^a$, and —$(CH_2)_xNR^a_2$, wherein x is an integer of from 1-4 and each $R^a$ is independently selected from the group consisting of $C_{1-6}$ alkyl and $C_{1-6}$ haloalkyl, or two $R^a$ groups are combined with the nitrogen to which they are attached to form an azetidinyl, pyrrolidinyl or piperidinyl group.

An illustrative Stretcher Unit is that of Formula Xa or Xb wherein $R^{17}$ is —$C_1$-$C_{10}$ alkylene-C(=O)—, —$C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, or —($C_3$-$C_8$ heterocyclo)-$C_1$-$C_{10}$ alkylene-C(=O)—.

Another illustrative Stretcher Unit is that of formula Xa wherein $R^{17}$ is —$C_2$-$C_5$ alkylene-C(=O)—, wherein the alkylene is optionally substituted by a Basic Unit (BU) such as an optionally substituted aminoalkyl, e.g., —(CH$_2$)$_x$NH$_2$, —(CH$_2$)$_x$NHR$^{op}$, and —(CH$_2$)$_x$N(R$^{op}$)$_2$, wherein x is an integer of from 1-4 and each R$^{op}$ is independently selected from the group consisting of C$_{1-6}$ alkyl and C$_{1-6}$ haloalkyl, or two R$^{op}$ groups are combined with the nitrogen to which they are attached to form an azetidinyl, pyrrolidinyl or piperidinyl group. During synthesis, the basic amino functional group of the Basic Unit can be protected by a protecting group.

Exemplary embodiments of Stretcher Units bonded to a Ligand Unit are as follows:

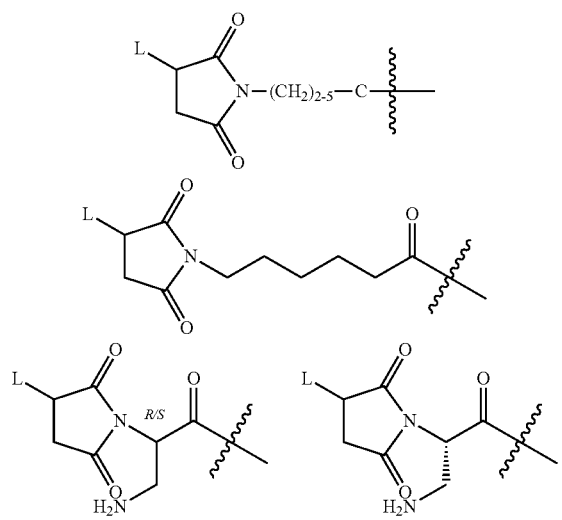

wherein the wavy line adjacent the carbonyl indicates attachment to B, A, or X of the Self Immolative Assembly Unit in formula II, IIa, IIb, II', IIa' or IIb',
or to B, A or W of formula III (i), IIa(i), IIb(i), III (i)', IIIa(i)' or IIIb(i)',
or to B, A or Y of formula III (ii), IIa(ii), IIb(ii), III (ii)', IIIa(ii)' or IIIb(ii)',
depending on the presence or absence of A and/or B.

It will be understood that a Ligand-substituted succinimide may exist in hydrolyzed form(s).

In some embodiments a Stretcher unit (Z) is comprised of an acid-amide moiety that when bonded to L is represented by the structure of formula Xd' or Xe':

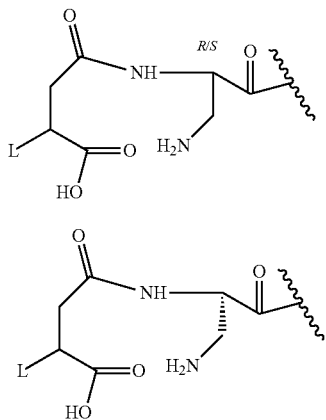

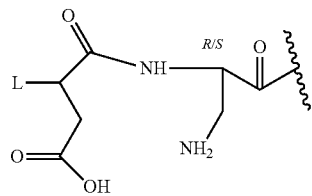

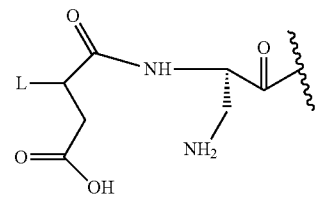

wherein the wavy line adjacent to the carbonyl indicates attachment to B, A, or X of the Self Immolative Assembly Unit in formula II, IIa, IIb, II', IIa' or IIb'.

In preferred embodiments a Stretcher unit (Z) is comprised of a succinimide moiety that when bonded to L is represented by the structure of

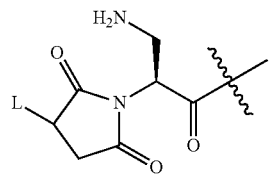

or is comprised of an acid-amide moiety that when bonded to L is represented by the structure of:

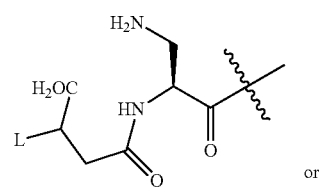

or

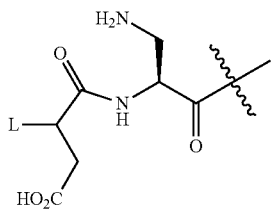

Illustrative Stretcher Units bonded to a Ligand Unit (L) and a Connector Unit (A) have the following structures:

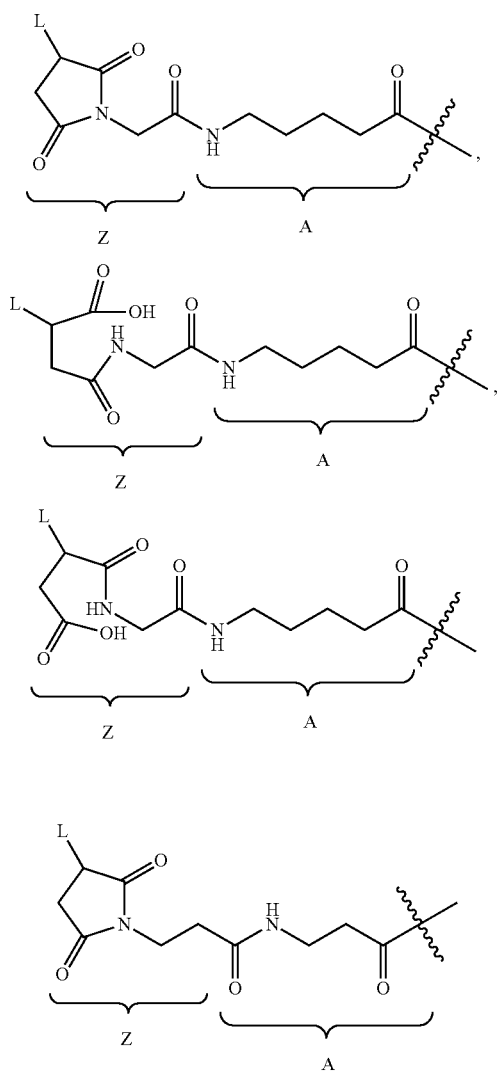

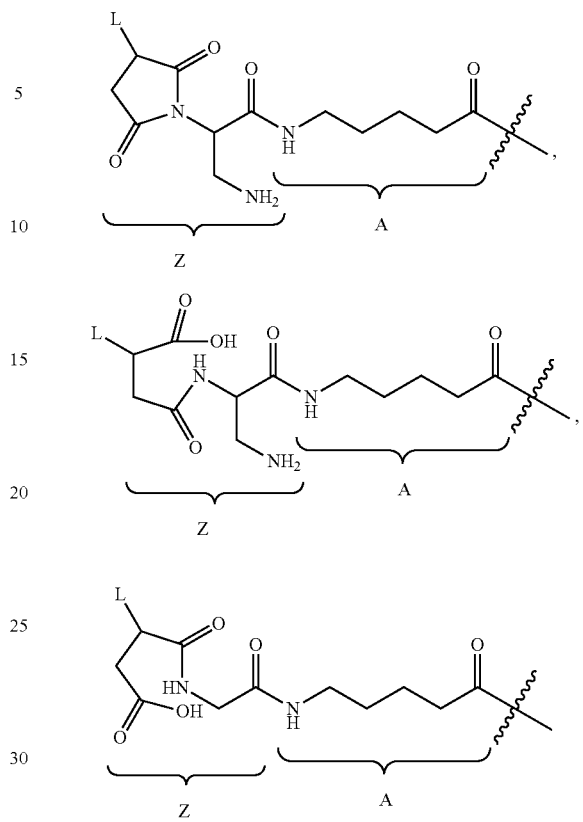

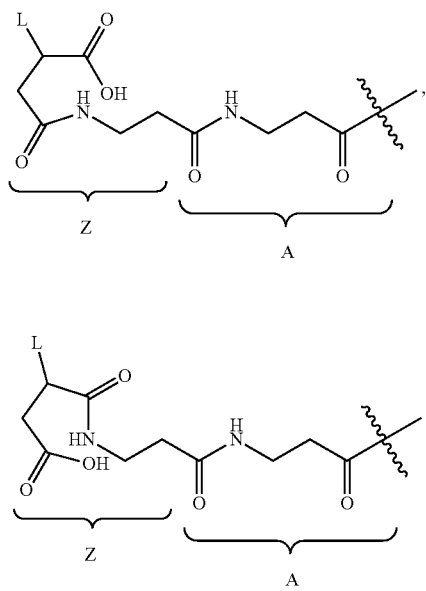

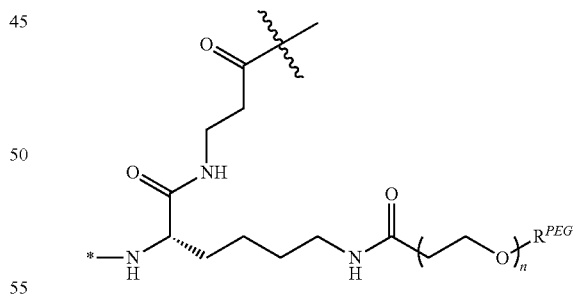

wherein the wavy line adjacent to the carbonyl indicates attachment to B, A, or X of the Self Immolative Assembly Unit in formula II, IIa, IIb, II', IIa' or IIb.

Other Stretcher Units bonded to a Ligand Unit (L) and a Connector Unit (A) have the structures above wherein A in the above Z-A structures is replaced by a Connector Unit having the structure of wherein n ranges from 8 to 24; $R^{PEG}$ is a PEG Unit capping group, preferably —$CH_3$ or —$CH_2CH_2CO_2H$, the asterisk (*) indicates covalent attachment to a Stretcher Unit corresponding in structure to formula Xa, and the wavy line indicates covalent attachment to X of a Self-immolative Assembly Unit.

Illustrative Stretcher Units prior to conjugation to the Ligand Unit (i.e., Stretcher Unit precursors) are comprised of a maleimide moiety and are represented by structures including that of formula XIa:

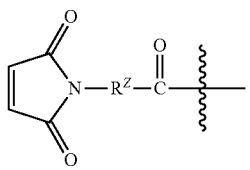
(XIa)

wherein the wavy line adjacent to the carbonyl indicates attachment to B, A, or X of the Self Immolative Assembly Unit in formula II, IIa, IIb, IIa' or IIb; and $R^Z$ is $-(CH_2)_{2-5}-$, optionally substituted with a Basic Unit such as an optionally substituted aminoalkyl, e.g., $-(CH_2)_xNH_2$, $-(CH_2)_xNHR^{op}$, and $-(CH_2)_xN(R^{op})_2$, wherein x is an integer of from 1-4 and each $R^{op}$ is independently selected from the group consisting of $C_{1-6}$ alkyl and $C_{1-6}$ haloalkyl, or two $R^{op}$ groups are combined with the nitrogen to which they are attached to form an azetidinyl, pyrrolidinyl or piperidinyl group.

In some preferred embodiments of formula XIa, a Stretcher Unit precursor (Z) is represented by one of the following structures:

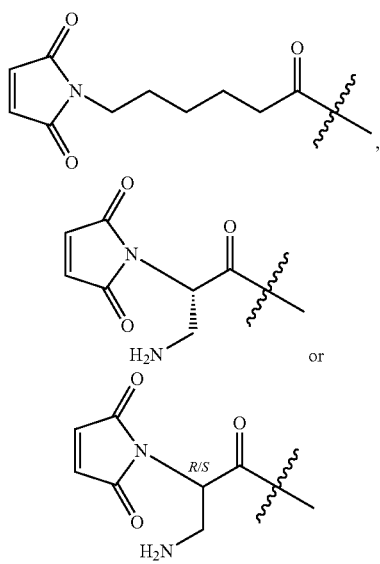

wherein the wavy line adjacent to the carbonyl indicates attachment to B, A, or X of the Self Immolative Assembly Unit in formula II, IIa, IIb, II', IIa' or IIb.

In more preferred embodiments the Stretcher unit precursor (Z') is comprised of a maleimide moiety and is represented by the structure of:

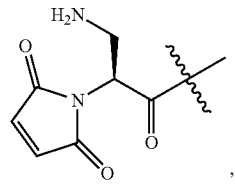 [SMILES: *C(=O)[C@H](CN)N1C(=O)C=CC1=O]

wherein the wavy line adjacent to the carbonyl indicates attachment to B, A, or X of the Self Immolative Assembly Unit in formula II, IIa, IIb, II', IIa' or IIb.

In Stretcher Units having a BU moiety, it will be understood that the amino functional group of that moiety may be protected by an amino protecting group during synthesis, e.g., an acid labile protecting group (e.g., BOC).

Illustrative Stretcher Unit precursors covalently attached to a Connector Unit have the following structures:

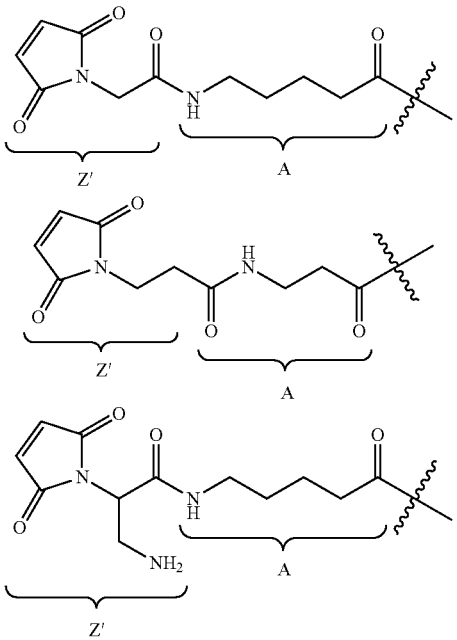

wherein the wavy line adjacent to the carbonyl indicates attachment to B, A, or X of the Self Immolative Assembly Unit in formula II, IIa, IIb, II', IIa' or IIb.

Other Stretcher Unit precursors bonded a Connector Unit (A) have the have the structures above wherein A in the above Z'-A structures is replaced by a Connector Unit having the structure of

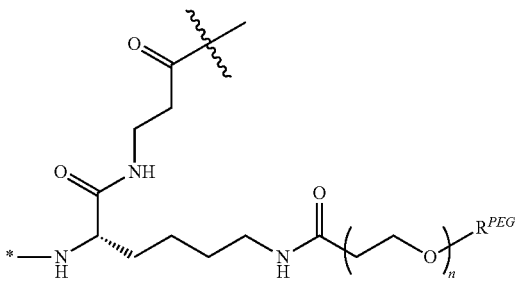

wherein n ranges from 8 to 24; $R^{PEG}$ is a PEG Unit capping group, preferably $-CH_3$ or $-CH_2CH_2CO_2H$, the asterisk (*) indicates covalent attachment to the Stretcher Unit precursor corresponding in structure to formula XIa and the wavy line indicates covalent attachment to X of a Self-immolative Assembly Unit.

In another embodiment, the Stretcher Unit is attached to the Ligand Unit via a disulfide bond between a sulfur atom of the Ligand unit and a sulfur atom of the Stretcher unit. A representative Stretcher Unit of this embodiment is depicted within the square brackets of Formula XIb:

(XIb)

wherein the wavy line indicates attachment to the Branching Unit (B), Connector Unit (A), if B is absent, or a self-immolative moiety (X) of a Self-Immolative Assembly Unit, if A and B are absent as defined herein and $R^{17}$ is —$C_1$-$C_{10}$ alkylene-, —$C_1$-$C_{10}$ heteroalkylene-, —$C_3$-$C_8$ carbocyclo-, —O—($C_1$-$C_8$-arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocycle-, —$C_1$-$C_{10}$alkylene-($C_3$-$C_8$ heterocyclo)-, —($C_3$-$C_8$ heterocyclo)-$C_1$-$C_{10}$ alkylene, —$C_1$-$C_{10}$ alkylene-C(=O)—, —$C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$-arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, —$C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In yet another embodiment, the reactive group of a Stretcher Unit precursor contains a reactive site that can form a bond with a primary or secondary amino group of a Ligand Unit. Examples of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher Units of this embodiment are depicted within the square brackets of Formulas XIIa, XIIb and XIIc:

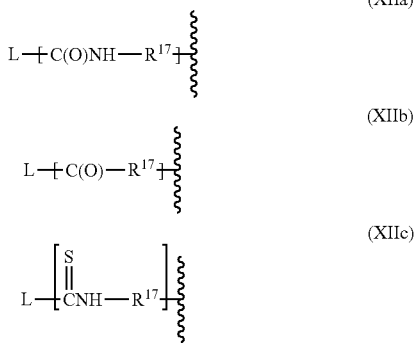

(XIIa)

(XIIb)

(XIIc)

wherein the wavy line indicates attachment to the Branching Unit (B), Connector Unit (A) or a self-immolative moiety (X) of a Self-Immolative Assembly Unit and $R^{17}$ is —$C_1$-$C_{10}$ alkylene-, —$C_1$-$C_{10}$ heteroalkylene-, —$C_3$-$C_8$ carbocyclo-, —O—($C_1$-$C_8$alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$ alkylene-, —$C_1$-$C_{10}$ alkylene-C(=O)—, —$C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$ alkylene-C(=O)—, —$C_1$-$C_{10}$ alkylene-NH—, $C_1$-$C_{10}$ heteroalkylene-NH—, —$C_3$-$C_8$ carbocyclo-NH—, —O—($C_1$-$C_8$alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, —$C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$carbocyclo)-S—, —($C_3$-$C_8$carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In yet another aspect, the reactive group of the Stretcher Unit precursor contains a reactive nucleophile that is capable of reacting with an electrophile present on, or introduced to, a Ligand. For example, a carbohydrate moiety on a targeting ligand can be mildly oxidized using a reagent such as sodium periodate and the resulting electrophilic functional group (—CHO) of the oxidized carbohydrate can be condensed with a Stretcher Unit precursor that contains a reactive nucleophile such as a hydrazide, an oxime, a primary or secondary amine, a hydrazine, a thiosemicarbazone, a hydrazine carboxylate, or an arylhydrazide such as those described by Kaneko, T. et al. (1991) Bioconjugate Chem. 2:133-41. Representative Stretcher Units of this embodiment are depicted within the square brackets of Formulas XIIIa, XIIIb, and XIIIc:

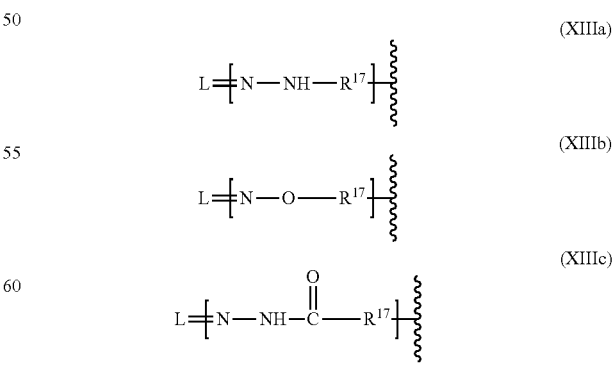

(XIIIa)

(XIIIb)

(XIIIc)

wherein the wavy line indicates attachment to the Branching Unit or Self-Immolative Assembly Unit, or Connector Unit as defined herein and $R^{17}$ is —$C_1$-$C_{10}$ alkylene-, $C_1$-$C_{10}$ heteroalkylene-, —$C_3$-$C_8$ carbocyclo-, —O—($C_1$-$C_8$ alkyl)-, -arylene-, —$C_1$-$C_{10}$ alkylene-arylene-, -arylene-$C_1$-$C_{10}$ alkylene-, —$C_1$-$C_{10}$ alkylene-($C_3$-$C_8$ carbocyclo)-, —($C_3$-$C_8$ carbocyclo)-$C_1$-$C_{10}$ alkylene-, —$C_3$-$C_8$ heterocyclo-, —$C_1$-$C_{10}$ alkylene-($C_3$-$C_8$ heterocyclo)-, —($C_3$-$C_8$ heterocyclo)-$C_1$-$C_{10}$alkylene-, —$C_1$-$C_{10}$ alkylene-C(=O)—, $C_1$-$C_{10}$ heteroalkylene-C(=O)—, —$C_3$-$C_8$ carbocyclo-C(=O)—, —O—($C_1$-$C_8$ alkyl)-C(=O)—, -arylene-C(=O)—, —$C_1$-$C_{10}$ alkylene-arylene-C(=O)—, -arylene-$C_1$-$C_{10}$ alkylene-C(=O)—, —$C_1$-$C_{10}$ alkylene-($C_3$-$C_8$ carbocyclo)-C(=O)—, —($C_3$-$C_8$ carbocyclo)-$C_1$-$C_{10}$ alkylene-C(=O)—, —$C_3$-$C_8$ heterocyclo-C(=O)—, —$C_1$-$C_{10}$ alkylene-($C_3$-$C_8$ heterocyclo)-C(=O)—, —($C_3$-$C_8$ heterocyclo)-$C_1$-$C_{10}$alkylene-C(=O)—, —$C_1$-$C_{10}$ alkylene-NH—, —$C_1$-$C_{10}$ heteroalkylene-NH—, —$C_3$-$C_8$ carbocyclo-NH—, —O—($C_1$-$C_8$ alkyl)-NH—, -arylene-NH—, —$C_1$-$C_{10}$ alkylene-arylene-NH—, -arylene-$C_1$-$C_{10}$ alkylene-NH—, —$C_1$-$C_{10}$ alkylene-($C_3$-$C_8$ carbocyclo)-NH—, —($C_3$-$C_8$ carbocyclo)-$C_1$-$C_{10}$ alkylene-NH—, —$C_3$-$C_8$ heterocyclo-NH—, —$C_1$-$C_{10}$ alkylene-($C_3$-$C_8$ heterocyclo)-NH—, —($C_3$-$C_8$ heterocyclo)-$C_1$-$C_{10}$ alkylene-NH—, —$C_1$-$C_{10}$ alkylene-S—, —$C_1$-$C_{10}$ heteroalkylene-S—, —$C_3$-$C_8$ carbocyclo-S—, —O—($C_1$-$C_8$ alkyl)-S—, -arylene-S—, —$C_1$-$C_{10}$ alkylene-arylene-S—, -arylene-$C_1$-$C_{10}$ alkylene-S—, —$C_1$-$C_{10}$ alkylene-($C_3$-$C_8$ carbocyclo)-S—, —($C_3$-$C_8$ carbocyclo)-$C_1$-$C_{10}$ alkylene-S—, —$C_3$-$C_8$ heterocyclo-S—, —$C_1$-$C_{10}$ alkylene-($C_3$-$C_8$ heterocyclo)-S—, or —($C_3$-$C_8$ heterocyclo)-$C_1$-$C_{10}$ alkylene-S—.

In some aspects of the prevent invention the Stretcher Unit has a mass of no more than about 1000 daltons, no more than about 500 daltons, no more than about 200 daltons, from about 30, 50 or 100 daltons to about 1000 daltons, from about 30, 50 or 100 daltons to about 500 daltons, or from about 30, 50 or 100 daltons to about 200 daltons.

Optional Branching Unit (B):

A Branching Unit (B) is included in Ligand-Drug Conjugates in instances where it is desirable to have multiple Self-immolative Assembly Units in a Linker Unit, and thus have multiple Drug Units for each drug-linker moiety attached to the Ligand Unit of an LDC and, ultimately, to increase the number of Drug Units in an LDC beyond the number of attachment sites in its Ligand Unit. A Branching Unit provides a covalent bond between B and a Stretcher Unit (Z) or precursor thereof (Z') and two, three or four Self-immolative (SI) Assembly Units, optionally each via an independently selected intervening Connector Unit, A. The skilled artisan will appreciate that a Branching Unit is designed in such a way to allow the required branching within the Linker Unit. For example, in order to act as a Branching Unit for two Drug Units (i.e., t is 2), the Branching Unit has at least a first, second and third attachment site within the conjugate (i.e., a first attachment site to Z, and a second and third attachment site for attachment to each A or X, depending on the presence or absence of each A. In other words, the Branching Unit must be at least trifunctional.

Contemplated in the present invention are those LDCs and Drug-Linker Compounds wherein the subscript t is 3 or 4. In such aspects, the Branching Unit will have four or five sites of covalent attachment within the conjugate. In some aspects, the Branching Unit is comprised of one or more (e.g., 1 to 10, preferably from 1 to 5, e.g., 1, 2, 3, 4, or 5) natural or non-natural amino acid, amino alcohol, amino aldehyde, or polyamine residues or combinations thereof that collectively provide the required functionality for branching. In some embodiment the Branching Unit is comprised of a tri-functional residue and may have flanking residues that are bi-functional to provide the first and second attachment sites. In embodiments having branching to accommodate 3 or 4 Drug Units in a single Linker Unit, the Branching Units is typically comprised of 2 or 3 tri-functional branching residues, and may be further comprised of flanking and/or intervening residues that are bi-functional.

It will be appreciated that when referring to natural or non-natural amino acids, amino alcohols, amino aldehydes, or polyamines as present in a Ligand Drug Conjugate or Intermediates thereof such as a Drug Linker Compound (whether it be part of a Branching Unit or other component of a LDC or Drug-Linker Intermediate thereof), the amino acid, amino alcohol, amino aldehyde, or polyamines will exist in residual form. For example, in embodiments, wherein the Branching Unit is two amino acids, the two amino acids will exist as residues with a peptide bond between them.

In embodiments where the Branching Unit is comprised of an amino alcohol, the amino alcohol will exist as a residue where, for example, its amino group is bonded to another residue of the Branching Unit or another component of the LDC or Drug-Linker Intermediate thereof through a carbonyl-containing functional group of that other residue/component while its hydroxyl group is bonded as an ether to, or is bonded through a carbonyl-containing functional group, of yet another residue of the Branching Unit or another component of the LDC or Drug-Linker Intermediate thereof.

In embodiments where the Branching Unit is comprised of an amino aldehyde, the amino aldehyde will exist as a residue where, for example, its amino group is bonded to another residue of the Branching Unit or another component of the LDC or Intermediate thereof through a carbonyl-containing functional group of that other residue/component while its aldehyde functional group is converted to an imino functional group or through its subsequent reduction to provide a nitrogen-carbon bond when bonded to an amino group of yet another residue of the Branching Unit or another component of the Conjugate. An amino aldehyde may be derived from a natural or unnatural amino acid by partial reduction of its carboxylic acid functional group to an aldehyde (i.e., —CHO) functional group.

To have a third functional group to serve as a tri-functional branching residue in a Branching Unit, an amino acid or other amine-containing acid residue within Branching Unit can have or can be substituted with a functionalized side chain to provide the requisite three points of attachment required for such a branching residue. For example, serine has three functional groups, i.e., acid, amino and hydroxyl functional groups and may be viewed as a combined amino acid and amino alcohol residue for purposes of acting as a Branching Unit. Tyrosine also contains a hydroxyl group, in this instance in its phenolic side chain, and may also be view similarly to serine for purposes of its incorporation as a trifunctional branching residue into a Branching Unit.

In another example, when the trifunctional branching residue of a Branching Unit is cysteine, its amino and carboxylic acid group will exist in residual form in a manner previously discussed for amino acids or amine-containing acids to provide two of the three requisite points of attachment for a branching residue while its thiol group will exist in residual form when bonded to a —X-D or -A-X-D moiety of a Linker Unit as a disulfide or in a sulfur-carbon bond as, for example, when the cysteine thiol functional group reacts with a maleimide-containing moiety of a Connector Unit precursor. In some instances, the residual thiol group is in its oxidized form (i.e., —S(=O)— or —S(=O)$_2$—) when bonded to another residue of the Branching Unit or to another component of the Linker Unit. In yet another example, the alpha amino and carboxylic acid group of a lysine will exist in residual form to provide two of the three requisite points of attachment required of a branching residue of a Branching Unit while it epsilon amino group in its residual form provides the third point of attachment. Histidine may also be viewed as an amino acid with two amino groups, where the second amino group is the NH of the imidazole-containing side chain.

In another example, when the trifunctional branching residue of a Branching Unit is aspartic or glutamic acid, the alpha amino and C-terminal carboxylic acid groups of the amino acid in their residual forms provide two of the three requisite points of attachment required for a branching residue of a Branching Unit, while its beta or gamma carboxylic acid group in its residual form provides the third point of attachment. In those instances when a naturally occurring amino acid is a residue of a Branching Unit, but does not naturally contain a functionalized amino acid side chain, yet is required to be a trifunctional branching residue within the Branching Unit, it is understood that the amino acid structure is modified to have an additional functional group besides its amino and carboxylic acid functional groups when in residual form in order to provide the requisite third point of attachment. For example, an amino acid having an aliphatic side chain may be substituted at a carbon of that side chain with a hydroxyl, amino, aldehyde, thiol, carboxylic acid group or other functional group or other moiety (e.g., an aryl or arylalkyl) substituted with any one of these functional groups to provide an unnatural amino acid having the requisite three points of attachment. Such unnatural amino acids are incorporated into a Branching Unit as described above for amino acids and residual forms of the introduced functional groups.

Similarly, when an amino aldehyde or amino alcohol is incorporated into a Branching Unit as a trifunctional branching residue that amino aldehyde or amino alcohol will have a third functional group to provide, along with its amino and aldehyde functional groups, the requisite three points of attachment. In those instances, an amino aldehyde or amino alcohol may correspond in structure to a natural amino acid that has a functionalized side chain or an unnatural amino acid having an functional group that was introduced into the side chain of a natural amino acid as described above in which a carboxylic acid of the natural or unnatural amino acid is reduced to a hydroxyl or aldehyde functional group.

An amino acid incorporated into a Branching Unit as a trifunctional branching residue can be an alpha, beta, or gamma amino acid or other amine-containing acid compound and can be in its D or L isomer if it contains a chiral carbon to which is bonded a natural or unnatural amino acid side chain. When the Branching Unit is made up of more than one natural or non-natural amino acid, amino alcohol, amino aldehyde, or polyamine residues, the amino acids, amino alcohols, amino aldehydes, polyamine residues or combinations thereof, wherein at least one of those residues is a trifunctional branching residue, these residues are linked together via covalent bonds to form the Branching Unit.

The amino acid, amino alcohol, or amino aldehyde can be non-natural and can be modified to have a functionalized side chain for attachment to components of the Conjugates or Intermediate Compounds (as described above for a branching residue of a Branching Unit), as the case may be. Exemplary functionalized amino acids, amino alcohols, or amino aldehydes include, for example, azido or alkyne functionalized amino acids, amino alcohols, or amino aldehydes (e.g., amino acid, amino alcohol, or amino aldehyde modified to have an azide group or alkyne group for attachment using click chemistry). Methods for the independent activation and reaction of the functional groups present on an amino acid—e.g., the amine portion, the carboxylic acid portion and the side chain portion (whether, for example, an amino moiety, a hydroxyl group, another carboxylic acid, thiol, azide or alkyne) are well known in the art.

A Branching Unit can comprise 1 or more (typically from 1 to 5 or 1 to 4 or 1 to 3 or 1 or 2) amino acids, optionally substituted $C_{1-20}$ heteroalkylenes (preferably optionally substituted $C_{1-12}$ heteroalkylene), optionally substituted $C_{3-8}$ heterocyclos, optionally substituted $C_{6-14}$ arylenes, optionally substituted $C_3$-$C_8$ carbocyclos, or combinations thereof. In some embodiments, the Branching Unit comprises no more than 2 or no more than one optionally substituted $C_{1-20}$ heteroalkylene, optionally substituted $C_3$-8 heterocyclo, optionally substituted $C_{6-14}$ arylene, or optionally substituted $C_3$-$C_8$ carbocyclo. Optional substituents include (=O), —X, —R, —OR, —SR, —NR$_2$, —NR$_3$, =NR, —CX$_3$, —CN, —OCN, —SCN, —N=C=O, —NCS, —NO, —NO$_2$, =N$_2$, —N$_3$, —NRC(=O)R, —C(=O)R, —C(=O)NR$_2$, —SO$_3^-$, —SO$_3$H, —S(=O)$_2$R, —OS(=O)$_2$OR, —S(=O)$_2$NR, —S(=O)R, —OP(=O)(OR)$_2$, —P(=O)(OR)$_2$, —PO$_{=3}$, —PO$_3$H$_2$, —AsO$_2$H$_2$, —C(=O)R, —C(=O)X, —C(=S)R, —CO$_2$R, —CO$_2^-$, —C(=S)OR, —C(=O)SR, —C(=S)SR, —C(=O)NR$_2$, —C(=S)NR$_2$, or —C(=NR)NR$_2$, where each X is independently a halogen: —F, —Cl, —Br, or —I; and each R is independently hydrogen, or —C$_1$ C$_{20}$ alkyl, —C$_6$ C$_{20}$ aryl, or —C$_3$ C$_{14}$ heterocycle, optionally substituted, or a protecting group or a prodrug moiety. Preferred optional substituents are (=O), —X, —R, —OR, —SR, and —NR$_2$. It will be understood that such moities acting a branching residue will be substituted with functionality to provide the requisite sites of attachment.

A Branching Unit or branching residue of a Branching Unit can be a straight chain or branched chain and can be represented by Formula A:

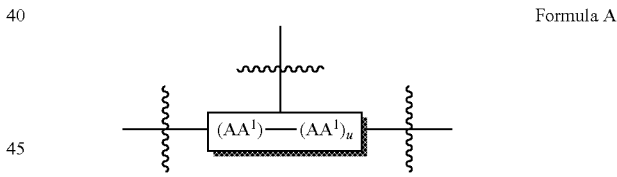

Formula A wherein

AA$^1$ is a subunit of a Branching Unit independently selected from an amino acid, optionally substituted $C_{1-20}$ heteroalkylene (preferably optionally substituted $C_{1-12}$ heteroalkylene), optionally substituted $C_{3-8}$ heterocyclo, optionally substituted $C_{6-14}$ arylene, or optionally substituted $C_3$-$C_8$ carbocyclo;

and the subscript u is independently selected from 0 to 4; and the wavy line indicates covalent attachment sites within the Ligand-Drug Conjugate or a Drug-Linker Intermediate thereof. The optionally substituted heteroalkylene, heterocycle, arylene or carbocyclo will have functional groups for attachments between the subunits of the Branching Unit and within a Ligand-Drug Conjugate or Drug-Linker Intermediate thereof having that Branching Unit.

In some embodiments at least one instance of AA' is an amino acid. The subscript u can be 0, 1, 2, 3, or 4. In some embodiments, AA' is an amino acid and u is 0. In some embodiments, a Branching Unit is comprised of no more than 2 optionally substituted $C_{1-20}$ heteroalkylenes, optionally substituted $C_{3-8}$ heterocyclos, optionally substituted $C_{6-14}$ arylenes, or optionally substituted $C_3$-$C_8$ carbocyclos. In some aspects, wherein the Branching Unit has formula A, the Branching Unit comprises no more than 1 optionally substituted $C_{1-20}$ heteroalkylene, optionally substituted $C_{3-8}$ heterocyclo, optionally substituted $C_{6-14}$ arylene, or optionally substituted $C_3$-$C_8$ carbocyclo.

A Branching Unit or an amino acid subunit thereof can be an alpha, beta, or gamma amino acid and can be natural or non-natural. The amino acid can be a D or L isomer. Attachment within the Branching Unit or with the other components of the LDC or Drug-Linker Intermediate thereof can be, for example, via amino, carboxyl, or other functional groups. Methods for the independent activation and reaction of the functional groups are well known in the art.

A Branching Unit or an amino acid subunit thereof can be independently selected from the D or L isomer of a thiol-containing amino acid. The thiol-containing amino acid can be, for example, cysteine, homocysteine, or penicillamine.

A Branching or an amino acid subunit thereof can be independently selected from the group consisting of the L- or D-isomers of the following amino acids: Alanine (including β-alanine), arginine, aspartic acid, asparagine, cysteine, histidine, glycine, glutamic acid, glutamine phenylalanine, lysine, leucine, methionine, serine, tyrosine, threonine, tryptophan, proline, ornithine, penicillamine, B-alanine, aminoalkynoic acid, aminoalkanedioic acid, heterocyclo-carboxylic acid, citrulline, statine, diaminoalkanoic acid, and derivatives thereof.

Preferred amino acids include cysteine, homocysteine, penicillamine, ornithine, lysine, serine, threonine, glutamine, alanine, aspartic acid, glutamic acid, selenocysteine, proline, glycine, isoleucine, leucine, methionine, valine, and alanine.

In some embodiments wherein the Branching Unit is capable of connecting two Self-immolative Assembly Units to a Stretcher Unit (each optionally via an independently selected Connector Unit, A), the Branching Unit, once assembled, has the formula denoted below:

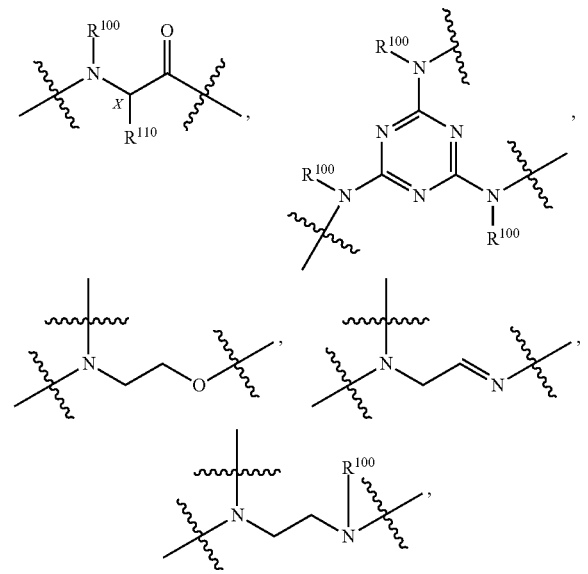

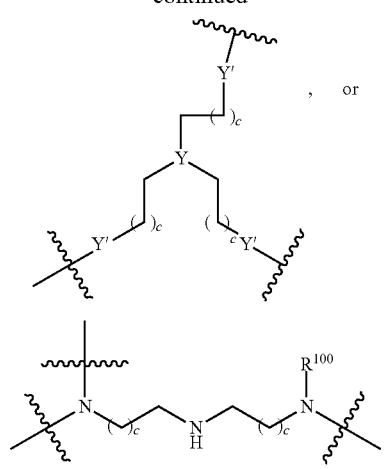

wherein the wavy line indicates the attachment sites to components of the Linker Unit, i.e., to the Stretcher Unit Z or its precursor Z' and to Self-immolative Assembly Unit(s) or the intervening Connector Unit(s), and wherein $R^{110}$ is

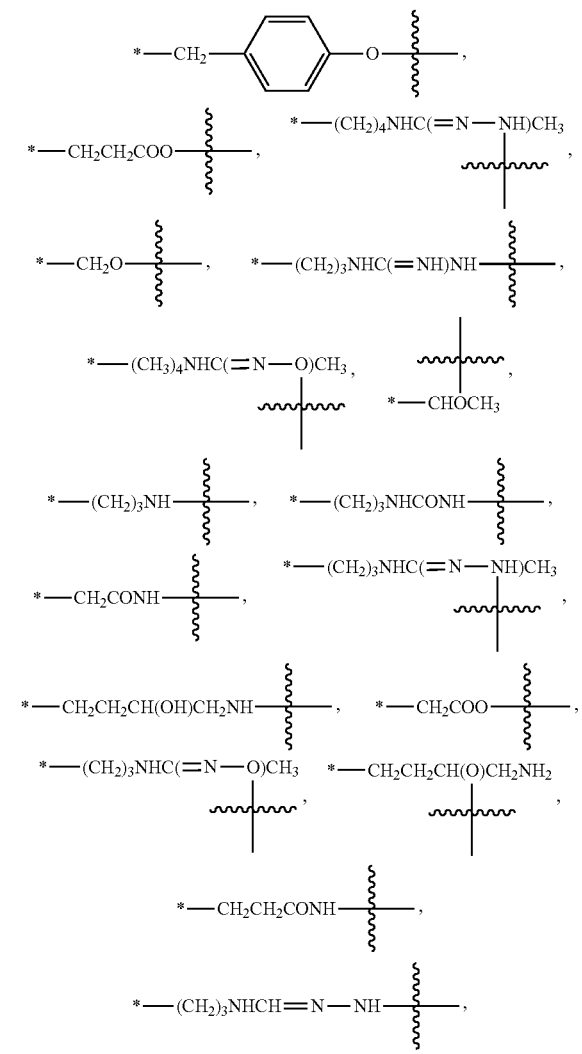

-continued

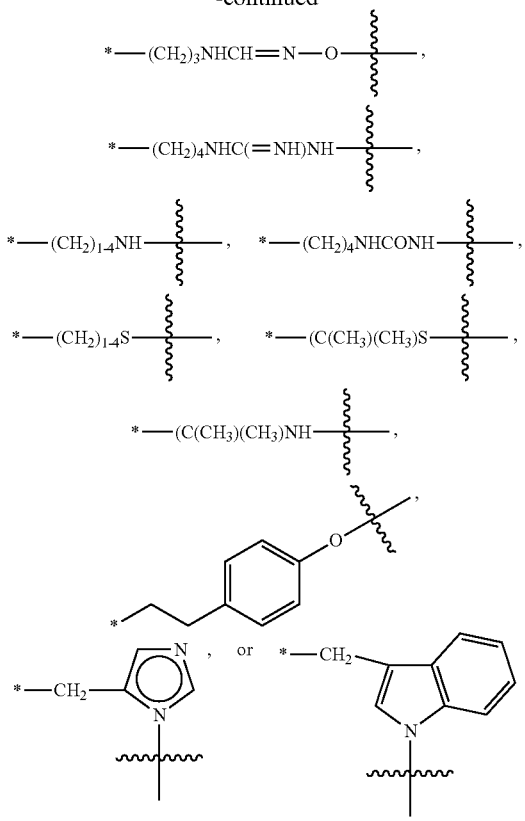

wherein the asterisk indicates attachment to the carbon labeled x and the wavy line indicates one of the attachment sites;
each $R^{100}$ is independently selected from hydrogen or —$C_1$-$C_3$ alkyl, preferably hydrogen or $CH_3$;
Y is independently selected from N or CH;
each Y' is independently selected from NH, O, or S; and
the subscript c is an integer independently selected from 1 to 10, preferably 1 to 3.

An exemplary Branching Unit or trifunctional branching residue in a Branching Unit is lysine as shown below wherein the wavy line and asterisks indicate covalent linkage within a the Linker Unit of a LDC or Drug-Linker intermediate thereof:

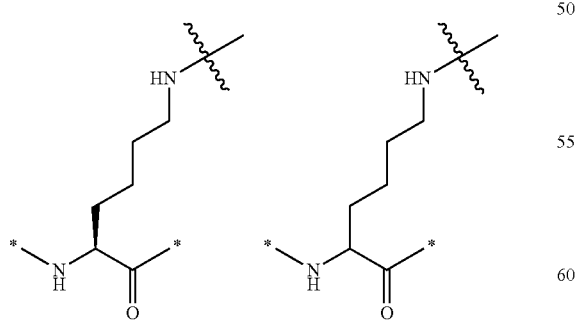

In some aspects of the prevent invention the Branching unit has a mass of no more than about 1000 daltons, no more than about 500 daltons, no more than about 200 daltons, from about 10, 50 or 100 daltons to about 1000 daltons, from about 10, 50 or 100 daltons to about 500 daltons, or from about 10, 50 or 100 daltons to about 200 daltons.

Connector Unit (A)

A Connector Unit, A, is included in a Ligand-Drug Conjugate or Drug-Linker Compound in instances where it is desirable to add additional distance between the Stretcher Unit (Z) or precursor thereof (Z') and a self-immolative moiety (X) of a Self-immolative Assembly Unit. In some aspects, the extra distance will aid with activation within X. Accordingly, the Connector Unit (A), when present, extends the framework of the Linker Unit. In that regard, a Connector Unit (A) is covalently bonded with the optional Branching Unit or Stretcher Unit (or its precursor) when B is absent at one terminus and is covalently bonded to the self-immolative moiety (X) of a Self-Immolative Assembly Unit at its other terminus. In one group of embodiments the self-immolative moiety (X) is comprised of a self-immolative Spacer Unit (Y) and Activation Unit (W) so that A is bonded to Y. In another group of embodiments the self-immolative moiety is comprised of a self-immolative Spacer Unit (Y) and Activation Unit (W) so that A is bonded to W.

The skilled artisan will appreciate that the Connector Unit can be any group that serves to provide for attachment of the Self-immolative Unit to the remainder of Linker Unit. The Connector Unit can be, for example, comprised of one or more (e.g., 1-10, preferably, 1, 2, 3, or 4) natural or non-natural amino acid, amino alcohol, amino aldehyde, diamino residues. In some aspects, the Connector Unit is a single natural or non-natural amino acid, amino alcohol, amino aldehyde, or diamino residue. An exemplary amino acid capable of acting as Connector units is β-alanine.

In some aspects, the Connector Unit has the formula denoted below:

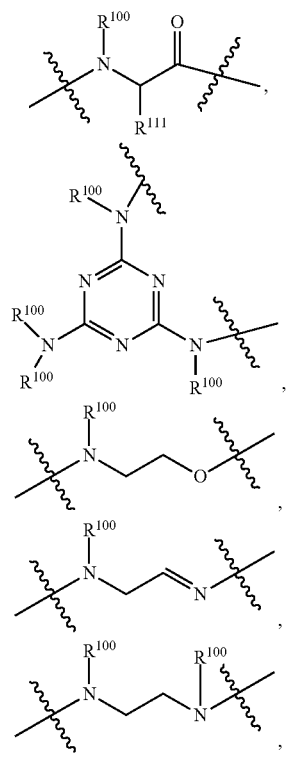

-continued

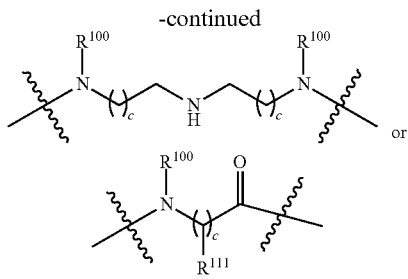

wherein the wavy lines indicate attachment of the Connector Unit within the Ligand Drug Conjugate or Drug-Linker Intermediate thereof;

wherein $R^{111}$ is independently selected from the group consisting of hydrogen, p-hydroxybenzyl, methyl, isopropyl, isobutyl, sec-butyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-,

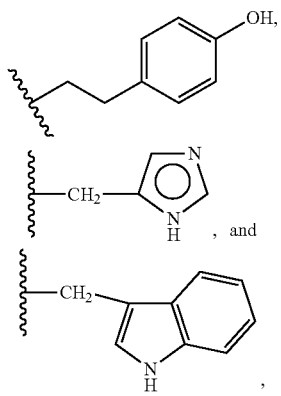, and wherein the wavy line indicates covalent attachment to the remainder of the Connector Unit;

each $R^{100}$ is independently selected from hydrogen or —$C_1$-$C_3$ alkyl, preferably hydrogen or $CH_3$; and c is independently selected integer ranging from 1 to 10, preferably 1 to 3.

A representative Connector Unit having a carbonyl group for attachment to the Activation Unit (W) or self-immolative Spacer Unit (Y) of a Self-immolative Assembly Unit's self-immolative moiety (X) is as follows:

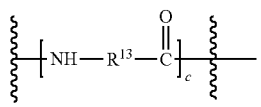

wherein in each instance $R^{13}$ is independently selected from the group consisting of —$C_1$-$C_6$ alkylene-, —$C_3$-$C_8$carbocyclo-, -arylene-, —$C_1$-$C_{10}$ heteroalkylene-, —$C_3$-$C_8$ heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, and —($C_3$-$C_8$ heterocyclo)-$C_1$-$C_{10}$ alkylene-, and the subscript c is an integer ranging from 1 to 4. In some embodiments $R^{13}$ is —$C_1$-$C_6$ alkylene and c is 1.

A representative Connector Unit having a carbonyl group for attachment to the to the Activation Unit (W) or Spacer Unit (Y) of a Self-immolative Assembly Unit's self-immolative moiety (X) is as follows:

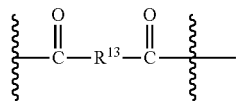

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-. In some embodiments $R^{13}$ is —$C_1$-$C_6$ alkylene.

A representative Connector Unit having a NH moiety that attaches to the Activation Unit (W) or Spacer Unit (Y) of a Self-immolative Assembly Unit's self-immolative moiety (X) is as follows:

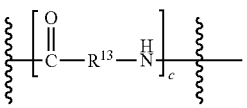

wherein in each instance, $R^{13}$ is independently selected from the group consisting of —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, and —($C_3$-$C_8$ heterocyclo)-$C_1$-$C_{10}$ alkylene-, and the subscript c is from 1 to 14. In some embodiments $R^{13}$ is —$C_1$-$C_6$ alkylene and the subscript c is 1.

A representative Connector Unit having a NH moiety that attaches to the Activation Unit (W) or Spacer Unit (Y) of a Self-immolative Assembly Unit's self-immolative moiety (X) is as follows:

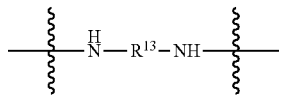

wherein $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene- or —C(=O)$C_1$-$C_6$ alkylene- or —$C_1$-$C_6$ alkylene-C(=O)—$C_1$-$C_6$ alkylene.

Selected embodiments of Connector Units include those having the following structure

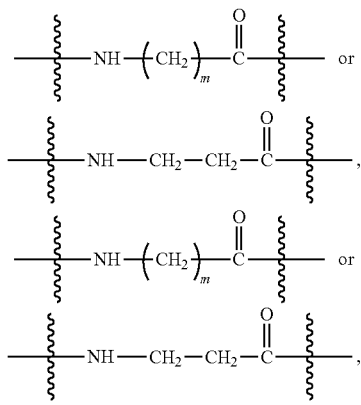

wherein the wavy line adjacent to the nitrogen indicates covalent attachment a Stretcher Unit (Z) (or its precursor Z'), either directly or indirectly via B, and the wavy line adjacent to the carbonyl indicates covalent attachment to Activation Unit (W) or Spacer Unit (Y) of a Self-immolative Assembly Unit's self-immolative moiety (X), or the wavy line adjacent to the carbonyl indicates covalent attachment to a Stretcher Unit (Z) (or its precursor Z'), either directly or indirectly via B, and the wavy line adjacent to the nitrogen indicates covalent attachment to Activation Unit (W) or Spacer Unit (Y) of a Self-immolative Assembly Unit's self-immolative moiety (X); and m is an integer ranging from 1 to 6, preferably 2 to 6, more preferably 2 to 4.

Self-Immolative Assembly Unit

The Self-Immolative Assembly Unit links the Drug Unit to the remainder of the Conjugate or it's Drug-Linker Intermediate. The main function of Self-immolative Assembly Unit is to conditionally release free drug at the site targeted by the Ligand Unit. In that vein, the Self-immolative Assembly Unit comprises an activateable self-immolative moiety (X) and a methylene carbamate linker. The activateable self-immolative moiety comprises an Activation Unit (W) and a self-immolative Spacer Unit (Y). The self-immolative Spacer Unit may be a single unit or can comprise two or more self-immolative subunits. Activation of W to induce self-immolation of Y is via cleavage at that Activation Unit and typically occurs at the bond between W and Y. Cleavage can be enzymatic (e.g., tumor associated protease or glycosidase such as glucuronidase) or via a disulfide reduction (e.g., disulfide cleavage (e.g., by glutathione-SH)). Upon cleavage, a self-immolative reaction sequence is initiated that leads to release of free drug. In one group of embodiments, the Self-immolative Assembly Unit can be attached to the remainder of a Ligand Drug Conjugate's Ligand Unit via the Activation Unit. In another group of embodiments, the self-immolative Assembly Unit can be attached to the remainder of a Ligand Drug Conjugate's Linker Unit via or the self-immolative Spacer Unit.

In certain embodiments a Self immolative Assembly Unit linked to a Drug Unit is represented by formula SIIa(i) or SIIa(ii):

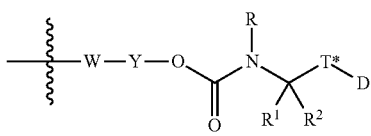

(SIIa(i))

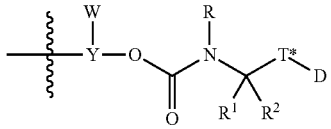

(SIIa(ii))

wherein
W is an Activation Unit;
Y is a self-immolative Spacer Unit;
D is a Drug Unit representing drug having a functional group prior to incorporation into the indicated methylene alkoxy carbamate unit;
T* is an optionally substituted heteroatom from said functional group that becomes incorporated into the indicated methylene carbamate unit;
R, $R^1$, and $R^2$ are as previously defined herein; and
the wavy line indicates the point of attachment to the remainder of the LDC or Drug-Linker Compound, wherein the Self-immolative Assembly Unit releases free drug following activation of the Activation Unit.

As indicated herein, activation of the Activation Unit is via cleavage of that unit, wherein cleavage is enzymatic (e.g., via tumor associated protease or glycosidase e.g., glucuronidase (e.g., beta-glucuronidase)) or via a disulfide reduction reaction (e.g., disulfide cleavage by glutathione-SH).

In some aspects of the prevent invention, a Self-immolative Assembly Unit has a mass of no more than about 5000 daltons, no more than about 4000 daltons, no more than about 3000 daltons, no more than about 2000 daltons, no more than about 1000 daltons, no more than about 800 daltons, or no more than about 500 daltons. In some aspects, a Self-immolative Assembly Unit has a mass of from about 100 daltons, or from about 200 daltons, or from about 300 daltons to about 5000 daltons, from about 100 daltons, or from about 200 daltons, or from about 300 daltons to about 4000 daltons, from about 100 daltons, or from about 200 daltons, or from about 300 daltons to about 3000 daltons, from about 100 daltons, or from about 200 daltons, or from about 300 daltons to about 2000 daltons, from about 100 daltons, or from about 200 daltons, or from about 300 daltons to about 1000 daltons, from about 100 daltons, or from about 200 daltons, or from about 300 daltons to about 800 daltons, or from about 100 daltons, or from about 200 daltons, or from about 300 daltons to about 500 daltons.

One of skill in the art will understand that the components of Drug-Linker Compounds can be linked in the same manner as Ligand-Drug Conjugates wherein in comparison to the corresponding LDC the Ligand Unit is absent and the Stretcher Unit (Z) when present is replaced by its corresponding Stretcher Unit precursor (Z').

Activation Unit (W)

W is an activation unit and may be referred to as a "trigger" or "activateable" trigger (i.e., capable of activation); that when activated initiates a self-immolative reaction sequence in a Spacer Unit (as a single unit or having 2 or more self-immolative subunits). In some aspects, the Activation Unit is an organic moiety attached via a cleavable bond to the self immolative Spacer Unit. Accordingly, in such embodiments, the structure and/or sequence of W is selected such that a cleavable bond is formed with the self-immolative Spacer Unit. In the various embodiments discussed herein, the nature of W can vary. For example, W can be designed such that the cleavable bond is cleaved by the action of enzymes present at the target site or via a reduction event in the case of a disulfide bond. Cleavable bonds include, for example, disulfide bonds, amide bonds, and glycosidic bonds.

In some embodiments, the Activation Unit will comprise one amino acid or one or more contiguous or non-contiguous sequences of amino acids (e.g., so that W has 1 to no more than 12 amino acids). The Activation Unit can comprise or consist of, for example, a monopeptide, a dipeptide, tripeptide, tetrapeptide, pentapeptide, hexapeptide, heptapeptide, octapeptide, nonapeptide, decapeptide, undecapeptide or dodecapeptide unit. In some aspects, in the presence of an enzyme (e.g., a tumor-associated protease), an amide linkage between the Activation Unit (W) and the self-immolative Spacer Unit (Y) is cleaved, which ultimately leads to release of free drug due to self-immolation of Y.

Each amino acid can be natural or unnatural and/or a D- or L-isomer provided of course that there is a cleavable bond formed that upon cleavage initiates self-immolation in Y. In some embodiments, the Activation Unit will comprise only natural amino acids. In some aspects, the Activation Unit will have from 1 to no more than 12 amino acids in contiguous sequence.

In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, selenocysteine, ornithine, penicillamine, β-alanine, aminoalkanoic acid, aminoalkynoic acid, aminoalkanedioic acid, aminobenzoic acid, amino-heterocyclo-alkanoic acid, heterocyclo-carboxylic acid, citrulline, statine, diaminoalkanoic acid, and derivatives thereof. In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, valine, cysteine, methionine, and selenocysteine. In some embodiments, each amino acid is independently selected from the group consisting of alanine, arginine, aspartic acid, asparagine, histidine, glycine, glutamic acid, glutamine, phenylalanine, lysine, leucine, serine, tyrosine, threonine, isoleucine, proline, tryptophan, and valine. In some embodiments, each amino acid is selected from the proteinogenic or the non-proteinogenic amino acids.

In another embodiment, each amino acid is independently selected from the group consisting of the following L-(natural) amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In another embodiment, each amino acid is independently selected from the group consisting of the following D-isomers of these natural amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In certain embodiments, the Activation Unit is comprised only of natural amino acids. In other embodiments, the Activation Unit is comprised only of non-natural amino acids. In some embodiments, the Activation Unit is comprised of a natural amino acid attached to a non-natural amino acid. In some embodiments, the Activation Unit is comprised of a natural amino acid attached to a D-isomer of a natural amino acid.

Exemplary Activation Units include dipeptides with -Val-Cit-, -Phe-Lys- or -Val-Ala.

Useful Activation Units can be designed and optimized in their selectivity for enzymatic cleavage by a particular enzyme, for example, a tumor-associated protease. In some embodiments, cleavage of a linkage (either through an intervening functional group or a bond) between the Activation Unit and the self-immolative Spacer Unit to initiate self-immolation in the self-immolative Spacer Unit is catalyzed by cathepsin B, C or D, or a plasmin protease.

In some embodiments, the Activation Unit will be represented by -(-AA-)$_{1-12}$-, or (-AA-AA-)$_{1-6}$ wherein AA is at each occurrence independently selected from natural or non-natural amino acids. In one aspect, AA is at each occurrence independently selected from natural amino acids.

In some embodiments, the Activation Unit has the formula denoted below in the square brackets, the wavy line adjacent to the carbonyl is attached to the self-immolative Spacer Unit and the other wavy line is attached to a Stretcher Unit (Z) (or its precursor Z'), directly or indirectly through an intervening Connector Unit (A), and/or Branching unit (B), and the subscript w is an integer ranging from 1 to 12:

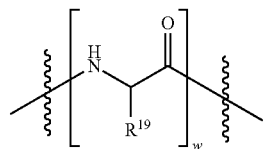

wherein $R^{19}$ is, in each instance, independently selected from the group consisting of hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

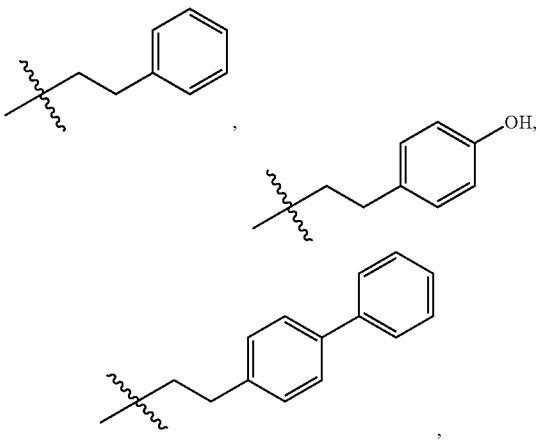

-continued

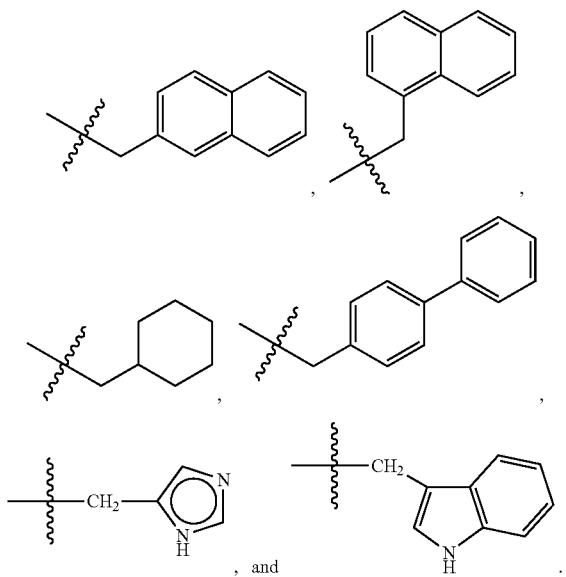

Illustrative Activation Units are represented by formulas (XV), (XVI) and (XVII)

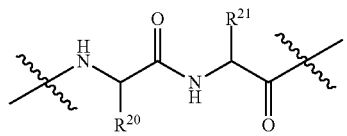
(XV)

wherein $R^{20}$ and $R^{21}$ are as follows:

| $R^{20}$ | $R^{21}$ |
| --- | --- |
| benzyl | $(CH_2)_4NH_2$; |
| methyl | $(CH_2)_4NH_2$; |
| isopropyl | $(CH_2)_4NH_2$; |
| isopropyl | $(CH_2)_3NHCONH_2$; |
| benzyl | $(CH_2)_3NHCONH_2$; |
| isobutyl | $(CH_2)_3NHCONH_2$; |
| sec-butyl | $(CH_2)_3NHCONH_2$; |
| 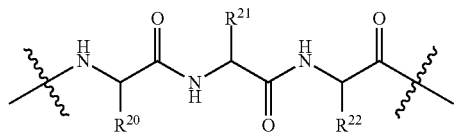 | $(CH_2)_3NHCONH_2$; |
| benzyl | methyl; and |
| benzyl | $(CH_2)_3NHC(=NH)NH_2$; |

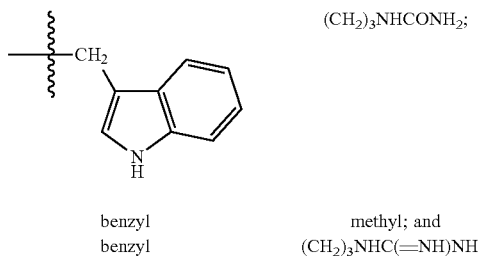
(XVI)

wherein $R^{20}$, $R^{21}$ and $R^{22}$ are as follows:

| $R^{20}$ | $R^{21}$ | $R^{22}$ |
| --- | --- | --- |
| benzyl | benzyl | $(CH_2)_4NH_2$; |
| isopropyl | benzyl | $(CH_2)_4NH_2$; and |
| H | benzyl | $(CH_2)_4NH_2$; |

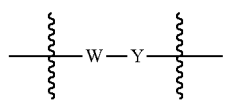
(XVII)

wherein $R^{20}$, $R^{21}$, $R^{22}$ and $R^{23}$ are as follows:

| $R^{20}$ | $R^{21}$ | $R^{22}$ | $R^{23}$ |
| --- | --- | --- | --- |
| H | benzyl | isobutyl | H; and |
| methyl | isobutyl | methyl | isobutyl. |

In some such aspects the self-immolative moiety X is

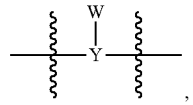

and is represented by structure of formula XVIII:

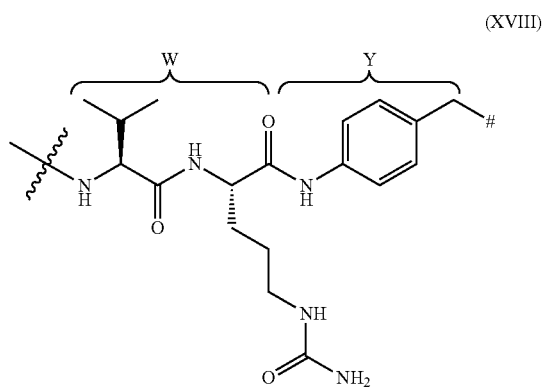
(XVIII)

wherein the wavy line indicates covalent attachment to the Stretcher Unit Z (or its precursor Z'), either directly or indirectly through the Connector Unit (A) or Branching Unit (B) or A and B, and the hash mark (#) indicates covalent attachment of the benzylic carbon to the methylene carbamate unit.

In other aspects, self-immolation is activated from cleavage by a glycosidase of a glycoside unit. The glycoside unit is another example of a self-immolative moiety (X) in which X has the structure of —Y(W)— shown below wherein one wavy line indicates covalent attachment to the Stretcher Unit Z (or its precursor Z'), either directly or indirectly through the Connector Unit (A) or Branching Unit (B) or A and B), and the other wavy line indicates covalent attachment to the remainder of the Self-immolative Assembly Unit (i.e., a methylene carbamate unit or MAC Unit).

A glycoside unit typically comprises a sugar moiety (Su) linked via an oxygen glycosidic bond to a self-immolative spacer, Y, having the structure represented by —Y(W)—. Cleavage of the oxygen glycosidic bond initiates the self-immolation reaction sequence that result in release of free drug. In such embodiments, the sugar represents the Activation Unit as it is attached to the self-immolative spacer via a cleavable bond and cleavage of that bond initiates the self-immolation reaction sequence.

In some aspects, the activateable self-immolative moiety (X) represented by —Y(W)— is activated from cleavage by β-glucuronidase of a Glucuronide unit, which is an exemplary glycoside unit. The Glucuronide unit comprises an activation unit and a self-immolative Spacer Unit. The Glucuronide unit comprises a sugar moiety (Su) linked via an oxygen glycosidic bond to a self-immolative Spacer Unit. Cleavage of the oxygen glycosidic bond initiates the self-immolation reaction sequence resulting in release of free drug. In such embodiments, the sugar represents the Activation Unit as it is attached to the self-immolative Spacer Unit via a cleavable bond and cleavage of that bond initiates the self-immolation reaction sequence.

In some embodiments, a Glycoside Unit or Glucuronide Unit comprises a sugar moiety (Su) linked via an oxygen glycoside bond (—O'—) to a self-immolative Spacer Unit (Y) of the formula:

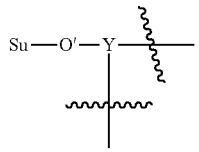

wherein the wavy lines indicate covalent attachment to the methylene carbamate unit and to the Stretcher Unit (Z) or its precursor (Z'), either directly or indirectly through the Connector Unit or Branching unit or Connector unit and Branching unit, as the case may be.

The oxygen glycosidic bond (—O'—) is typically a β-glucuronidase-cleavage site (i.e., Su is from glucuronide), such as a glycoside bond cleavable by human, lysosomal β-glucuronidase.

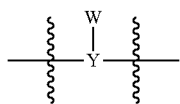

The activateable self-immolative moiety X having the structure of that is cleavable by a glycosidase to initiate the self-immolative reaction sequence can be represented by formula XIXa or XIXb:

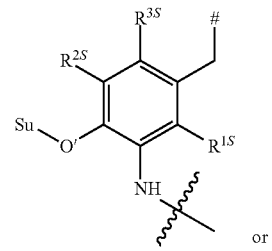

(XIXa)

or (XIXb)

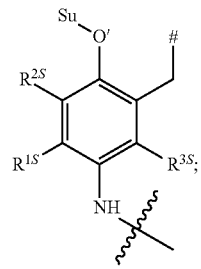

wherein Su is a Sugar moiety, —O'— represents an oxygen glycosidic bond;

$R_{1S}$, $R^{2S}$ and $R^{3S}$ independently are hydrogen, a halogen, —CN, —NO$_2$, or other electron withdrawing group, or an electron donating group; and wherein the wavy line indicates attachment to a Stretcher Unit (Z) (or its precursor (Z'), either directly or indirectly through a Connector Unit or Branching unit or Connector unit and Branching unit);

and # indicates attachment to the methylene carbamate unit (either directly or indirectly via an intervening functional group or other moiety).

In preferred embodiments $R^{1S}$, $R^{2S}$ and $R^{3S}$ are independently selected from hydrogen, halogen, —CN, or —NO$_2$ In other preferred embodiments, $R^{1S}$, $R^{2S}$ and $R^{3S}$ are each hydrogen. In other preferred embodiments $R^{2S}$ is an electron withdrawing group, preferably NO$_2$, and TVs and $R^{3S}$ are each hydrogen.

In some such aspects the activateable self-immolative group capable of glycosidase cleavage to initiate the self-immolative reaction sequence is represented by the formula XIXc:

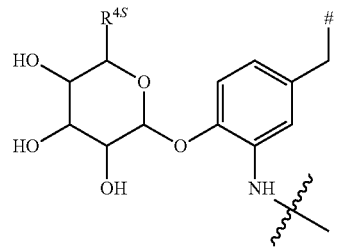

(XIXc)

wherein $R^{4S}$ is CH$_2$OH or —CO$_2$H, the wavy line indicates covalent attachment to a Stretcher Unit (Z) (or its precursor Z), either directly or indirectly through a Connector Unit or Branching Unit or Connector unit and Branching unit, and the hash mark (#) indicates covalent attachment to the methylene carbamate unit.

In some embodiments wherein the activateable self-immolative moiety is comprised of a Glucuronide Unit, it is represented by the following formula XVId:

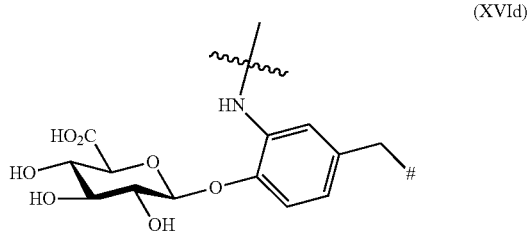

(XVId)

wherein the wavy line indicates covalent attachment to a Stretcher Unit (Z) (or its precursor Z'), either directly or indirectly through a Connector Unit or Branching Unit or Connector unit and Branching unit and the hash mark (#) indicates covalent attachment of the benzylic carbon of Y to the methylene carbamate unit.

Without being bound by theory, Scheme 1 depicts a mechanism of free drug release from a Drug Unit attached to a methylene carbamate unit in an LDC having a self-immolative moiety with the structure of —Y(W)— as in formula XVId.

mentation) that results in release of free drug. They are typically two types of self-immolative Spacer Units. The first can be referred to as an electronic cascade self-immolative Spacer Unit. The electronic cascade within such a self-immolative Spacer Unit causes an elimination reaction as a consequence of shifting conjugated electronic pairs. That rearrangement of electron pair is followed by spontaneous decomposition of the methylene carbamate unit ultimately leading to release free drug from the Drug Unit. Activation of the Activation Unit initiates the elimination reaction (e.g., 1,6- or 1,4-elimination reaction) The second type of self-immolative Spacer Unit is a cyclization self-immolative Spacer Unit. The cyclization self-immolative Spacer Unit acts by causing spontaneous decomposition of a methylene carbamate unit following an intramolecular cyclization reaction thereby leading to free drug release. Activation of the Activation Unit initiates the cyclization reaction. Accordingly, the self-immolative Spacer Unit is a chemical moiety that is capable of undergoing a fragmentation or cyclization reaction following activation of the Activation Unit whereby the fragmentation or cyclization reaction results in spontaneous decomposition of the methylene carbamate unit and release of free drug.

In some aspects, a self-immolative Spacer Unit is a chemical moiety that is capable of covalently linking

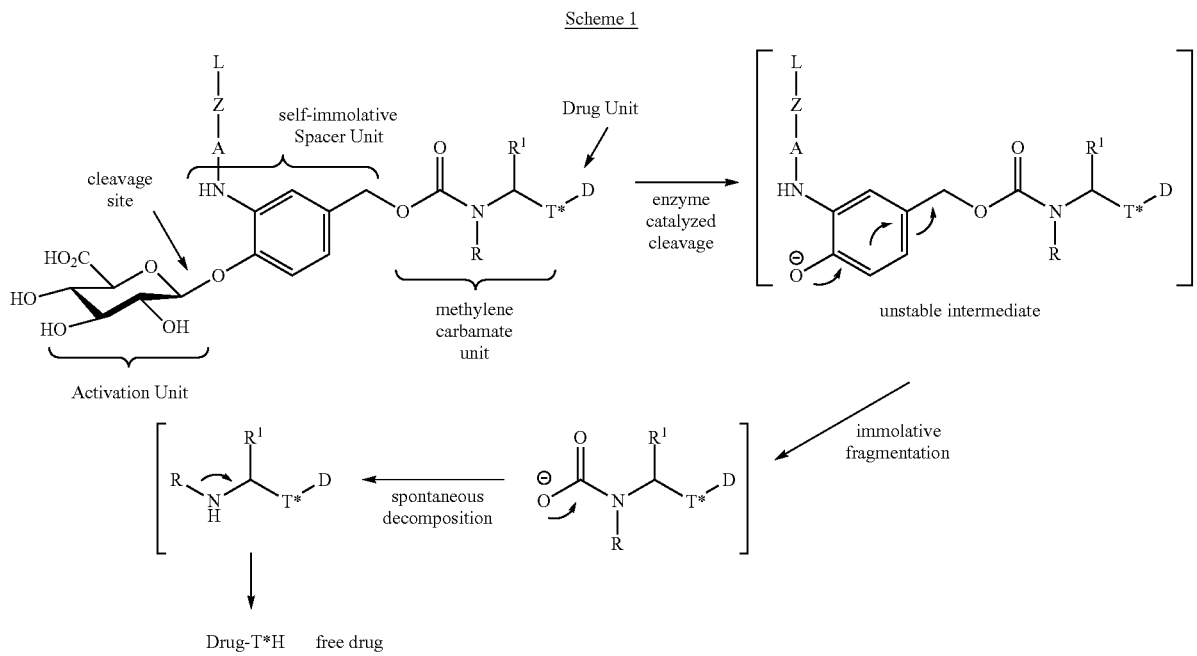

Scheme 1

In some embodiments, the cleavage event that initiates a self-immolation reaction sequence is cleavage of a disulfide bond. In some such aspects, a reducing agent (e.g., glutathione-SH) will act to cleave the disulfide bond thereby initiating the self-immolation reaction sequence. Accordingly, in such embodiments, the Activation Unit is a chemical moiety containing a sulfur atom that participates in a cleavable disulfide bond between the Activation Unit and the self-immolative Spacer Unit.

Self-Immolative Spacer Unit (Y)

The self-immolative Spacer Unit is a chemical moiety that can undergo a self-immolation reaction sequence (i.e., fragtogether three spatially distinct chemical moieties (e.g., an Activation Unit (W), an methylene carbamate unit, and a Stretcher (Z) (or its precursor Z), either directly or indirectly through a Connector Unit or Branching Unit, or Connector Unit and Branching Unit. In other aspects, a Self-immolative Spacer Unit is a chemical moiety that is capable of covalently linking together two spatially distinct chemical moieties (e.g., an Activation Unit and a methylene carbamate unit) wherein attachment to a Stretcher Unit is via the Activation Unit. In some such embodiments, an exemplary self-immolative Spacer Unit is a PAB group having the structure as shown below:

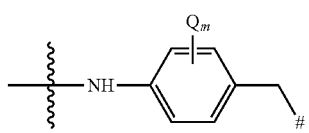

wherein the wavy line indicates covalent attachment to the Activation Unit and the hashtag (#) indicates covalent attachment of the benzylic carbon of the PAB group to the methylene carbamate unit, Q is —$C_1$-$C_8$ alkyl, —O—($C_1$-$C_8$ alkyl), or other electron donating group, -halogen, -nitro or -cyano or other electron withdrawing group (preferably, Q is —$C_1$-$C_8$ alkyl, —O—($C_1$-$C_8$ alkyl), halogen, nitro or cyano); and m is an integer ranging from 0-4 (i.e., the central arylene has no other substituents or 1-4 other substituents). In preferred embodiments m is 0. In other preferred embodiments m is 1 or 2 and each Q is an independently selected electron donating group.

Scheme 2 depicts a possible mechanism of Drug release of an exemplary PAB group of a self-immolative Spacer Unit (Y) that is attached directly to -D via a methylene carbamate unit, wherein the self-immolative moiety has the structure of —W—Y—.

tronically similar to the PAB group such as 2-aminoimidazol-5-methanol derivatives (see, e.g., Hay et al., 1999, *Bioorg. Med. Chem. Lett.* 9:2237) and ortho or para-aminobenzylacetals as well as five ring heterocycles and N-heterocyclic quaternary ammonium salts. Self-immolative Spacer Units can also be used that undergo cyclization upon amide bond hydrolysis, such as substituted and unsubstituted 4-aminobutyric acid amides (see, e.g., Rodrigues et al., 1995, *Chemistry Biology* 2:223), appropriately substituted bicyclo[2.2.1] and bicyclo[2.2.2] ring systems (see, e.g., Storm et al., 1972, *J. Amer. Chem. Soc.* 94:5815) 2-aminophenylpropionic acid amides (see, e.g., Amsberry et al., 1990, *J. Org. Chem.* 55:5867), and trimethyl lock based spacers. Elimination of amine-containing drugs that are substituted at the α-position of glycine (see, e.g., Kingsbury et al., 1984, *J. Med. Chem.* 27:1447) are also examples of self-immolative Spacer Units useful in exemplary Ligand Drug Conjugates as are thiophenols. (see, e.g. Senter, P et al., 1990, J. Org. Chem. 55:2975).

Exemplary self-immolative Spacer Units further include, for example, a thiophenyl, whose sulfhydryl sulfur participates in a disulfide bond from which free drug is released as shown below in Scheme 3:

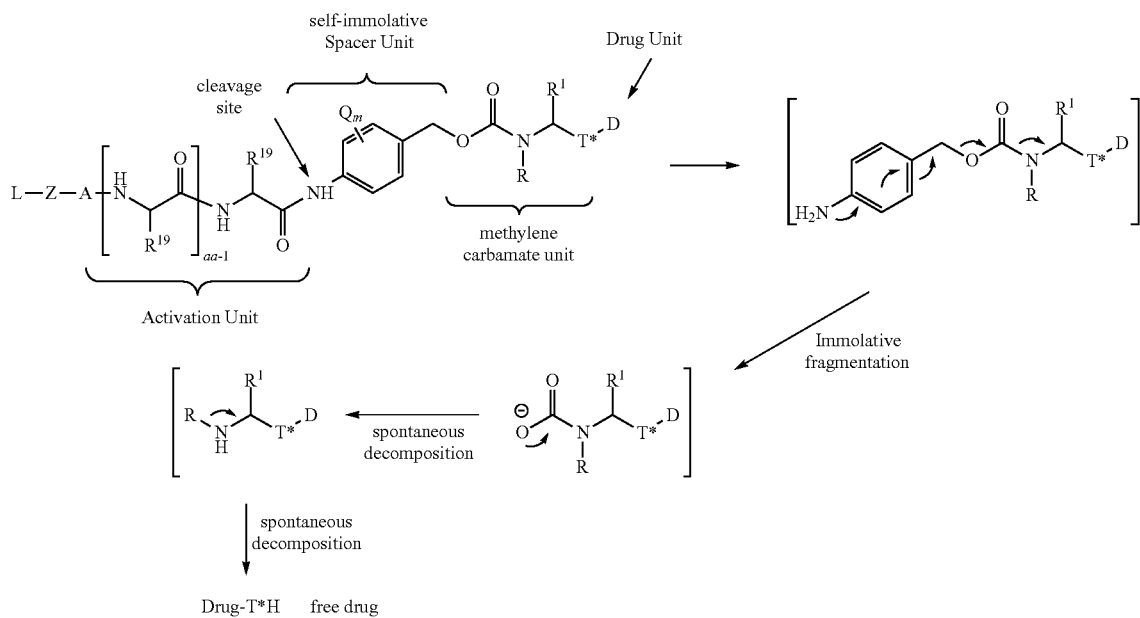

wherein Q is —$C_1$-$C_8$ alkyl or —O—($C_1$-$C_8$ alkyl) or other electron donating group, or -halogen, -nitro, -cyano or other electron withdrawing group (Q is preferably $C_1$-$C_8$ alkyl, —O—($C_1$-$C_8$ alkyl), halogen, nitro, or cyano); and m is an integer ranging from 0-4; and $R^{19}$, independently selected, and aa are as defined for peptide-based Activation Units Other examples of self-immolative Spacer Units include, but are not limited to, aromatic compounds that are elec-

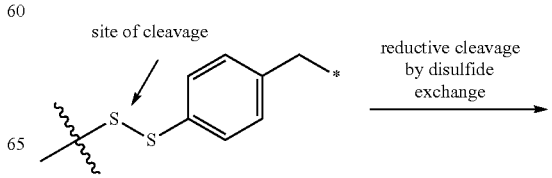

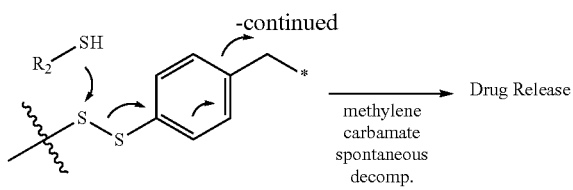

Drug Release
methylene
carbamate
spontaneous
decomp.

wherein the wavy line indicates the site of attachment to a Stretcher Unit (Z) (or its precursor Z'), either directly or indirectly through a Connector Unit or Branching Unit or Connector unit and Branching unit, and the asterisk (*) indicates the site of attachment of the benzylic carbon of Y to the methylene carbamate unit.

Exemplary self-immolative Spacer Units further include, for example, a 5-ringed heterocycle which releases drug as shown below in Scheme 4.

Scheme 4

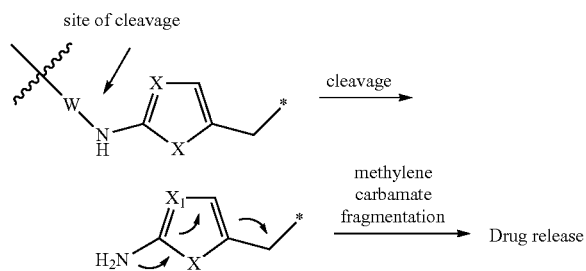

cleavage methylene carbamate fragmentation

Drug release wherein X is C, O, or S, W is an Activation Unit, the wavy line indicates the site of attachment to a Stretcher Unit (Z) (or its precursor Z), either directly or indirectly through a Connector Unit or Branching Unit or Connector unit and Branching unit, and the asterisk indicates the site of attachment to the methylene carbamate unit.

In some aspects of the prevent invention the self-immolative Spacer Unit has a mass of no more than about 1000 daltons, no more than about 500 daltons, no more than about 400 daltons, no more than about 300 daltons, or from about 10, 50 or 100 to about 1000 daltons, from about 10, 50 or 100 to about 500 daltons, from about 10, 50 or 100 daltons to about 400 daltons, from about 10, 50 or 100 daltons to about 300 daltons or from about 10, 50 or 100 daltons to about 200 daltons.

The Subscript "p"

In one aspect of the invention, the subscript p represents the number of drug linker moieties on a Ligand unit of an individual Ligand Drug Conjugate (LDC) and is an integer preferably ranging from 1 to 16, 1 to 12, 1 to 10, or 1 to 8. Individual LDCs can be also be referred to as a LDC compound. In any of the embodiments herein, there can be 1, 2, 3, 4, 5, 6, 7, 8, 9, 10, 11, 12, 13, 14, 15, or 16 drug linker moieties conjugated to a Ligand Unit of an individual LDC. In another aspect of the invention, one group of embodiments describes a population of individual Ligand Drug Conjugates substantially identical except for the number of drug linker moieties bound to each Ligand Unit (i.e., a LDC composition) so that p represents the average number of drug-linker moieties bound to the Ligand Units of the LDC composition. In that group of embodiments, p is a number ranging from 1 to about 16, 1 to about 12, 1 to about 10, or 1 to about 8, from 2 to about 16, 2 to about 12, 2 to about 10, or 2 to about 8. In some aspects, the p value refers to the average drug loading as well as the drug loading of the predominate ADC in the composition.

In some aspects, conjugation will be via the interchain disulfides and there will from 1 to about 8 drug linker molecules conjugated to a ligand molecule. In some aspects, conjugation will be via an introduced cysteine residue as well as interchain disulfides and there will be from 1 to 10 or 1 to 12 or 1 to 14 or 1 to 16 drug linker molecules conjugated to a ligand molecule. In some aspects, conjugation will be via an introduced cysteine residue and there will be 2 or 4 drug linker molecules conjugated to a ligand molecule.

Ligand-Drug Conjugate Mixtures and Compositions

The present invention provides Ligand-Drug Conjugate mixtures and pharmaceutical compositions comprising any of the Ligand-Drug Conjugates described herein. The mixtures and pharmaceutical compositions comprise a plurality of conjugates. In some aspects, each of the conjugates in the mixture or composition is identical or substantially identical, however, the distribution of drug-linkers on the ligands in the mixture or compositions may vary as well as the drug loading. For example, the conjugation technology used to conjugate drug-linkers to antibodies as the targeting ligand can result in a composition or mixture that is heterogeneous with respect to the distribution of drug-linkers on the Antibody Ligand Units within the mixture and/or composition and/or with respect to loading of drug-linkers on the ligand molecules within the mixture and/or composition. In some aspects, the loading of drug-linkers on each of the antibody molecules in a mixture or composition of such molecules is an integer that ranges from 1 to 14.

In those aspects, when referring to the composition as a whole the loading of drug-linkers is a number ranging from 1 to about 14. Within the composition or mixture, there may also be a small percentage of unconjugated antibodies. The average number of drug-linkers per Ligand Unit in the mixture or composition (i.e., average drug-load) is an important attribute as it determines the maximum amount of drug that can be delivered to the target cell. When the Linker Units in an LDC are not branched, the average number of drug-linkers in a mixture or composition of such LDCs represents the average drug load and is a number that can range from 1 to about 14, preferably from about 2 to about 10 or about 8. The average drug load can be 1, 2 or about 2, 3 or about 3, 4 or about 4, 5 or about 5, 6 or about 6, 7 or about 7, 8 or about 8, 9 or about 9, 10 or about 10, 11 or about 11, 12 or about 12, 13 or about 13, 14 or about 14, 15 or about 15, 16 or about 16. When the Linker Units in an LDC are branched, the average number of drug linkers in mixtures or compositions of such LDCs have ranges corresponding to unbranched LDCs, but the average drug loading will be some multiple of those average drug-linker loads depending on the number of branch points in each Linker Unit.

In some aspects, the mixtures and pharmaceutical compositions comprise a plurality (i.e., population) of conjugates, however, the conjugates are identical or substantial identical and are substantially homogenous with respect to the distribution of drug-linkers on the ligand molecules within the mixture and/or composition and with respect to loading of drug-linkers on the ligand molecules within the mixture and/or composition. In some such aspects, the loading of drug-linkers on the Antibody Ligand Unit is 2 or 4. Within the composition or mixture, there may also be a small percentage of unconjugated antibodies. The average drug load in such embodiments is about 2 or about 4. Typically, such compositions and mixtures result from the use of site specific conjugation techniques and conjugation is due to an introduced cysteine residue.

The average number of Drugs units or Drug-Linkers per Ligand Unit in a preparation from a conjugation reaction may be characterized by conventional means such as mass spectrometry, ELISA assay, HPLC (e.g., HIC). The quantitative distribution of Ligand-Drug Conjugates in terms of p may also be determined. In some instances, separation, purification, and characterization of homogeneous Ligand-Drug Conjugates may be achieved by means such as reverse phase HPLC or electrophoresis.

In some aspects, the compositions are pharmaceutical compositions comprising the Ligand-Drug Conjugates described herein and a pharmaceutically acceptable carrier. In some aspect, the pharmaceutical composition will be in liquid form. In some aspects, it will be a lyophilized powder.

The compositions, including pharmaceutical compositions, can be provided in purified form. As used herein, "purified" means that when isolated, the isolate contains at least 95%, and in another aspect at least 98%, of Conjugate by weight of the isolate.

Methods of Use

Treatment of Cancer

The Ligand-Drug Conjugates are useful for inhibiting the multiplication of a tumor cell or cancer cell, causing apoptosis in a tumor or cancer cell, or for treating cancer in a patient. The Ligand-Drug Conjugates can be used accordingly in a variety of settings for the treatment of cancers. The Ligand-Drug Conjugates can be used to deliver a drug to a tumor cell or cancer cell. Without being bound by theory, in one embodiment, the Ligand unit of a Ligand-Drug Conjugate binds to or associates with a cancer-cell or a tumor-cell-associated antigen, and the Ligand-Drug Conjugate can be taken up (internalized) inside the tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, via activation of the Activation Unit, the drug is released within the cell. In an alternative embodiment, the free drug is released from the Ligand-Drug Conjugate outside the tumor cell or cancer cell, and the free drug subsequently penetrates the cell.

In one embodiment, the Ligand Unit binds to the tumor cell or cancer cell.

In another embodiment, the Ligand Unit binds to a tumor cell or cancer cell antigen which is on the surface of the tumor cell or cancer cell.

In another embodiment, the Ligand Unit binds to a tumor cell or cancer cell antigen which is an extracellular matrix protein associated with the tumor cell or cancer cell.

The specificity of the Ligand Unit for a particular tumor cell or cancer cell can be important for determining the tumors or cancers that are most effectively treated. For example, Ligand-Drug Conjugates that target a cancer cell antigen present in hematopoietic cancers can be useful treating hematologic malignancies (e.g., anti-CD30, anti-CD70, anti-CD19, anti-CD33 binding Ligand Unit (e.g., antibody) can be useful for treating hematologic malignancies). Ligand-Drug Conjugates that target a cancer cell antigen present on solid tumors can be useful treating such solid tumors.

Cancers that can be treated with a Ligand-Drug Conjugate include, but are not limited to, hematopoietic cancers such as, for example, lymphomas (Hodgkin Lymphoma and Non-Hodgkin Lymphomas) and leukemias and solid tumors. Examples of hematopoietic cancers include, follicular lymphoma, anaplastic large cell lymphoma, mantle cell lymphoma, acute myeloblastic leukemia, chronic myelocytic leukemia, chronic lymphocytic leukemia, diffuse large B cell lymphoma, and multiple myeloma. Examples of solid tumors include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

In preferred embodiments, the cancers treated are any one of the above-listed lymphomas and leukemias.

Multi-Modality Therapy for Cancer

Cancers, including, but not limited to, a tumor, metastasis, or other disease or disorder characterized by uncontrolled cell growth, can be treated or inhibited by administration of a Ligand-Drug Conjugate.

In other embodiments, methods for treating cancer are provided, including administering to a patient in need thereof an effective amount of a Ligand-Drug Conjugate and a chemotherapeutic agent. In one embodiment the chemotherapeutic agent is that with which treatment of the cancer has not been found to be refractory. In another embodiment, the chemotherapeutic agent is that with which the treatment of cancer has been found to be refractory. The Ligand-Drug Conjugates can be administered to a patient that has also undergone surgery as treatment for the cancer.

In some embodiments, the patient also receives an additional treatment, such as radiation therapy. In a specific embodiment, the Ligand-Drug Conjugate is administered concurrently with the chemotherapeutic agent or with radiation therapy. In another specific embodiment, the chemotherapeutic agent or radiation therapy is administered prior or subsequent to administration of a Ligand-Drug Conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a Ligand-Drug Conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Treatment of Autoimmune Diseases

The Ligand-Drug Conjugates are useful for killing or inhibiting the unwanted replication of cells that produces an autoimmune disease or for treating an autoimmune disease. The Ligand-Drug Conjugates can be used accordingly in a variety of settings for the treatment of an autoimmune disease in a patient. The Ligand-Drug Conjugates can be used to deliver a drug to a target cell. Without being bound by theory, in one embodiment, the Ligand-Drug Conjugate associates with an antigen on the surface of a pro-inflammatory or inappropriately-stimulated immune cell, and the Ligand-Drug Conjugate is then taken up inside the targeted cell through receptor-mediated endocytosis. Once inside the cell, the Linker unit is cleaved, resulting in release of the Drug or Drug unit. The released Drug is then free to migrate in the cytosol and induce cytotoxic or cytostatic activities. In an alternative embodiment, the Drug is cleaved from the Ligand-Drug Conjugate outside the target cell, and the Drug or Drug unit subsequently penetrates the cell.

In one embodiment, the Ligand Unit binds to an autoimmune antigen. In one aspect, the antigen is on the surface of a cell involved in an autoimmune condition.

In one embodiment, the Ligand Unit binds to activated lymphocytes that are associated with the autoimmune disease state.

In a further embodiment, the Ligand-Drug Conjugate kills or inhibits the multiplication of cells that produce an autoimmune antibody associated with a particular autoimmune disease.

Particular types of autoimmune diseases that can be treated with the Ligand-Drug Conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); and activated B lymphocyte-related disorders (e.g., systemic lupus erythematosus, Goodpasture's syndrome, rheumatoid arthritis, and type I diabetes).

Multi-Drug Therapy of Autoimmune Diseases

Methods for treating an autoimmune disease are also disclosed including administering to a patient in need thereof an effective amount of a Ligand-Drug Conjugate and another therapeutic agent known for the treatment of an autoimmune disease.

Compositions and Methods of Administration

The present invention provides pharmaceutical compositions comprising the Ligand-Drug Conjugates described herein and a pharmaceutically acceptable carrier. The Ligand-Drug Conjugates can be in any form that allows for the compound to be administered to a patient for treatment of a disorder associated with expression of the antigen to which the Ligand unit binds. For example, the conjugates can be in the form of a liquid or solid. The preferred route of administration is parenteral. Parenteral administration includes subcutaneous injections, intravenous, intramuscular, intrasternal injection or infusion techniques. In one aspect, the compositions are administered parenterally. In one aspect, the conjugates are administered intravenously. Administration can be by any convenient route, for example by infusion or bolus injection Pharmaceutical compositions can be formulated so as to allow a compound to be bioavailable upon administration of the composition to a patient. Compositions can take the form of one or more dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or digylcerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition.

For intravenous administration, the composition can comprise from about 0.01 to about 100 mg of a Ligand-Drug Conjugate per kg of the animal's body weight. In one aspect, the composition can include from about 1 to about 100 mg of a Ligand-Drug Conjugate per kg of the animal's body weight. In another aspect, the amount administered will be in the range from about 0.1 to about 25 mg/kg of body weight of a compound. Depending on the drug used, the dosage can be even lower, for example, 1.0 µg/kg to 5.0 mg/kg, 4.0 mg/kg, 3.0 mg/kg, 2.0 mg/kg or 1.0 mg/kg, or 1.0 µg/kg to 500.0 µg/kg of the subject's body weight.

Generally, the dosage of a conjugate administered to a patient is typically about 0.01 mg/kg to about 100 mg/kg of the subject's body weight or from 1.0 µg/kg to 5.0 mg/kg of the subject's body weight. In some embodiments, the dosage administered to a patient is between about 0.01 mg/kg to about 15 mg/kg of the subject's body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. In some embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The term "carrier" refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a patient, the compound or compositions and pharmaceutically acceptable carriers are sterile.

Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol. The present compositions, if desired, can also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachets indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Methods of Preparing Ligand-Drug Conjugates

The Ligand-Drug Conjugates described herein can be prepared in either a serial construction of antibodies, linkers, and drug units, or in a convergent fashion by assembling portions followed by a completed assembly step. The Curtius Rearrangement or a Chloramine synthesis can be used to provide a methylene carbamate linker which is a common feature of all of the Conjugates described herein.

Scheme 5: Preparation of Exemplary Drug-Linkers using the Curtius Rearrangement Reaction

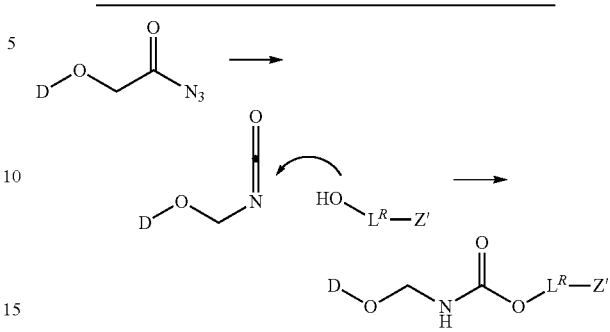

Scheme 5 illustrates a synthetic strategy involving a Curtius rearrangement of an acyl azide derivative of the free drug, wherein D is a drug unit representing having a hydroxyl functional group whose hydrogen atom is incorporated into the methylene alkoxy carbamate unit formed as a consequence of the rearrangement, Z' is a Stretcher Unit precursor and $L^R$ is the remainder of the Linker Unit (e.g., —Y(W)-A or —Y—W-A-, wherein Y is bonded to the carbamate oxygen and A is bonded to Z'). That strategy may be applied to drugs containing multiple alcohols, or other heteroatoms, as a means for acquiring regioselectivity, as there a many complementary methods of alkylation to form an acyl azide such as: halo ester alkylation, halo acid alkylation or metal carbene insertion with ethyl or methyl diazoacetate, see Doyle, M. et al. Modern Catalytic Methods for Organic Synthesis with Diazo Compounds; Wiley: New York, 1998. The acyl azide is then heated with at least a stoichiometric amount of alcohol-containing Linker Unit intermediate, such as structure 1.1. (see examples).

Scheme 6: Preparation of Exemplary Drug-Linkers via N-chloromethylamine synthesis

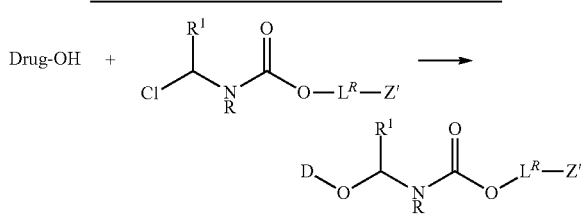

The N-chloromethylamine synthesis is an alternative to the Curtius rearrangement in that it allows for the introduction of an unmodified alcohol or other heteroatom containing-drug, whose use may not be compatible with the conditions required to form the acyl azide of Scheme 5, and proceeds by condensation with a reactive N-chloromethylamine such as structure 1.5 (see examples). That methodology is also more appropriate for introducing certain types of methylene carbamate units as shown for example by Scheme 7.

Scheme 7 demonstrates synthesis of exemplary Drug-Linker Compounds of the present invention having a Self-immolative Assembly Unit comprising an methylene carbamate of formula Ib. Reaction of the p-nitro-phenyl carbonate with the cyclic aminol provides a carbamate, which is then converted to the chlorcycloalkylamine for alkylation with a nucleophile from the thiol, hydroxyl, amine or amide functional group of free drug. Alternatively, the carbamate can be treated with acid in the presence of the drug moiety to assemble the drug-linker intermediate shown. The alkylation product is deprotected followed by condensation of the resulting free amine with 3-maleimido-propionic acid N-hydroxysuccimide ester, which introduces a Stretcher Unit precursor covalently attached to a Connector Unit thus providing Drug-Linker Compounds of formula. The resulting Drug-Linker Compounds are then condensed with a thiol-containing targeting ligand to provide Ligand Drug Conjugates having a Self-immolative Assembly unit comprised of a —Y(W)-self-immolative moiety and a methylene carbamate unit of formula Ib.

For Drug Linker Compounds and Ligand Drug Conjugates having a methylene carbamate unit wherein T* is the nitrogen heteroatom from an primary aliphatic amine or the substituted heteroatom from a secondary aliphatic (cyclic or acyclic), direct alkylation with a chlormethylamine following the generalized procedures provided by Scheme 6 or Scheme 7 may not be suitable due to excessive or undesired over-alkylation of the nitrogen heteroatom from the amine functional group of free drug. In those instances the method embodied by Scheme 8 may be used.

Scheme 7

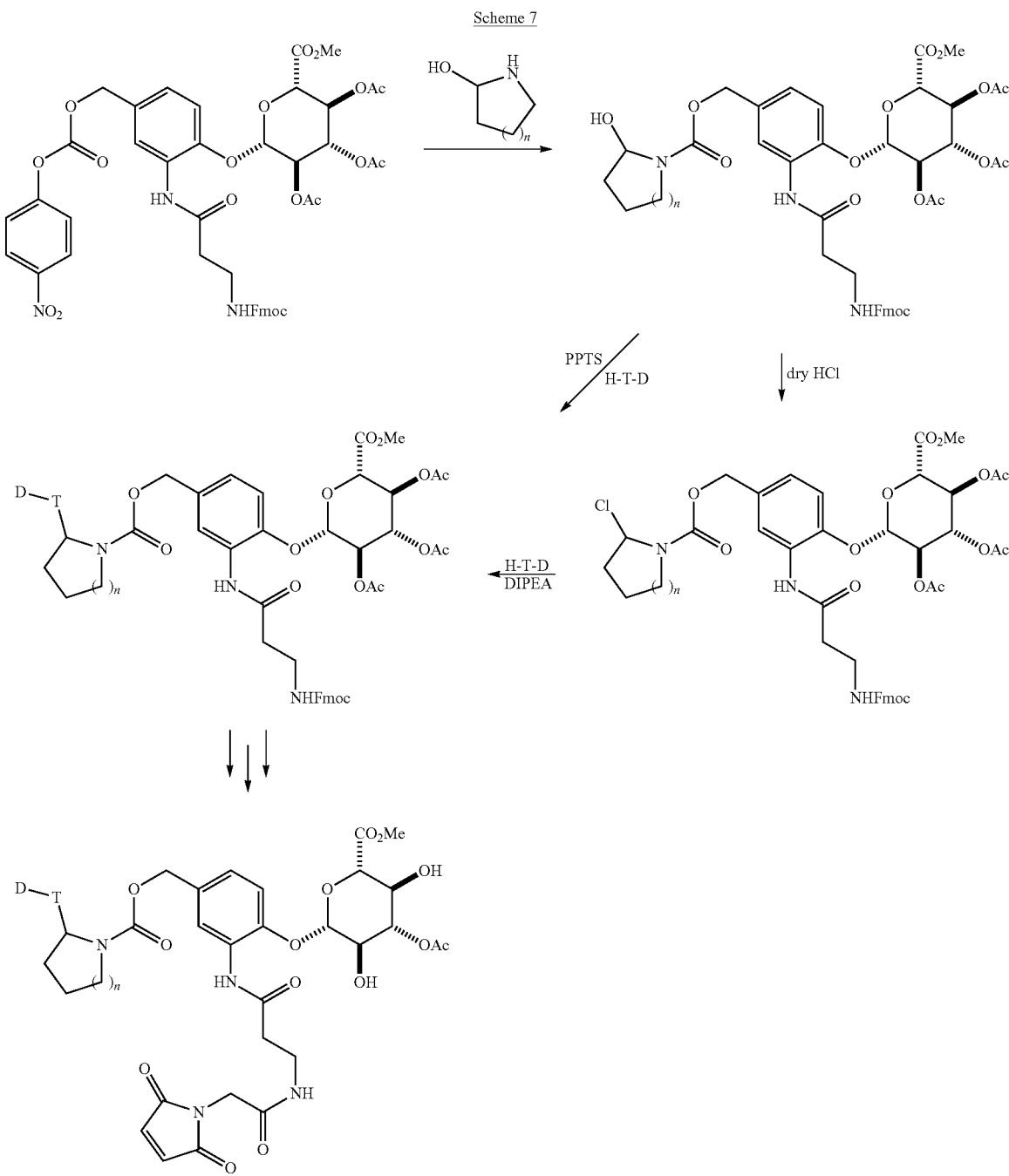

Scheme 8.

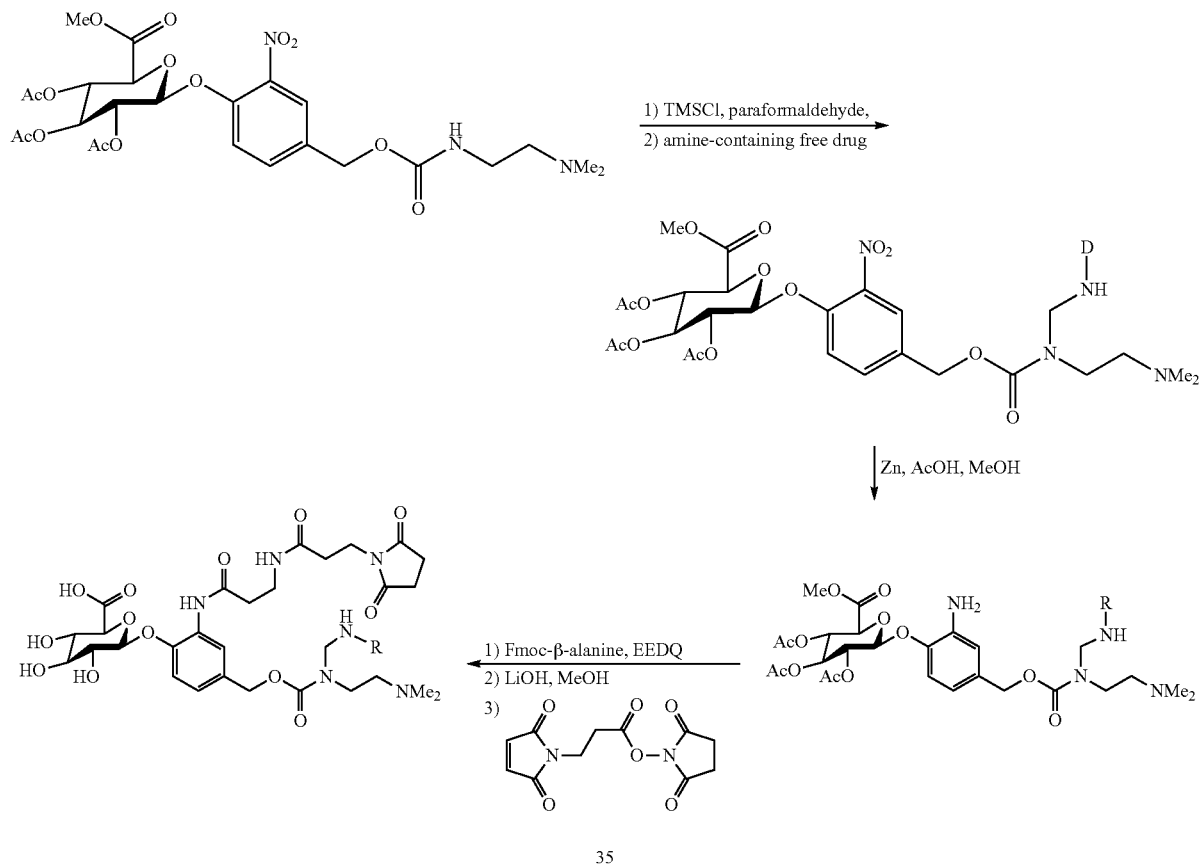

In Scheme 8 an intermediate carbamate is prepared already having a Basic Unit (i.e., the dimethylaminoethyl moiety) as the R substituent for a formula Ia methylene carbamate unit. The nitrogen of that carbamate is condensed with formaldehyde and the resulting intermediate quenched with the amine functional group of an aliphatic amine-containing drug. That condensation forms the methylene carbamate covalently attached to a Drug Unit of formula Ia, wherein IV is hydrogen and R is dimethylaminoethyl. The phenyl nitro group is then reduced to by the general method of Example 8 to provide a handle for sequential introduction of a Connector Unit (A) and a Stretcher Unit precursor (Z').

NUMBERED EMBODIMENTS

The following embodiments further exemplify the invention and are not meant to limit the invention in any manner.

1. A Ligand-Drug Conjugate Compound comprising a Ligand Unit, a Drug Unit and a Linker Unit, wherein the Linker Unit is comprised of a Self-immolative (SI) Assembly Unit having a methylene carbamate unit and an activateable self-immolative moiety wherein the methylene carbamate unit is covalently attached to the Drug Unit, and wherein the SI Assembly Unit covalently attached to the Drug Unit is represented by the structure of formula SI:

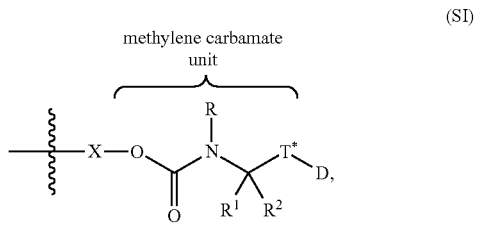

(SI)

or a pharmaceutically acceptable salt thereof, wherein the wavy line indicates covalent attachment to the remainder of the Linker Unit; D is the Drug Unit having a hydroxyl, thiol, amine or amide functional group that has been incorporated into the methylene carbamate unit; T* is the oxygen, sulfur or optionally substituted nitrogen heteroatom from said functional group that becomes incorporated into the indicated methylene carbamate unit; X is the activateable self-immolative moiety; R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or both R and R' together with the nitrogen and carbon atoms to which they are attached comprise an azetidinyl, pyrrolodinyl, piperidinyl or homopiperidinyl moiety and $R^2$ is hydrogen.

2. The Ligand-Drug Conjugate Compound of embodiment 1 wherein the SI Assembly Unit covalently attached to the Drug Unit is represented by the structure of formula SIa or SIb:

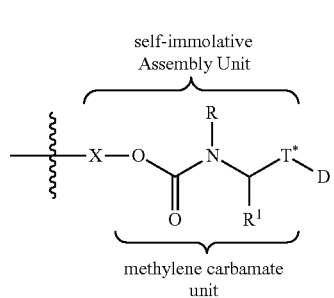

(SIa)

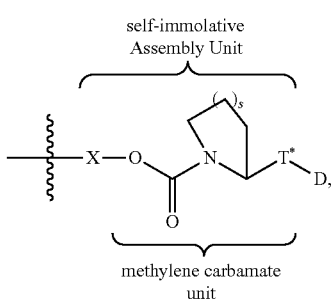

(SIb)

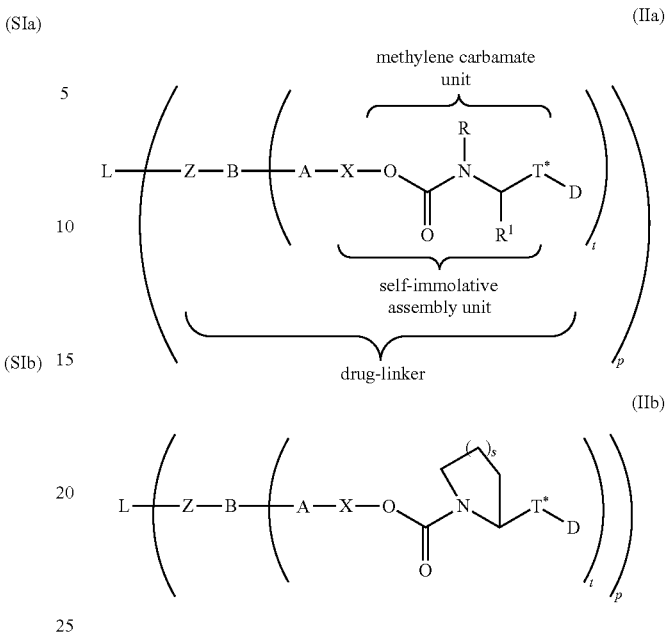

or a pharmaceutically acceptable salt thereof, wherein s is 0, 1, 2 or 3.

3. The Ligand-Drug Conjugate Compound of claim 2 wherein R and $R^1$ are independently selected from hydrogen, optionally substituted $C_1$-$C_6$ alkyl or optionally substituted $C_{6\text{-}14}$ aryl; and the subscript s is 0, 1, or 2.

4. The Ligand-Drug Conjugate Compound of embodiment 1 having Formula II:

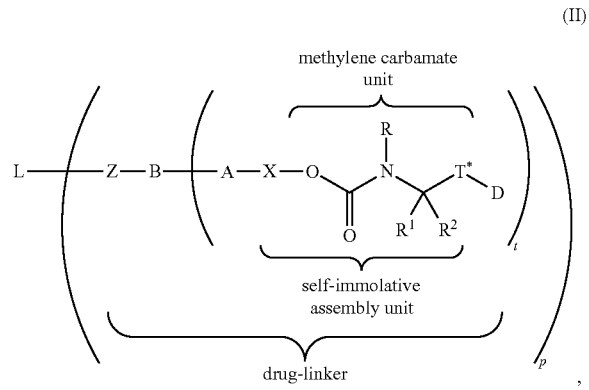

(II)

or a pharmaceutically acceptable salt thereof, wherein L is a Ligand Unit; Z is a Stretcher Unit; B is an optional branching unit and is present when t is greater than 1 and is absent when t is 1; A is an optional Connector Unit; the subscript t ranges from 1 to 4; and the subscript p is an integer ranging from 1 to 16.

5. The Ligand-Drug Conjugate Compound of embodiment 4 having Formula IIa or IIb:

or a pharmaceutically acceptable salt thereof, wherein s is 0, 1, 2, or 3.

6. The Ligand-Drug Conjugate Compound of embodiment 4 wherein R and IV are independently selected from hydrogen, optionally substituted $C_1$-$C_6$ alkyl or optionally substituted $C_{6\text{-}14}$ aryl, and the subscript s is 0, 1, or 2.

7. The Ligand-Drug Conjugate Compound of embodiment 5 wherein R and $R^1$ are independently selected from hydrogen, optionally substituted $C_1$-$C_6$ alkyl or optionally substituted $C_{6\text{-}14}$ aryl; and the subscript s is 0, 1, or 2.

8. The Ligand-Drug Conjugate Compound of any one of embodiments 4 to 7 wherein $R^1$ is not substituted.

9. The Ligand-Drug Conjugate Compound of any one of embodiments 4 to 7 wherein $R^1$ and $R^2$ are not substituted.

10. The Ligand-Drug Conjugate Compound of embodiment 4 or 5 wherein R, and $R^2$ are not substituted.

11. The Ligand-Drug Conjugate Compound of any one of embodiments 4 to 9 wherein the optional substituents are independently selected from the group consisting of —X, —$R^{op}$, —OH, —O$R^{op}$, —S$R^{op}$, —N($R^{op}$)$_2$, —N($R^{op}$)$_3$, =N$R^{op}$, —CX$_3$, —CN, —NO$_2$, —N$R^{op}$C(=O)$R^{op}$, —C(=O)$R^{op}$, —C(=O)N($R^{op}$)$_2$, —S(=O)$_2$$R^{op}$, —S(=O)$_2$ N$R^{op}$, —S(=O)$R^{op}$, —OP(=O)(O$R^{op}$)$_2$, —P(=O)(O$R^{op}$)$_2$, —PO$_3^=$, PO$_3$H$_2$, —C(=O)$R^{op}$, —C(=S)$R^{op}$, —CO$_2$$R^{op}$, —CO$_2^-$, —C(=S)O$R^{op}$, —C(=O)S$R^{op}$, —C(=S)S$R^{op}$, —C(=O)N($R^{op}$)$_2$, —C(=S)N($R^{op}$)$_2$, and —C(=N$R^{op}$)N($R^{op}$)$_2$, wherein each X is independently selected from the group consisting of a halogen: —F, —Cl, —Br, and —I; and each $R^{op}$ is independently selected from the group consisting of hydrogen, —$C_1$-$C_{20}$ alkyl, —$C_6$-$C_{20}$ aryl, —$C_3$-$C_{14}$ heterocycle, a protecting group, and a prodrug moiety.

12. The Ligand-Drug Conjugate Compound of embodiment 11 wherein the optional substituents are selected from the group consisting of —X, —$R^{op}$, —OH, —O$R^{op}$, —S$R^{op}$, —N($R^{op}$)$_2$, N($R^{op}$)$_3$, =N$R^{op}$, —N$R^{op}$C(=O)$R^{op}$, —C(=O)$R^{op}$, —C(=O)N($R^{op}$)$_2$, —S(=O)$_2$$R^{op}$, —S(=O)$_2$ N$R^{op}$, —S(=O)$R^{op}$, —C(=O)$R^{op}$, —C(=S) $R^{op}$, —C(=O)N($R^{op}$)$_2$, —C(=S)N($R^{op}$)$_2$, and —C(=N$R^{op}$)N($R^{op}$)$_2$, wherein each X is selected from the group consisting of —F and —Cl; and each $R^{op}$ is independently selected from the group consisting of hydrogen, —$C_1$-$C_{20}$ alkyl, —$C_6$-$C_{20}$ aryl, —$C_3$-$C_{14}$ heterocycle, a protecting group, and a prodrug moiety.

13. The Ligand-Drug Conjugate Compound of embodiment 11 wherein the optional substituents are selected from the group consisting of —X, —$R^{op}$, —OH, —$OR^{op}$, —$N(R^{op})_2$, —$N(R^{op})_3$, —$NR^{op}C(=O)R^{op}$, —$C(=O)N(R^{op})_2$, —$S(=O)_2R^{op}$, —$S(=O)_2NR^{op}$, —$S(=O)R^{op}$, —$C(=O)R^{op}$, —$C(=O)N(R^{op})_2$, and —$C(=NR^{op})N(R^{op})_2$, wherein X is —F.

14. The Ligand-Drug Conjugate Compound of embodiment 11 wherein the optional substituent is selected from the group consisting of —$N(R^{op})_2$, —$N(R^{op})_3$ and —$C(=NR)N(R^{op})_2$.

15. The Ligand-Drug Conjugate Compound of any one of embodiments 1 to 9 wherein R is $C_{1-6}$ alkyl, optionally substituted with a basic group.

16. The Ligand-Drug Conjugate Compound of claim any one of claims 1 to 9 wherein R is a saturated $C_{1-6}$ alkyl, optionally substituted with a basic group.

17. The Ligand-Drug Conjugate Compound of any one of embodiments 1 to 9 wherein R is a Basic Unit wherein the basic functional group of the Basic Unit is an amine or a nitrogen-containing 3, 4, 5, or 6 membered heterocycle that is C-linked or N-linked and can be optionally substituted.

18. The Ligand-Drug Conjugate Compound of embodiment 17 wherein R is a Basic Unit, wherein the basic functional group of the Basic Unit is —$N(R^{op})_2$, wherein $R^{op}$ are independently selected from the group consisting of hydrogen and $C_{1-6}$ alkyl.

19. The Ligand-Drug Conjugate Compound of embodiment 17 wherein R is a Basic Unit, wherein the basic functional group of the Basic Unit is —$N(R^{op})_2$, wherein $R^{op}$ are independently selected from the group consisting of hydrogen and methyl.

20. The Ligand-Drug Conjugate Compound of embodiment 17 wherein R is a Basic Unit, wherein, the basic functional group of the Basic Unit is —$N(R^{op})_2$, wherein each $R^{op}$ is methyl.

21. The Ligand Drug Conjugate Compound of embodiment 17 wherein R is a Basic Unit, wherein the Basic Unit is —$CH_2CH_2N(R^{op})_2$, wherein $R^{op}$ are independently selected from the group consisting of hydrogen and methyl.

22. The Ligand-Drug Conjugate Compound of any one of embodiment 15 to 21 wherein IV is hydrogen.

23. The Ligand-Drug Conjugate Compound of any one of embodiment 1 to 22 wherein D is a Drug Unit corresponding to a drug having a hydroxyl functional group that has been incorporated into the methylene carbamate unit so that T* represents the oxygen heteroatom from that functional group.

24. The Ligand-Drug Conjugate Compound of embodiment 23 wherein D is a Drug Unit corresponding to an aliphatic alcohol-containing drug, wherein attachment of D within the conjugate is via the oxygen heteroatom of the hydroxyl functional group of the aliphatic alcohol, so that T* represents the oxygen atom from that functional group.

25. The Ligand-Drug Conjugate Compound of embodiment 23 wherein D is a Drug Unit corresponding to an aromatic alcohol-containing drug, wherein attachment of D within the conjugate is via the oxygen atom of the aromatic alcohol, so that T* represents the oxygen atom from that functional group.

26. The Ligand-Drug Conjugate Compound of embodiment 25 wherein the aromatic alcohol is not a phenolic alcohol.

27. The Ligand-Drug Conjugate Compound of any one of embodiments 4 to 26 wherein B is absent and the subscript t is 1.

28. The Ligand-Drug Conjugate Compound of any one of embodiments 4 to 27 wherein the structure representing the indicated activateable self-immolative moiety (X) within the Linker Unit is represented by formula (i)

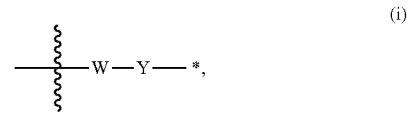

wherein the way line indicates covalent attachment of W to A, B or Z depending on the presence or absence of A and/or B and the asterisk (*) indicates covalent attachment of Y to a methylene carbamate unit and wherein; W is an Activation Unit; and Y is a self-immolative Spacer Unit, wherein activation of self-immolation of Y results in release of free drug.

29. The Ligand-Drug Conjugate Compound of embodiment 28 wherein activation for self-immolation of Y is by enzymatic cleavage of a covalent bond between W and Y.

30. The Ligand-Drug Conjugate Compound of embodiment 29 wherein enzymatic cleavage is by a tumor associated protease.

31. The Ligand-Drug Conjugate Compound of embodiment 30 wherein the tumor associated protease is cathepsin B.

32. The Ligand-Drug Conjugate Compound of embodiments 30 wherein W is -Val-Cit-, -Phe-Lys- or -Val-Ala-.

33. The Ligand-Drug Conjugate Compound of embodiment 30 wherein —W—Y— is represented by the structure of:

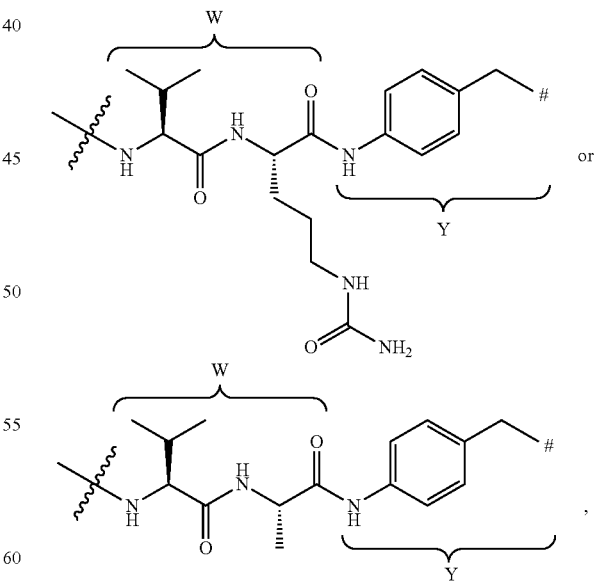

wherein the wavy bond to the nitrogen of W indicates covalent linkage to Z, A or B, depending on the presence or absence of A and/or B, and the hash mark (#) indicates covalent attachment of the benzylic carbon of Y to a methylene carbamate unit.

34. The Ligand-Drug Conjugate Compound of any one of embodiments 4 to 27 wherein the structure representing the indicated activateable self-immolative moiety (X) within the Linker Unit is represented by formula (ii):

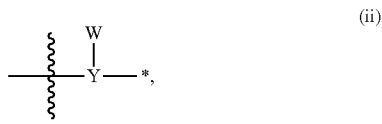

(ii)

wherein the wavy line indicates covalent attachment of Y to A, B or Z depending on the presence or absence of A and/or B, and the asterisk (*) indicates covalent attachment of Y to the methylene carbamate moiety, and wherein; W is an Activation Unit; and Y is a self-immolative Spacer Unit, wherein activation of self-immolation of Y results in release of free drug.

35. The Ligand-Drug Conjugate Compound of embodiment 34 wherein activation for self-immolation of Y is by enzymatic cleavage of a covalent bond between W and Y, wherein enzymatic cleavage is by a glycosidase.

36. The Ligand-Drug Conjugate Compound of embodiment 35 wherein the glycosidase is a glucuronidase.

37. The Ligand-Drug Conjugate Compound of embodiment 35 wherein W is a sugar moiety connected to Y via a glycosidic bond capable of cleavable by a glycosidase for activation of self-immolation of Y.

38. The Ligand-Drug Conjugate Compound of embodiment 33 wherein —Y(W)— is represented by the structure of:

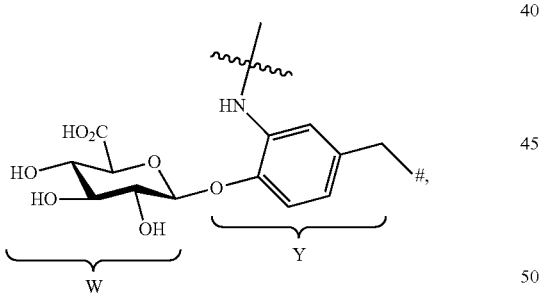

wherein the wavy bond adjacent to the nitrogen of Y indicates covalent attachment of Y to Z, A or B, depending on the presence or absence of A and/or B, and the hash mark (#) indicates covalent attachment of the benzylic carbon of Y to a methylene carbamate unit.

39. The Ligand-Drug Conjugate Compound of any one of embodiments 4 to 38 wherein the Stretcher unit (Z) comprises a succinimide moiety or an acid-amide moiety, wherein that moiety is attached to a sulfur atom of the Ligand Unit.

40. The Ligand-Drug Conjugate Compound of embodiment 39 wherein the Stretcher unit (Z) is comprised of a succinimide moiety and is represented by the structure of formula Xa':

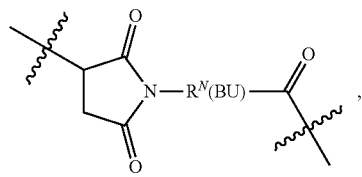

(Xa')

wherein the wavy line adjacent to the succinimide ring system indicates covalent attachment to a sulfur atom of a Ligand Unit; the wavy line adjacent to the carbonyl indicates attachment within the linker; and RN is $—C_2-C_5$ alkylene, wherein the alkylene is optionally substituted by a Basic Unit (BU), wherein BU is $—(CH_2)_xNH_2$, $—(CH_2)_xNHR^{op}$, or $—(CH_2)_xN(R^{op})_2$, wherein x is an integer ranging from 1-4; and $R^{op}$ is $C_{1-6}$ alkyl.

41. The Ligand-Drug Conjugate Compound of embodiment 39 wherein the Stretcher unit (Z) is comprised of a succinimide moiety and is represented by the structure:

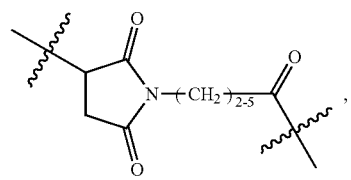

wherein the wavy line adjacent to the succinimide ring system indicates covalent attachment to a sulfur atom of a Ligand Unit, and the wavy line adjacent to the carbonyl indicates attachment within the linker.

42. The Ligand-Drug Conjugate Compound of embodiment 39 wherein the Stretcher unit (Z) is comprised of a succinimide moiety or an acid-amide moiety and is represented by the structure of:

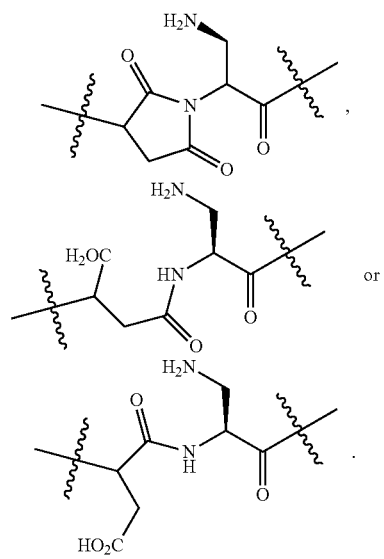

43. The Ligand-Drug Conjugate Compound of any one of embodiments 2 to 42 wherein a Connector Unit (A) is present.

44. The Ligand-Drug Conjugate Compound of embodiment 43 wherein A is:

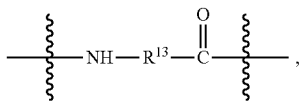

wherein the wavy line adjacent to the carbonyl indicates covalent attachment to the activateable self-immolative moiety X of the Self-immolative Assembly Unit, and the other wavy line indicates attachment to B, if present, or to Z if B is absent; and $R^{13}$ is —$C_1$-$C_6$ alkylene-, —$C_3$-$C_8$carbocyclo-, -arylene-, —$C_1$-$C_{10}$ heteroalkylene-, —$C_3$-$C_8$heterocyclo-, —$C_1$-$C_{10}$alkylene-arylene-, -arylene-$C_1$-$C_{10}$alkylene-, —$C_1$-$C_{10}$alkylene-($C_3$-$C_8$carbocyclo)-, —($C_3$-$C_8$carbocyclo)-$C_1$-$C_{10}$alkylene-, —$C_1$-$C_{10}$alkylene-($C_3$-$C_8$ heterocyclo)-, or —($C_3$-$C_8$ heterocyclo)-$C_1$-$C_{10}$ alkylene-.

45. The Ligand-Drug Conjugate Compound of embodiment 44 wherein A has the formula

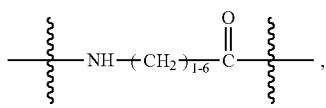

46. The Ligand-Drug Conjugate Compound of any one of embodiments 4 to 42 wherein A is absent.

47. The Ligand-Drug Conjugate Compound of any one of embodiments 4 to 46 wherein p ranges from 1 to 10.

48. The Ligand-Drug Conjugate Compound of any one of embodiments 4 to 46 wherein p ranges from 1 to 8.

49. The Ligand-Drug Conjugate Compound of any one of embodiments 1 to 48 wherein the Ligand Unit corresponds to a targeting antibody.

50. A Drug-Linker compound, wherein the compound comprises a Drug Unit and a Linker Unit, wherein the Linker Unit is comprised of a Self-Immolative Assembly Unit having a methylene carbamate unit and an activateable self-immolative moiety wherein the Drug Unit is covalently attached to the methylene carbamate unit, wherein the Drug-Linker compound has the structure of formula V:

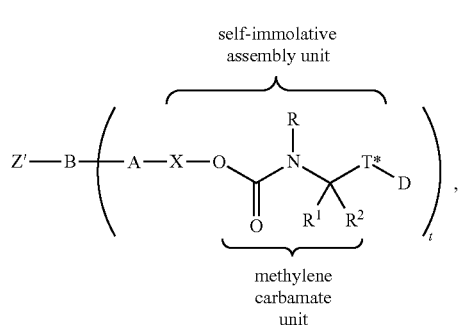

or a pharmaceutically acceptable salt thereof; wherein D is a Drug Unit having a hydroxyl, thiol, amine or amide functional group that has been incorporated into the indicated methylene carbamate unit; T* is the oxygen, sulfur or optionally substituted nitrogen heteroatom from said functional group that becomes incorporated into the indicated methylene carbamate unit; R, $R^1$ and $R^2$ independently are hydrogen, optionally substituted $C_1$-$C_6$ alkyl, optionally substituted $C_{6-14}$ aryl, or optionally substituted C-linked $C_3$-$C_8$ heteroaryl, or both R and $R^1$ together with the nitrogen and carbon atoms to which they are attached comprise an azetidinyl, pyrrolodinyl, piperidinyl or homopiperidinyl moiety (preferably a pyrrolodinyl or piperidinyl moiety) and $R^2$ is hydrogen; X is an activateable self-immolative moiety; Z' is a Stretcher Unit precursor to a Stretcher Unit (Z) and is comprised of a functional group that provides for covalent attachment of a Ligand Unit to Z; B is an optional Branching Unit that is present when t is greater than 1 and absent when t is 1; A is an optional Connector Unit; and the subscript t ranges from 1 to 4.

51. The Drug-Linker compound of embodiment 50 wherein D is a Drug Unit corresponding to a drug having a hydroxyl functional group that has been incorporated into the methylene carbamate unit of the Self-immolative Assembly Unit; and T* is the oxygen atom from that functional group.

52. The Drug-Linker compound of embodiment 50 or 51 wherein X is —Y(W)—, wherein —Y(W)— is represented by the structure of:

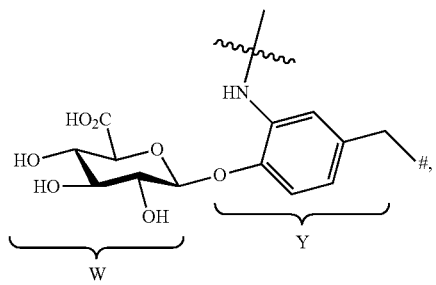

wherein the wavy bond adjacent to the nitrogen of Y indicates covalent attachment to Z', A or B, depending on the presence or absence of A and/or B, and the hash mark (#) indicates covalent attachment of the benzylic carbon of Y to the methylene carbamate unit.

53. The Drug-Linker compound of embodiment 50 or 51, wherein X is —W—Y, wherein —W—Y— is represented by the structure of:

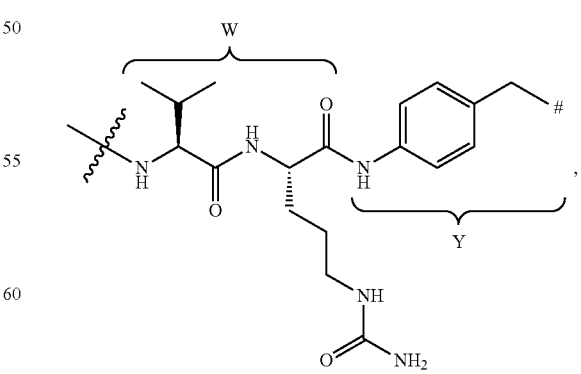

wherein the wavy bond adjacent to the nitrogen heteroatom of W indicates covalent attachment of W to Z', A or B, depending on the presence or absence of A and/or B and the hash mark (#) indicates covalent attachment of the benzylic carbon of Y to the methylene carbamate unit.

54. The Drug-Linker compound of any one of embodiments 50 to 53 wherein Z' comprises a maleimide moiety.

55. The Drug-Linker compound of embodiment 54 wherein Z' has the formula:

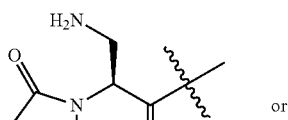 or

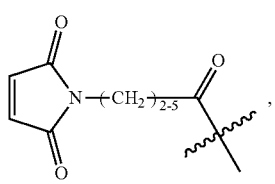, wherein the wavy line adjacent to the carbonyl indicates covalent attachment of Z' to A, B or X, depending on the presence or absence of A and/or B.

56. The Drug-Linker compound any one of claims 50 to 55 wherein A is present and has the formula

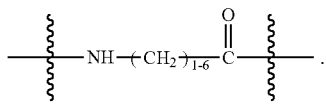.

57. The Drug-Linker compound of any one of embodiments 50 to 56 wherein B is absent and t is 1.

58. The Drug-Linker compound of any one of claims 50 to 56 wherein B is present and t is 2.

59. A Ligand-Drug Conjugate composition comprising a plurality of conjugate compounds, wherein each has the structure of a Ligand-Drug Conjugate Compound of any one of claims 1 to 49, wherein the Conjugate Compounds are differentiated by their p integer values; and a pharmaceutically acceptable carrier.

60. The Ligand-Drug Conjugate composition of embodiment 59 wherein there is an average of 2 to 10 drug-linkers per Ligand Unit.

61. The Ligand-Drug Conjugate composition of embodiment 59 wherein there is an average of 2 to 8 drug-linkers per Ligand Unit.

62. The Ligand-Drug Conjugate Compound of any one of embodiments 1-49, the Drug-Linker compound of any one of claims 50-58 or the Ligand-Drug Conjugate composition of any one of claims 59-61, wherein the Drug Unit corresponds in structure to a compound having hydroxyl functional group whose oxygen heteroatom is capable of incorporation into a methylene carbamate unit, wherein the compound binds to FKBP to inhibit mTOR or calcineurin effector function.

63. The Ligand-Drug Conjugate Compound, Drug-Linker compound or Ligand-Drug Conjugate composition of embodiment 62, wherein the FKBP binding compound is everolimus, tacrolimus or sirolimus.

64. The Ligand-Drug Conjugate Compound, Drug-Linker compound or Ligand-Drug Conjugate composition of embodiment 62, wherein the compound or composition has the structure of:

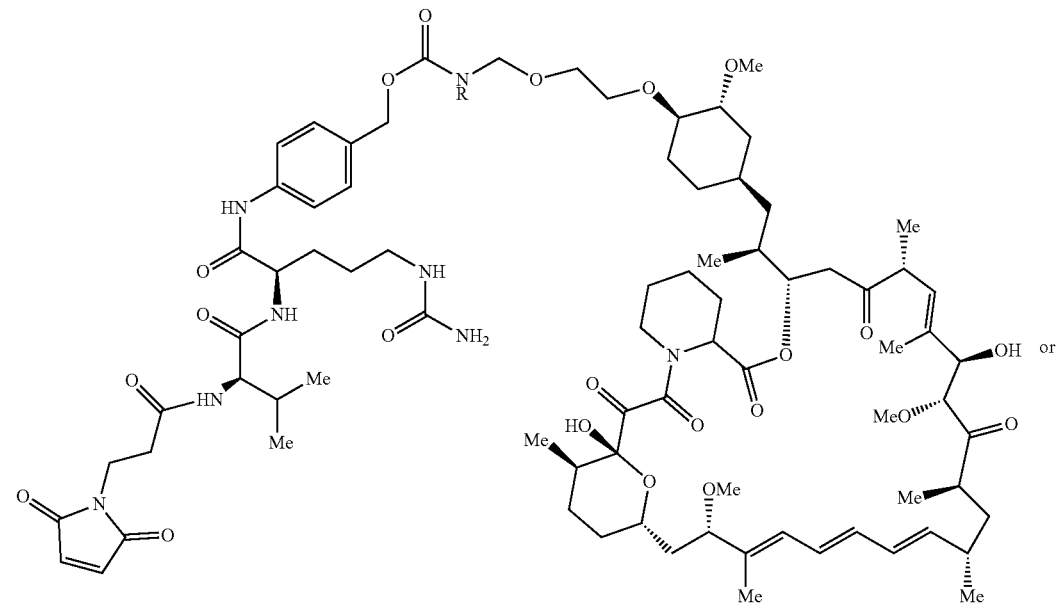

-continued
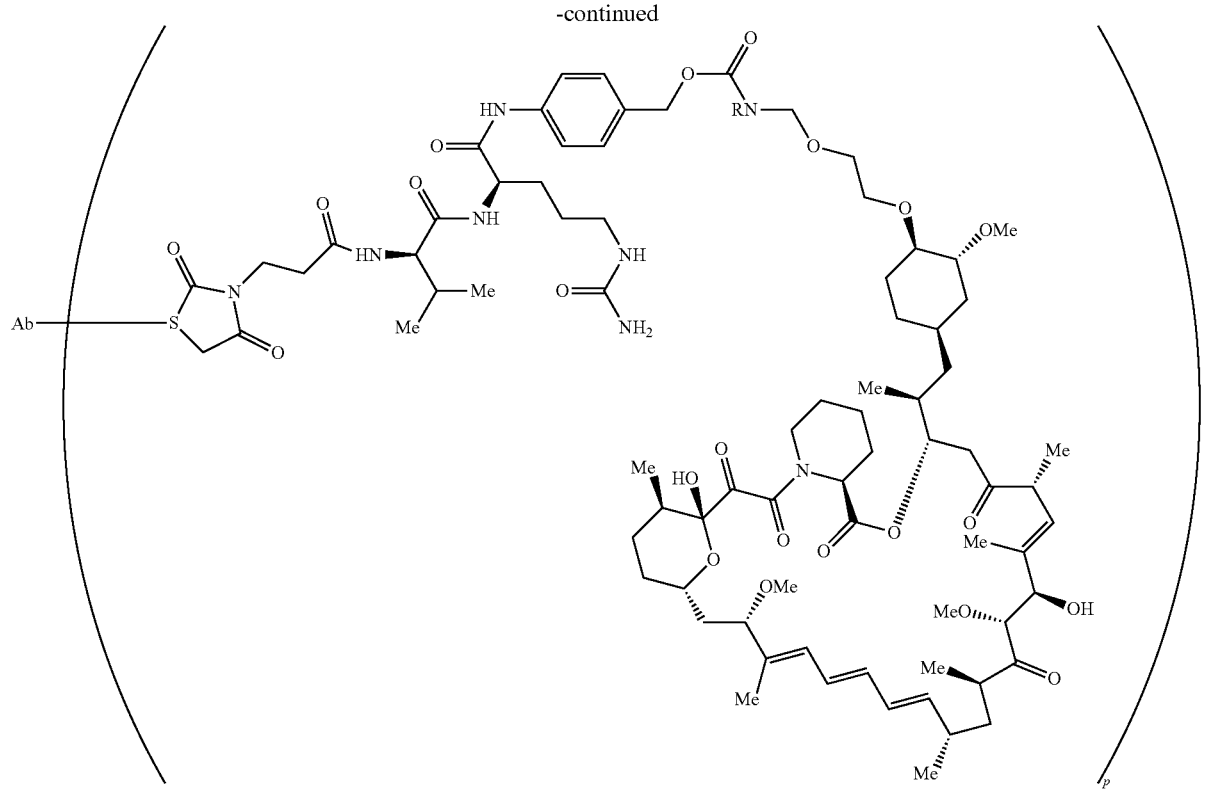
wherein the Ab-S— moiety is a Ligand Unit from a targeting antibody; R is hydrogen, ethyl or $CH_2CH_2N(CH_3)_2$; and p ranges from 1 to 20, 1 to 16 or 1 to 8.
65. The Ligand-Drug Conjugate Compound, Drug-Linker compound or Ligand-Drug Conjugate composition of embodiment 62, wherein the compound or composition has the structure of:
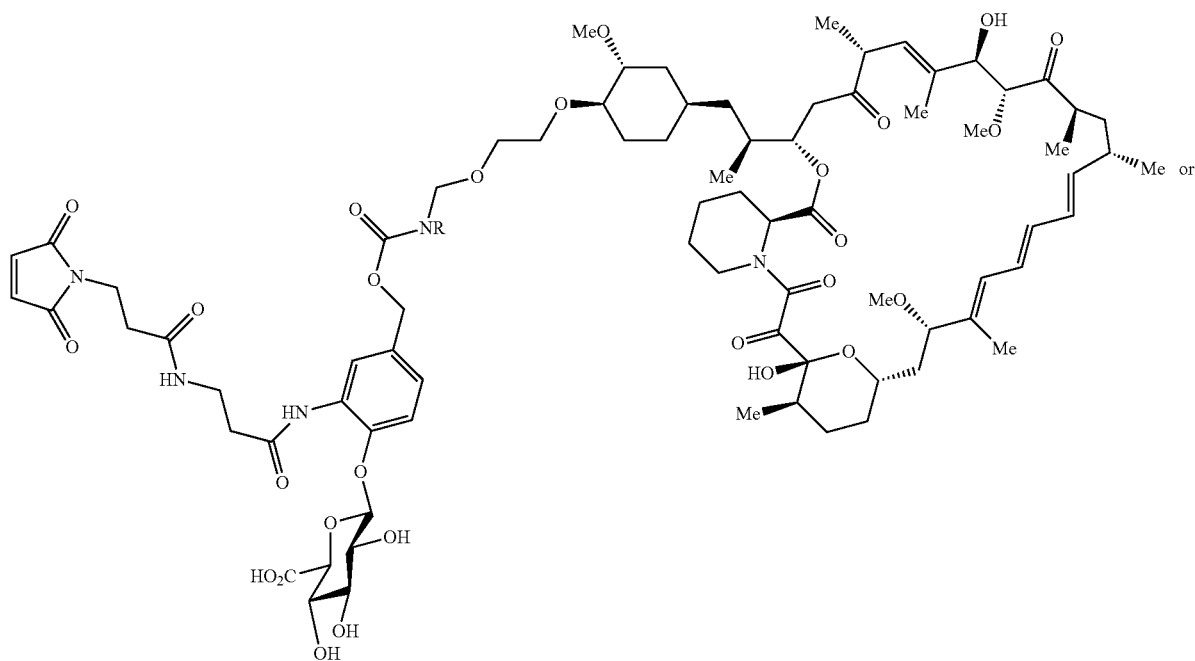

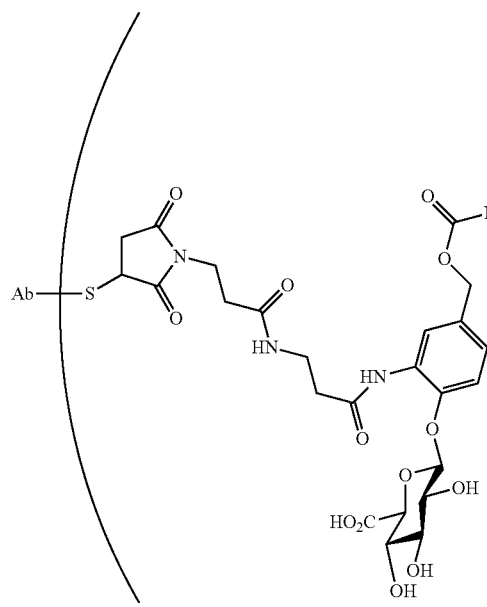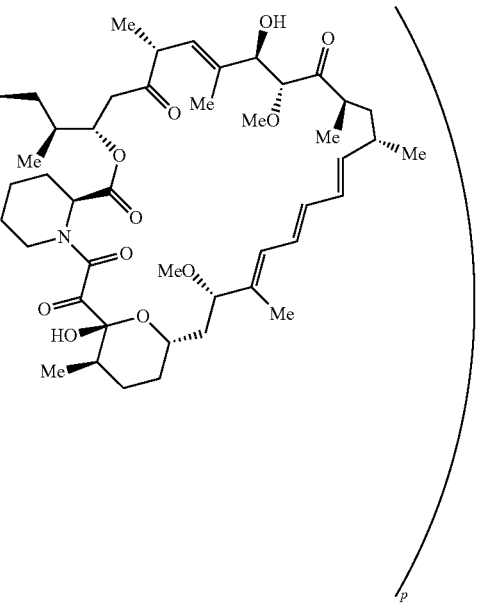
wherein the Ab-S— moiety is a Ligand Unit from a targeting antibody; R is hydrogen, ethyl or $CH_2CH_2N(CH_3)_2$; and p ranges from 1 to 20, 1 to 16 or 1 to 8.
66. The Ligand-Drug Conjugate Compound, Drug-Linker compound or Ligand-Drug Conjugate composition of embodiment 62, wherein the compound or composition has the structure of:
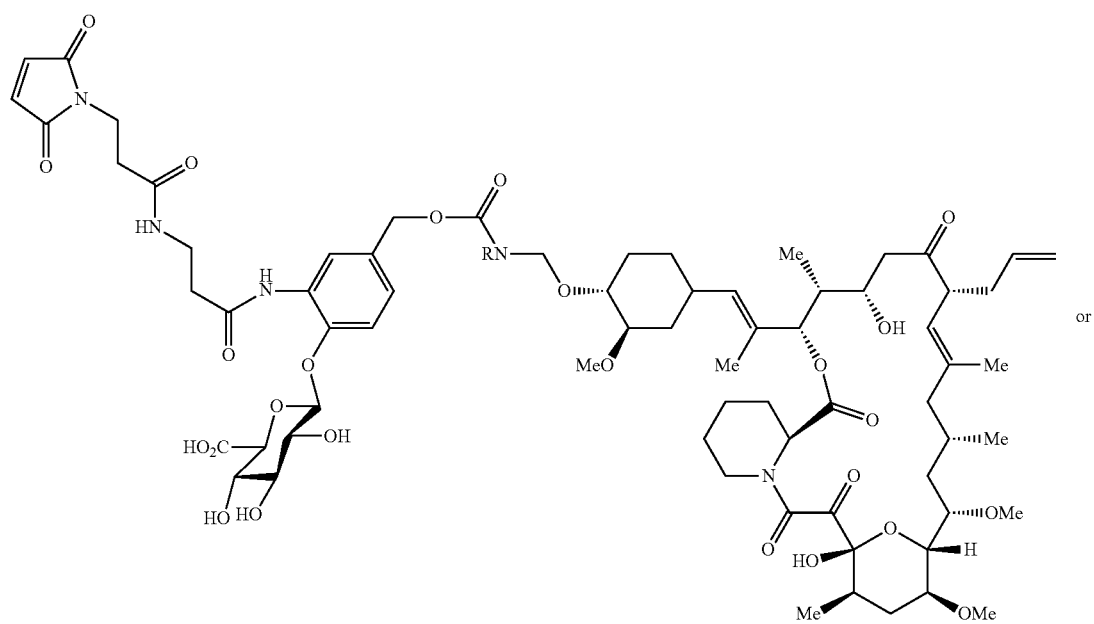
or -continued

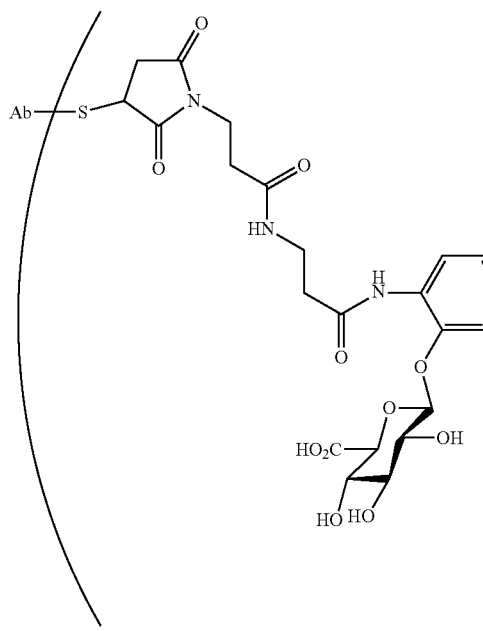

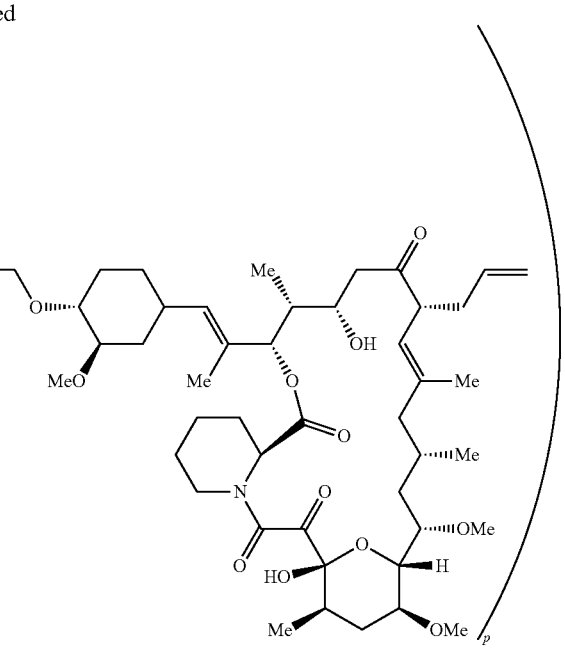

wherein the Ab-S— moiety is a Ligand Unit from a targeting antibody; R is hydrogen, ethyl or CH$_2$CH$_2$N(CH$_3$)$_2$; and p ranges from 1 to 20, 1 to 16 or 1 to 8.

67. The Ligand-Drug Conjugate Compound of any one of embodiments 1-49, the Drug-Linker compound of any one of embodiments 50-58 or the Ligand-Drug Conjugate composition of any one of embodiments 59-61, wherein the Drug Unit corresponds in structure to a auristatin having hydroxyl functional group whose oxygen heteroatom is capable of incorporation into a methylene carbamate unit, wherein the compound binds to tubulin to disrupt tubulin function.

68. The Ligand-Drug Conjugate Compound, Drug-Linker compound or Ligand-Drug Conjugate composition of embodiment 67 wherein the auristatin is MMAE or auristatin T.

69. A method of treating cancer or an autoimmune disease comprising administering to a subject in need thereof, an effective amount of a Ligand-Drug Conjugate of any one of embodiments 1 to 49 or a Ligand-Drug Conjugate composition any one of embodiments 59 to 70. A method of preparing a Drug-Linker Compound having the structure of

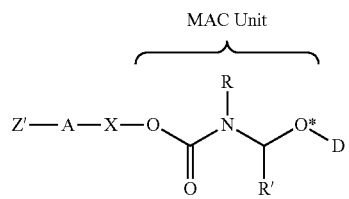

said method comprising: contacting a modified free drug having the structure of:

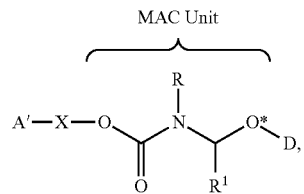

with an intermediate linker moiety represented by: Z'-A-X'—OH under conditions sufficient for providing the indicated MAC unit through Curtius rearrangement, wherein D is a Drug Unit having a hydroxyl functional group that has been incorporated into the MAC, the oxygen heteroatom from which is designated by O*; Z' is a stretcher unit precursor to a Stretcher Unit (Z) in a Ligand-Drug Conjugate and is comprised of a functional group capable of conjugation to a targeting ligand; A is an optional Connector Unit; X is an activeatable self-immolative moiety; X' is a self-immolative moiety precursor to X and has a hydroxyl functional group that participates in the Curtius rearrangement; R is hydrogen; and R$^1$ is hydrogen, or C$_1$-C$_6$ alkyl, C$_6$-C$_{14}$ aryl or C-linked heteroaryl, optionally substituted with suitable protection as required.

71. A method of preparing an intermediate of a Drug-Linker compound wherein the intermediate has the structure of:

said method comprising: contacting a modified free drug having the structure of:

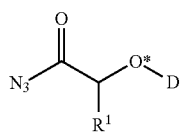

with a self-immolative intermediate represented by: A'-X—OH, under conditions sufficient for providing the indicated MAC Unit through Curtius rearrangement, wherein D is a Drug Unit having a hydroxyl functional group that has been incorporated into the MAC, the oxygen heteroatom from which is designated by O*, A' is a Connector Unit precursor to a Connector Unit (A) and is comprised of a functional group for bond formation to the remainder of the Linker Unit of the Drug-Linker compound; X is an activeatable self-immolative moiety; R is hydrogen; and $R^1$ is hydrogen, or $C_1$-$C_6$ alkyl, $C_6$-$C_{14}$ aryl or C-linked heteroaryl, optionally substituted with suitable protection as required.

72. A method of preparing a Drug-Linker Compound wherein the compound has the structure of:

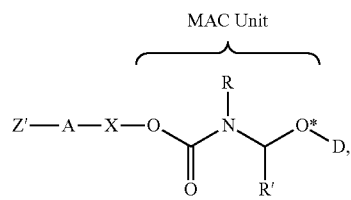

said method comprising: contacting a drug having a free hydroxyl functional group with a N-chloromethylamine having the structure of:

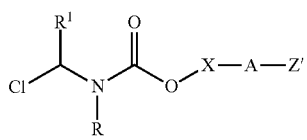

under conditions sufficient for substitution of the chorine atom with the oxygen heteroatom from said free drug functional group, wherein Z' is a Stretcher Unit precursor to a Stretcher Unit (Z) of the Drug-Linker Compound and comprises a functional group for attachment of a targeting ligand; A is an optional Connector Unit; X is an activeatable self-immolative moiety; R is hydrogen, or $C_1$-$C_6$ alkyl, $C_6$-$C_{14}$ aryl or C-linked heteroaryl, optionally substituted with suitable protection; and IV is hydrogen, or $C_1$-$C_6$ alkyl, $C_6$-$C_{14}$ aryl or C-linked heteroaryl, optionally substituted with suitable protection as required, or R and $R^1$ together with the nitrogen and carbon atoms to which they are attached comprise a pyrrolodinyl or piperidinyl moiety.

73. A method of preparing an intermediate of a Drug-Linker Compound wherein the intermediate has the structure of:

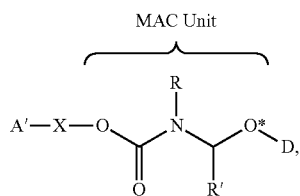

said method comprising: contacting a drug having a free hydroxyl functional group with a N-chloromethylamine having the structure of:

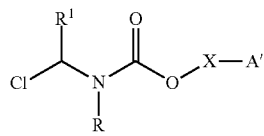

under conditions sufficient for substitution of the chorine atom with the oxygen heteroatom from said free drug functional group, wherein Z' is a Stretcher Unit precursor to a Stretcher Unit (Z) of the Drug-Linker Compound and comprises a functional group for attachment of a targeting ligand; A' is a Connector Unit precursor to a Connector Unit (A) and is comprised of a functional group for bond formation to the remainder of the Linker Unit of the Drug-Linker compound; X is an activatable self-immolative moiety; R is hydrogen, or $C_1$-$C_6$ alkyl, $C_6$-$C_{14}$ aryl or C-linked heteroaryl, optionally substituted with suitable protection; and $R^1$ is hydrogen, or $C_1$-$C_6$ alkyl, $C_6$-$C_{14}$ aryl or C-linked heteroaryl, optionally substituted with suitable protection as required, or R and $R^1$ together with the nitrogen and carbon atoms to which they are attached comprise a pyrrolodinyl or piperidinyl moiety.

EXAMPLES

Summary

Examples 1 and 2 describe alternative preparations of a Drug-Linker Compound having a Drug Unit (D) covalently attached to a methylene alkoxy carbamate unit of formula Ia' wherein the Drug Unit is from auristatin E. The resultant Drug-Linker Compound has the generalized structure of formula V':

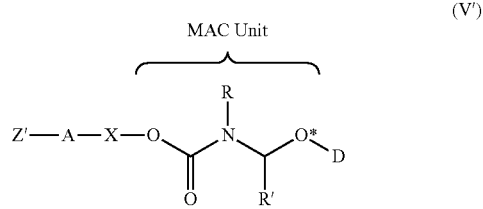

wherein R and R' are hydrogen and the activateable moiety X is —Y(W)— wherein —Y(W)— has the structure of formula XVId:

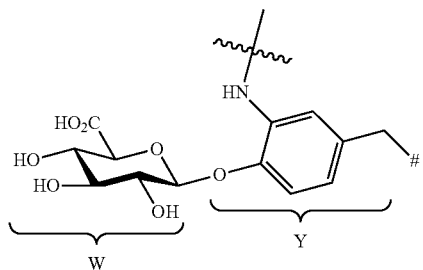

(XVId)

wherein the wavy line to the nitrogen heteroatom of the self-immolative Spacer Unit (Y) indicates covalent attachment to the Connector Unit (A) and the hash mark (#) indicates covalent attachment of the benzylic carbon of Y to the MAC Unit, wherein O* is the oxygen heteroatom from the hydroxyl functional group of free drug.

Example 3 describes the synthesis of a model self-immolative assembly unit having a cyclic MAC Unit and its conditional self-immolation.

Examples 4, 5 and 6 describes the synthesis of Drug-Linker Compounds wherein the Drug Units are from triptolide, everolimus and tacrolimus (FK-506), respectively, in which a hydroxyl functional group of free drug is used in conjugation so that its oxygen heteroatom becomes incorporated into a formula Ia' MAC Unit. For two of those drugs (tacrolimus and triptolide) the hydroxyl functional group is a sterically hindered secondary hydroxyl functional group.

Example 7 describes the synthesis of a Drug-Linker Compound having a Drug Unit (D) covalently attached to a methylene carbamate unit of formula Ia wherein the Drug Unit is from a tetrahydroquinoline-containing compound (BMN-673). The resultant Drug-Linker Compound has the generalized structure of formula V:

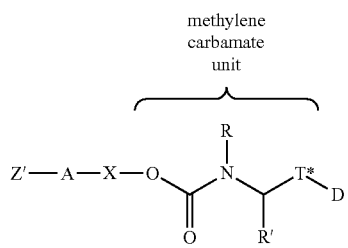

(V)

wherein R and R' are hydrogen and the activateable moiety X is —Y(W)— having the structure of formula XVId and wherein T* represents the cyclized nitrogen heteroatom from the amine functional group (—NH—) in the tetrahydroquinoline ring system of BMN-673 that has been incorporated into a methylene carbamate unit. The example demonstrates a variant of the MAC Unit adapted for use for conjugation of amine-containing drugs, in this instance where T* is a cyclic aniline nitrogen.

Example 8 describes the preparation of model Self-immolative Assembly Units each comprised of a MAC Units and its variant covalently attached to a Drug Unit corresponding to model drug compounds for thiol-containing drugs, primary, secondary and tertiary aliphatic alcohol-containing drugs, and phenolic alcohol-containing drugs wherein each Self-immolative Assembly Units is capable of releasing the model drug compound subsequent to initiation of self-immolation within the Self-immolative Assembly Unit.

Example 9 describes the in vitro stability to spontaneous hydrolysis of MAC Units and their variants in Self-immolative Assembly Units of drug-linker moieties in model Ligand Drug Conjugates and the unexpected increase in half-life at pH 7.0 resulting from a Basic Unit tethered to the MAC unit's carbamate nitrogen.

Example 10 describes in vitro stabilities of N-acetyl cysteine (NAC) conjugates wherein the N-acetyl cysteinyl moiety is a stand-in for a Ligand Unit, to spontaneous hydrolysis of its methylene carbamate unit.

Example 11 describes the ex vivo stability of an ADC to spontaneous hydrolysis of its methylene carbamate unit.

Example 12 describes the release of drug or model compounds for a thiol-containing drug, primary, secondary and tertiary aliphatic alcohol-containing drugs, and an aromatic alcohol-containing drug from NAC-conjugates having a Self-immolative Assembly Unit comprised of a MAC Unit or variant thereof subsequent to glucuronidase activation of that unit.

Example 13 describes the efficient release of an tetrahydroquinoline-containing compound (BMN-673) whose aromatic amine nitrogen corresponds to the optionally substituted nitrogen heteroatom of a methylene carbamate unit covalently attached to a Drug Unit from a NAC conjugate comprised of a Self-immolative assembly unit upon conditional activation that initiates self-immolation within Self-immolative Assembly Units comprised of these methylene carbamate units.

Example 14 describes the cytotoxicity of Antibody Drug Conjugates to cancer cells targeted by its antibody Ligand Unit each having a MAC Unit that conditionally releases a cytotoxic free drug.

General Information:

The following information is applicable to the synthetic procedures described in this section unless indicated otherwise. All commercially available anhydrous solvents were used without further purification. Analytical thin layer chromatography was performed on silica gel 60 F254 aluminum sheets (EMD Chemicals, Gibbstown, N.J.). Radial chromatography was performed on Chromatotron™ apparatus (Harris Research, Palo Alto, Calif.). Column chromatography was performed on a Biotage Isolera One™ flash purification system (Charlotte, N.C.). Analytical HPLC was performed on a Varian ProStar™ 210 solvent delivery system configured with a Varian ProStar 330 PDA detector. Samples were eluted over a C12 Phenomenex Synergi™ 2.0×150 mm, 4 μm, 80 Å reverse-phase column. The acidic mobile phase consisted of acetonitrile and water both containing either 0.05% trifluoroacetic acid or 0.1% formic acid. Compounds were eluted with a linear gradient of acidic acetonitrile from 5% at 1 min post injection, to 95% at 11 min, followed by isocratic 95% acetonitrile to 15 min (flow rate=1.0 mL/min). LC-MS was performed on a Waters Xevo™ G2 Tof mass spectrometer interfaced to a Waters 2695 Separations Module equipped with a C12 Phenomenex Synergi 2.0×150 mm, 4 μm, 80 Å reverse phase column with a Waters 2996 Photodiode Array Detector. The acidic eluent consisted of a linear gradient of acetonitrile from 5% to 95% in 0.1% aqueous formic acid over 10 min, followed by isocratic 95% acetonitrile for 5 min (flow rate=0.4 mL/min). UPLC-MS was performed on a Waters SQ mass detector interfaced to an Acquity Ultra Performance™ LC equipped with an Acquity UPLC BEH C18 2.1×50 mm, 1.7 μm reverse phase column. The acidic mobile phase (0.1% formic acid) consisted of a gradient of 3% acetonitrile/97% water to 100% acetonitrile (flow rate=0.5 mL/min unless otherwise indicated). Preparative HPLC was carried out on a Varian ProStar 210 solvent delivery system configured with a Varian ProStar 330 PDA detector. Products were purified over a C12 Phenomenex Synergi 10.0×250 mm, 4 μm, 80 Å reverse phase column eluting with 0.1% trifluoroacetic acid in water (solvent A) and 0.1% trifluoroacetic acid in acetonitrile (solvent B). The purification method consisted of the following gradient of solvent A to solvent B: 90:10 from 0 to 5 min; 90:10 to 10:90 from 5 min to 80 min; followed by isocratic 10:90 for 5 min. The flow rate was 4.6 mL/min with monitoring at 254 nm.

Example 1: Synthesis of an Auristatin E Drug-Linker Compound Comprising the MAC Linker Using the Curtius Rearrangement Synthesis of (2S,3R,4S,5S,6S)-6-(2-(3-((((9H-fluoren-9-yl)methoxy)carbonyl)amino)propanamido)-4-((7S,8R,11R,12R)-12-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-8,11-dimethyl-3,10-dioxo-7-phenyl-2,6,13-trioxa-4,9-diazatetradecyl)phenoxy)-5-(methoxycarbonyl)tetrahydro-2H-pyran-2,3,4-triyl triacetate (1.2) via Curtius Rearrangement

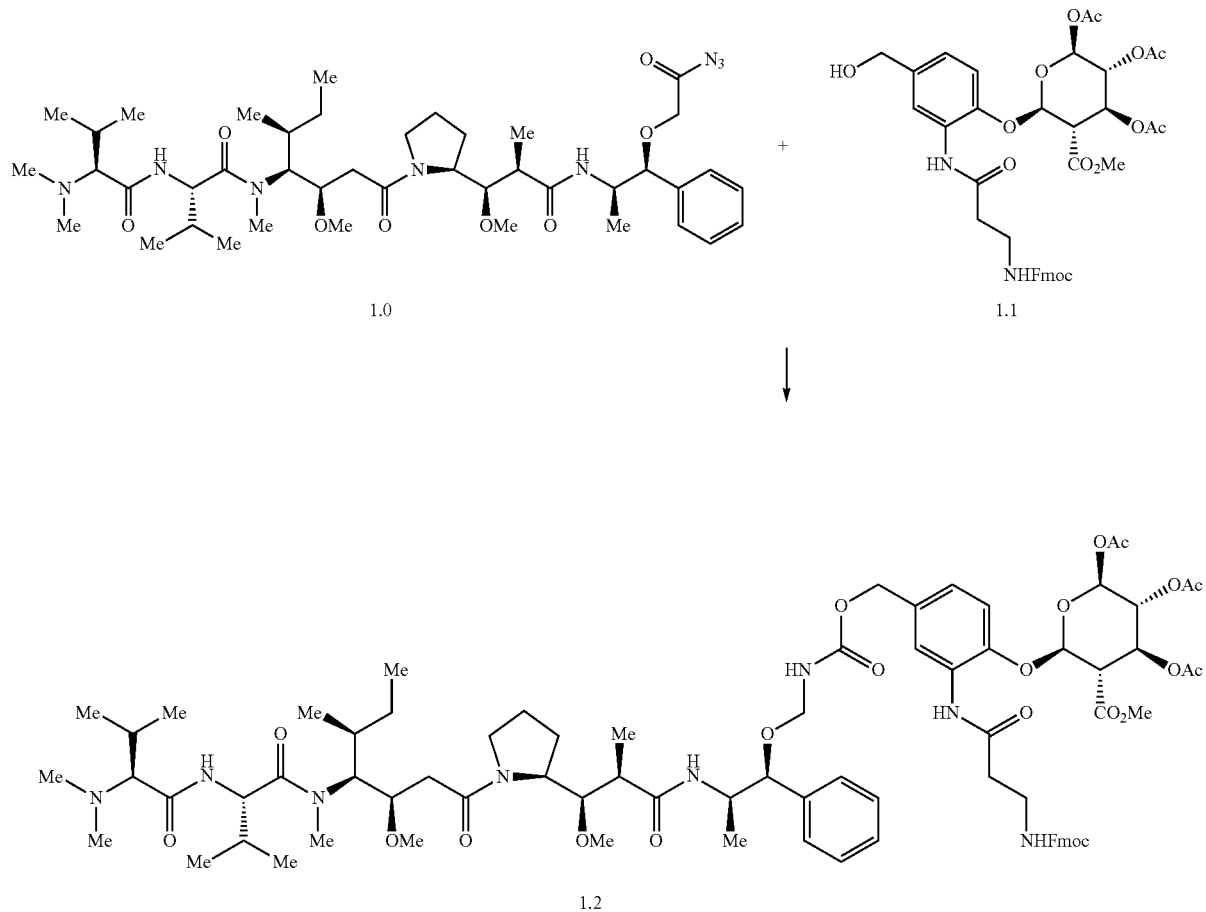

To azido ketone 1.0 (30 mg, 37 μmol), synthesized from the corresponding free auristatin alcohol (for synthesis of 1.1 see Jeffrey et al., Org. Lett. (2010) 12:277) in of DMF (250 μmol) at RT was added 1.1 (90 mg, 120 μmol) to the solution followed by 5 μL of dibutyl tin dilaurate. The reaction mixture was then stirred at 60° C. for 1 hour at which time LC/MS showed the reaction was complete. Subsequently, the reaction was directly purified by preparatory HPLC (gradient 5-95 acetonitrile/water 0.05 TFA) to yield 22 mg of 1.2. MS (m/z) [M+H]$^+$ calc for $C_{80}C_{110}N_8O_{22}$ 1535.77, found 1535.80.

Synthesis of (2S,3S,4S,5R,6R)-2-(4-((7S,8R,11R, 12R)-12-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-8,11-dimethyl-3,10-dioxo-7-phenyl-2,6,13-trioxa-4,9-diazatetradecyl)-2-(3-(3-(2,5-dioxo-2,5-dihydro-1H-pyrrol-1-yl)propanamido)propanamido)phenoxy)-4,5,6-trihydroxytetrahydro-2H-pyran-3-carboxylic acid (1.3)
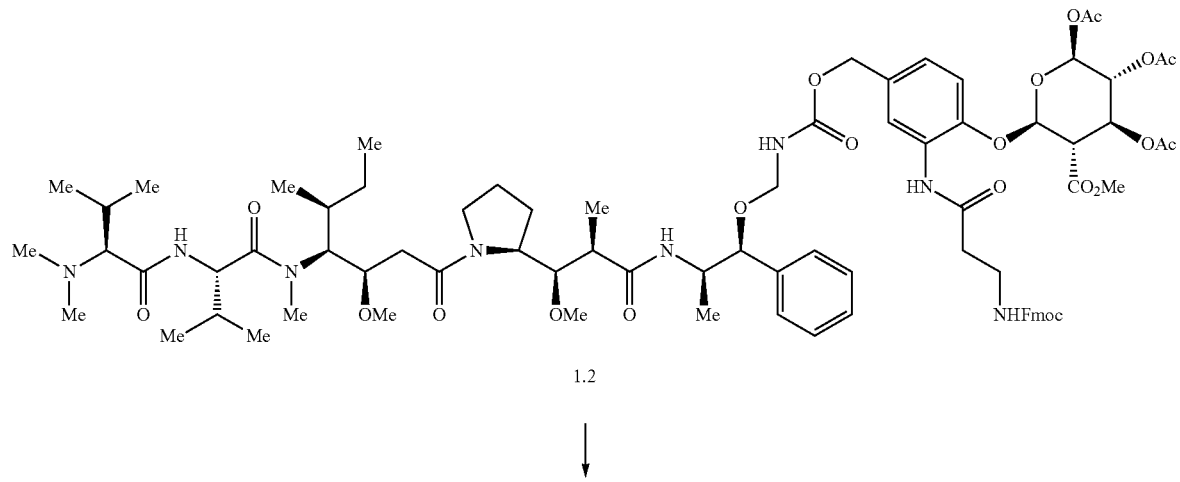
1.2
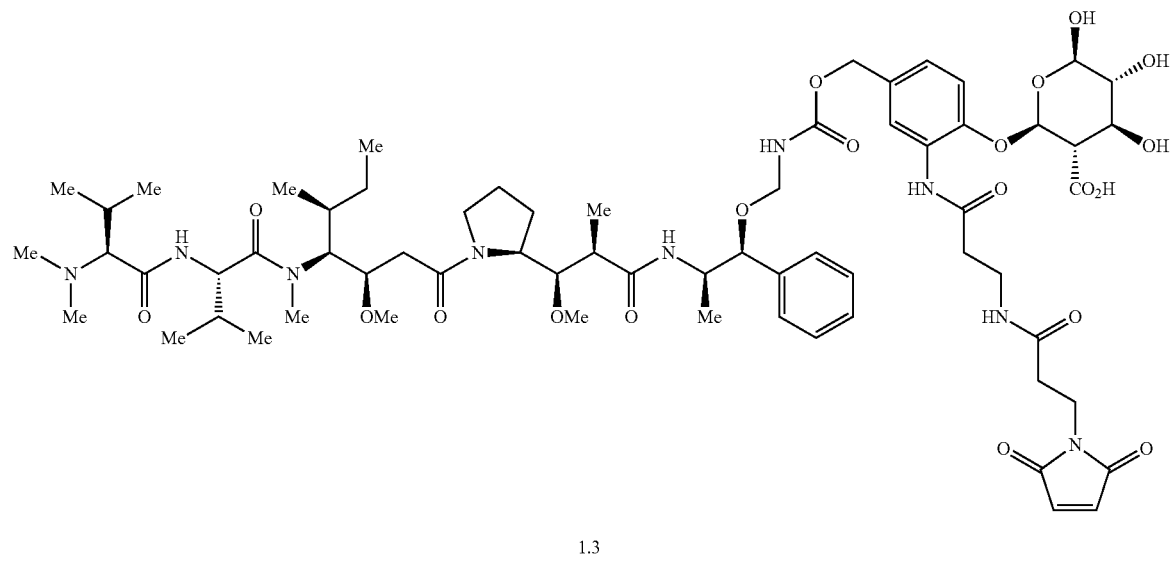
1.3

To a MeOH:Water 1:1 solution of 1.2 (15 mg, 10 μmol) was added LiOH (5 mg). The resulting reaction mixture was vigorously stirred for 10 min at RT at which time LC/MS showed the reaction was complete. The reaction mixture was then directly purified by preparatory HPLC (gradient 5-95 acetonitrile/water 0.05 TFA) to yield 8 mg of deprotected 1.2. Subsequently, DMF (100 μL) was added to a vial containing 8 mg of deprotected 1.2 followed by 20 μL Hünig's base and 10 mg (40 mmol) 3-maleimidopropionic acid N-hydroxysuccimide ester. The reaction was then stirred for 10 minutes at RT at which time LC/MS indicated the reaction was complete. Afterwards, the reaction was directly purified by preparatory HPLC (gradient 5-95 acetonitrile/water 0.05 TFA) to yield 7 mg of 1.3, 60 yield. MS (m/z) [M+H]+ calc for $C_{65}H_{97}N_9O_{20}$, 1324.68, found 1324.60.

Example 2: Synthesis of an Auristatin E Drug-Linker Compound Comprising the MAC Linker Via N-Chlormethylamine Synthesis Synthesis of (2S,3R,4S,5S,6S)-2-(4-((((chloromethyl)(ethyl)carbamoyl)oxy)methyl)-2-nitrophenoxy)-6-(methoxycarbonyl)tetrahydro-2H-pyran-3,4,5-triyl triacetate (1.5)

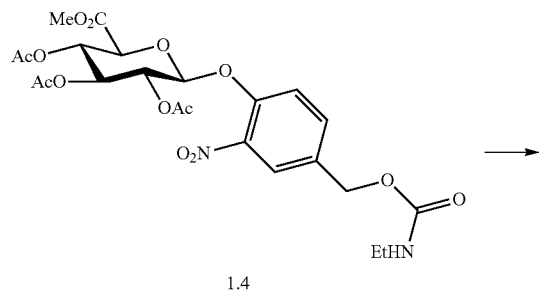

1.4

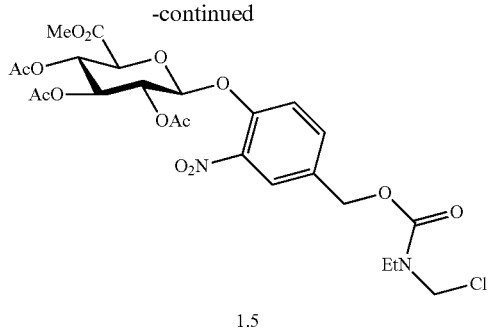

1.5

To a solution of 1.4 (400 mg, 0.36 mmol) (for preparation of 1.4 see Bosslet et al., 1998, J. Med. Chem. 41:3572) in DCM (4 mL) was added paraformaldehyde (32 mg, 0.54 mmol) and TMSCl (0.212 mL, 1.1 mmol). The reaction was stirred for additional 2 hours at RT with monitoring by utilizing methanol as a diluent and following the formation of the methanol adduct by LC/MS. Subsequently, the reaction was filtered and dried in vacuo 450 mg of crude 1.5, which was then used in the subsequent reaction without further purification (see procedure from Barnes et al., 2009, Org. Lett. 11:273). MS (m/z) [M+H]+ calc for the methanol adduct $C_{25}H_{32}N_2O_{15}$ 601.18, found 601.21.

Synthesis of (2R,3S,4R,5R,6R)-2-(4-((7S,8R,11R,12R)-12-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-4-ethyl-8,11-dimethyl-3,10-dioxo-7-phenyl-2,6,13-trioxa-4,9-diazatetradecyl)-2-nitrophenoxy)-6-(methoxycarbonyl)tetrahydro-2H-pyran-3,4,5-triyl triacetate (1.7) via N-chloromethylamine substitution

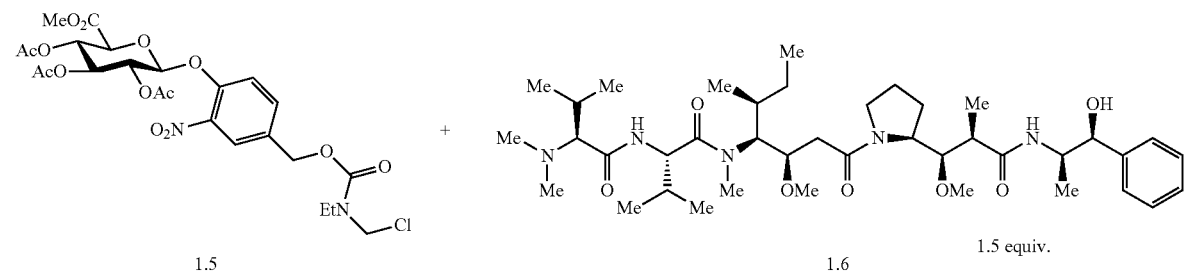

1.5    1.6    1.5 equiv.

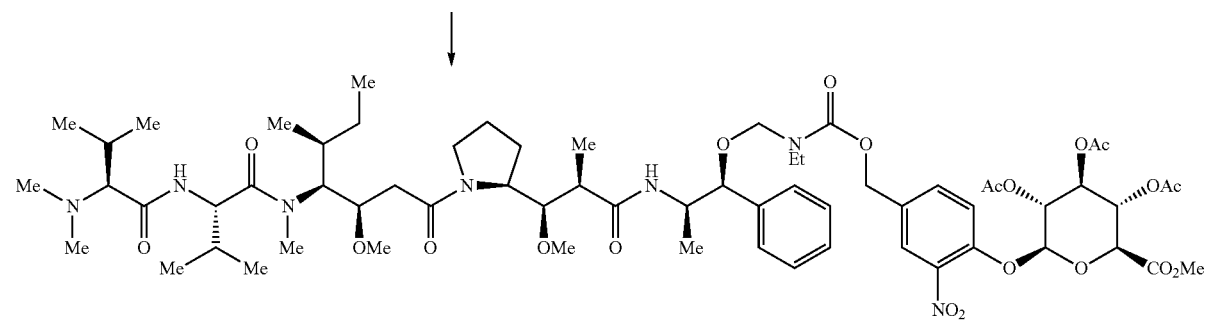

1.7

To a solution of 1.5 (60 mg, 100 μmol) in DCM (300 μL) was added 1.6 (110 mg, 150 μmol) and Hünig's base (50 μL). The reaction was stirred for an additional 90 minutes at RT which time LC/MS showed the reaction was complete. The reaction was then directly purified by preparatory HPLC (gradient 5-95 acetonitrile/water 0.05 TFA) to yield 45 mg of 1.7. MS (m/z) [M+H]+ calc $C_{64}H_{97}N_7O_{21}$ 1300.67, found 1300.71.

Synthesis of (2R,3S,4R,5R,6R)-2-(2-amino-4-((7S, 8R,11R,12R)-12-((S)-1-((3R,4S,5S)-4-((S)-2-((S)-2-(dimethylamino)-3-methylbutanamido)-N,3-dimethylbutanamido)-3-methoxy-5-methylheptanoyl) pyrrolidin-2-yl)-4-ethyl-8,11-dimethyl-3,10-dioxo-7-phenyl-2,6,13-trioxa-4,9-diazatetradecyl)phenoxy)-6-(methoxycarbonyl)tetrahydro-2H-pyran-3,4,5-triyl triacetate (1.8)

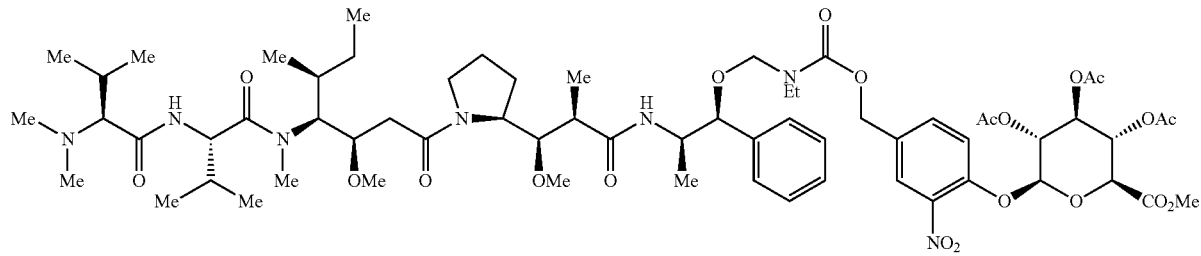

1.7

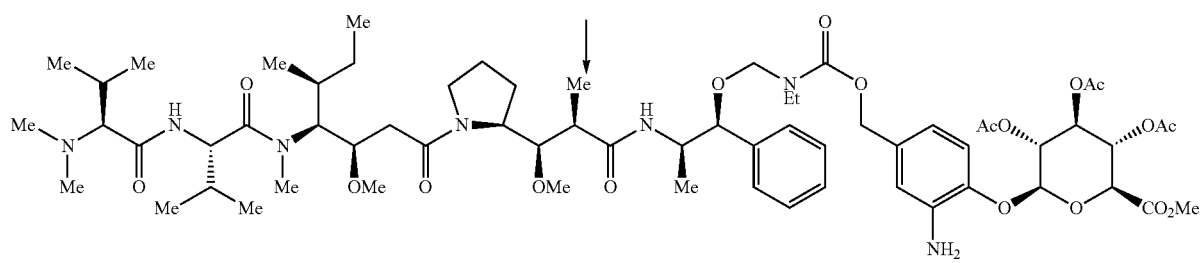

1.8

To 1.7 (10 mg, 6 μmol) in of MeOH (200 μL) at RT was added samarium metal (10 mg, 66 μmol) and ammonium chloride (10 mg, 100 μmol). The reaction mixture was sonicated for 10 minutes at which time LC/MS showed the reaction was complete. Hünig's base (50 μL) was then added to the reaction, which was subsequently filtered via a fritted funnel. The reaction mixture was then taken up in water and purified by preparatory HPLC (gradient 5-95 acetonitrile/water 0.05% TFA) to yield 22 mg of 1.8. MS (m/z) [M+H]+ cald for $C_{64}H_{99}N_7O_{19}$ 1448.75, found 1448.71.

The synthesis of (2R,3S,4R,5R,6R)-2-(2-amino-4-((7S,8R,11R,12R)-12-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-4-ethyl-8,11-dimethyl-3,10-dioxo-7-phenyl-2,6,13-trioxa-4,9-diazatetradecyl)phenoxy)-6-(methoxycarbonyl) tetrahydro-2H-pyran-3,4,5-triyl triacetate (1.9

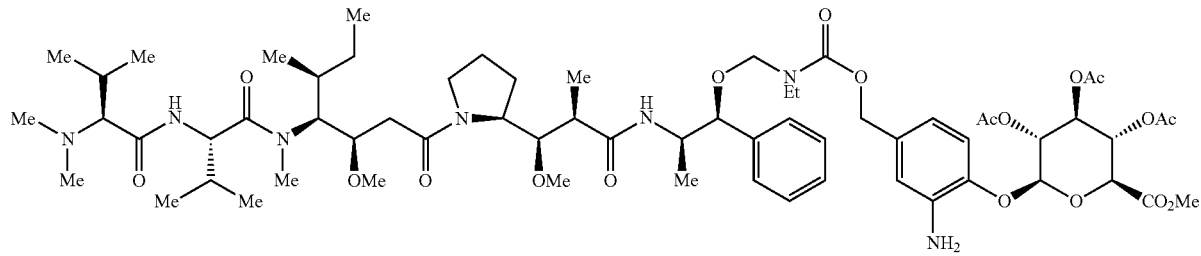

1.8

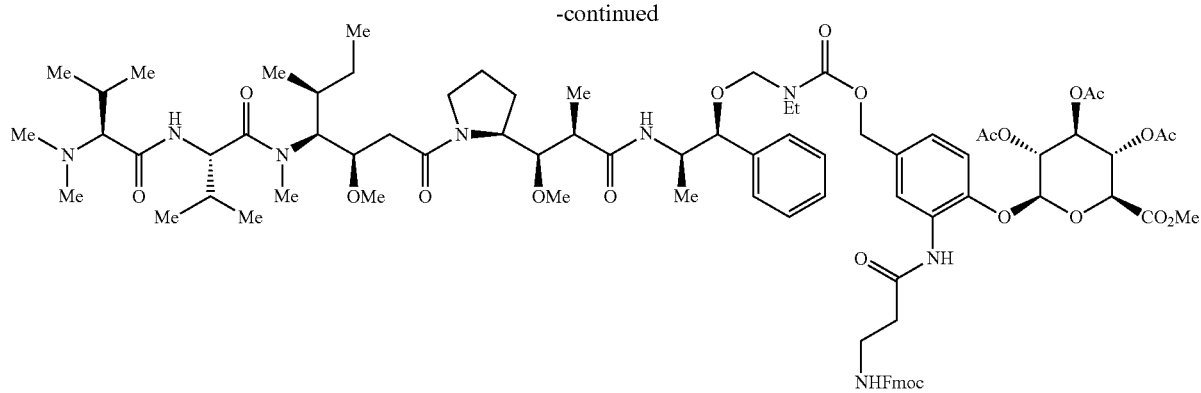

1.9

To a 1 dram vial equipped with a stir bar was added 100 µL of DCM followed by 5 mg (4.0 µmol) 1.8, Fmoc β-alanine (3 mg, 14 µmol) and 5 mg (21 µmol)N-ethoxy-carbonyl-2-ethoxy-1,2-dihydroquinoline. The reaction mixture was then stirred for 3 h at RT at which time LC/MS indicated the reaction was complete. The reaction was purified directly by preparatory HPLC (gradient 5-95 acetonitrile/water 0.05% TFA) to yield 5 mg of 1.9, 83%. MS (m/z) [M+H]$^+$ cald $C_{82}H_{114}N_8O_{22}$ 1563.80, found 1563.84.

The synthesis of (2R,3R, 4R, 5S, 6R)-6-(4-((7S,8R, 11R,12R)-12-((S)-1-((3R,4S,5S)-4-((S)-2-((S)-2-(dimethylamino)-3-methylbutanamido)-N,3-dimethylbutanamido)-3-methoxy-5-methylheptanoyl)pyrrolidin-2-yl)-4-ethyl-8,11-dimethyl-3,10-dioxo-7-phenyl-2,6,13-trioxa-4,9-diazatetradecyl)-2-(3-(3-(2, 5-dioxo-2,5-dihydro-1H-pyrrol-1-yl)propanamido) propanamido)phenoxy)-3,4,5-trihydroxytetrahydro-2H-pyran-2-carboxylic acid, (2.0)

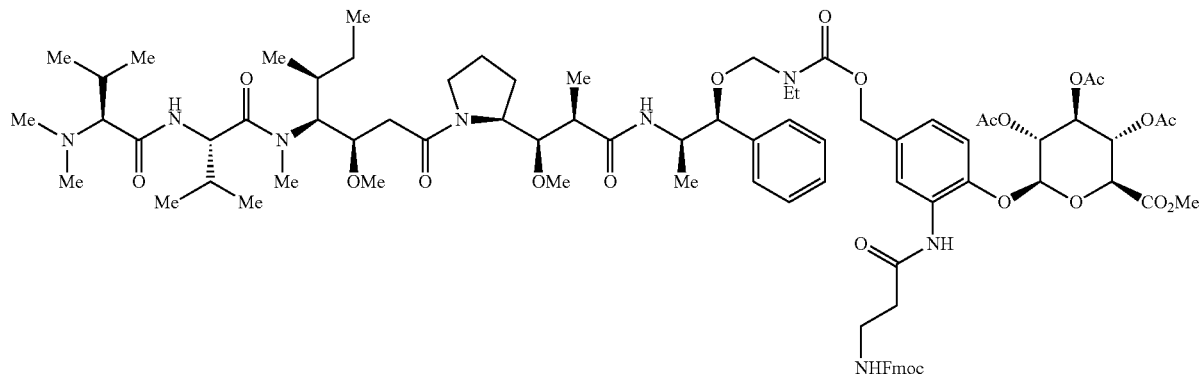

1.9

-continued

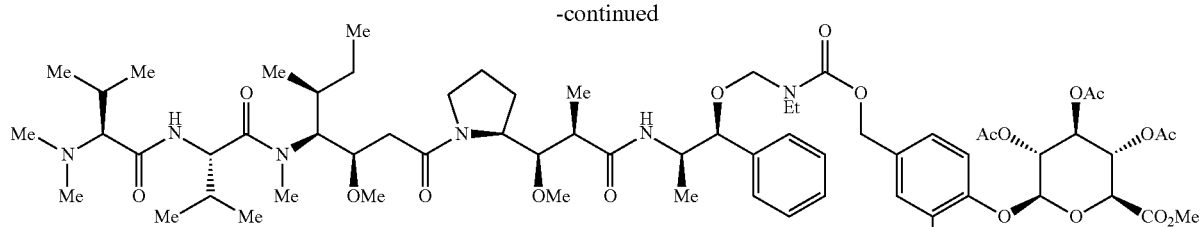

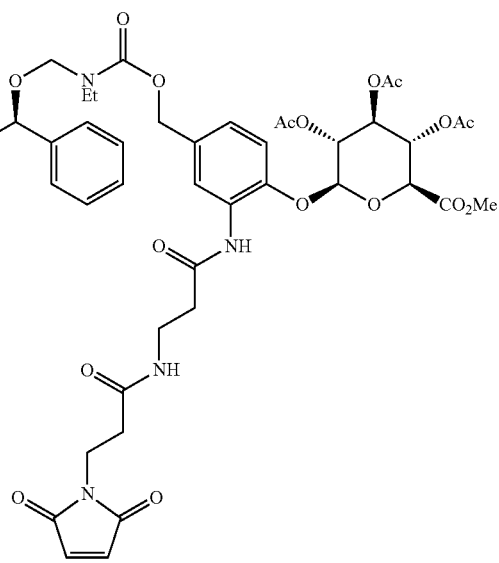

2.0

To a MeOH:Water 1:1 solution of 1.9 (5 mg, 3 µmol) was added LiOH (5 mg). The resulting reaction mixture was then vigorously stirred for 10 min at RT at which time LC/MS showed the reaction was complete. Subsequently, the reaction mixture was directly purified by preparatory HPLC (gradient 5-95 acetonitrile/water 0.05 TFA) to yield 4 mg of deprotected 1.9. DMF (100 µL) was added to a vial containing 4 mg of deprotected 1.9 followed by Hünig's base (20 µL) and 3-maleimidopropionic acid N-hydroxysuccimide ester (10 mg, 40 µmol). The reaction was stirred for 10 minutes at RT at which time LC/MS indicated the reaction was complete. The reaction mixture was subsequently purified directly by preparatory HPLC by first quenching with 3 mL of 2% TFA:water (HPLC gradient 5-95 acetonitrile/water 0.05% TFA) to yield 4.0 mg of 2.0. MS (m/z) [M+H]$^+$ cald for $C_{67}H_{101}N_9O_{20}$, 1351.72, found 1351.65.

Similarly to Examples 1 and 2 monomethyl auristatin E (MMAE) and auristatin T Drug-Linker Compounds comprising the MAC having the following structures are prepared:

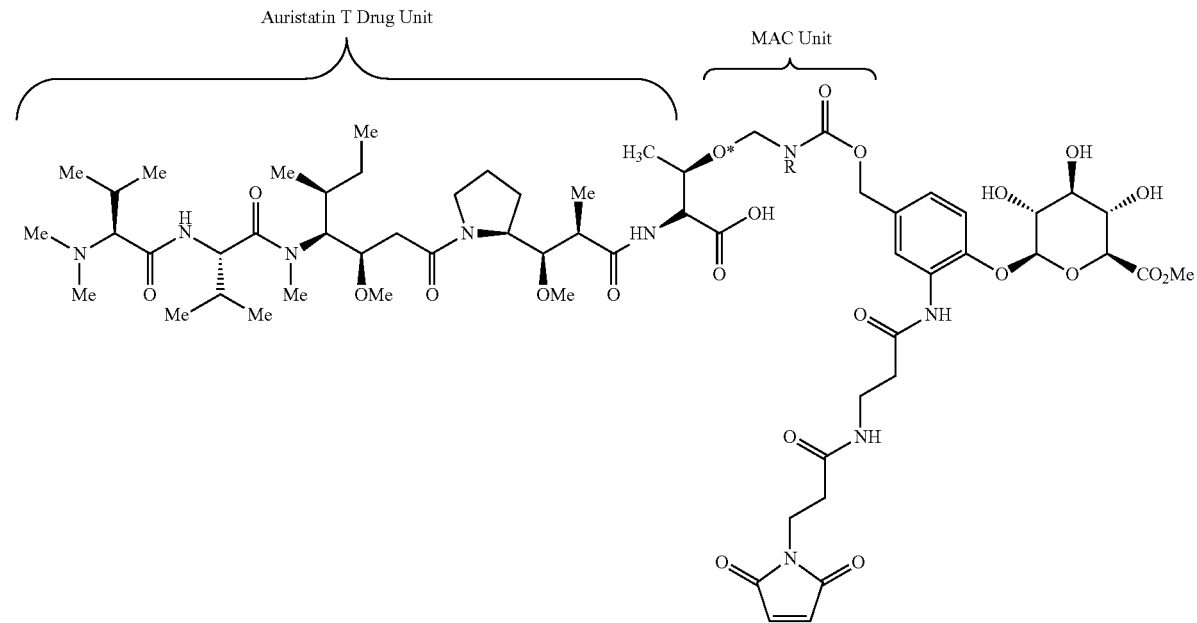

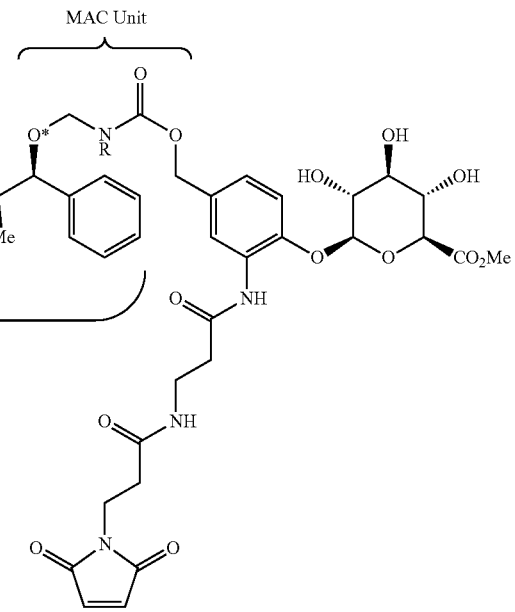

wherein R is hydrogen or ethyl and O* is the oxygen heteroatom of the MAC unit from the secondary hydroxyl functional group of auristatin T or MMAE.

Example 3: Synthesis of a Model Self-Immolative Assembly Unit Having a Cyclic MAC Unit and its Conditional Self-Immolation

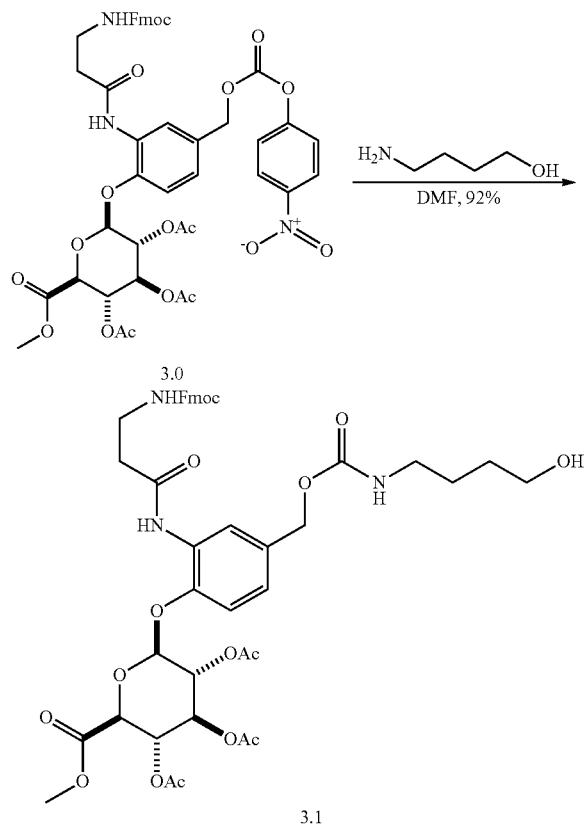

Synthesis of (2S,3R,4S,5S,6S)-2-(2-(3-((((9H-fluoren-9-yl)methoxy)carbonyl)amino)propanamido)-4-(((((4-hydroxybutyl)carbamoyl)oxy)methyl)phenoxy)-6-(methoxycarbonyl)tetrahydro-2H-pyran-3,4,5-triyl triacetate (3.1)

To a mixture of the para-nitrophenyl carbonate 3.0 (300 mg, 0.33 mmol) in DMF (5 mL) was added the 4-aminobutan-1-ol (58 mg, 0.66 mmol). Upon addition of the 4-aminobutan-1-ol, the reaction was complete as judged by UPLC-MS. The mixture was poured into ethyl acetate (100 mL) which was washed with water (3×50 mL) and brine (1×50 mL). The organic phase was dried over sodium sulfate, decanted and concentrated to a residue which was purified by radial chromatography on a 2 mm radial chromatotron plate eluting with ethyl acetate. Product-containing fractions were concentrated under reduced pressure to give 260 mg (92%) of 3.1: $^1$H NMR (CDCl3) δ 8.40 (s, 1H), 8.07 (s, 1H)), 7.75 (d, 2H, J=7.9 Hz), 7.60 (d, 2H, J=7.4 Hz), 7.38 (t, 2H, J=7.4 Hz), 7.29 (m, 2H), 7.01 (d, 1H, J=2.0 Hz), 6.91 (d, 1H, J=6.2 Hz), 5.73 (bs, 1H), 5.4 (t, 1H, J=9.4 Hz), 5.29 (m, 2H), 5.05-5.03 (m, 3H), 4.95 (m, 1H), 4.38 (pent, 2H, J=7.5 Hz), 4.23 (t, 1H, J=7.1 Hz), 4.16 (d, 1H, J=9.7 Hz), 3.73 (s, 3H), 3.65-3.50 (m, 7H), 3.21 (m, 2H), 2.73 (m, 2H), 2.06-2.04 (m, 9H), 1.65-1.59 (m, 4H); UPLC-MS (m/z) (AP+) 864.44 (M+H), $t_r$=1.44 min (flow rate 0.7 mL/min).

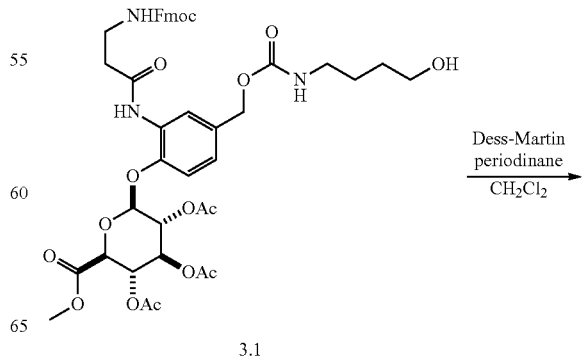

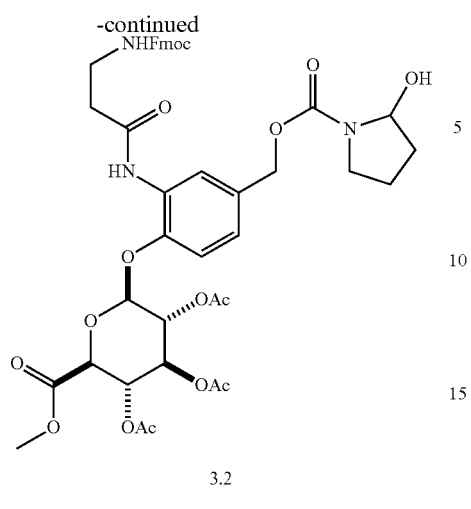

3.2

(2S,3R,4S,5S,6S)-2-(2-(3-((((9H-fluoren-9-yl)methoxy)carbonyl)amino)propanamido)-4-(((2-hydroxypyrrolidine-1-carbonyl)oxy)methyl)phenoxy)-6-(methoxycarbonyl)tetrahydro-2H-pyran-3,4,5-triyl triacetate (3.2)

To a mixture of the alcohol 3.1 (50 mg, 0.056 mmol) in dichloromethane (2 mL) was added Dess-Martin periodinane (30 mg, 0.067 mmol). The reaction mixture was stirred for 3 h before being purified directly on a 1 mm radial chromatotron plate, eluting with 50% ethyl acetate in hexanes, followed by 100% ethyl acetate to provide 19.4 mg (39%) of 3.2: $^1$H NMR (CD$_3$OD) δ 8.04 (d, 2H, J=6.3 Hz), 7.78 (d, 2H, J=7.4 Hz), 7.63 (d, 2H, J=7.5 Hz), 7.37 (t, 2H, J=7.4 Hz), 7.25 (q, 2H, J=7.4 Hz), 7.22 (m, 2H), 7.11 (t, 2H, J=8.2 Hz), 5.49 (t, 1H, J=10.2 Hz), 5.46 (bs, 1H), 5.40 (d, 1H, J=7.9 Hz), 5.19 (t, 1H, J=9.8 Hz), 5.06-5.00 (m, 2H), 4.76 (d, 1H, J=10.1 Hz), 4.37-4.30 (m, 2H), 4.25 (t, 1H, J=6.2 Hz) 3.69 (s, 3H), 3.55-3.45 (m, 4H), 2.65 (pent, 2H, J=6.7 Hz), 2.07-1.95 (m, 11H), 1.24 (m, 3H); UPLC-MS (ink) (AP+) 884.41 (M+Na$^+$), t$_r$=1.48 min (flow rate 0.7 mL/min).

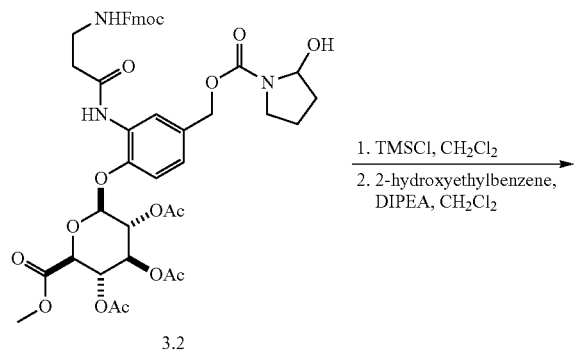

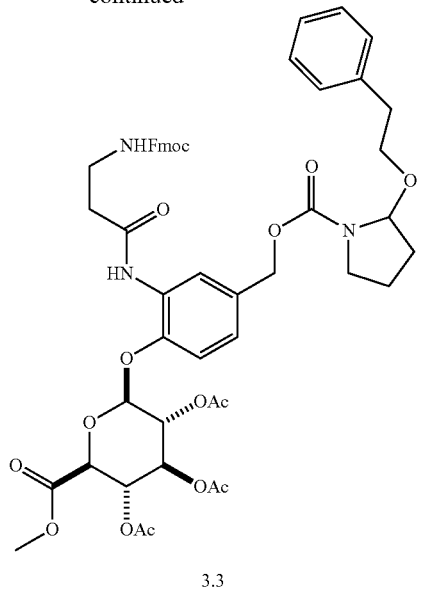

3.3

Synthesis of (2S,3R,4S,5S,6S)-2-(2-(3-((((9H-fluoren-9-yl)methoxy)carbonyl)amino)propanamido)-4-(((2-phenethoxypyrrolidine-1-carbonyl)oxy)methyl)phenoxy)-6-(methoxycarbonyl)tetrahydro-2H-pyran-3,4,5-triyl triacetate (3.3)

To a mixture of the pyrrolidinol 3.2 (19.4 mg, 22.4 μmol) in dichloromethane (2 mL) was added TMSCl (20 μL) and the reaction mixture was stirred for 1 h. The mixture was concentrated under reduced pressure, including high vacuum for 10 min. The resulting residue was dissolved in dichloromethane (1 mL) followed by a 2-hydroxyethylbenzene (10 μL) along with DIPEA (10 μL) Immediately post addition of the alcohol and DIPEA, the reaction was complete as judged by UPLC-MS. The mixture was aspirated directly onto a 1 mm radial chromatotron plate and eluted with 50% ethyl acetate in hexanes to give 13.8 mg (63%) of 3.3: $^1$H NMR (CD3OD) δ 8.13 (bs, 1H), 8.08 (bs, 1H), 7.76 (d, 2H, J=7.4 Hz), 7.61 (d, 2H, J=7.4 Hz), 7.35 (t, 2H, J=7.4 Hz), 7.27-7.03 (m, 8H), 5.48 (t, 1H, J=9 Hz), 5.37 (d, 1H, J=7.9 Hz), 5.3-5.17 (m, 3H), 5.05-4.99 (m, 2H), 4.44 (d, 1H, J=9.8 Hz), 4.34-4.30 (m, 2H), 4.22 (bs, 1H), 3.79-3.67 (m, 1H), 3.66 (s, 3H), 3.64-3.55 (m, 2H), 3.49 (bs, 1H), 3.30 (m, 1H), 2.79 (bs, 1H), 2.66 (m, 3H), 2.01 (s, 6H), 1.96 (s, 3H), 1.81 (m, 2H), 1.75-1.65 (m, 2H); Analytical UPLC-MS: MS (m/z) (ESI+) 988.48 (M+Na$^+$), t$_r$=1.65 min (flow rate 0.7 mL/min).

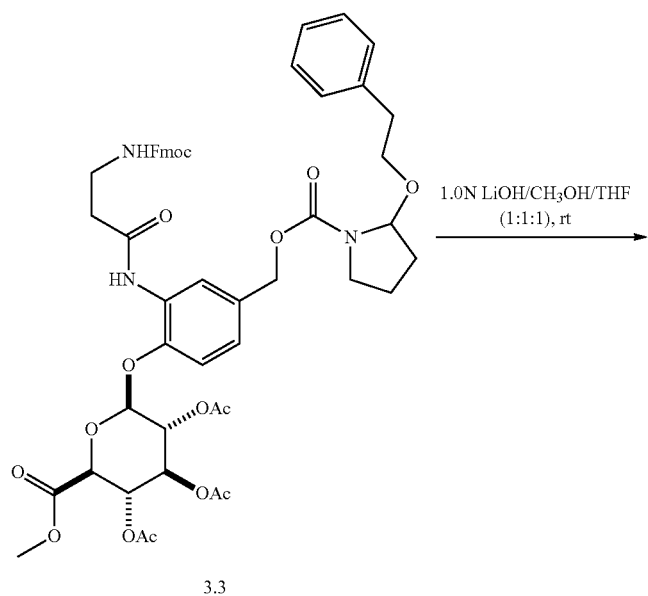

3.3

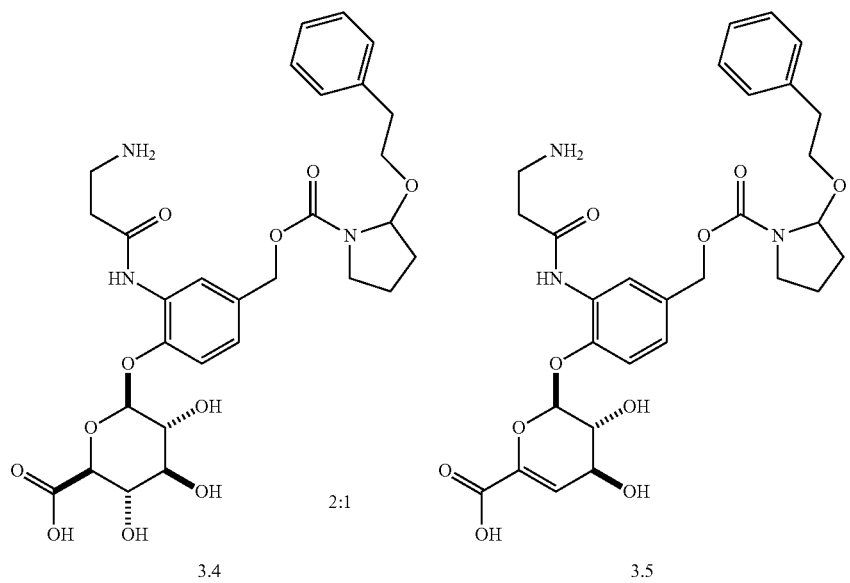

3.4     2:1     3.5

Synthesis of (2S,3S,4S,5R,6S)-6-(2-(3-aminopropanamido)-4-(((2-phenethoxypyrrolidine-1-carbonyl)oxy)methyl)phenoxy)-3,4,5-trihydroxytetrahydro-2H-pyran-2-carboxylic acid (3.4)

To a mixture of the pyrrolidine 3.3 (50 mg) in methanol (2 mL) and THF (2 mL) was added drop-wise an aqueous solution of 1.0 N lithium hydroxide (2 mL). The reaction mixture was stirred for 1 h at an ambient temperature. Inspection of the reaction mixture by UPLC-MS revealed complete deprotection to a ~2:1 mixture of desired product 3.4 to elimination product 3.5. The reaction mixture was neutralized to pH 7 by the drop-wise addition of acetic acid. The mixture was concentrated under reduced pressure and the resulting residue was taken up in deionized water (2 mL) and filtered. This solution was used directly to assess in vitro stability using conditions described in example 8: Analytical UPLC-MS: MS (m/z) 604.35 (M+H$^+$), t$_r$ (3.4)=0.88 min (flow rate 0.7 mL/min).

Example 4: Synthesis of a Triptolide Drug-Linker Compound Comprising a MAC Unit Synthesis of (2S,3R,4S,5S,6S)-2-(4-(((ethyl((((5bS,5cS,6aR,7S,7aR,8aS,8bS,9aS,9bS)-7a-isopropyl-9b-methyl-3-oxo-1,3,5,5b,5c,6a,6b,7,7a,8a,8b,9b-dodecahydro-2H tris(oxireno)[2',3':4b,5;2'',3'':6,7;2''',3''':9,10] phenanthro[1,2-c]furan-7-yl)oxy)methyl)carbamoyl)oxy)methyl)-2-nitrophenoxy)-6-(methoxycarbonyl)tetrahydro-2H-pyran-3,4,5-triyl triacetate (4.1)

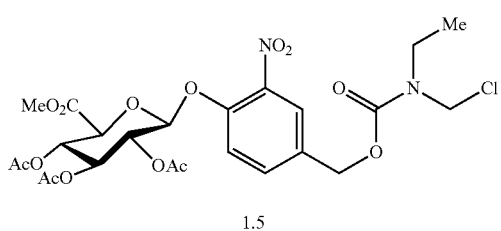

1.5

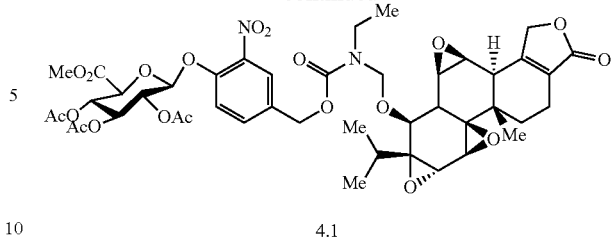

4.1

Following the chloramine procedure from Example 2 for preparing compound 1.7: Utilizing 109 mg (0.17 mmol) of 250 mg (0.13 mmol) 1.5, (, of 7.0 and 65 µl (4.30 mmol) of Hünig's base provided 85 mg of 7.1, 72% yield. Analytical UPLC-MS: $t_r$=2.21 min. MS (m/z) $[M+H]^+$ cald $C_{44}H_{52}N_2O_{20}$ 929.31, found 929.29.

Synthesis of (2S,3R,4S,5S,6S)-2-(2-amino-4-(((ethyl(a(5bS,5cS,6aR,7S,7aR,8aS,8bS,9aS,9bS)-7a-isopropyl-9b-methyl-3-oxo-1,3,5,5b,5c,6a,6b,7,7a,8a,8b,9b-dodecahydro-2H-tris(oxireno) [2',3': 4b,5;2'',3'':6,7;2''', 3''':9,10] phenanthro[1,2-c]furan-7-yl)oxy) methyl)carbamoyl)oxy) methyl)phenoxy)-6-(methoxycarbonyl)tetrahydro-2H-pyran-3,4,5-triyl triacetate (4.2)

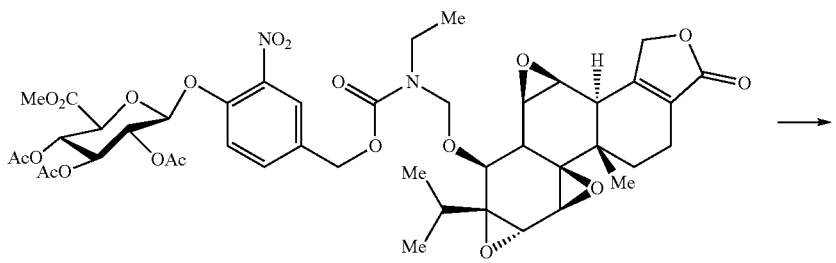

4.1

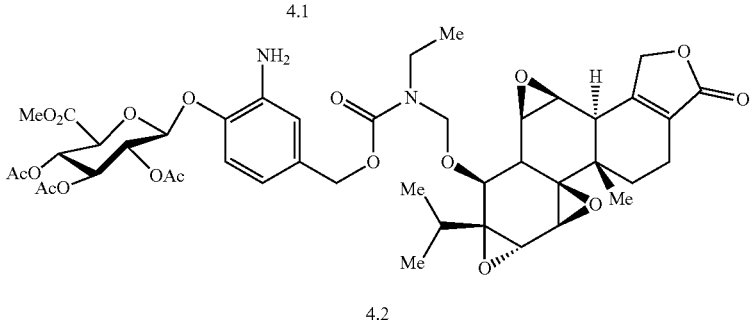

4.2

-continued

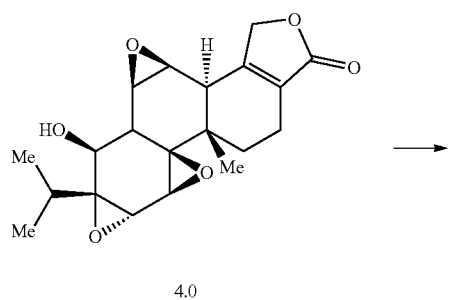

4.0

A 25 mL round bottom flask was equipped with an argon balloon was charged with 370 µL of MeOH, 85 mg (0.1 mmol) of 4.1 and 5 mg of 10% Pd/C. The reaction mixture was then vacuumed, purged and flushed with hydrogen via balloon 3 times. Equipped with a hydrogen balloon the reaction mixture was vigorously stirred for 1 h at RT at which time LC/MS indicated the reactions was complete. The reaction mixture was then filtered and purified by preparatory HPLC (gradient 5-95 acetonitrile/water 0.05 TFA) to yield 35 mg of 4.2, 44% yield. Analytical UPLC-MS: $t_r$=2.14 min MS (m/z) $[M+H]^+$ cald $C_{44}H_{54}N_2O_{18}$ 899.34, found 899.37.

Synthesis of (2S,3R,4S,5S,6S)-2-(2-(3-((((9H-fluoren-9-yl)methoxy)carbonyl)amino) propanamido)-4-(((ethyl((((5bS,5c5,6aR,7S,7aR,8aS,8bS,9aS,9bS)-7a-isopropyl-9b-methyl-3-oxo-1,3,5,5b,5c,6a,6b,7,7a,8a,8b,9b-dodecahydro-2H-tris(oxireno)[2',3':4b,5;2",3":6, 7;2',3'":9,10] phenanthro[1,2-c]furan-7-yl)oxy)methyl)carbamoyl)oxy)methyl)phenoxy)-6-(methoxycarbonyl)tetrahydro-2H-pyran-3,4,5-triyl triacetate (4.3)

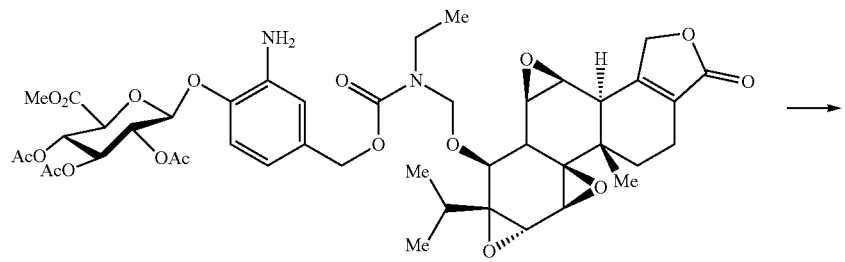

4.2

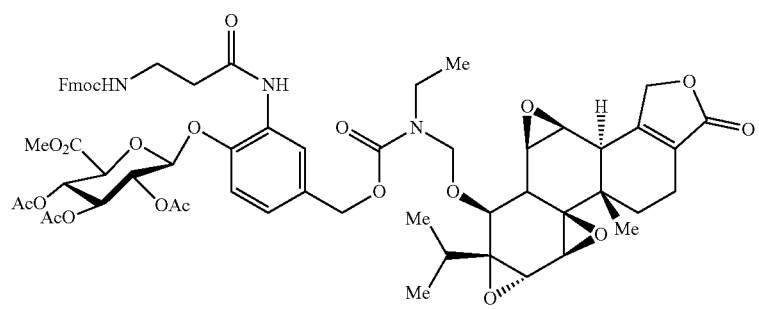

4.3

To a 1 dram vial equipped with a stir bar was added 200 µL of DCM followed by 6 mg (7.0 µmol) 4.2, Fmoc β-alanine (8 mg, 28 µmol) and 7 mg (0.28 µmol)N-ethoxycarbonyl-2-ethoxy-1,2-dihydroquinoline. The reaction mixture was then stirred for an additional 3 h at RT at which time LC/MS indicated the reaction was complete. The reaction was purified directly by preparatory HPLC (gradient 5-95 acetonitrile/water 0.05 TFA) to yield 6 mg of 4.3, 75%.

Analytical UPLC-MS: $t_r$=2.34 min MS (m/z) [M+H]$^+$ cald $C_{62}H_{69}N_3O_{21}$ 1192.44, found 1192.45.

Synthesis of (2S,3S,4S,5R,6S)-6-(2-(3-aminopropanamido)-4-(((ethyl(a(5bS,5cS,6aR, 7S, 7aR, 8aS, 8bS,9aS,9bS)-7a-isopropyl-9b-methyl-3-oxo-1,3,5,5b,5c,6a,6b,7,7a,8a,8b,9b-dodecahydro-2H-tris(oxireno) [2',3':4b,5;2",3": 6,7;2'",3'":9,10] phenanthro[1,2-c]furan-7-yl)oxy)methyl) carbamoyl)oxy)methyl)phenoxy)-3,4,5-trihydroxytetrahydro-2H-pyran-2-carboxylic acid (4.4)

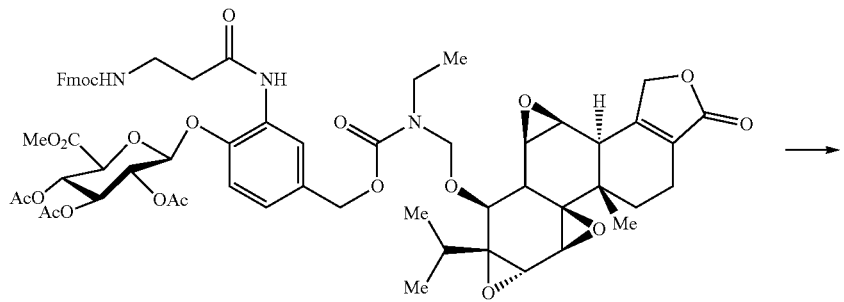

4.3

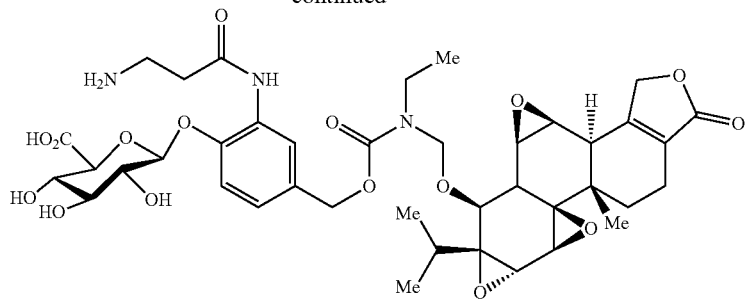

4.4

Following the deprotection method in Example 2 for obtaining compound 2.0: Compound 4.3 (4.0 mg, 3 μmol) was converted to 2.8 mg of 4.4, 95% yield. Analytical UPLC-MS: $t_r$=1.14 min MS (m/z) [M+H]$^+$ cald $C_{40}H_{51}N_3O_{16}$ 830.33, found 830.32.

Synthesis of (2S,3S,4S,5R,6S)-6-(2-(3-(3-(2,5-dioxo-2,5-dihydro-1H-pyrrol-1-yl) propanamido)propanamido)-4-(((ethyl(a(5bS,5c5,6aR,7S,7aR,8aS, 8bS,9aS,9bS)-7a-isopropyl-9b-methyl-3-oxo1,3,5, 5b,5c,6a,6b,7,7a,8a,8b,9b-dodecahydro-2H tris (oxireno) [2',3':4b,5;2",3":6,7;2'",3'":9,10] phenanthro[1,2-c]furan-7yl)oxy)methyl) carbamoyl) oxy)methyl)phenoxy)-3,4,5-trihydroxytetrahydro-2H-pyran-2-carboxylic acid (4.5)

To a 1 dram vial containing 2 mg of 4.4 (2 μmol) was added 100 μL of DMF followed by 20 μL (0.1 mmol) of Hünig's base and 2.5 mg (9 μmol) of 3-maleimidopropionic acid N-hydroxysuccimide ester. The reaction mixture was then stirred for an additional 10 minutes at RT at which time LC/MS indicated the reaction was complete. The reaction was directly purified by preparatory HPLC (gradient 5-95 acetonitrile/water 0.05 TFA) by first quenching with 2% TFA:water (3 mL) to yield 1.8 mg, 90% yield, of 4.5. Analytical UPLC-MS: $t_r$=1.61 min MS (m/z) [M+H]$^+$ cald for $C_{47}H_{56}N_4O_{19}$, 981.35, found 981.38.

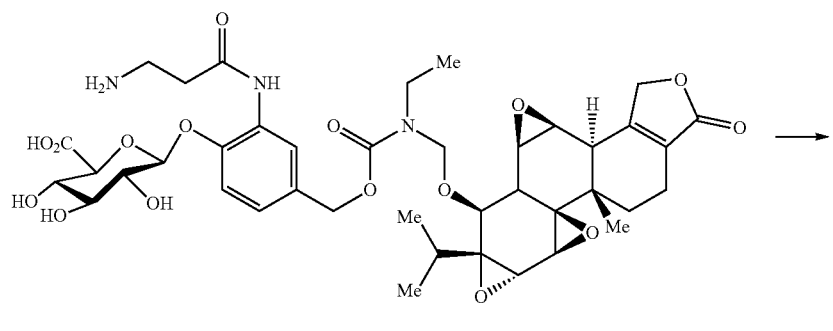

4.4

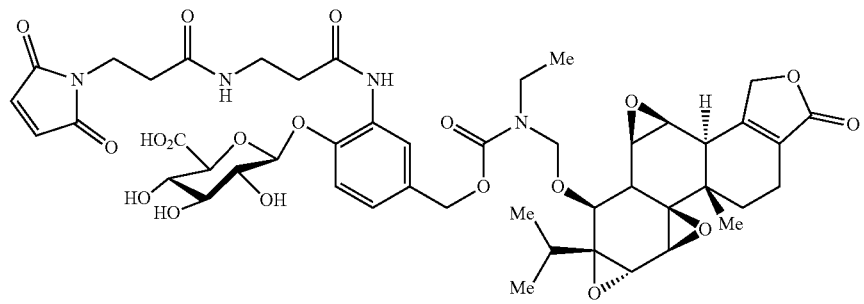

4.5

Example 5: Synthesis of an Everolimus Drug-Linker Compound Comprising a MAC Unit Synthesis of 2-(trimethylsilyl)ethyl 2-{[(1R,2R,4R)-4-[(2S)-2-[(1R,9S,12S,15R,16E,18R,19R, 21R,23S, 24E,26E,28E,30S,32S,35R)-1,18-dihydroxy-19,30-dimethoxy-15,17,21,23,29,35 hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl]oxy}ethoxy)acetate (5.1)

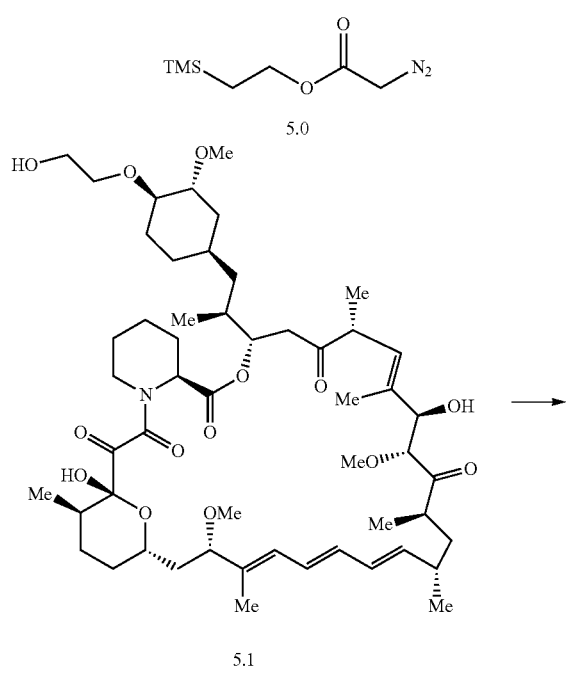

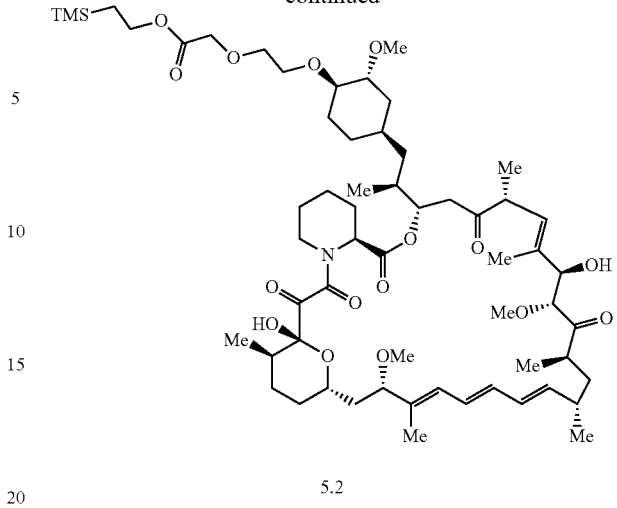

A 1 dram vial equipped with a septa screw cap and stir bar was charged with 1 mL of dry DCM, 2 mg (1 μmol) rhodium diacetate and 100 mg (0.1 mmol) of everolimus (5.1). Added dropwise to the reaction mixture with stirring at RT was 40 μL (0.2 mmol) trimethyl-ethyl diazoacetate (5.0). LC/MS indicated the reaction was complete after 1 hour. Afterwards, 1 mL of MeOH was added and the reaction was filtered and dried in vacuo. The resultant oil and then purified by preparatory TLC (hexanes:ethyl acetate, 1:1, rf=0.50) to yield 73 mg, 68% yield, of 5.2. Analytical UPLC-MS: $t_r$=1.92 min MS (m/z) [M+H]$^+$ cald for $C_{60}H_{97}NO_{16}Si$, 1116.66, found 1116.66.

Synthesis 2-(2{[(1R,2R,4R)-4-[(2S)-2[(1R,9S,12S, 15R,16E,18R,19R,21R,23S,24E,26E,28E,30S,32S, 35R)-1,18-dihydroxy-19,30-dimethoxy-15,17,21,23, 29,35-hexamethyl-2,3,10,14,20-pentaoxo-11,36-dioxa-4-azatricyclo[30.3.1.0$^{4,9}$]hexatriaconta-16,24, 26,28-tetraen-12-yl]propyl]-2-methoxycyclohexyl] oxy}ethoxy)acetic acid (5.3)

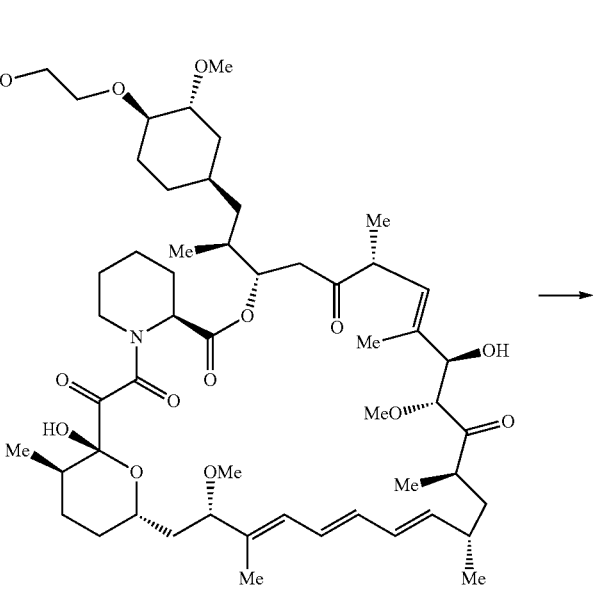

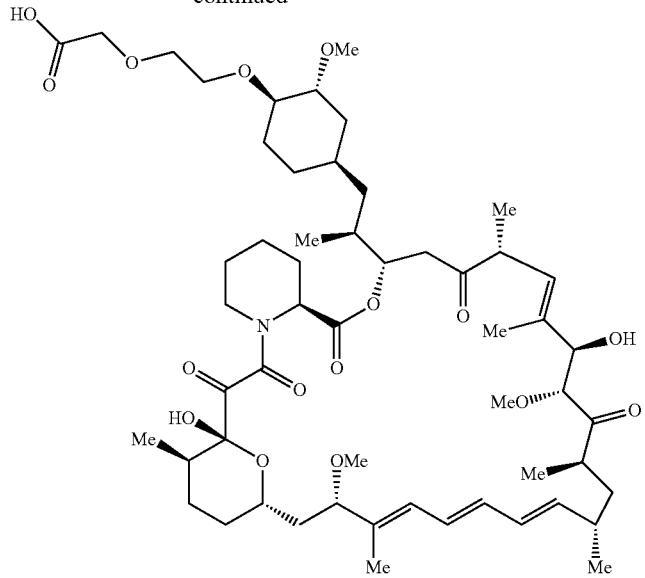

5.3

A 1 dram vial equipped with a septa screw cap and stir bar was charged with 1 mL of dry DMF, 70 mg (63 µmol) of 5.2 and 52 mg (1.89 mmol) of tris(dimethylamino)sulfonium difluorotrimethylsilicate. The stirred reaction at RT was monitored by LC/MS and was complete after 20 min. The reaction mixture was then treated with 5 mL of 10 M phosphate buffered saline and extracted ethyl ether 3×5 ml. The organic layer was dried in vacuo. The resultant oil was then purified by preparatory TLC (DCM:MeOH:AcOH, 8.9:1:0.1, rf=0.45) to yield 57 mg, 89% yield, of 5.3.

Analytical UPLC-MS: $t_r$=1.79 min MS (m/z) [M+H]$^+$ cald for $C_{55}H_{85}NO_{16}$, 1016.59, found 1016.61.

Synthesis of {4-[(2R)-2-[(2R)-2-amino-3-methylbutanamido]-5(carbamoylamino) pentanamido] phenyl}methyl N-[(2-{[(1R,2R,4R)-4-[(2S)-2-[(1R, 9S,12S,15R,16E,18R,19R,21R,23S,24E,26E,28E, 30S,32S,35R)-1,18-dihydroxy-19,30-dimethoxy-15, 17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl]oxy}ethoxy)methyl]carbamate (5.5)

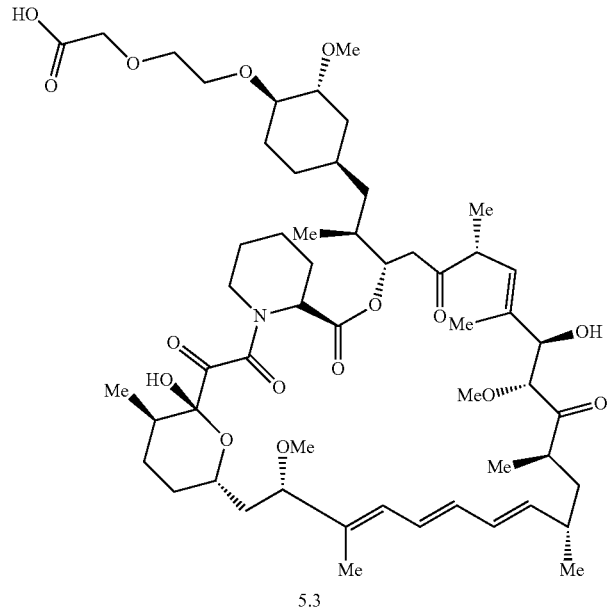

5.3

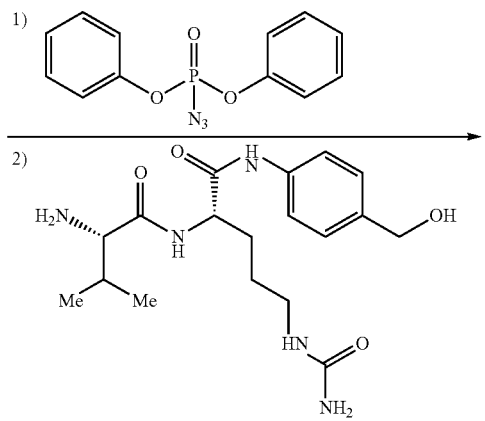

5.4

-continued

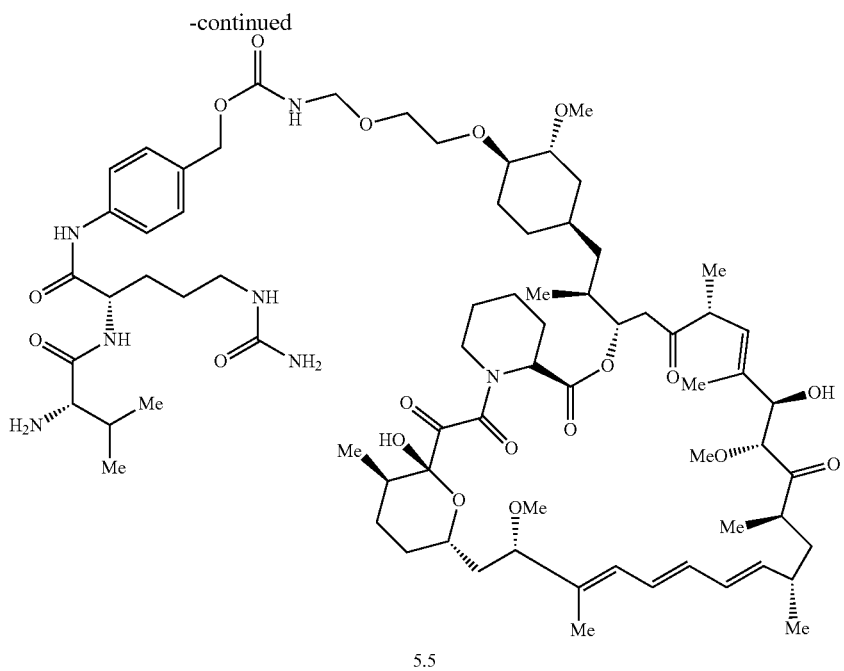

5.5

To a 1 dram vial containing 15 mg (15 µmol) of 5.3 was added 300 µL DMF followed by 8 µL (30 µmol) of diphenylphosphoryl azide and 6 µL (45 µmol) of Hünig's base. The resulting mixture was stirred at RT for 1 h at which time, 44 mg (75 µmol) of 5.4 and 2 µl (3 µmol) of dibutyltin dilaurate was added to the reaction mixture at 60° C. The reaction was stirred for an additional 2 h at 60° C. at which time LC/MS indicated the reaction was complete. The reaction mixture was quenched with 100 µL of diethyl amine and then directly purified by preparatory HPLC (gradient 5-95 acetonitrile/water 0.05% TFA) to yield 10 mg, 47% yield, of 5.5. Analytical UPLC-MS: $t_r$=1.49 min MS (m/z) [M+H]$^+$ cald for $C_{73}H_{113}N_7O_{19}$, 1392.81, found 1392.80.

Synthesis of {4-[(2R)-5-(carbamoylamino)-2-[(2R)-2-[3-(2,5-dioxo-2,5-dihydro-1H-pyrrol-1-yl) propanamido]-3-methylbutanamido]pentanamido] phenyl}methyl N-[(2-{[(1R,2R,4R)-4-[(2S)-21(1R,9S,12S,15R,16E,18R,19R,21R,23S,24E,26E,28E,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$]hexatriaconta-16,24,26,28-tetraen-12-yl]propyl]-2-methoxycyclohexyl] oxy}ethoxy) methyl]carbamate (5.6)

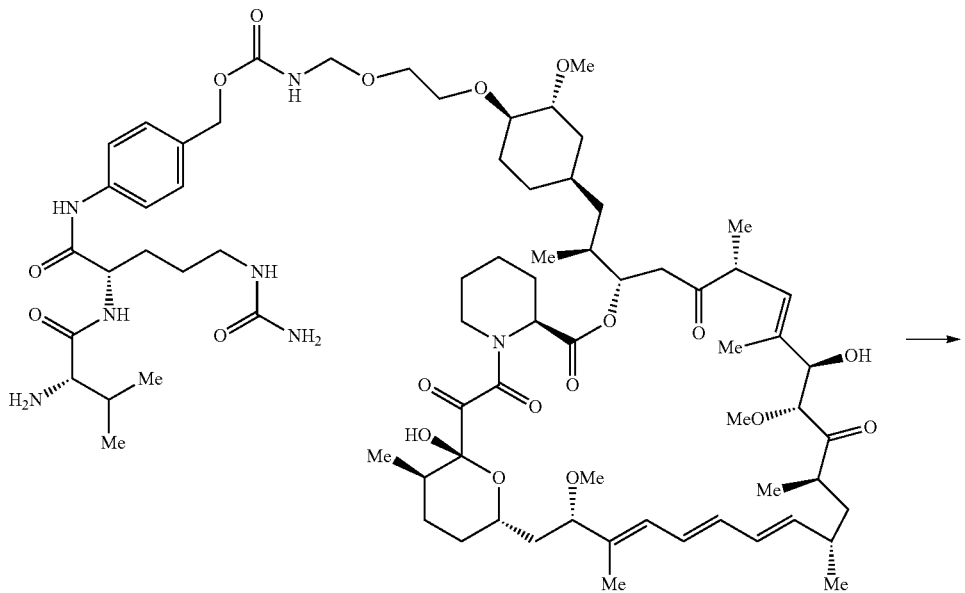

5.5

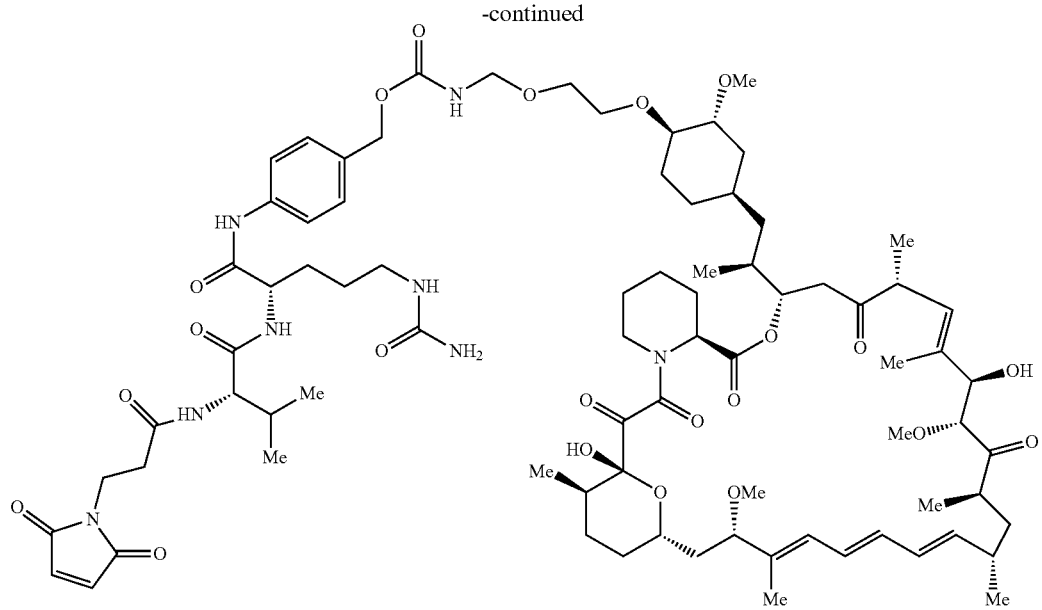

5.6

To a 1 dram vial containing 8 mg (5 mol) of 5.5 was added 100 µL of DMF followed by 20 µl (0.15 mmol) of Hünig's base and 3-maleimidopropionic acid 5 mg (18 µmol)N-hydroxysuccimide ester. The reaction was then stirred for an additional 30 minutes at RT at which time LC/MS indicated the reaction was complete. The reaction was directly purified by preparatory HPLC (gradient 5-95 acetonitrile/water 0.05 TFA) by first quenching with 2% TFA:water (3 mL) to yield 5 mg, 62% yield, of 9.3. Analytical UPLC-MS: $t_r$=1.69 min MS (m/z) MS (m/z) [M+H]$^+$ cald for $C_{80}H_{118}N_8O_{22}$, 1543.84, found 1543.86.

Example 6: Synthesis of a Tacrolimus Drug-Linker Compound Comprising a MAC Unit

Synthesis of 2-{[(1R,2R)-4-[(1E)-2-[(1R,9S,12S, 13R,14S,17R,18E,21S,23S,24R,25S,27R)-1,14-di-hydroxy-23,25-dimethoxy-13,19,21,27-tetramethyl-2,3,10,16-tetraoxo-17-(prop-2-en-1-yl)-11,28-dioxa-4-azatricyclo[22.3.1.0$^{4,9}$]octacos-18-en-12-yl]prop-1-en-1-yl]-2-methoxycyclohexyl]oxy}acetic acid (6.3)

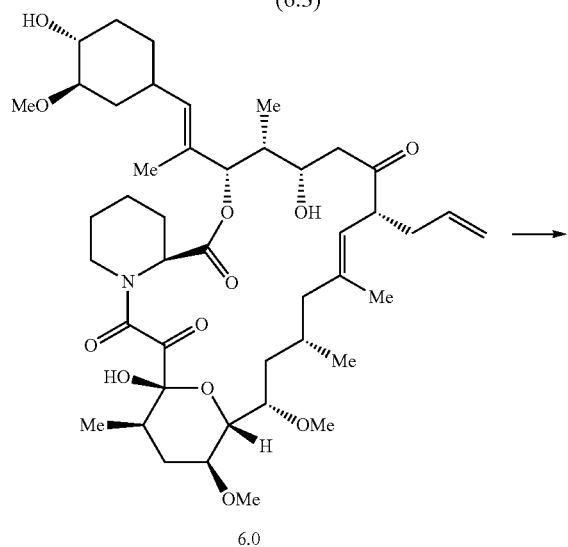

6.0

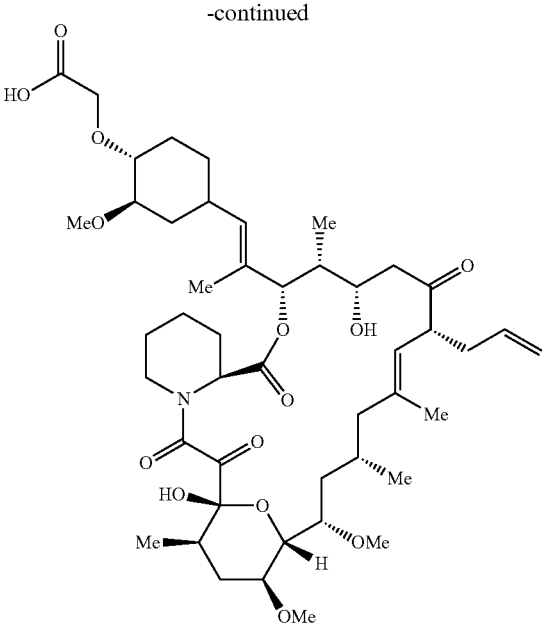

6.1

To a 4 dram vial equipped with a septa screw cap and an argon balloon was charged with 3 mL of dry DCM, 13 mg (60 µmol) of rhodium diacetate and 500 mg (0.6 mmol) of FK-506 (6.1). Afterwards, 200 µL (1.2 mmol) of tert-butyl diazoacetate in 200 µL of DCM was added dropwise to the stirred reaction mixture at 39° C. via syringe pump. LC/MS indicated the reaction was complete after 1 hour whereupon 1 mL of MeOH was added. The reaction mixture was then filtered and dried in vacuo. The resultant oil was treated with 4 mL of a DCM and trifluoroacetic acid (5:1) solution. The deprotection reaction was complete after 1 h as indicated by LC/MS. The resulting reaction mixture was then dried in vacuo and purified by preparatory TLC (10% MeOH:DCM, rf=0.20) to yield 378 mg, 71% yield, of 6.1. Analytical UPLC-MS: $t_r$=1.89 min MS (m/z) [M+H]$^+$ cald for $C_{46}H_{71}NO_{14}$, 862.49, found 862.52.

Synthesis {4-[(2S)-2-[(2S)-2-amino-3-methylbutanamido]-5(carbamoylamino) pentanamido] phenyl}methyl N-({[(1R,2R)-4-[(1E)-2-[(1R,9S,12S,13R,14S,17R,18E,21S,23S,24R,25S,27R)-1,14-dihydroxy-23,25-dimethoxy-13,19,21,27-tetramethyl-2,3,10,16-tetraoxo-17-(prop-2-en-1-yl)-11,28-dioxa-4-azatricyclo[22.3.1.0$^{4,9}$]octacos-18-en-12-yl]prop-1-en-1-yl]-2-methoxycyclohexyl] oxy}methyl) carbamate (6.3)

To a 4 dram vial containing 50 mg (58 µmol) of 6.1 was added 300 µL of DMF followed by 23 µl (87 µmol) of diphenylphosphoryl azide and 14 µL (1.2 mmol) of Hünig's base. The reaction mixture was then stirred at RT for 1 h. Afterwards, 52 mg (87 µmol) of 6.2, and 2 µL (3 µmol) of dibutyltin dilaurate was added at 60° C. The reaction was then stirred for an additional 2 h at 60° C. at which time LC/MS indicated the reaction was complete. After quenching with a 100 µL of diethyl amine, the reaction mixture was directly purified by preparatory HPLC (gradient 5-95 acetonitrile/water 0.05% TFA) to yield 15 mg, 21% yield, of

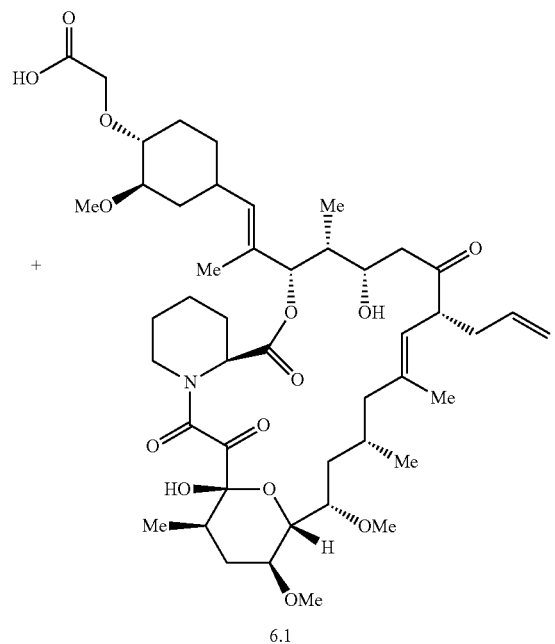

6.1

+

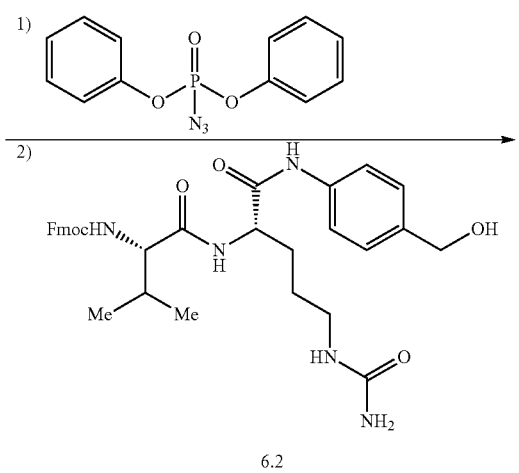

6.2

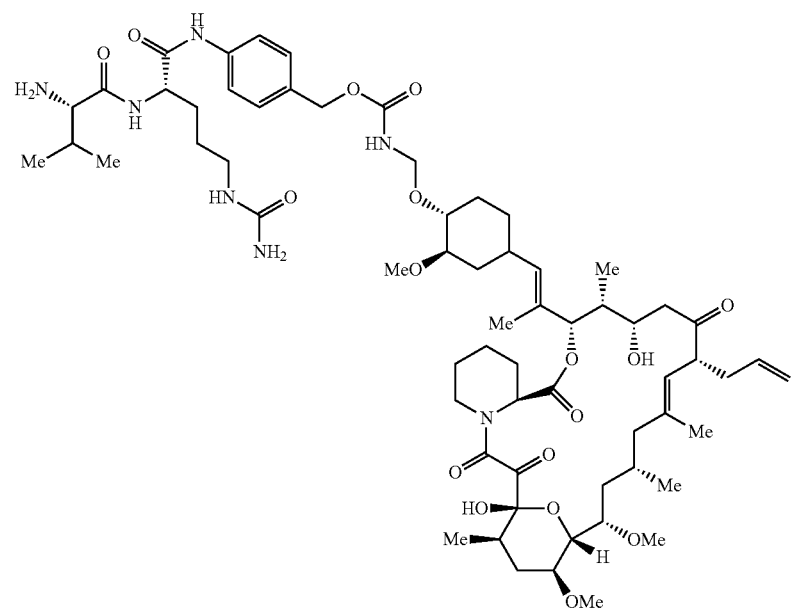

6.3

6.3. Analytical UPLC-MS: $t_r$=1.82 min MS (m/z) [M+H]$^+$ cald for $C_{74}H_{114}N_{10}O_{22}$, 1238.71, found 1238.70.

The synthesis of {4-[(2S)-5-(carbamoylamino)-2-[(2S)-2-[3-(2,5-dioxo-2,5-dihydro-1H-pyrrol-1-yl)propanamido]-3-methylbutanamido]pentanamido]phenyl}methyl-N-({[(1R,2R)-4-[(1E)-2[(1R,9S,12S,13R,14S,17R,18E,21S,23S,24R,25S,27R)-1,14-dihydroxy-23,25-dimethoxy-13,19,21,27-tetramethyl-2,3,10,16-tetraoxo-17-(prop-2-en-1-yl)-11,28-dioxa-4-azatricyclo[22.3.1.0$^{4,9}$]octacos-18-en-12-yl]prop-1-en-1-yl]-2 methoxycyclohexyl]oxy}methyl)carbamate (6.4)

To a 1 dram vial containing 4 mg (3 μmol) of 6.3 was added 100 μL of DMF followed by 20 μl (0.1 mmol) of Hünig's base and 2.5 mg (9 μmol) 3-maleimidopropionic acid N-hydroxysuccimide ester. Afterwards, the reaction was stirred for an additional 30 minutes at RT at which time LC/MS indicated the reaction was complete. The reaction was directly purified by preparatory HPLC (gradient 5-95 acetonitrile/water 0.05 TFA) by first quenching the reaction with 2% TFA:water (3 mL) to yield 3.4 mg, 85% yield, of 6.4. Analytical UPLC-MS: $t_r$=1.78 min MS (m/z) [M+H]$^+$ cald for $C_{71}H_{104}N_8O_{20}$, 1389.74, found 1389.77. Half-life in 0.1 M PBS buffer, pH 7.4 at 37° C. determined according to the method of Example 8 is 10 hrs.

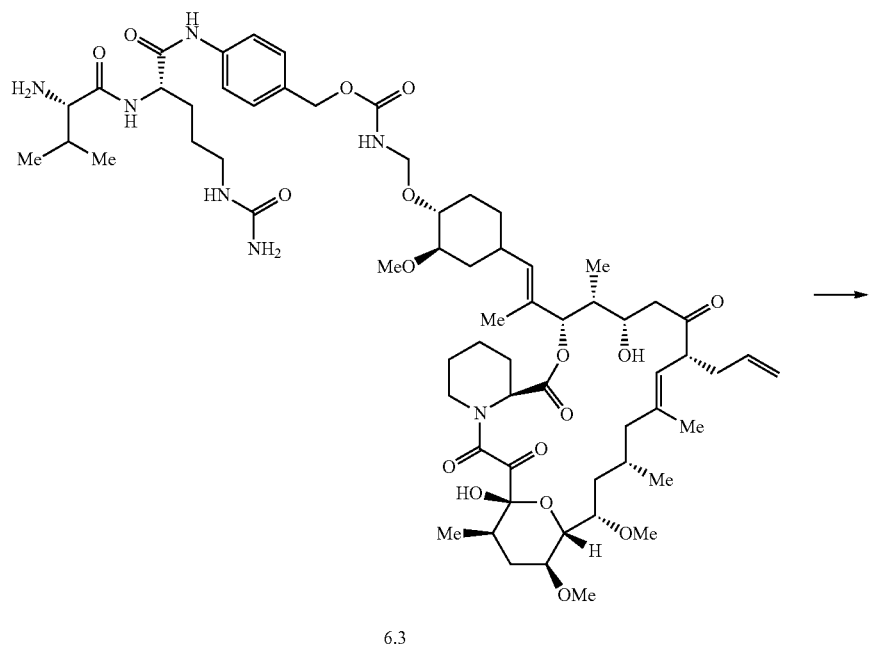

6.3

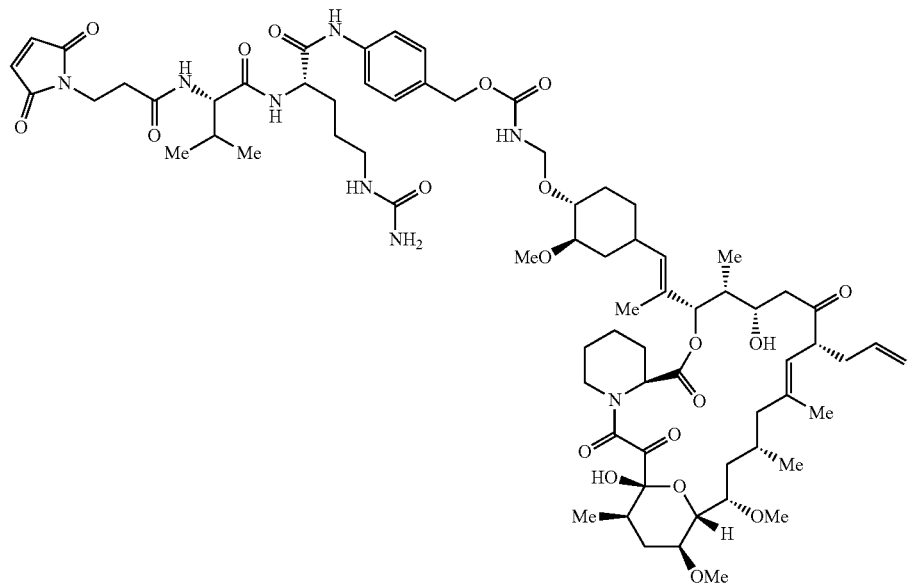

6.4

Example 7: Synthesis of an Tetrahydroquinoline-Containing Drug-Linker Compound Comprising a MAC Unit Variant
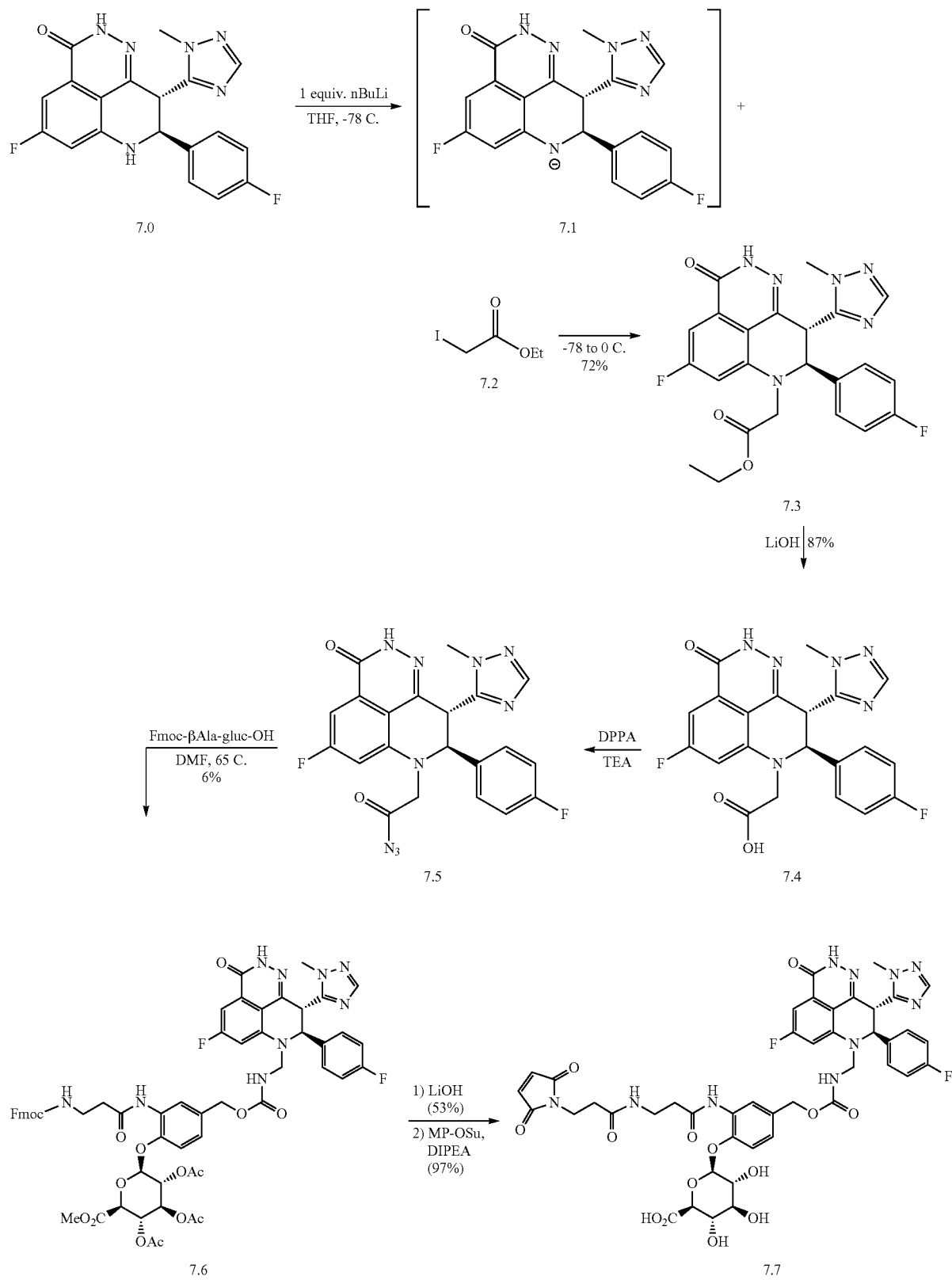

Synthesis of ethyl 2-((8S,9R)-5-fluoro-8-(4-fluorophenyl)-9-(1-methyl-1H-1,2,4-triazol-5-yl)-3-oxo-8,9-dihydro-2H-pyrido[4,3,2-de]phthalazin-7(3H)-yl) acetate (7.3)

A flame dried flask was charged with (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (7.0, 49 mg, 129 µmol) in 2.2 mL anhydrous THF. The solution was stirred at −80° C. under $N_2$ and n-butyl lithium (77 µL, 188 µmol) as a 2.5 M solution was added dropwise and the resulting reaction was stirred for an additional 10 min at −80° C. Ethyl iodoacetate (7.2, 31 µL, 258 µmol) was then added as a solution in 1 mL of anhydrous THF. Subsequently, the reaction mixture was stirred under nitrogen at 0° C. until LC/MS revealed conversion to product was complete. The reaction mixture was then cooled to −80° C. and quenched with saturated ammonium chloride, diluted with dichloromethane, and washed with sodium bicarbonate. The aqueous layer was then extracted with dichloromethane, and the combined organics were washed with brine, dried over sodium sulfate, and concentrated to dryness. The crude product was purified over silica via a Biotage column eluting with methanol:dichloromethane mixtures to provide 7.3 (43 mg, 72%). Analytical UPLC-MS: $t_r$=1.79 min, m/z (ES+) found 467.55.

Synthesis of 2-((8S,9R)-5-fluoro-8-(4-fluorophenyl)-9-(1-methyl-1H-1,2,4-triazol-5-yl)-3-oxo-8,9-dihydro-2H-pyrido[4,3,2-de]phthalazin-7(3H)-yl) acetic acid (7.4)

A flask was charged with 43 mg ester 7.3 (92 µmol) which was then dissolved in THF (1.5 mL) and MeOH (1.5 mL). The resulting solution was stirred under $N_2$ and cooled to 0° C. Lithium hydroxide monohydrate (7.8 mg, 184 µmol) solubilized in $H_2O$ (1.5 mL) was then added dropwise. Afterwards, the reaction was allowed to warm to RT and stirred for 2 hours. The reaction was then quenched with acetic acid (10.5 µL, 184 µmol) and condensed under reduced pressure. The residue was taken up in minimal DMSO and purified by preparative LC to provide 7.4 (35 mg, 87%). Analytical UPLC-MS: $t_r$=1.47 min, m/z (ES+) found 439.42.

Synthesis of 2-((8S,9R)-5-fluoro-8-(4-fluorophenyl)-9-(1-methyl-1H-1,2,4-triazol-5-yl)-3-oxo-8,9-dihydro-2H-pyrido[4,3,2-de]phthalazin-7(3H)-yl) acetyl azide (7.5)

A flask was charged with free carboxylic acid (7.4, 28 mg, 64 µmol), which was then dissolved in anhydrous THF (1.3 mL). Triethylamine (22 µL, 160 µmol) was added and the resulting reaction mixture was stirred for 10 minutes at RT under nitrogen. Diphenylphosphoryl azide (14 µL, 64 µmol) was then added and the resulting reaction mixture was stirred for 2 hours at RT, at which time UPLC/MS revealed conversion to product. The material was then concentrated under reduced pressure to provide crude acyl azide 7.5, which was carried forward without further characterization. Analytical LC-MS: $t_r$=12.80 min, m/z (ES+) found 436.16 (M+H−$N_2$).

Synthesis of (2S,3R,4S,5S,6S)-2-(2-(3-((((9H-fluoren-9-yl)methoxy)carbonyl)amino)propanamido)-4-(((a(8S,9R)-5-fluoro-8-(4-fluorophenyl)-9-(1-methyl-1H-1,2,4-triazol-5-yl)-3-oxo-8,9-dihydro-2H-pyrido[4,3,2-de]phthalazin-7(3H)-yl)methyl)carbamoyl)oxy)methyl)phenoxy)-6-(methoxycarbonyl)tetrahydro-2H-pyran-3,4,5-triyl triacetate (7.6)

To a flask containing acyl azide (7.5, 64 µmol) in anhydrous DMF (0.3 mL) was added the previously described (Bioconjugate Chem. 2006, 17, 831-840) glucuronide-containing compound Fmoc-βAla-glucuronide benzyl alcohol (96 mg, 128 µmol).

Subsequently, the reaction mixture was heated to and stirred at 65° C. to promote the rearrangement of the acyl azide to the isocyanate with subsequent trapping to form the carbamate functional group. After 2 hours, catalytic dibutyltin dilaurate was added. Continued stirring at 65° C. for 5 hours resulted in modest conversion to product. The reaction was diluted in acetonitrile and dimethylsulfoxide and purified by preparative HPLC to provide 7.6 (4.4 mg, 6%). Analytical UPLC-MS: $t_r$=2.27 min, m/z (ES+) found 1185.29.

Synthesis of (2S,3S,4S,5R,6S)-6-(2-(3-(3-(2,5-dioxo-2,5-dihydro-1H-pyrrol-1-yl)propanamido)propanamido)-4-(((((8S,9R)-5-fluoro-8-(4-fluorophenyl)-9-(1-methyl-1H-1,2,4-triazol-5-yl)-3-oxo-8,9-dihydro-2H-pyrido[4,3,2-de]phthalazin-7(3H)-yl)methyl)carbamoyl)oxy)methyl)phenoxy)-3,4,5-trihydroxytetrahydro-2H-pyran-2-carboxylic acid (7.7)

A flask charged with 4.4 mg protected glucuronide linker intermediate 7.6 (3.7 µmol) was dissolved in THF (0.13 mL) and MeOH (0.13 mL). The resulting solution was stirred under $N_2$ and cooled to 0° C. LiOH.$H_2O$ (0.9 mg, 22 µmol) solubilized in $H_2O$ (0.13 mL) was then added dropwise. The reaction was then allowed to warm to RT and stirred for an additional 4 hours. The reaction mixture was then quenched with acetic acid (1.3 µL, 22 µmol) and condensed under reduced pressure. The residue obtained was taken up in minimal DMSO and purified by preparative LC to provide the deprotected glucuronide linker (1.6 mg, 53%). Analytical UPLC-MS: $t_r$=1.20 min, m/z (ES+) found 822.49. Maleimidopropionyl NHS ester (0.8 mg, 2.9 µmol) was dissolved in anhydrous DMF (0.19) and added to a flask containing the globally deprotected glucuronide linker (1.6 mg, 1.9 mol). DIPEA (1.7 µL, 9.5 µmol) was then added and the reaction was stirred under nitrogen at RT for 3 hours. Subsequently, the reaction was diluted in acetonitrile and dimethylsulfoxide and purified by preparative HPLC to provide drug-linker 7.7 (2 mg, 97%). Analytical UPLC-MS: $t_r$=1.41 min, m/z (ES+) found 973.43.

Example 8: Preparation of Drug-Linker Model Systems Having Self-Immolative Assembly Units that Release Hydroxyl and Thiol-Containing Compounds as Model Free Drugs Exemplary Self-immolative Assembly Units with covalent attachment to Drug Units incorporating structures of model drugs were prepared via N-chloromethylamine synthesis according to the following scheme, wherein each Self-immolative Assembly Unit prepared is comprised of a self-immolative moiety of structure XVId (i.e., -PABA(gluc)-) and a MAC Unit:

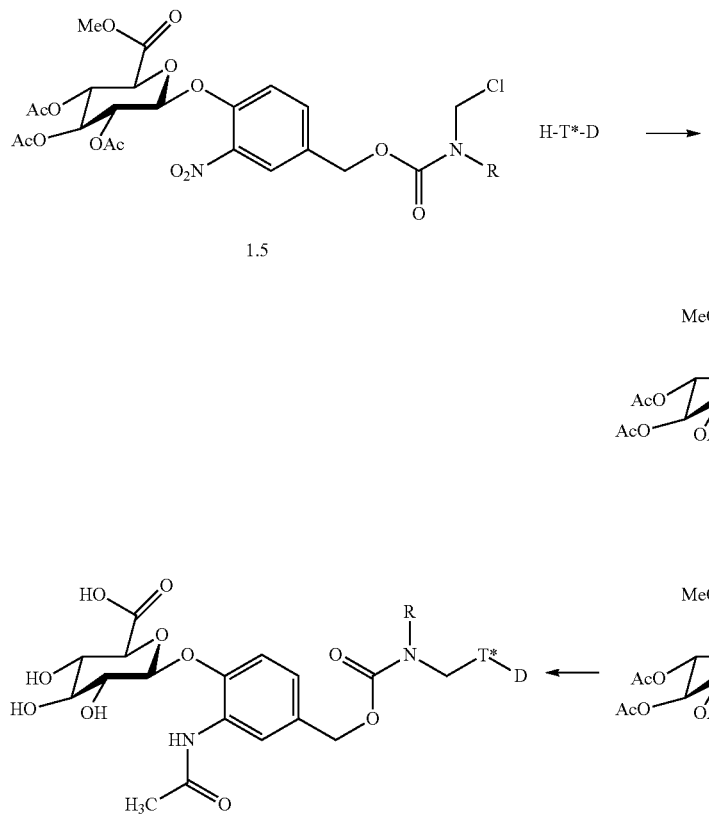

wherein variations in R and D-T*-H free drug, which is used in the synthesis and released upon activation of the PABA (gluc) self-immolative moiety, are as follows in Table 1:

TABLE 1

| Hydroxyl- and thiol-containing compounds as model free drugs with variation in MAC Unit substitution | | |
|---|---|---|
| D—T*—H | | R |
| HO-CH2-phenyl | HO-naphthyl | —CH2CH3 |
| HO-CH(CH3)-CH2-phenyl | HS-CH2CH2-phenyl | —PEG |
| HO-CH2-C(CH3)2-CH2-phenyl | | —CH2CH2N(CH3)2 |

General procedure for alkylation of a nucleophile from D-T*-H with 1.5: To a round bottom flask equipped with a stir bar, septa and argon balloon and charged with 5 mL of dry DCM, 1 mmol of D-T*-H, 5 mmol of Hünig's base was added followed by 2 mmol of N-chlormethylamine compound 1.5 via syringe at once. The reaction was monitored by LC/MS until starting material D-T*-H was consumed;

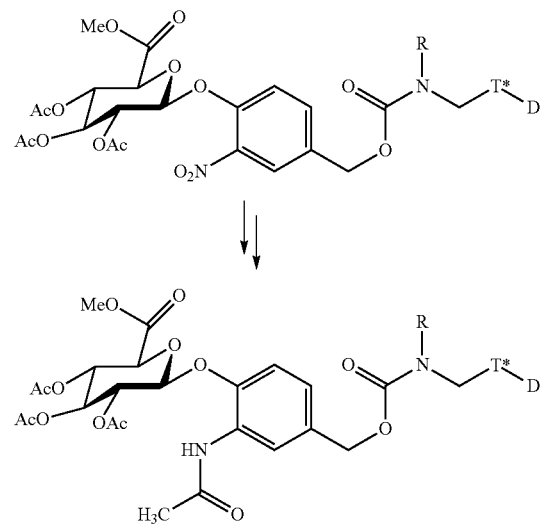

reactions were typically completed within 2 h. The reaction mixture was dried in vacuo via rotoevaporation. The resultant oil was then purified via Biotage FCC with ethyl acetate and hexanes gradient.

Synthesis of (2S,3R,4S,5S,6S)-2-(4-(((ethyl (phenethoxymethyl)carbamoyl)oxy)methyl)-2-nitrophenoxy)-6-(methoxycarbonyl)tetrahydro-2H-pyran-3,4,5-triyl triacetate (8.1)

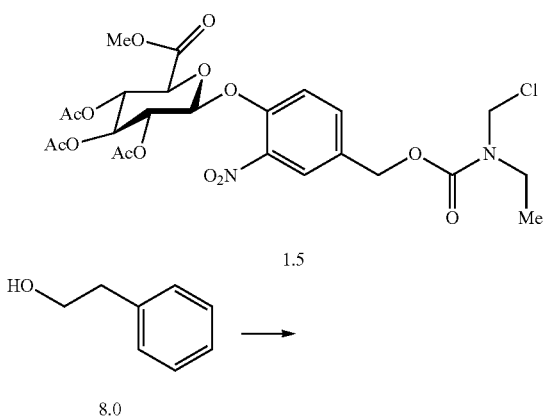

-continued

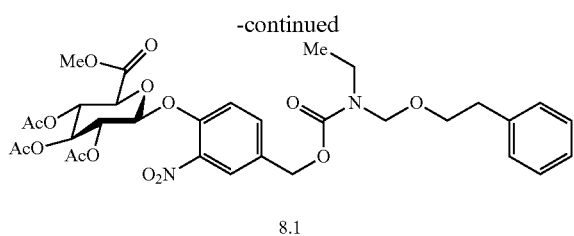

8.1

Following general alkylation procedure: Utilizing (621 mg, 1.05 mmol) of 1.5, (250 µL, 2.1 mmol) of 8.0 and (939 µL, 5.25 mmol) of Hünig's base provided 615 mg of 8.1, 85% yield. MS (m/z) [M+H]+ cald $C_{32}H_{38}N_2O_{15}$ 691.23, found 691.25, $^1$H NMR (400 MHz, CDCl$_3$) δ=7.80 (s, 1H), 7.52 (dd, J=9.2, 8.1 Hz, 1H), 7.37-7.30 (m, 1H), 7.27 (t, J=3.5, 2H), 7.23-7.14 (m, 3H), 5.38-5.27 (m, 3H), 5.20 (d, J=5.9, 1H), 5.12 (d, J=5.4, 2H), 4.71 (d, J=14.0, 2H), 4.20 (d, J=11.3, 1H), 3.73 (s, 3H), 3.65 (dt, J=12.5, 3.5, 2H), 3.39-3.26 (m, 2H), 2.80 (m, 2H), 2.11 (s, 3H), 2.06 (s, 6H), 1.14-1.06 (m, 3H).

Synthesis of (2S,3R,4S,5S,6S)-2-(4-(((ethyl(((1-phenylpropan-2yl)oxy) methyl)carbamoyl)oxy) methyl)-2-nitrophenoxy)-6-(methoxycarbonyl)tetrahydro-2H-pyran-3,4,5-triyl triacetate (8.3)

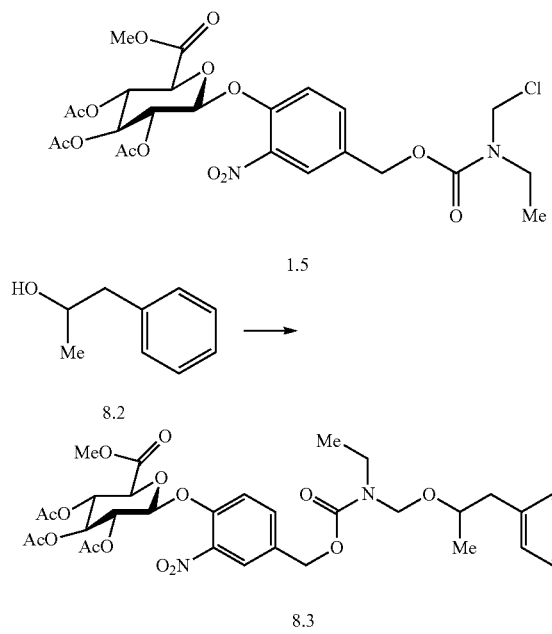

Following general alkylation procedure: Utilizing (105 mg, 0.175 mmol) of 1.5, (47 µL, 0.35 mmol) of 8.2 and (156.6 µL, 0.87 mmol) of Hünig's base provided 111 mg of 8.3, 90% yield. MS (m/z) [M+H]+ cald $C_{33}H_{40}N_2O_{15}$ 705.68, found 705.65, $^1$H NMR (400 MHz, CDCl$_3$) δ=7.80 (s, 1H), 7.52 (dd, J=9.2, 8.1 Hz, 1H), 7.37-7.10 (m, 5H), 5.38-5.27 (m, 3H), 5.25-5.01 (m, 3H), 4.80-4.63 (m, 2H), 4.19 (d, J=14.0, 2H), 4.20 (d, J=8.78, 1H), 3.73 (d, J=2.74, 3H), 3.3-3.03 (m, 2H), 2.80 (m, 2H), 2.60 (dd, J=13.11, 4.64, 1H), 2.11 (s, 3H), 2.06 (s, 6H), 1.14-1.06 (t, J=7.37, 3H).

Synthesis of (2S,3R,4S,5S,6S)-2-(4-(((ethyl(((2-methyl-1-phenylpropan-2-yl)oxy)methyl)carbamoyl) oxy)methyl)-2-nitrophenoxy)-6-(methoxycarbonyl) tetrahydro-2H-pyran-3,4,5-triyl triacetate (8.5)

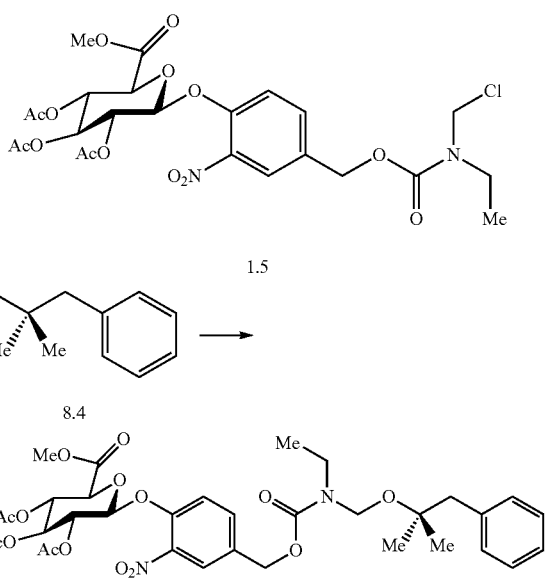

Following general alkylation procedure: Utilizing (534 mg, 0.885 mmol) of 1.5, (260 µL, 0.17 mmol) of 7.5 and (795 µL, 4.4 mmol) of Hünig's base provided 390 mg of 7.6, 61% yield. MS (m/z) [M+H]+ cald $C_{34}H_{42}N_2O_{15}$ 719.26, found 719.24, $^1$H NMR (400 MHz, CDCl$_3$) δ=7.80 (d, J=7.2 1H), 7.52 (dd, J=9.7, 8.4 Hz, 1H), 7.40-7.29 (m, 1H), 7.25-7.13 (m, 5H), 5.37-5.26 (m, 3H), 5.12-5.09 (m, 2H), 4.81 (d, J=32.0, 2H), 4.18 (m, 1H), 3.73 (s, 3H), 3.41-3.31 (m, 2H), 2.81-2.72 (d, J=16.9, 2H), 2.11 (m, 3H), 2.11 (s, 3H), 2.05 (s, 6H), 1.19-1.10 (m, 9H).

Synthesis of (2S,3R,4S,5S,6S)-2-(4-(((ethyl((naphthalen-1-yloxy)methyl)carbamoyl)oxy)methyl)-2-nitrophenoxy)-6-(methoxycarbonyl)tetrahydro-2H-pyran-3,4,5-triyl triacetate (8.7)

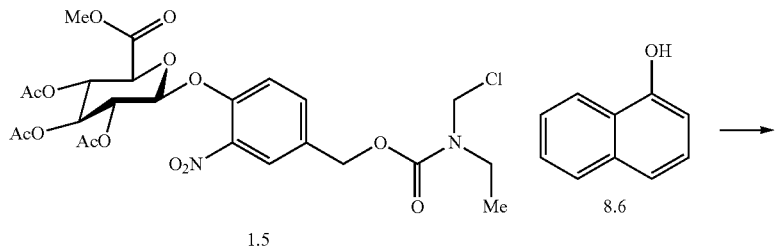

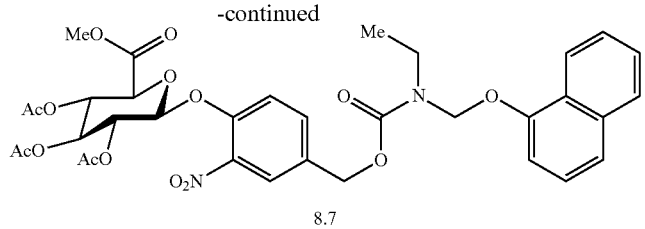

8.7

Following general alkylation procedure: Utilizing (791 mg, 1.3 mmol) of 1.5, (377 mg, 2.6 mmol) of 8.6 and (1.7 ml, 6.5 mmol) of Hünig's base provided 768 mg of 8.7, 82% yield. MS (m/z) [M+H]$^+$ cald C$_{34}$H$_{36}$N$_2$O$_{15}$ 713.39, found 713.37, $^1$H NMR (400 MHz, CDCl$_3$) δ=8.19 (dd, J=16.3, 8.5 Hz, 1H), 7.80 (d, J=7.2 1H), 7.47 (m, 3H), 7.34 (t, J=10.5 2H), 7.25 (m, 1H), 7.18 (m, 2H), 6.9 (dd, J=39.5, 6.7 Hz, 1H) 5.49 (d, J=14.9, 2H), 5.30 (m, 3H), 5.21-5.02 (m, 3H), 4.18 (m, 1H), 3.73 (s, 3H), 3.64-3.49 (m, 2H), 2.31 (s, 2H), 2.12 (s, 3H), 2.06 (s, 6H), 1.32-1.18 (m, 3H).

Synthesis of (2S,3R,4S,5S,6S)-2-(4-(((ethyl((phenethylthio)methyl)carbamoyl)oxy)methyl)-2-nitrophenoxy)-6-(methoxycarbonyl)tetrahydro-2H-pyran-3,4,5-triyl triacetate (8.9)

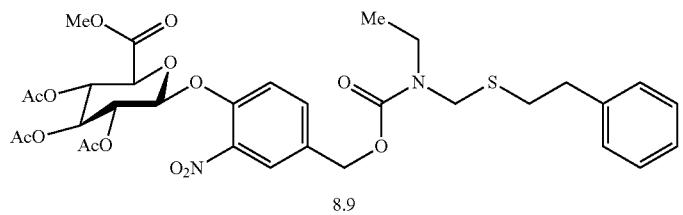

1.5

8.8

8.9

Following general alkylation procedure: Utilizing (43 mg, 0.070 mmol) of 1.5, (19 µL, 0.140 mmol) of 8.8 and (62 µL, 6.5 mmol) of Hünig's base provided 42 mg of 8.9, 86% yield. MS (m/z) [M+H]$^+$ cald C$_{32}$H$_{38}$N$_2$O$_{14}$S 707.20, found 707.18, $^1$H NMR (400 MHz, CDCl$_3$) δ=7.79 (s, 1H), 7.50 (dd, J=10.2, 8.7 Hz, 1H), 7.37-7.08 (m, 6H), 5.38-5.26 (m, 3H), 5.17-5.08 (m, 3H), 4.47 (d, J=31.3, 2H), 4.17 (d, J=9.6, 2H), 4.20 (d, J=11.3, 1H), 3.73 (s, 3H), 3.40 (m, 2H), 2.90-2.75 (m, 2H), 2.11 (s, 3H), 2.06 (d, J=2.8, 6H), 1.14 (t, J=6.6, 3H).

Synthesis of (2S,3R,4S,5S,6S)-2-(4-((((2-(dimethylamino)ethyl)carbamoyl)oxy)methyl)-2-nitrophenoxy)-6-(methoxycarbonyl)tetrahydro-2H-pyran-3,4,5-triyl triacetate (8.11)

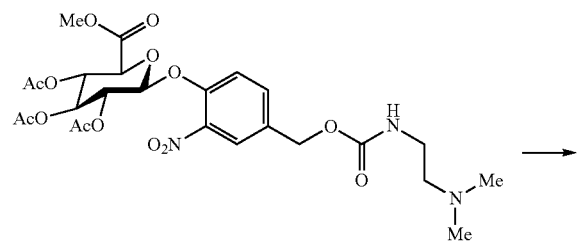

8.10

-continued

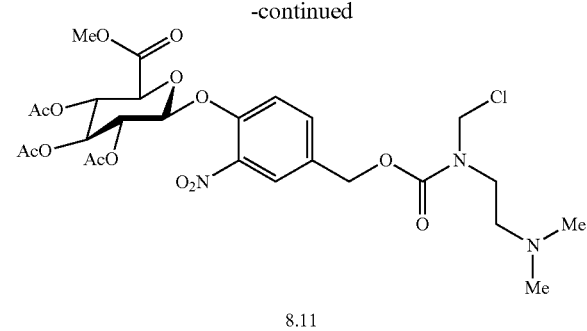

8.11

Compound 8.11 was synthesized using the procedure for 1.5. Utilizing (150 mg, 0.2 mM) 8.10 (for synthesis of 8.10 see Bosslet et al., 1998, J. Med. Chem. 41:3572) provided 155 mg of 8.11, 95% yield. Analytical UPLC samples are prepared with MeOH to quench the reactive chloride in 8.1. Analytical UPLC-MS: $t_r$=1.40 min, MS (m/z) [M+Na]$^+$ cald for $C_{27}H_{37}N_3NO_{15}$ 666.21, found 666.19.

Synthesis of (2S,3R,4S,5S,6S)-2-(4-((((2-(dimethyl-amino)ethyl)(phenethoxymethyl)carbamoyl)oxy) methyl)-2-nitrophenoxy)-6-(methoxycarbonyl)tetra-hydro-2H-pyran-3,4,5-triyl triacetate (8.12)

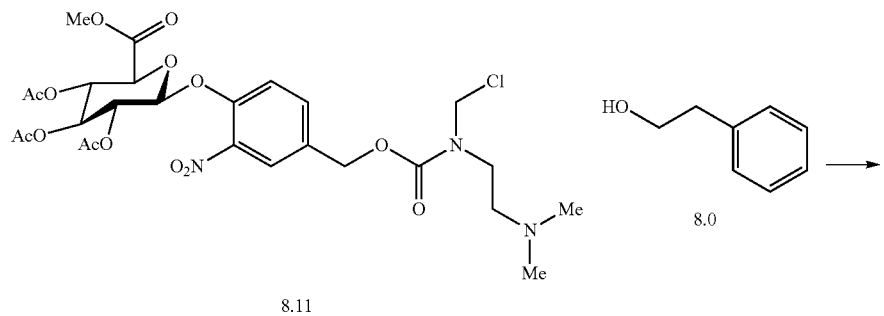

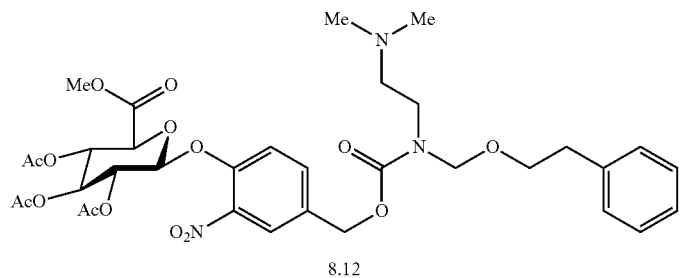

Following general alkylation procedure: Utilizing (97 mg, 0.150 mmol) of 8.11, (37 µL, 0.30 mmol) of 8.0 and (102 µL, 1.1 mmol) of Hünig's base provided 76 mg of 8.12, 72% yield. $^1$H NMR (400 MHz, CDCl$_3$) δ=7.84-7.77 (m, 1H), 7.53 (dd, J=46.5, 9.6 Hz, 1H), 7.35 (t, J=8.2, 1H), 7.30-7.14 (m, 5H), 5.38-5.26 (m, 3H), 5.21 (t, J=6.21, 3H), 5.12 (d, J=7.86, 2H), 4.76 (d, J=15.7, 2H), 4.22 (dd, J=13.2, 7.4, 1H), 3.73 (s, 3H), 3.70-3.54 (m, 5H), 3.0 (t, J=5.9, 1H), 2.83 (t, J=6.6, 2H), 2.78 (s, 6H), 2.59 (s, 2H), 2.12 (s, 3H), 2.06 (d, J=2.19, 6H).

Synthesis of (2S,3R,4S,5S,6S)-2-(4-((((2-(dimethyl-amino)ethyl)(((2-methyl-1-phenylpropan-2-yl)oxy) methyl)carbamoyl)oxy)methyl)-2-nitrophenoxy)-6-(methoxycarbonyl)tetrahydro-2H-pyran-3,4,5-triyl triacetate (8.13)

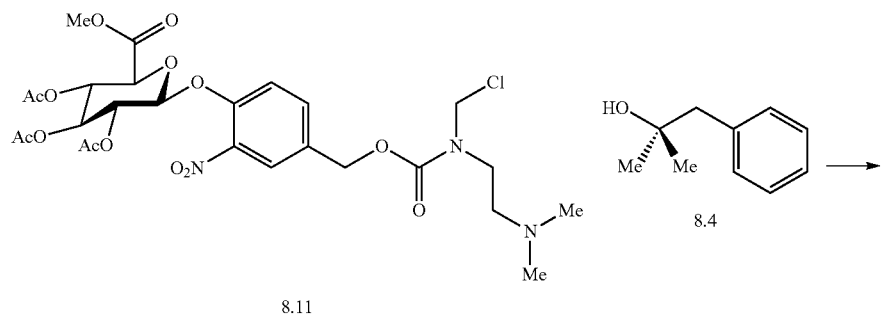

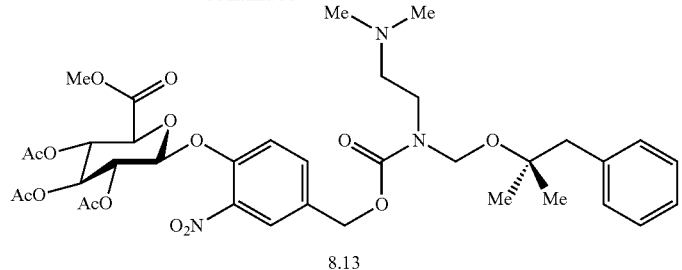

8.13

Following general alkylation procedure: Utilizing (150 mg, 0.23 mmol) of 8.11, (104 μL, 0.69 mmol) of 8.4 and (102 μL, 1.1 mmol) of Hünig's base provided 118 mg of 8.13, 67% yield. MS (m/z) [M+H]$^+$ cald C$_{36}$H$_{47}$N$_4$O$_{15}$ 762.30, found 762.32, $^1$H NMR (400 MHz, CDCl$_3$) δ=7.80 (d, J=24.6 1H), 7.53 (dd, J=12.3, 8.4 Hz, 1H), 7.34 (t, J=11.1, 1H), 7.26-7.13 (m, 5H), 5.38-5.26 (m, 3H), 5.21-5.09 (m, 3H), 4.47 (d, J=27.2, 2H), 4.20 (t, J=9.74, 1H), 3.73 (s, 3H), 3.55 (td, J=27.2, 7.7 2H), 2.84 (t, J=9.7, 1H), 2.76 (t, J=14.9, 2H), 2.84 (t, J=9.0, 1H), 2.51 (s, 3H), 2.12 (s, 3H), 2.05 (s, 9H), 1.16 (d, J=12.2, 6H).

Synthesis of (2S,3S,4S,5R,6S)-2-(methoxycarbonyl)-6-(4-(4-(methoxymethyl)-3-oxo-2,7,10,13,16,19,22,25,28-nonaoxa-4-azanonacosyl)-2-nitrophenoxy)tetrahydro-2H-pyran-3,4,5-triyl triacetate (8.15)

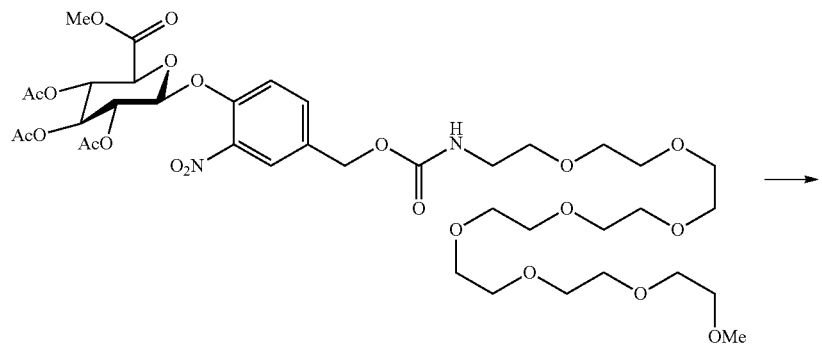

8.14

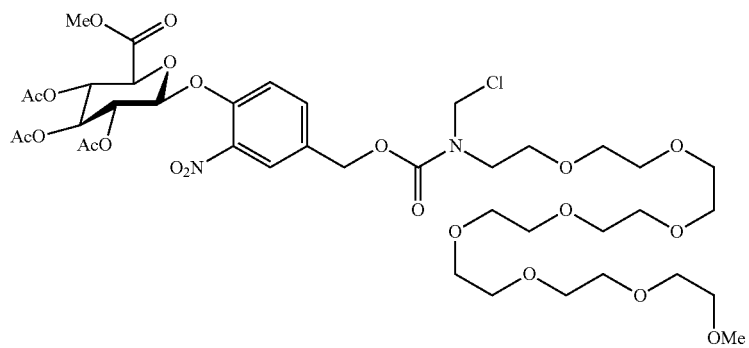

8.15

Compound 8.15 was synthesized using the procedure for 1.5. Utilizing (500 mg, 0.56 mM) 8.14 (for synthesis of 8.14 see Bosslet et al., 1998, J. Med. Chem. 41:3572) provided 516 mg of 8.15, 98% yield. Analytical UPLC samples are prepared with MeOH to quench the reactive chloride in 8.15. Analytical UPLC-MS: $t_r$=1.91 min, MS (m/z) [M+Na]$^+$ cald for $C_{40}H_{62}N_2NO_{23}$ 961.36, found 921.40.

Synthesis of (2S,3S,4S,5R,6S)-2-(methoxycarbonyl)-6-(2-nitro-4-(3-oxo-4-(((1-phenylpropan-2-yl)oxy)methyl)-2,7,10,13,16,19,22,25,28-nonaoxa-4-azanonacosyl)phenoxy)tetrahydro-2H-pyran-3,4,5-triyl triacetate (8.16)

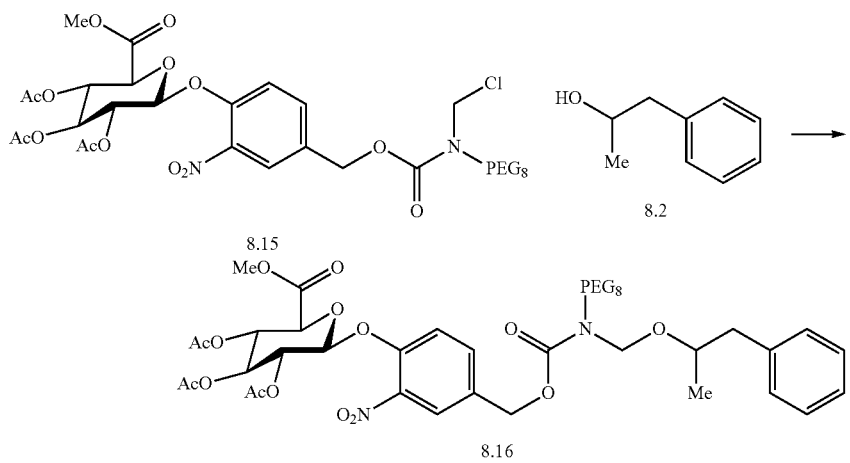

Following general alkylation procedure: Utilizing (60 mg, 0.064 mmol) of 8.15, (17 μL, 0.128 mmol) of 8.2 and (41 μL, 0.32 mmol) of Hünig's base provided 51 mg of 8.16, 84% yield. MS (m/z) [M+H]$^+$ cald $C_{48}H_{70}N_2O_{23}$ 1043.44, found 1043.47, $^1$H NMR (400 MHz, CDCl$_3$) δ=7.79 (s, 1H), 7.53 (t, J=8.0 Hz, 1H), 7.35 (dd, J=9.9, 6.1 Hz, 1H), 7.26-7.07 (m, 5H), 5.38-5.27 (m, 3H), 5.20-5.16 (m, 3H), 4.80-4.70 (m, 1H), 4.20 (m, 1H), 3.73 (s, 3H), 3.66-3.49 (m, 32H), 3.45 (t, J=7.08, 1H), 3.37 (s, 3H), 3.21 (m, 1H), 2.78 (m, 1H) 2.64 (dd, J=13.1, 5.7, 1H), 2.12 (s, 3H), 2.05 (d, J=2.12, 6H), 1.14 (m, 3H).

General procedure for reduction of the aryl nitro group to the aryl amine: A 1 dram vial equipped with a stir bar and rubber septum was charged with 1 mmol of aryl nitro compound and a 10:1 MeOH:AcOH (v/v %) for final concentration of 0.2 M. Activated zinc, 20 mmol, was then added in one scoop and the resulting mixture was vigorously stirred at RT. The reaction was monitored by LC/MS until its completion, which generally occurred within 30 minutes. The reaction mixture was then filtered and the resultant solid was washed with excess MeOH. The filtrate was then azeotroped to dryness with toluene in vacuo. The crude oil was then purified by Biotage FCC with an ethyl acetate and hexanes gradient.

The synthesis of (2S,3S,4R,5R,6S)-6-(2-amino-4-(((ethyl(phenethoxymethyl)carbamoyl)oxy)methyl)phenoxy)-5-hydroxy-2-(methoxycarbonyl)tetrahydro-2H-pyran-3,4-diyl diacetate (8.17)

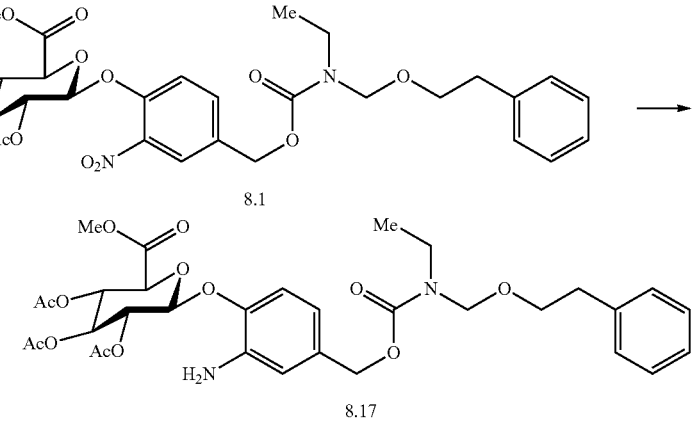

Following general reduction procedure: In 400 µL of MeOH:AcOH 8.1 (52 mg, 0.075 mmol) was treated with zinc (96 mg, 1.5 mmol). Purification of the reaction mixture yielded 43 mg of 8.17, 86% yield. MS (m/z) [M+H]⁺ cald $C_{32}H_{40}N_2O_{13}$ 661.25, found 661.23, ¹H NMR (400 MHz, CDCl₃) δ=7.30-7.25 (m, 2H), 7.23-7.13 (m, 3H), 6.86 (dd, J=13.6, 7.02, 1H), 6.66 (m, 2H), 5.38-5.27 (m, 3H), 5.00 (m, 3H), 4.77 (d, J=15.5, 2H), 4.15 (d, J=9.6, 1H), 3.80 (m, 2H), 3.74 (s, 3H), 3.68 (t, J=7.02, 1H), 3.60 (m, 1H), 3.36-3.24 (m, 1H), 2.90-2.79 (m, 1H), 2.07 (s, 3H), 2.05 (d, J=3.8 6H), 1.09 (q, 3H).

Synthesis of (2S,3R,4S,5S,6S)-2-(2-amino-4-(((ethyl(((1-phenylpropan-2-yl)oxy)methyl)carbamoyl)oxy)methyl)phenoxy)-6-(methoxycarbonyl)tetrahydro-2H-pyran-3,4,5-triyl triacetate (8.18)

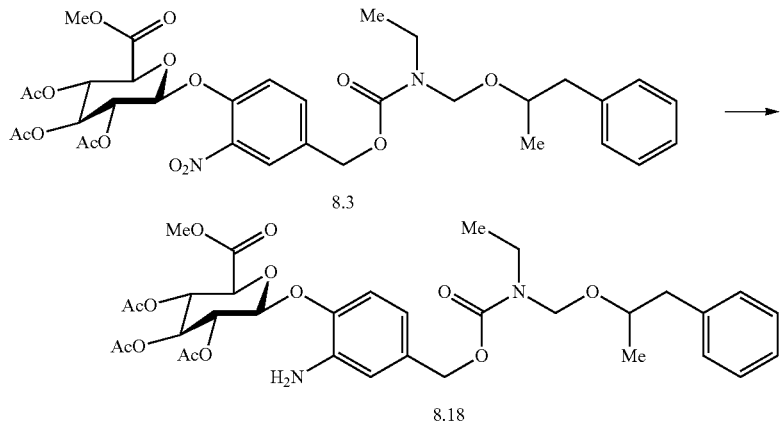

Following general reduction procedure: In 350 µL of MeOH:AcOH 8.3 (49 mg, 0.070 mmol) was treated with zinc (88 mg, 1.4 mmol). Purification of the reaction mixture yielded 44 mg of 8.18, 93% yield. MS (m/z) [M+H]⁺ cald $C_3H_{42}N_2O_{13}$ 675.27, found 675.28, ¹H NMR (400 MHz, CDCl₃) δ=7.92 (s, 1), 7.41-6.85 (m, 7H) 5.44-5.21 (m, 3H), 5.1 (m, 3H), 4.77 (d, J=5.8, 2H), 4.18 (d, J=8.7, 1H), 3.74 (d, J=5.8, 2H), 3.73-3.45 (m, 2H), 3.34-3.23 (m, 2H), 2.89-2.78 (m, 2H), 2.45 (s, 1H), 2.21 (s, 2H), 2.00 (m, 9H), 1.09 (t, J=6.7, 3H).

Synthesis of (2S,3R,4S,5S,6S)-2-(2-amino-4-(((ethyl(((2-methyl-1-phenylpropan-2-yl)oxy)methyl)carbamoyl)oxy)methyl)phenoxy)-6-(methoxycarbonyl)tetrahydro-2H-pyran-3,4,5-triyl triacetate (8.19)

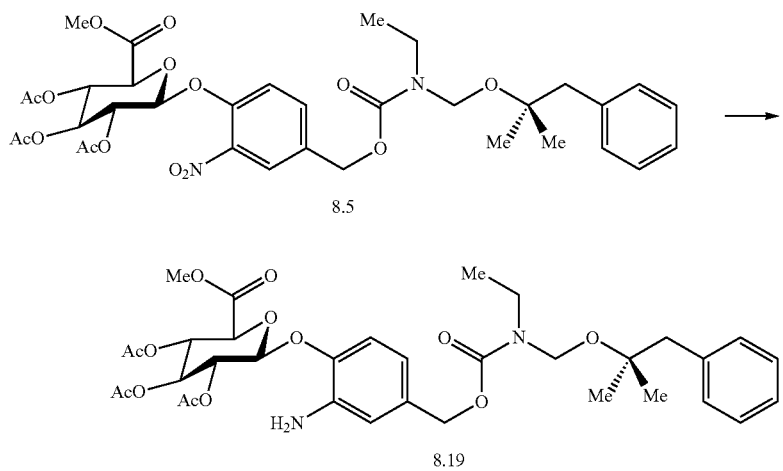

Following general reduction procedure: Compound 8.5 (56 mg, 0.074 mmol) in 390 μL of MeOH:AcOH was treated with zinc (90 mg, 1.42 mmol). Purification of the reaction mixture yielded 44 mg of 8.19, 93% yield. MS (m/z) [M+H]+ cald $C_{34}H_{44}N_2O_{13}$ 689.28, found 689.30, $^1$H NMR (400 MHz, CDCl$_3$) δ=7.26-7.14 (m, 5H), 6.86 (t, J=7.0, 1H), 7.47 (m, 2H), 5.38-5.26 (m, 3H), 5.00 (s, 3H), 4.87-4.74 (d, J=38.0, 2H), 4.14 (m, 1H), 3.80 (m, 2H), 3.74 (s, 3H), 3.49 (s, 6H), 3.35 (m, 2H), 2.77 (d, J=22.0, 2H), 2.08 (s, 3H), 2.05 (d, J=4.8, 6H), 1.13 (t, J=6.7, 3H).

Synthesis of (2S,3R,4S,5S,6S)-2-(2-amino-4-(((ethyl((naphthalen-1-yloxy)methyl)carbamoyl)oxy)methyl)phenoxy)-6-(methoxycarbonyl)tetrahydro-2H-pyran-3,4,5-triyl triacetate (8.20)

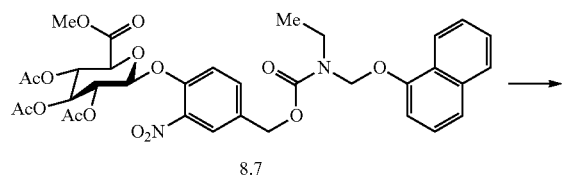

8.7

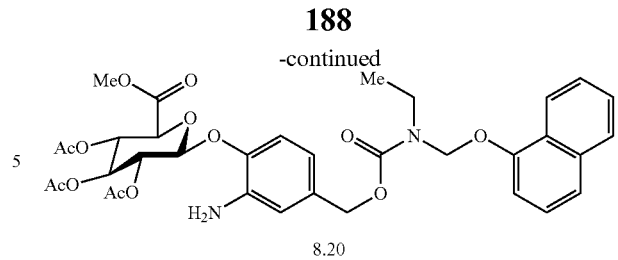

8.20

Following general reduction procedure: In 630 μL of MeOH:AcOH 8.7 (89 mg, 0.125 mmol) was treated with zinc (160 mg, 2.50 mmol). Purification of the reaction mixture yielded 78 mg of 8.20, 88% yield. MS (m/z) [M+H]+ cald $C_{34}H_{38}N_2O_{13}$ 683.24, found 683.21, $^1$H NMR (400 MHz, CDCl$_3$) δ=8.23 (m, 1H), 7.80 (m, 1H), 7.48 (m, 2H), 7.36-7.27 (m, 1H), 7.26-6.40 (m, 5H), 4.4 (d, J=36.0 2H), 5.38-5.27 (m, 3H), 5.00 (m, 3H), 4.15 (m, 1H), 3.80 (s, 3H), 3.66-3.45 (m, 2H), 2.36 (s, 3H), 2.05 (m, 9H), 3.60 (m, 1H), 1.25 (dt, J=30.0, 7.84, 1H).

Synthesis of (2S,3R,4S,5S,6S)-2-(2-amino-4-(((ethyl((phenethylthio)methyl)carbamoyl)oxy)methyl)phenoxy)-6-(methoxycarbonyl)tetrahydro-2H-pyran-3,4,5-triyl triacetate (8.21)

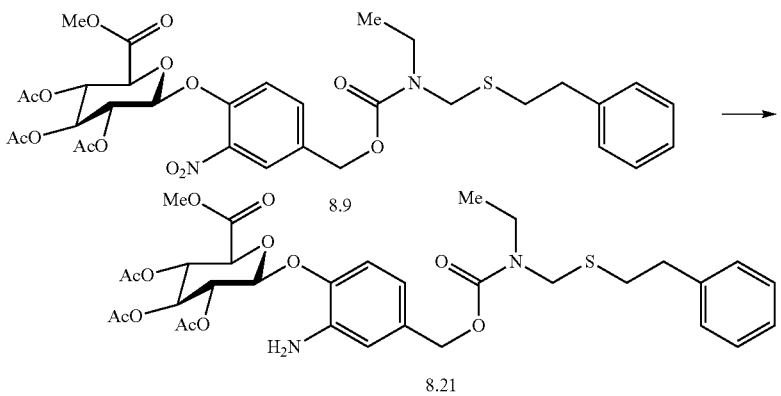

8.9

8.21

Following general reduction procedure: In 320 μL of MeOH:AcOH 8.9 (45 mg, 0.064 mmol) was treated with zinc (81 mg, 1.27 mmol). Purification of the reaction mixture yielded 38 mg of 8.21, 84% yield. MS (m/z) [M+H]+ cald $C_{34}H_{40}N_2O_{12}S$ 677.23, found 677.20, $^1$H NMR (400 MHz, CDCl$_3$) δ=7.81 (s, 1H), 7.51 (dd, J=18.1, 8.6 Hz, 1H), 7.35-7.27 (m, 3H), 7.25-7.08 (m, 3H), 5.38-5.27 (m, 3H), 5.14 (m, 3H), 4.49 (d, J=34.0, 2H), 4.20 (d, J=7.90, 2H), 3.74 (s, 3H), 3.50 (s, 2H), 3.46-3.37 (m, 2H), 3.95-2.71 (m, 3H), 2.13 (s, 3H), 2.06 (d, J=2.8, 6H), 1.15 (t, J=6.6, 3H).

Synthesis of (2S,3R,4S,5S,6S)-2-(2-amino-4-((((2-(dimethylamino)ethyl)(phenethoxymethyl)carbamoyl)oxy)methyl)phenoxy)-6-(methoxycarbonyl)tetrahydro-2H-pyran-3,4,5-triyl triacetate (8.22)

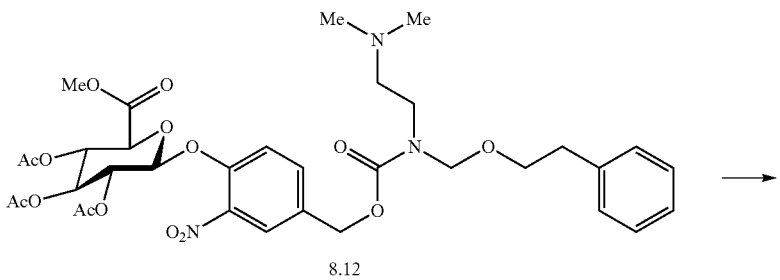

8.12

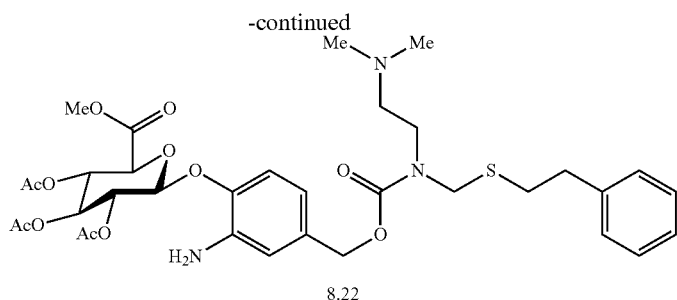

8.22

Following general reduction procedure: Compound 8.12 (51 mg, 0.070 mmol) in 380 μL of MeOH:AcOH was treated with zinc (97 mg, 1.52 mmol). Purification of the reaction mixture yielded 40 mg of 8.22, 78% yield. MS (m/z) [M+H]$^+$ cald C$_{34}$H$_{45}$N$_3$O$_{13}$ 704.30, found 704.27, $^1$H NMR (400 MHz, DMSO) δ=7.29-7.11 (m, 5H), 6.82 (t, J=6.8, 1H), 6.62 (d, J=1.8, 1H), 6.50 (t, J=7.3, 1H), 5.52-5.42 (m, 2H), 5.13-5.01 (m, 2H), 4.72-4.63 (m, 5H), 3.62 (s, 3H), 3.54 (m, 2H), 3.24 (m, 2H), 2.75 (m, 2H), 2.40-2.29 (m, 2H), 2.16 (s, 3H), 2.09 (s, 3H), 2.02 (s, 3H), 1.99 (s, 6H).

Synthesis of (2S,3R,4S,5S,6S)-2-(2-amino-4-((((2-(dimethylamino)ethyl)(((2-methyl-1-phenylpropan-2-yl)oxy)methyl)carbamoyl)oxy)methyl)phenoxy)-6-(methoxycarbonyl)tetrahydro-2H-pyran-3,4,5-triyl triacetate (8.23)

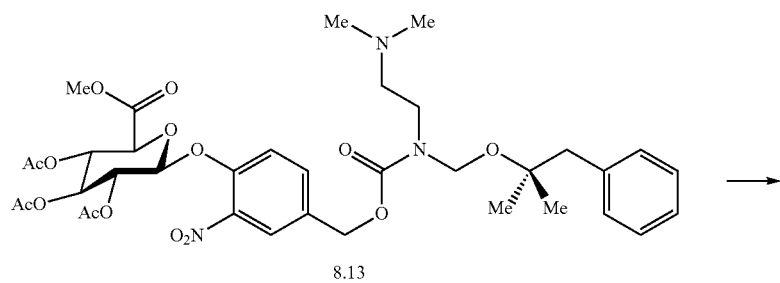

8.13

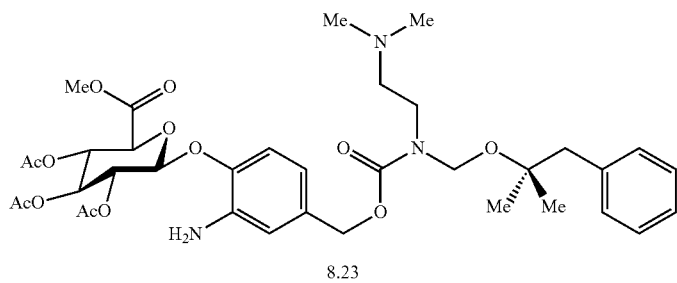

8.23

Following general reduction procedure: In 330 μL of MeOH:AcOH 8.13 (50 mg, 0.066 mmol) was treated with zinc (84 mg, 1.31 mmol). Purification of the reaction mixture yielded 46 mg of 8.23, 92% yield. MS (m/z) [M+H]$^+$ cald C$_{36}$H$_{49}$N$_3$O$_{13}$ 732.33, found 732.29, $^1$H NMR (400 MHz, CDCl$_3$) δ=7.39 (s, 1H), 7.42 (m, 2H), 7.19-7.11 (m, 4H), 6.89 (d, J=8.4 Hz, 1H), 5.40-5.25 (m, 3H), 5.15-4.98 (m, 3H), 4.85 (d, J=32.0 Hz, 2H), 3.73 (s, 2H), 2.89 (m, 2H), 2.77 (t, J=24.0, 2H), 2.11 (m, 15H), 1.21 (s, 6H).-

Synthesis of (2S,3S,4S,5R,6S)-2-(methoxycarbonyl)-6-(2-amino-4-(3-oxo-4-(((1-phenylpropan-2-yl)oxy)methyl)-2,7,10,13,16,19,22,25,28-nonaoxa-4-azanonacosyl)phenoxy)tetrahydro-2H-pyran-3,4,5-triyl triacetate (8.24)

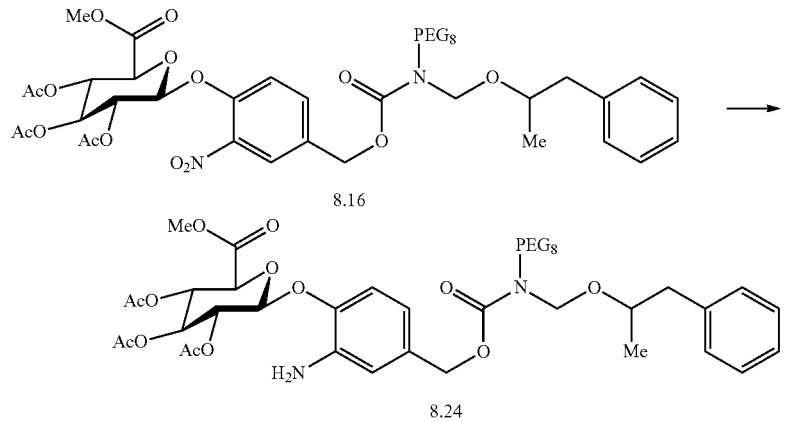

To a 1 dram vial equipped with septa screw top and an argon balloon was charged with 8.16, (56 mg, 0.048 mmol), tin dichloride (54 mg, 0.288 mmol), pyridine (37 μL, 480 mmol) and 240 μL of ethanol. The reaction was stirred for 16 h at which time LC/MS showed consumption of the starting materials. The reaction mixture was filtered over a Celite plug and the filtrate was purified by flash column chromatography to yield 22 mg of 8.24 as clear oil, 44%. MS (m/z) [M+H]$^+$ cald $C_{34}H_{44}N_2O_{13}$ 1013.46, found 1013.43.

General procedure for acetamide formation followed by lithium hydroxide aryl glucuronide deprotection. To a 1 dram vial equipped with a stir bar and PTFE lined cap was added 1 mmol of aniline glucuronide, 5 mmol of acetic anhydride, 6 mmol of Hünig's base and 5 mL of dichloromethane at RT. The reaction was monitored by LC/MS to completion, which generally occurred within 1 hour. Afterwards, the reaction mixture was azeotroped to dryness with toluene in vacuo. The crude oil was then treated with a 1 mL of 1:1 MeOH and saturated aqueous LiOH solution at RT. The hydrolysis deprotection reaction was monitored by LC/MS and was generally complete within 1 hour. The reaction mixture was then purified using preparatory HPLC (gradient 5-95 acetonitrile/water 0.05% TFA).

Synthesis of (2S,3S,4S,5R,6S)-6-(2-acetamido-4-(((ethyl(phenethoxymethyl)carbamoyl)oxy)methyl)phenoxy)-3,4,5-trihydroxytetrahydro-2H-pyran-2-carboxylic acid (8.25)

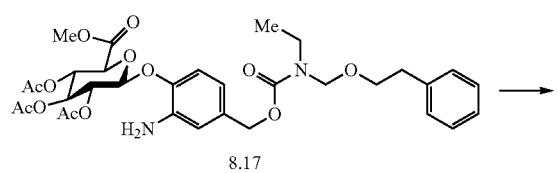

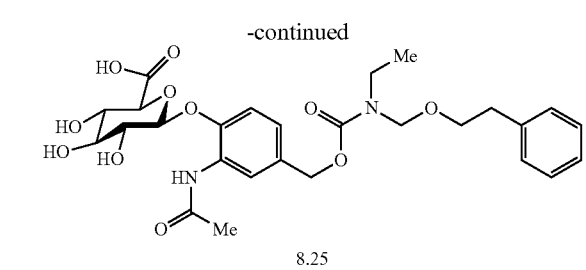

Following general procedure: Compound 8.17 (63 mg, 0.090 mmol) was converted to 40 mg of 8.25, 80% yield. MS (m/z) [M+H]$^+$ cald $C_{27}H_{34}N_2O_{11}$ 563.22, found 563.18.

Synthesis of (2S,3S,4S,5R,6S)-6-(2-acetamido-4-(((ethyl(((-phenylpropan-2-yl)oxy)methyl)carbamoyl)oxy)methyl)phenoxy)-3,4,5-trihydroxytetrahydro-2H-pyran-2-carboxylic acid (8.26)

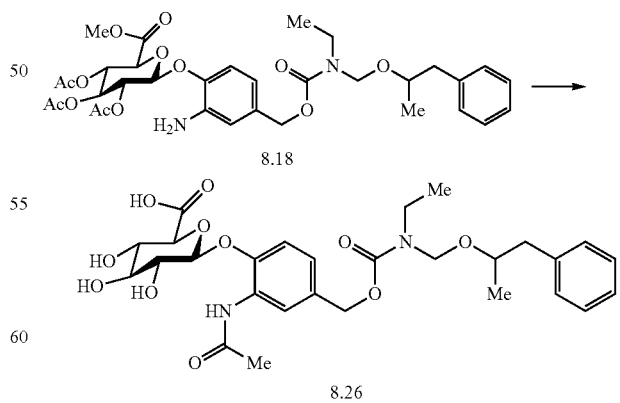

Following general procedure: Compound 8.16 (56 mg, 0.078 mmol) was converted to 33 mg of 8.24, 73% yield. MS (m/z) [M+H]$^+$ cald $C_{28}H_{36}N_2O_{11}$ 577.23, found 577.25.

Synthesis of (2S,3S,4S,5R,6S)-6-(2-acetamido-4-(((ethyl(((2-methyl-1-phenylpropan-2-yl)oxy)methyl)carbamoyl)oxy)methyl)phenoxy)-3,4,5-trihydroxytetrahydro-2H-pyran-2-carboxylic acid (8.27)

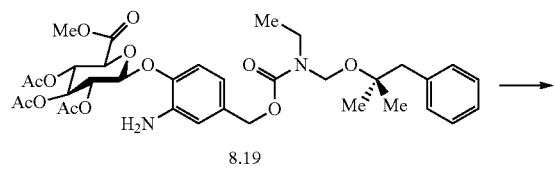

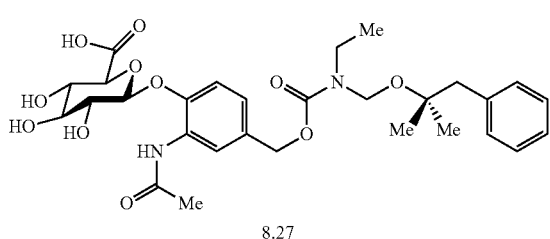

Following general procedure: Compound 8.19 (29 mg, 0.040 mmol) was converted to 18 mg of 8.27, 78% yield. MS (m/z) [N+H]⁺ cald $C_{29}H_{38}N_2O_{11}$ 591.25, found 591.27.

Synthesis of (2S,3S,4S,5R,6S)-6-(2-acetamido-4-(((ethyl((naphthalen-1-yloxy)methyl)carbamoyl)oxy)methyl)phenoxy)-3,4,5-trihydroxytetrahydro-2H-pyran-2-carboxylic acid (8.28)

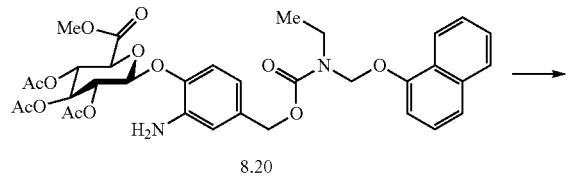

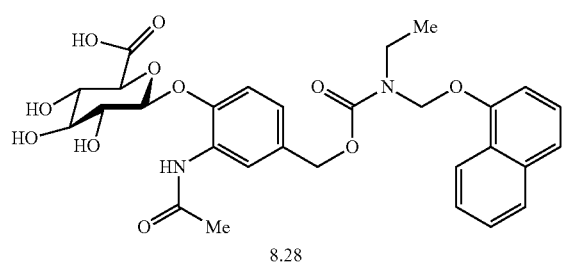

Following general procedure: Compound 8.20 (197 mg, 0.270 mmol) was converted to 103 mg of 8.28, 66% yield. MS (m/z) [M+H]⁺ cald $C_{29}H_{32}N_2O_{11}$ 585.20, found 585.23.

Synthesis of (2S,3S,4S,5R,6S)-6-(2-acetamido-4-(((ethyl((phenethylthio)methyl)carbamoyl)oxy)methyl)phenoxy)-3,4,5-trihydroxytetrahydro-2H-pyran-2-carboxylic acid (8.29)

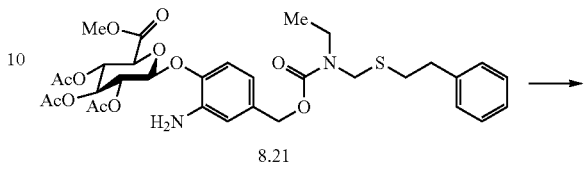

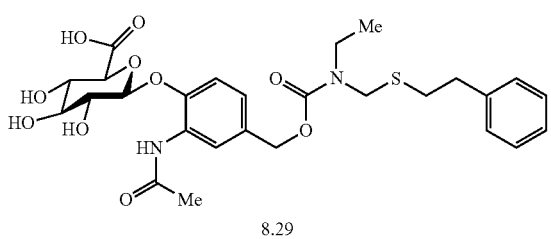

Following general procedure: Compound 8.21 (48 mg, 0.067 mmol) was converted to 32 mg of 8.29, 71% yield. MS (m/z) [M+H]⁺ cald $C_{27}H_{34}N_2O_{10}S$, 579.79, found 579.76.

Synthesis of (2S,3S,4S,5R,6S)-6-(2-acetamido-4-((((2-(dimethylamino)ethyl)(phenethoxymethyl)carbamoyl)oxy)methyl)phenoxy)-3,4,5-trihydroxytetrahydro-2H-pyran-2-carboxylic acid (8.30)

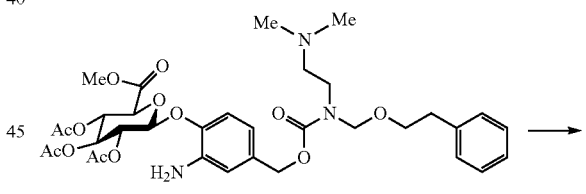

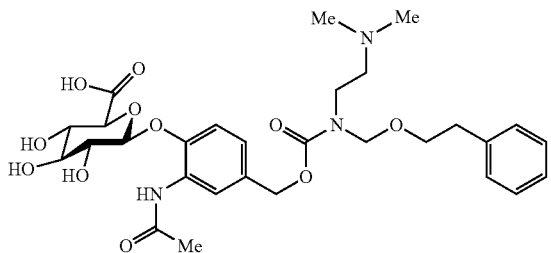

Following general procedure: Compound 8.22 (45 mg, 0.062 mmol) was converted to 28 mg of 8.30, 75% yield. MS (m/z) [M+H]⁺ cald $C_{29}H_{39}N_3O_{11}$ 606.26, found 606.25.

Synthesis of (2S,3S,4S,5R,6S)-6-(2-acetamido-4-((((2-(dimethylamino)ethyl)(((2-methyl-1-phenyl-propan-2-yl)oxy)methyl)carbamoyl)oxy)methyl)phenoxy)-3,4,5-trihydroxytetrahydro-2H-pyran-2-carboxylic acid (8.31)

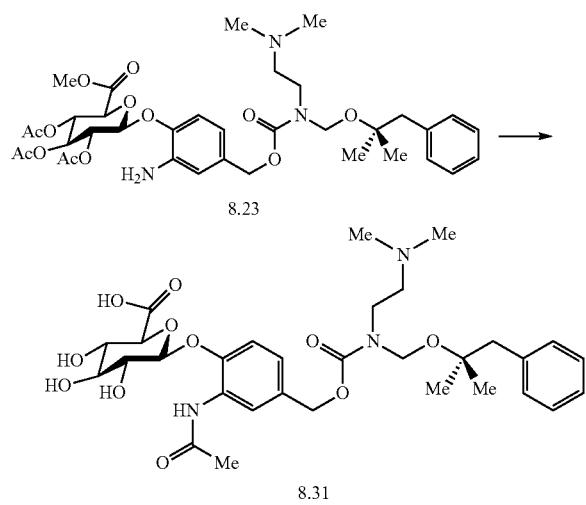

Following general procedure: Compound 8.23 (50 mg, 0.066 mmol) was converted to 31 mg of 8.31, 72% yield. MS (m/z) [M+H]$^+$ cald $C_{31}H_{43}N_3O_{11}$ 634.29, found 634.32.

Synthesis of (2S,3S,4S,5R,6S)-6-(2-acetamido-4-(3-oxo-4-(((1-phenylpropan-2-yl)oxy)methyl)-2,7,10,13,16,19,22,25,28-nonaoxa-4-azanonacosyl)phenoxy)-3,4,5-trihydroxytetrahydro-2H-pyran-2-carboxylic acid (8.32)

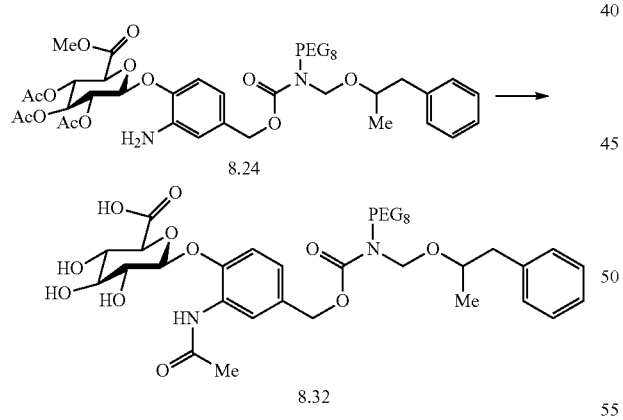

Following general procedure: Compound 7.26 (52 mg, 0.050 mmol) was converted to 28 mg of 7.34, 62% yield. MS (m/z) [M+H]$^+$ cald $C_{29}H_{32}N_2O_{11}$ 915.43, found 915.41.

Example 9: In Vitro Stability of Model Systems Having Self-Immolative Assembly Units Each Comprising a MAC Unit, or Variant Thereof, to Spontaneous Hydrolysis The final N-acetyl products of Example 8 contain Self-immolative Assembly Units, each having a methylene carbamate unit of formula I covalently attached to a Drug Unit from a model drug compound, that have been capped off with acetyl in lieu of a Stretcher Unit. As such, the compounds represent model Drug-Linker compounds. The stability of those moieties to spontaneous hydrolysis was determined using the following general procedure.

General procedure for testing Drug-Linker stability: Final N-acetyl products of Example 8 were dissolved in 1 mL 0.1 M phosphate buffered saline, pH 7.4, in a vial at 37° C. LC/MS samples were prepared by adding 2 μL aliquots of incubated compound solution to 100 μL of MeOH in an HPLC vial. Each conjugate was tested every 24 h for 7 days.

For model drug-linker compounds having a methylene carbamate unit of formula I with R as ethyl or PEG, the secondary aliphatic alcohol (standing in for an aliphatic alcohol-containing free drug) provided model Drug-Linker compounds (8.26 and 8.32, respectively) that showed no signs of degradation after 7 days. The model Drug-Linker compound from the thiol-containing model drug compound having a methylene carbamate unit with R as ethyl (8.29) also showed no sign of degradation after 7 days. With R as ethyl and the Drug Unit from naphthol (standing in for an aromatic alcohol-containing drug) provided a model drug-linker compound having a MAC unit covalently attached to a Drug Unit (8.28) that had excellent stability, which was indistinguishable during the course of the study to the corresponding model Drug-Linker compound (8.26) from the secondary aliphatic alcohol. That outcome was unexpected since a MAC unit incorporating the oxygen heteroatom of an aromatic alcohol may not be as hydrolytic stable as one incorporating a secondary alcohol due to its lower pKa and thus the better leaving group ability of the aryl-OH compared to aliphatic-OH. In contrast, the primary and tertiary aliphatic alcohols standing in for primary and secondary aliphatic alcohol-containing free drugs provided model Drug-Linker compounds (8.25 and 8.27, respectively) with R as ethyl that had suitable stability but not to the same extent as that observed for the model Drug Linker compound from the secondary alcohol. Unexpectedly, when R is dimethylaminoethyl instead of ethyl, the primary and tertiary alcohol model drug compounds provided model Drug-Linker compounds (8.25 and 8.27) that were shown to have the same excellent stability as the model Drug-Linker compound (8.26) from the secondary aliphatic alcohol.

We believe that stability of a drug linker may be improved by substitution of the carbamate nitrogen of its methylene carbamate unit with a Basic Unit as defined herein including without limitation a dimethylaminoalkyl moiety.

Example 10: In Vitro Stability of Drug-Linker Compounds Having a Self-Immolative Assembly Unit to Spontaneous Hydrolysis of its Methylene Carbamate Unit Stability of the MAC Unit variant in drug-linker moieties represented by corresponding moieties within Linker-Drug compounds 4.5 (triptolide), 5.6 (everolimus), 6.4 (tricolimus) and 7.7 (BMN-673) of Examples 4, 5, 6 and 7 respectively, were evaluated in the following manner.

For evaluation of in vitro stability of Compound 7.7 this Drug-Linker compound was converted to its N-acetylcysteine conjugate (NAC-7.7), which provide a model LDC with NAC serving as a surrogate for a targeting antibody Ligand Unit. For that purpose eight microliters of a 8 mM DMSO stock of Drug-Linker Compound was diluted in phosphate-buffered saline (0.39 mL). The maleimide moiety in each Drug-Linker Compound was then quenched with N-acetylcysteine (0.8 µL, 100 mM stock), and the material was stored in a 37° C. incubator. Aliquots were drawn at various time points out to 14 days and analyzed by UPLC-MS for drug-linker integrity.

Stability testing was conducted as in Example 9. No indication of drug-linker degradation was noted after 14 da incubation in 0.1 M PBS, pH 7.4, at 37° C. for model Drug Linker Compounds 4.5, 5.6 and 6.4, and the model conjugate NAC-7.7 in 4 mM PBS, pH 7.4, 37° C. In the case of NAC-7.7, the corresponding acid-amide from hydrolysis of the succinimide moiety was observed. Unexpectedly, the model Drug-Linker compound (8.26), which incorporates the secondary aliphatic alcohol as the stand-in for a secondary aliphatic-alcohol containing free had increase stability in comparison to the acceptable stability of the Drug-Linker Compound 6.4, which derived form a secondary aliphatic-alcohol containing free drug (tricolimus), Furthermore, the Drug-Linker Compound 5.6, which is derived from a primary aliphatic alcohol-containing free drug (everolimus) was found to have even better hydrolytic stability compared to the model Drug-Linker Compound (8.23), which was derived from the primary aliphatic alcohol as the stand-in for a primary aliphatic alcohol-containing free drug.

Thus, each model drug compound provided a drug-linker moiety having a methylene carbamate unit of acceptable stability, the degree of which appears to be independent on the identity of the heteroatom T*, and thus of the functional group on the drug through which it is conjugated, but may be also dependent on the remaining structure of the Drug Unit. Results with methylene carbamate units that are N-substituted with a basic moiety provide drug linker moieties of exceptional stability.

Example 11: Ex Vivo Stability of an Antibody Drug Conjugate Having a Self-Immolative Assembly Unit to Spontaneous Hydrolysis of its Methylene Carbamate Unit ADC with four drug-liner moieties from Drug-Linker compound 1.3 (i.e., an ADC composition having an average drug loading of about 4), prepared as in Example 14, was incubated at 1 mg/mL in 200 µL sterile aliquots of commercially available rat and mouse plasma (Bioreclamation). Aliquots were incubated at 37° C. and frozen at −80° C. at each time point. After the incubations were complete, samples were thawed and 50 µL net IgSelect resin (GE Healthcare) was added to each aliquot. Samples were rotated at 4° C. for at least three hours and transferred to a 96-well filter plate (Seahorse) on a vacuum manifold. The resin was washed three times with 3 mM PBS (Gibco) and eluted by centrifugation with two 50 µL aliquots of IgG Elution Buffer (Pierce). Purified ADC's were neutralized with 15 µL of 1M Tris (pH 7.4) and deglycosylated at 37° C. for one hour using PNGaseF (New England Biolabs). A 40 µL injection of each sample was resolved on a Polyhydroxyethyl A SEC column (PolyLC) in-line with a QTOF (Agilent) mass spectrometer such that the ADC could be analyzed in a native, intact state (see Valliere-Douglass, John et. al. "Native Intact Mass Determination of Antibodies Conjugated with Monomethyl Auristatin E and F at Interchain Cysteine Residues" Analytical Chemistry 2012, 84, 2843-2849). The raw mass spectrum of the intact ADC was deconvoluted, and the area under each deconvoluted peak was integrated to determine an average drug-antibody ratio for each sample. FIG. 1 shows the plasma stability of the AE drug conjugate as a function of drug-antibody ratio determined by the above mass spectroscopy method over time in days.

The mass spectral data confirms that any drug loss that had occurred was due to complete elimination of the drug-linker from the Ligand Unit and not due to linker degradation attributable to hydrolytic instability the MAC Unit. The mass spectral data also demonstrates that after complete hydrolysis of the succinimide ring system of the Stretcher Unit's succinimide moiety to the corresponding acid-amide moiety the drug:antibody ratio remained constant.

Stability data for various constructs described herein having a Self-immolative Assembly unit having a methylene carbamate unit covalently attached to a Drug unit corresponding in structure to a drug or model drug is summarized in Table 4.

TABLE 4

Summary of Self-immolative Assembly Unit Stability

| Drug or model drug (carbamate R) | Construct (drug functional group) | Relative Degradation Half-life Observed by LC/MS |
|---|---|---|
| 1.3 (H) | cAC10-AE Conjugate (2°OH)* | None Observed |
| 4.5 (Et) | Triptolide-Linker Compound (2°OH) | None Observed |
| 5.6 (H) | Everolimus-Linker Compound (2°OH) | 7 days |
| 6.4 (H) | Tricolimus-Linker Compound (1°OH) | None Observed |
| 7.7 (H) | NAC-(BMN-673) Conjugate (2°NH) | None Observed |
| 8.25 (Et) | Model Drug-Linker Compound (1°OH) | 7 days |
| 8.30 (BU)** | Model Drug-Linker Compound (1°OH) | None Observed |
| 8.26 (Et) | Model Drug-Linker Compound (2°OH) | None Observed |
| 8.32 (PEG$_8$) | Model Drug-Linker Compound (2°OH) | None Observed |
| 8.27 (Et) | Model Drug-Linker Compound (3°OH) | 7 days |
| 8.31 (BU) | Model Drug-Linker Compound (3°OH) | None Observed |
| 8.28 (Et) | Model Drug-Linker Compound (Ar—OH) | None Observed |
| 8.29 (Et) | Model Drug-Linker Compound (1°SH) | None Observed |

*Incubated in rat or mouse plasma at 37° C., all others in 0.1M PBS, pH 7.4, at 37° C.
**BU is —CH$_2$CH$_2$—N(CH$_3$)$_2$

Example 12. Release of Free Drug or Model Compounds for Thiol-Containing Drugs, Primary, Secondary and Tertiary Aliphatic Alcohol-Containing Drugs, and Phenolic Alcohol-Containing Drug from NAC-Conjugates Having a Self-Immolative Assembly Unit Comprised of a MAC Unit or Variant Thereof Subsequent to Glucuronidase Activation of that Unit Release of free drug from the NAC-7.7 conjugate derived from the Drug-Linker Compound of Example 7 was evaluated in the following manner: An enzyme stock was prepared by dissolving Type B-1 β-glucuronidase (bovine liver, 1,644,000 units/g solid) in pH 5 100 mM sodium acetate buffer to a working concentration of 0.5 mg/mL. Five microliters of 8 mM drug-linker stock of compound 7.7 was added to 12.5 µL DMSO, 26.3 µL of phosphate-buffered saline, and 6.75 µL of 100 mM N-acetylcysteine. The quenched linker was then diluted with 0.45 mL enzyme stock. The enzymatic reaction was then incubated at 37 C, with multiple time points taken at 1, 10, 20, and 40 minutes. Each time point sample consisted of 20 µL reaction diluted in 5 volumes ice cold methanol and cooled to −20 C until all the samples were withdrawn. The samples were then centrifuged at 12,000 g for 5 minutes and 20 µL of supernatant was analyzed by UPLC-MS. After 20 minutes of enzyme digestion the drug-linker was completely consumed. By 40 minutes, the majority of the material was free drug, indicating effectively complete drug release from the linker system.

In contrast to the cAC10-2.0 conjugate, which rapidly released free drug from the MAC unit with no detectable intermediate after self-immolation of the Self-immolative Assembly Unit, the NAC-7.7 conjugate showed build-up of an intermediate, NH$_2$—CH$_2$-7.0, the structure for which is shown in the following scheme.

replacing the N-acetyl capping group with N-3-(propionoyl)-maleimide, which introduces a maleimide Stretcher Unit precursor, in the amino intermediates used for the preparation of model drug linker compounds 8.23-8.30. The maleimide moieties are then quenched with N-acetyl-cyste-

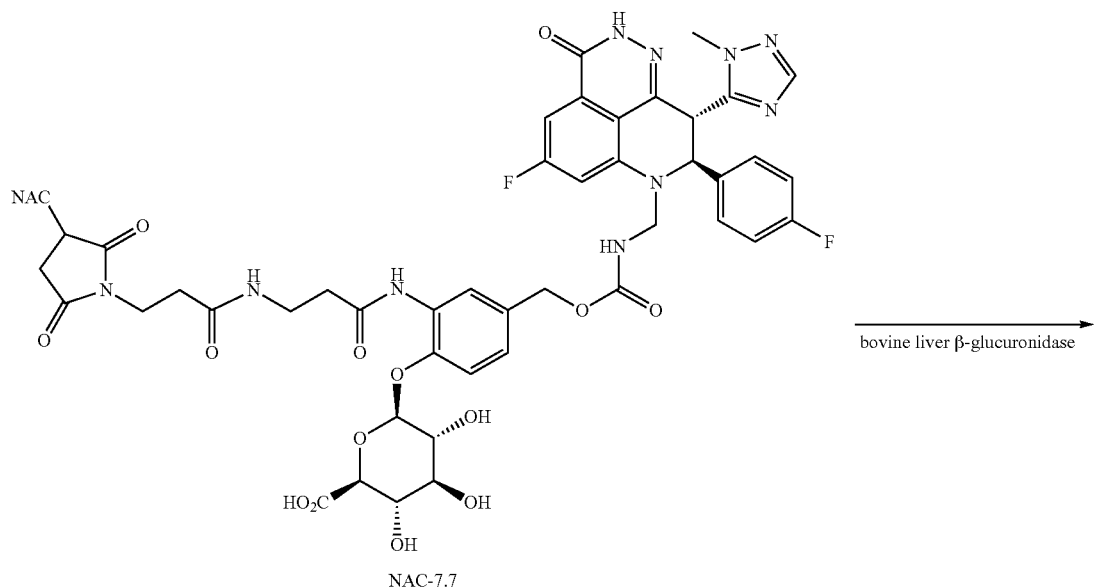

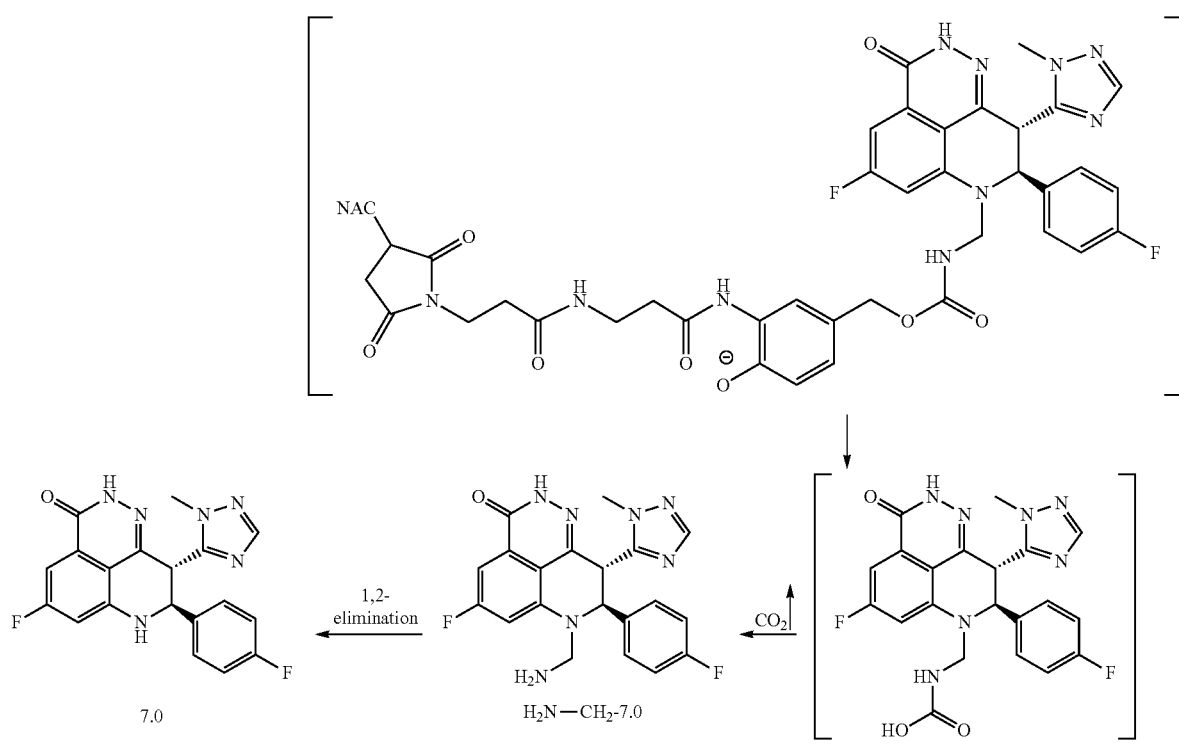

Releases of stand-in "free drugs" from NAC conjugates incorporating the Drug-Linker moieties from Example 8 were also studied. Those compounds were prepared by ine as previously described for the preparation of NAC-7.7. The NAC-conjugates derived from the amino intermediates of Example 8 have the generalized structure of

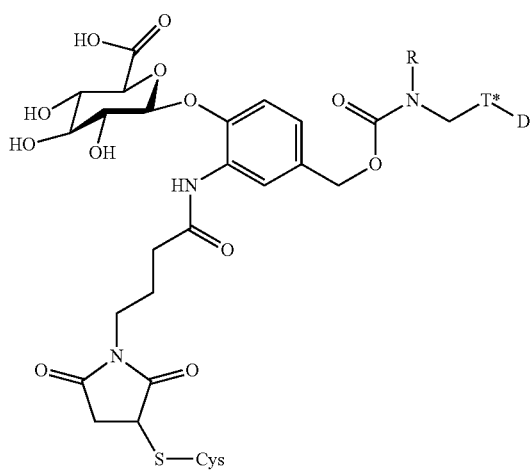

wherein T* is the oxygen or sulfur heteroatom from the hydroxyl or sulfhydryl functional group of the primary alcohol or thiol-containing compound or the oxygen heteroatom from the hydroxyl functional group of the secondary or tertiary alcohol-containing compound or from the phenolic-containing compound of Table 3. The time to complete D-T*-H release with variations in R and released compound are shown in Table 5.

TABLE 5

Free Drug Release Efficiency Subsequent to Activation of Self-immolation

| D-T*-H (corresponding model drug-linker compd) | R | Time to 100% Release (min.) |
|---|---|---|
| Primary alcohol (8.25) | —$CH_2CH_3$ | 15 |
| Primary alcohol (8.30) | —$CH_2CH_2N(CH_3)_2$ | 15 |
| Secondary alcohol (8.26) | —$CH_2CH_3$ | 45 |
| Secondary alcohol (8.32) | -$PEG_8$ | 15 |
| Tertiary alcohol (8.27) | —$CH_2CH_3$ | 15 |
| Tertiary alcohol (8.31) | —$CH_2CH_2N(CH_3)_2$ | 15 |
| Aromatic alcohol (8.28) | —$CH_2CH_3$ | 25 |
| Thiol (8.29) | —$CH_2CH_3$ | 40 |

Figure 2:
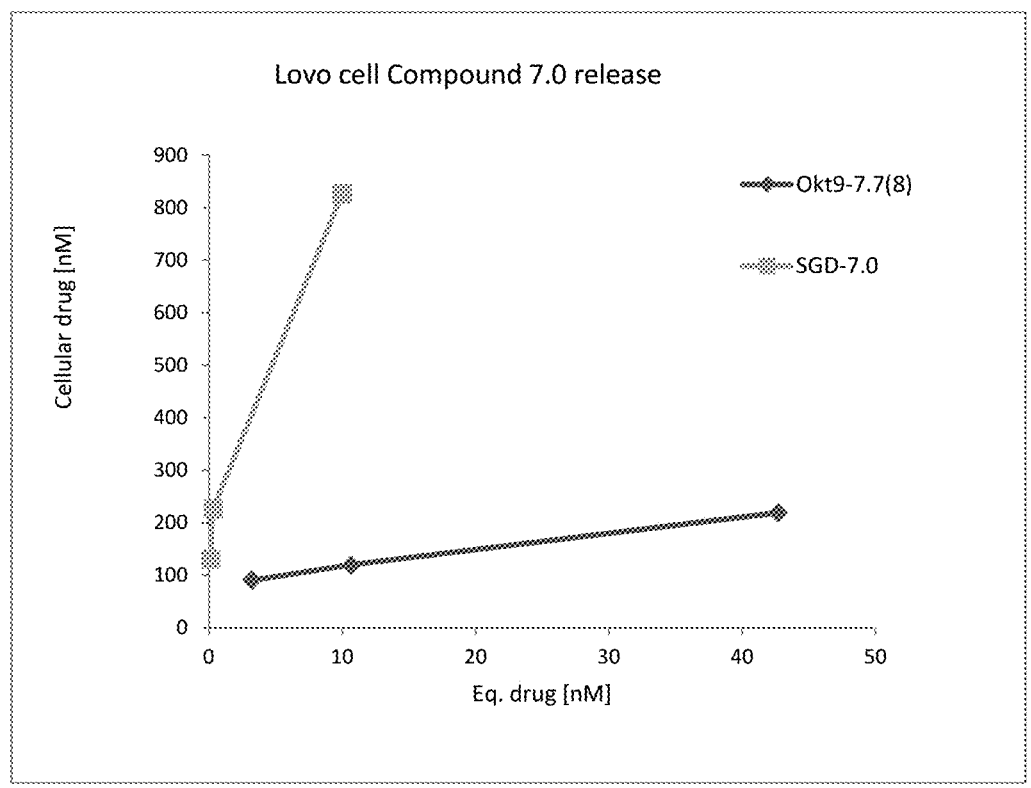
FIG. 2 demonstrates the intracellular accumulation of free drug from targeted delivery by a Ligand Drug Conjugate having a variant MAC Unit attached to a Drug Unit from the PARP inhibitor BMN-673.

Example 13: Intracellular Delivery of Cytotoxic Free Drug to Targeted Cancer Cells Released from a MAC Unit of an Antibody Drug Conjugate Due to Conditional Activation of its Self-Immolative Assembly Unit Lovo cells (human colon adenocarcinoma cell line) contacted with 8 drug loaded cOKT9-7.7 conjugate, which targets $CD70^+$ cells, having drug-linker moiety of Example 7 and prepared in the manner of Example 14, was found to have greater amounts of intracellular free drug (i.e., compound 7.0) than when contacted with an equivalent amount of untargeted free drug as shown in FIG. 2. Those results indicate that the ADC is targeting the desired cells and is efficiently releasing free drug upon its cellular internalization.

Example 14: Preparation of ADC's Having a MAC Unit and their In Vitro Cytotoxicities The targeting antibody ligands cAC10 and h1F6 are described in U.S. Pat. No. 8,257,706 and US 2009/0148942, respectively. cAC10 targets $CD30^+$ cells, which includes Karpas 299, L540cy and L-428. h1F6 targets $CD70^+$ cells, which includes 786-0, L-428 and Caki-1.

For ADC compositions having a homogeneous drug loading of 8, full reduction of interchain disulfide bonds of the targeting antibody ligand was accomplished by the method of US 2003/00883263. Briefly, the targeting antibody (5-10 mg/mL) in phosphate buffered saline with 1 mM ethylenediaminetetraacetic acid (EDTA) was treated with 10 eq. tris(2-carboxyethyl)phosphine (TCEP) neutralized to pH 7.4 using potassium phosphate dibasic and incubated at 37 C for 45 minutes. Separation of low molecular weight agents is achieved by size exclusion chromatography on a Sephadex G25 column.

Partial reduction of the targeting antibody ligand to provide ADC compositions having an average drug loading of about 4 was accomplished using the method of US 2005/0238649. Briefly, the antibody in phosphate buffered saline with 1 mM EDTA, pH 7.4, was treated with 2.1 eq. TCEP and then incubated at 37° C. for about 45 minutes. The thiol/Ab value was checked by determining the reduced antibody concentration from the absorbance at 280 nm of the solution and the thiol concentration by reaction with DTNB and determination of the absorbance at 412 nm.

Drug-Linker compounds were conjugated to the fully and partially reduced targeting antibody ligands using the method of US 2005/0238649. Briefly, a Drug-Linker compound in DMSO, was added to the reduced antibody in PBS with EDTA along with excess DMSO to a total reaction co-solvent of 15%. After 30 minutes at ambient temperature, an excess of n-acetyl cysteine was added to the mixture to quench all unreacted maleimide groups. The reaction mixture was purified by desalting using Sephadex G25 resin into PBS buffer.

The protein concentration of the resulting ADC composition was determined at 280 nm. Bound drug was quantified by analysis using hydrophobic interaction (HIC) HPLC.

cAC10-1006 and hF16-1006, referenced in the following tables, is the chimeric AC10 antibody and the humanized F16 antibody, respectively, conjugated to monomethyl auristatin E (MMAE) at its N terminus via a carbamate functional group to a val-cit-PABA self-immolative moiety having formula XVIII and was used as a control. The resultant ADCs were tested against multiple cell lines to determine in vitro activity, the results from which are summarized in Tables 5 and 6.

TABLE 6

In vitro cytotoxic activity of ADCs prepared with MAC linkers; values represent $IC_{50}$s in ng/mL.

| ADC | Dr/Ab | Karpas 299 CD30+ CD70− | L540cy CD30+ CD70 (low) | 786-0 CD70+ | Caki-1 CD70+ |
|---|---|---|---|---|---|
| h1F6-1.3 | 3.6 | >1000 | >1000* | >1000** | 19 |
| cAC10-1.3 | 3.7 | 0.8 | 3 | >1000 | >1000 |
| cAC10-1006 | 4.0 | 1 | 8 | >1000 | >1000 |
| h1F6-1006 | 4.0 | >1000 | >1000 | >1000** | 7 |

TABLE 7

In vitro cytotoxic activity of ADCs prepared with MAC linkers; values represent $IC_{50}s$ in ng/mL.

| ADC | Dr/Ab | Karpas 299 CD30+ CD70− | L540cy CD30+ CD70− | L-428 CD30 (med) CD70 (low) | HEL92.1.7 CD30− CD70− |
|---|---|---|---|---|---|
| cAC10-2.0 | 8.0 | 0.4 | 3 | 65 | >1000 |
| cAC10-1006 | 4.0 | 0.6 | 9 | >1000* | >1000 |
| h1F6-1006 | 4.0 | >1000 | >1000 | >1000* | >1000 |

*Cell lines are known to be resistant to MMAE
**Cell line known to be resistant to auristatins

What is claimed is:

1. A Ligand-Drug Conjugate Compound having the structure of Formula II:

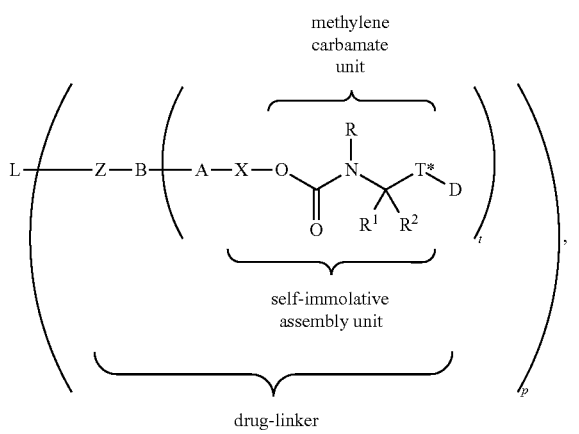

drug-linker or a pharmaceutically acceptable salt thereof, wherein
L is a Ligand Unit;
Z is a Stretcher Unit;
B is an optional branching unit and is present when subscript t is greater than 1 and is absent when subscript t is 1;
A is an optional Connector Unit;
D is a Drug Unit incorporating a free drug having a hydroxyl; thiol; amine or amide functional group; wherein the functional group has been incorporated into the indicated methylene carbamate unit;
T* is the oxygen; sulfur or optionally substituted nitrogen heteroatom from said functional group;
X is an activateable self-immolative moiety;
R; $R^1$ and $R^2$ independently are hydrogen; optionally substituted $C_1$–$C_6$ alkyl; optionally substituted $C_6$–$C_{14}$ aryl; or optionally substituted C-linked heteroaryl having from 3 to 8 carbon atom ring members and one to four heteroatom ring members independently selected from the group consisting of N, O, P and S; or
wherein R is a Basic Unit wherein the basic functional group of the Basic Unit is an amine or a nitrogen-containing 3, 4, 5, or 6 membered heterocycle, optionally substituted, wherein the heterocycle is C-linked or N-linked, or the basic functional group of the Basic Unit is $-N(R^{op})_2$, wherein each $R^{op}$ is independently selected from the group consisting of hydrogen and $C_1$–$C_6$ alkyl or each $R^{op}$ is methyl;
subscript t ranges from 1 to 4; and
subscript p is an integer ranging from 1 to 16.

2. The Ligand-Drug Conjugate Compound of claim 1 having Formula IIa:

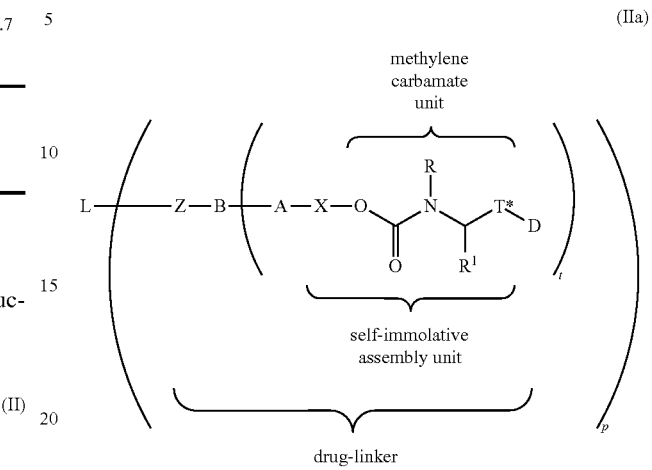

drug-linker or a pharmaceutically acceptable salt thereof.

3. The Ligand-Drug Conjugate Compound of claim 2 wherein R and $R^1$ are independently selected from the group consisting of hydrogen, optionally substituted $C_1$–$C_6$ alkyl and optionally substituted $C_6$–$C_{14}$ aryl.

4. The Ligand-Drug Conjugate Compound of claim 3 wherein one or more of R, $R^1$ and $R^2$ is not substituted.

5. The Ligand-Drug Conjugate Compound of claim 3 wherein the optional substituent is selected from the group consisting of $-N(R^{op})_2$, $-N(R^{op})_3$ and $-C(=NR)N(R^{op})_2$, wherein each $R^{op}$ is independently selected from the group consisting of hydrogen, $C_1$–$C_{20}$ alkyl, $C_6$–$C_{20}$ aryl, $C_3$–$C_{14}$ heterocycle, and a protecting group.

6. The Ligand-Drug Conjugate Compound of claim 2 wherein R is a Basic Unit wherein the basic functional group of the Basic Unit is an amine or a nitrogen-containing 3, 4, 5, or 6 membered heterocycle, optionally substituted, wherein the heterocycle is C-linked or N-linked, or the basic functional group of the Basic Unit is $-N(R^{op})_2$, wherein each $R^{op}$ is independently selected from the group consisting of hydrogen and $C_1$–$C_6$ alkyl or each $R^{op}$ is methyl.

7. The Ligand Drug Conjugate Compound of claim 6 wherein the Basic Unit is $-CH_2CH_2N(R^{op})_2$, wherein each $R^{op}$ is independently selected from the group consisting of hydrogen and methyl.

8. The Ligand-Drug Conjugate Compound of claim 7 wherein $R^1$ is hydrogen.

9. The Ligand-Drug Conjugate Compound of claim 8 wherein the free drug has a hydroxyl functional group that has been incorporated into the methylene carbamate unit so that T* represents the oxygen heteroatom from that functional group.

10. The Ligand-Drug Conjugate Compound of claim 9 wherein the free drug is an aliphatic alcohol-containing drug or an aromatic alcohol-containing drug, and wherein attachment of D within the Ligand Drug Conjugate compound is via the oxygen heteroatom of the hydroxyl functional group of the aliphatic or aromatic alcohol, so that T* represents the oxygen atom from that functional group.

11. The Ligand-Drug Conjugate Compound of claim 1 wherein B is absent and subscript t is 1.

12. The Ligand-Drug Conjugate Compound of claim 11 wherein the activateable self-immolative moiety (X) has the structure of formula (i)

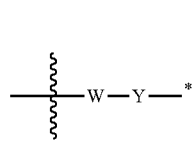
(i)

wherein the way line indicates covalent attachment of W to A, B or Z depending on the presence or absence of A and/or B and the asterisk (*) indicates covalent attachment of Y to the methylene carbamate unit and wherein;
W is an Activation Unit; and
Y is a self-immolative Spacer Unit,
wherein activation of self-immolation of Y results in release of the free drug.

13. The Ligand-Drug Conjugate Compound of claim 12 wherein activation for self-immolation of Y is by enzymatic cleavage of a covalent bond between W and Y.

14. The Ligand-Drug Conjugate Compound of claim 13 wherein enzymatic cleavage is by a tumor associated protease.

15. The Ligand-Drug Conjugate Compound of claim 14 wherein the tumor associated protease is cathepsin B and W is -Val-Cit-, -Phe-Lys- or -Val-Ala-.

16. The Ligand-Drug Conjugate Compound of claim 15 wherein -W-Y- has the structure of:

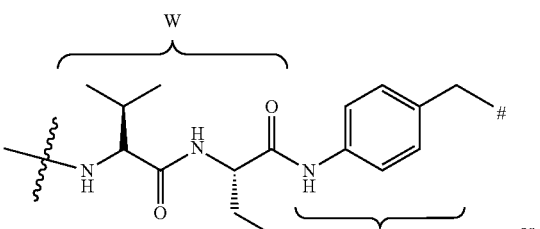

or

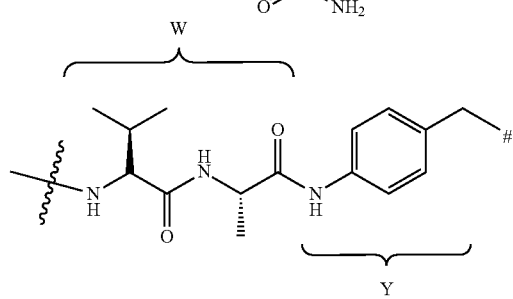

wherein the wavy bond to the nitrogen of W indicates covalent linkage to Z, A or B, depending on the presence or absence of A and/or B, and the hash mark (#) indicates covalent attachment of the benzylic carbon of Y to the methylene carbamate unit.

17. The Ligand-Drug Conjugate Compound claim 1 wherein the activateable self-immolative moiety (X) has the structure of formula (ii):

(ii)

wherein the wavy line indicates covalent attachment of Y to A, B or Z depending on the presence or absence of A and/or B, and the asterisk (*) indicates covalent attachment of Y to the methylene carbamate moiety, and wherein;
W is an Activation Unit; and
Y is a self-immolative Spacer Unit,
wherein activation of self-immolation of Y results in release of the free drug.

18. The Ligand-Drug Conjugate Compound of claim 17 wherein activation for self-immolation of Y is by enzymatic cleavage of a covalent bond between W and Y, wherein enzymatic cleavage is by a glycosidase.

19. The Ligand-Drug Conjugate Compound of claim 18 wherein W is a sugar moiety connected to Y via a glycosidic bond cleavable by a glycosidase for activation of self-immolation of Y, wherein the glycosidase is a glucuronidase.

20. The Ligand-Drug Conjugate Compound of claim 19 wherein -Y(W)- has the structure of:

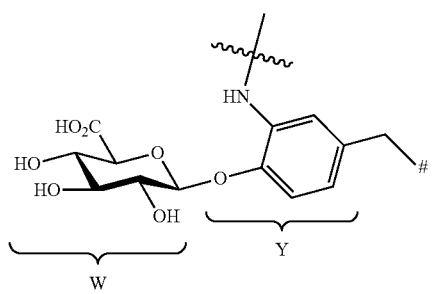

wherein the wavy line adjacent to the nitrogen of Y indicates covalent attachment of Y to Z, A or B, depending on the presence or absence of A and/or B, and the hash mark (#) indicates covalent attachment of the benzylic carbon of Y to the methylene carbamate unit.

21. The Ligand-Drug Conjugate Compound of claim 1 wherein the Stretcher unit (Z) is comprised of a succinimide moiety or an acid-amide moiety and optionally a Basic Unit, wherein the succinimide or acid-amide moiety is attached to a sulfur atom of the Ligand Unit.

22. The Ligand-Drug Conjugate Compound of claim 21 wherein the Stretcher unit (Z) has the structure of formula Xa':

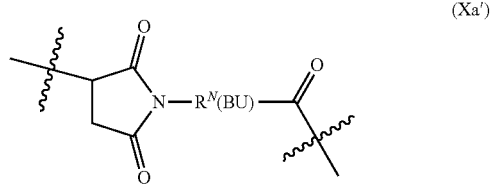
(Xa')

wherein the wavy line adjacent to the succinimide ring system indicates covalent attachment to a sulfur atom of the Ligand Unit;

the wavy line adjacent to the carbonyl indicates attachment within the remainder of the Ligand Drug Conjugate Compound;

and $R^N$ is $-C_2-C_5$ alkylene; wherein the alkylene is substituted by a Basic Unit (BU), wherein BU is $-(CH_2)_xNH_2$, $-(CH_2)_xNHR^{op}$; or $-(CH_2)_xN(R^{op})_2$, wherein subscript x is an integer ranging from 1 to 4; and $R^{op}$ is $C_1-C_6$ alkyl.

23. The Ligand-Drug Conjugate Compound of claim 21 wherein the Stretcher unit (Z) has the structure of:

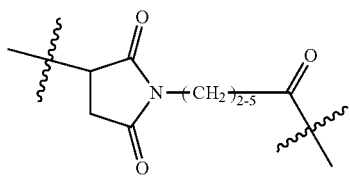

wherein the wavy line adjacent to the succinimide ring system indicates covalent attachment to a sulfur atom of the Ligand Unit, and the wavy line adjacent to the carbonyl indicates attachment to the remainder of the Ligand Drug Conjugate compound.

24. The Ligand-Drug Conjugate Compound of claim 21 wherein the Stretcher unit (Z) has the structure of:

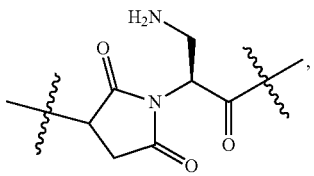

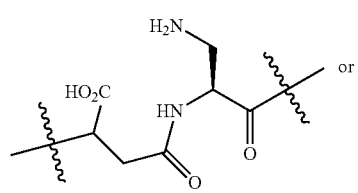

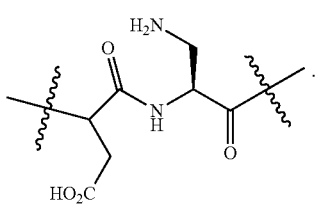

25. The Ligand-Drug Conjugate Compound of claim 24 wherein the Connector Unit (A) is present and has the structure of:

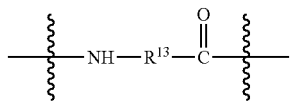

wherein the wavy line adjacent to the carbonyl indicates covalent attachment to the activateable self-immolative moiety X, and the other wavy line indicates attachment to B, if present, or to Z if B is absent; and $R^{13}$ is $-C_1-C_6$ alkylene-, $-C_3-C_8$carbocyclo-, -arylene-, $-C_1-C_{10}$ heteroalkylene-, $-C_3-C_8$heterocyclo-, $-C_1-C_{10}$alkylene-arylene-, -arylene-$C_1-C_{10}$alkylene-, $-C_1-C_{10}$alkylene-($C_3-C_8$carbocyclo)-, -($C_3-C_8$carbocyclo)-$C_1-C_{10}$alkylene-, $-C_1-C_{10}$alkylene-($C_3-C_8$ heterocyclo)-, or -($C_3-C_8$ heterocyclo)-$C_1-C_{10}$ alkylene-.

26. The Ligand-Drug Conjugate Compound of claim 25 wherein the Connector Unit (A) is present and has the structure of:

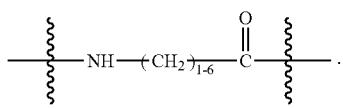

27. The Ligand-Drug Conjugate Compound of claim 1 wherein the Ligand Unit is an antibody Ligand Unit.

28. A Ligand-Drug Conjugate composition comprising a plurality of conjugate compounds, each having the structure of Formula (II) of claim 1 in which subscript p is an integer ranging from 1 to 8, wherein the remaining variable groups are as defined in claim 1; and a pharmaceutically acceptable carrier.

29. The Ligand-Drug Conjugate Compound of claim 1, wherein the free drug binds to FKBP to inhibit mTOR or calcineurin effector function.

30. The Ligand-Drug Conjugate Compound of claim 29, wherein the FKBP binding free drug is everolimus, tacrolimus or sirolimus.

31. The Ligand-Drug Conjugate Compound of claim 29, wherein the Ligand-Drug Conjugate Compound has the structure of:

209
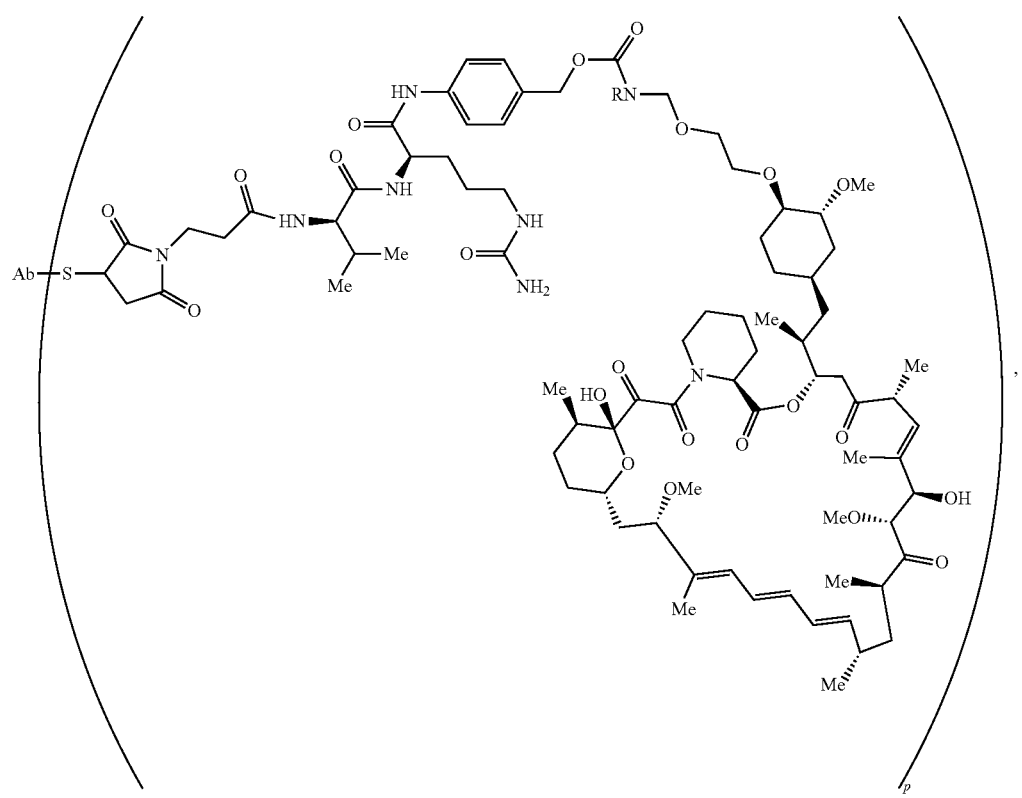
210
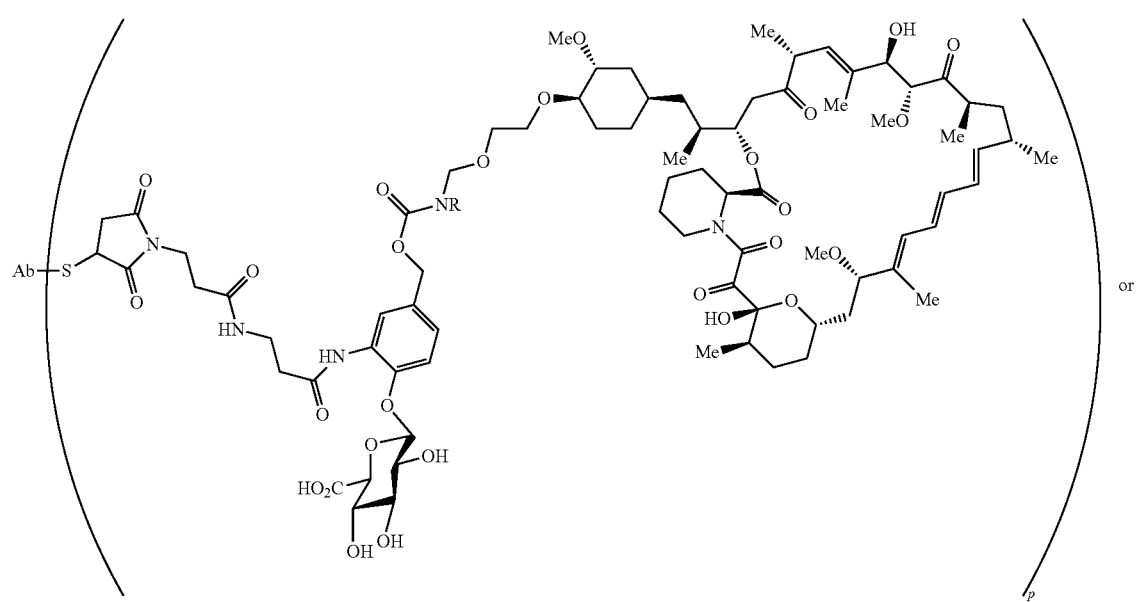
or

-continued

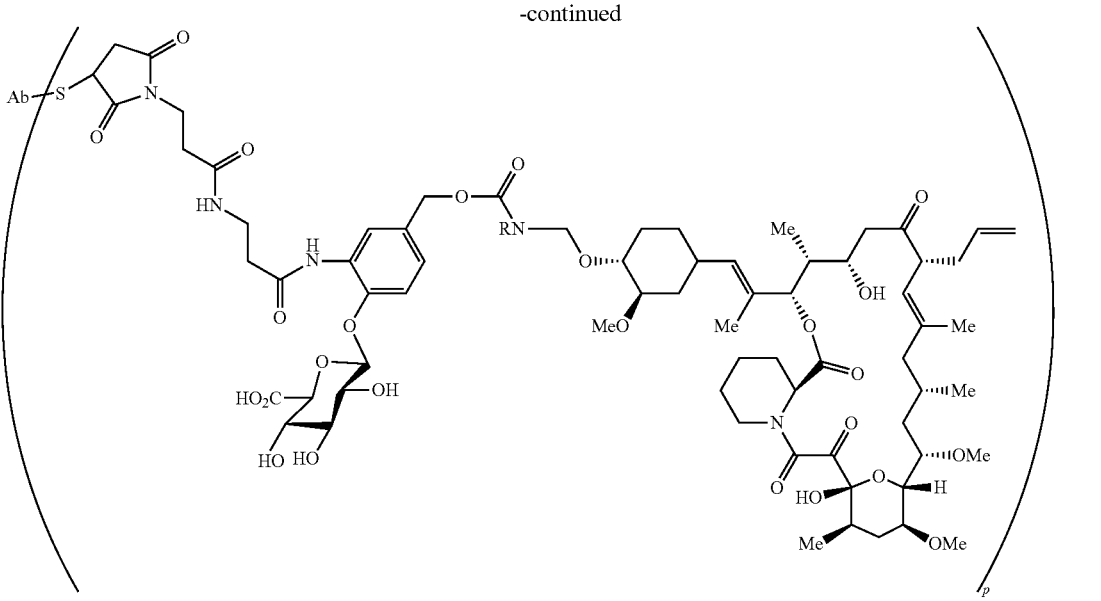

wherein the Ab-S- moiety is an antibody Ligand Unit; R is hydrogen, ethyl or –CH$_2$CH$_2$N(CH$_3$)$_2$; and subscript p ranges from 1 to 16 or 1 to 8.

32. The Ligand-Drug Conjugate Compound of claim 1, wherein the Drug Unit incorporates an auristatin free drug having a hydroxyl functional group, wherein the functional group has been incorporated into the indicated methylene carbamate unit of Formula (II);
  T* is the oxygen heteroatom from said functional group; and
  wherein the free auristatin drug binds to tubulin to disrupt tubulin function.

33. The Ligand-Drug Conjugate Compound of claim 32 wherein the auristatin free drug is MMAE or auristatin T.

34. A method of treating cancer or an autoimmune disease comprising administering to a subject in need thereof, an effective amount of a Ligand-Drug Conjugate composition of claim 28, wherein the cancer is Hodgkin's disease, prostate cancer, melanoma, renal cell (kidney) cancer, non-Hodgkin's disease, or erythroleukemia.

35. The Ligand-Drug Conjugate Compound of claim 33 wherein the compound has the structure of:

or a pharmaceutically acceptable salt thereof, wherein the Ab-S- moiety is an antibody Ligand Unit; subscript p is 4; and the Ab-S antibody Ligand Unit is of the chimeric antibody cAC10.

36. The Ligand-Drug Conjugate Compound of claim 2, wherein R is a Basic Unit, wherein the basic functional group of the Basic Unit is –N(R$^{op}$)$_2$, wherein each R$^{op}$ is independently selected from the group consisting of hydrogen and C$_1$–C$_6$ alkyl.

37. The Ligand-Drug Conjugate Compound of claim 2, wherein R is a Basic Unit, wherein the basic functional group of the Basic Unit is –N(R$^{op}$)$_2$, wherein one R$^{op}$ is hydrogen and the other R$^{op}$ is methyl, or both R$^{op}$ are methyl.

38. The Ligand-Drug Conjugate Compound of claim 14, wherein the tumor associated protease is cathepsin B.

39. The Ligand-Drug Conjugate Compound of claim 14, wherein W is -Val-Cit-, -Phe-Lys-, or -Val-Ala-.

40. The Ligand-Drug Conjugate Compound of claim 25, wherein R$^{13}$ is –C$_1$–C$_6$ alkylene–.

41. The Ligand-Drug Conjugate Compound of claim 1, wherein subscript p is an integer ranging from 1 to 8.

42. The Ligand-Drug Conjugate Compound of claim 1, wherein the Stretcher unit (Z) has the structure of:

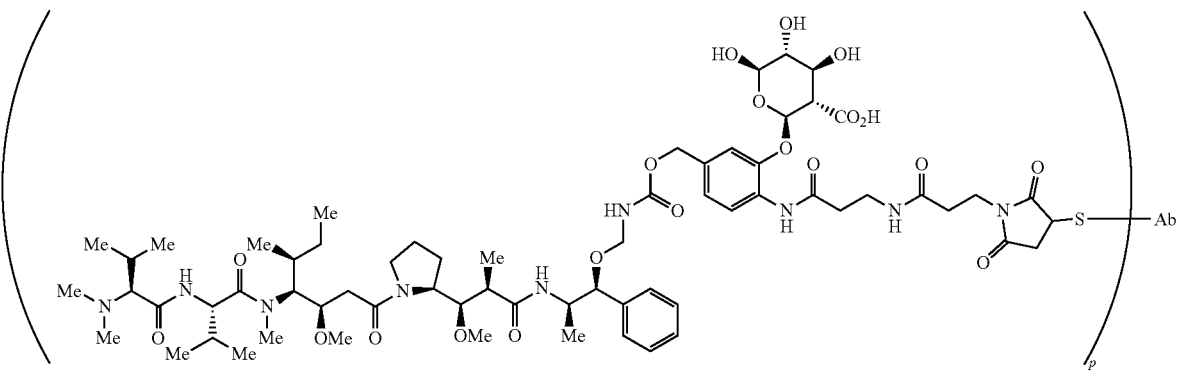

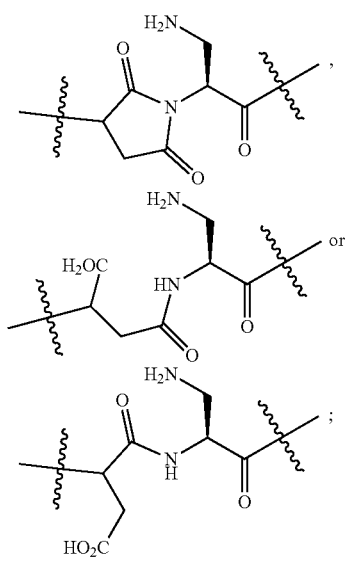

wherein the Connector Unit (A) is present and has the structure of:

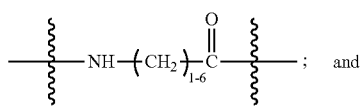; and wherein subscript p is an integer ranging from 1 to 8.

43. The Ligand-Drug Conjugate Compound of claim 1, wherein the Stretcher unit (Z) has the structure of:

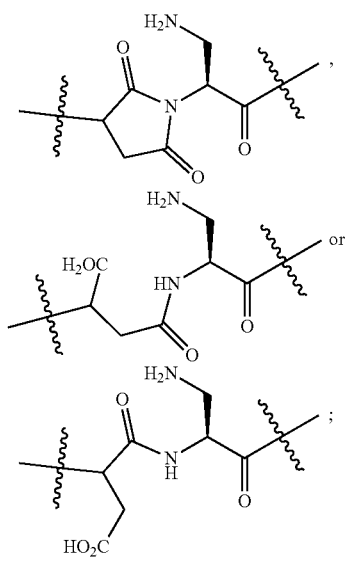

wherein the Connector Unit (A) is absent; and wherein subscript p is an integer ranging from 1 to 8.

44. The Ligand-Drug Conjugate Compound of claim 2, wherein R is a Basic Unit having the structure $-CH_2CH_2N(R^{op})_2$, wherein each $R^{op}$ is independently selected from the group consisting of hydrogen and methyl;

wherein the Stretcher unit (Z) has the structure of:

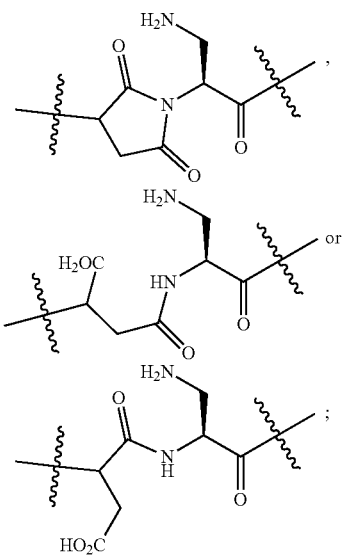

wherein the Connector Unit (A) is present and has the structure of:

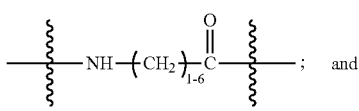; and wherein subscript p is an integer ranging from 1 to 8.

45. The Ligand-Drug Conjugate Compound of claim 2, wherein R is a Basic Unit having the structure $-CH_2CH_2N(R^{op})_2$, wherein each $R^{op}$ is independently selected from the group consisting of hydrogen and methyl;

wherein the Stretcher unit (Z) has the structure of:

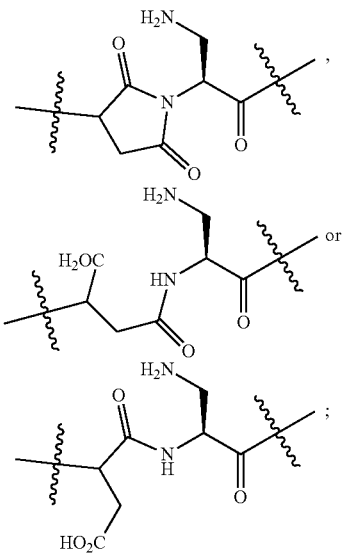

wherein the Connector Unit (A) is absent; and wherein subscript p is an integer ranging from 1 to 8.

46. The Ligand-Drug Conjugate Compound of claim 12, wherein Y has the structure:

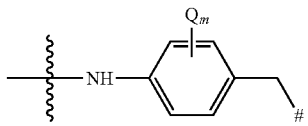

wherein the wavy line indicates covalent attachment to the Activation Unit (W) and the hashtag (#) indicates covalent attachment of the benzylic carbon to the methylene carbamate unit;
wherein Q is C1–C6 alkyl, –O–($C_1$–$C_6$ alkyl), halogen, nitro, or cyano; and
m is an integer ranging from 0 to 4.

47. The Ligand-Drug Conjugate Compound of claim 2, wherein the activateable self-immolative moiety (X) has the structure of formula (i)

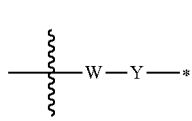 (i)

wherein the way line indicates covalent attachment of W to A, B or Z depending on the presence or absence of A and/or B and the asterisk (*) indicates covalent attachment of Y to the methylene carbamate unit and wherein;
W is an Activation Unit;
wherein Y has the structure:

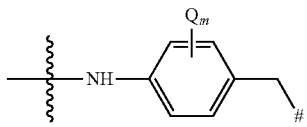

wherein the wavy line indicates covalent attachment to the Activation Unit (W) and the hashtag (#) indicates covalent attachment of the benzylic carbon to the methylene carbamate unit;
wherein Q is $C_1$–$C_6$ alkyl, –O–($C_1$–$C_6$ alkyl), halogen, nitro, or cyano; and
m is an integer ranging from 0 to 4.

48. The Ligand-Drug Conjugate Compound of claim 42, wherein
wherein the activateable self-immolative moiety (X) has the structure of formula (i)

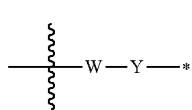 (i)

wherein the way line indicates covalent attachment of W to A, B or Z depending on the presence or absence of A and/or B and the asterisk (*) indicates covalent attachment of Y to the methylene carbamate unit and wherein;
W is an Activation Unit;
Y has the structure:

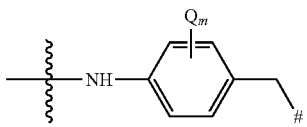

wherein the wavy line indicates covalent attachment to the Activation Unit (W) and the hashtag (#) indicates covalent attachment of the benzylic carbon to the methylene carbamate unit;
wherein Q is $C_1$–$C_6$ alkyl, –O–($C_1$–$C_6$ alkyl), halogen, nitro, or cyano; and
m is an integer ranging from 0 to 4.

49. The Ligand-Drug Conjugate Compound of claim 43, wherein
wherein the activateable self-immolative moiety (X) has the structure of formula (i)

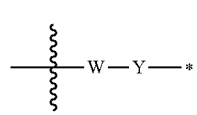 (i)

wherein the way line indicates covalent attachment of W to A, B or Z depending on the presence or absence of A and/or B and the asterisk (*) indicates covalent attachment of Y to the methylene carbamate unit and wherein;
W is an Activation Unit;
Y has the structure:

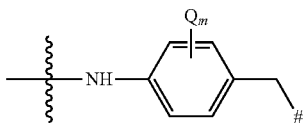

wherein the wavy line indicates covalent attachment to the Activation Unit (W) and the hashtag (#) indicates covalent attachment of the benzylic carbon to the methylene carbamate unit;
wherein Q is $C_1$–$C_6$ alkyl, –O–($C_1$–$C_6$ alkyl), halogen, nitro, or cyano; and
m is an integer ranging from 0 to 4.

50. The Ligand-Drug Conjugate Compound of claim 1,
wherein R is a Basic Unit having the structure –$CH_2CH_2N(R^{op})_2$, wherein each $R^{op}$ is independently selected from the group consisting of hydrogen and methyl;
wherein the Stretcher unit (Z) has the structure of:

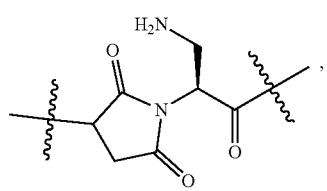

-continued

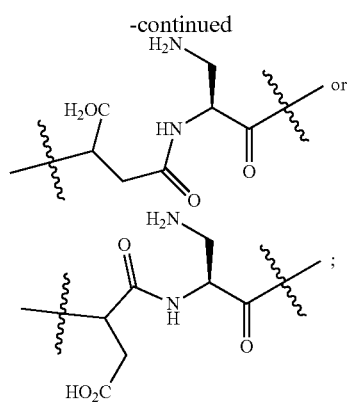

wherein the Connector Unit (A) is present and has the structure of:

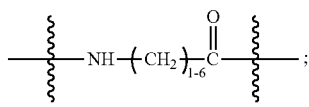

wherein subscript p is an integer ranging from 1 to 8;
wherein the activateable self-immolative moiety (X) has the structure of formula (i)

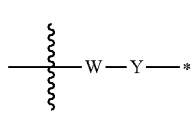
(i)

wherein the way line indicates covalent attachment of W to A, B or Z depending on the presence or absence of A and/or B and the asterisk (*) indicates covalent attachment of Y to the methylene carbamate unit and wherein;
W is an Activation Unit;
Y has the structure:

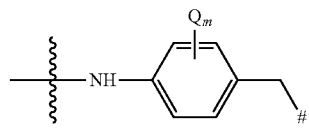

wherein the wavy line indicates covalent attachment to the Activation Unit (W) and the hashtag (#) indicates covalent attachment of the benzylic carbon to the methylene carbamate unit;
wherein Q is $C_1$-$C_6$ alkyl; –O–($C_1$-$C_6$ alkyl); halogen, nitro; or cyano; and
m is an integer ranging from 0 to 4.

51. The Ligand-Drug Conjugate Compound of claim 2;
wherein R is a Basic Unit having the structure –$CH_2CH_2N(R^{op})_2$; wherein each $R^{op}$ is independently selected from the group consisting of hydrogen and methyl;

wherein the Stretcher unit (Z) has the structure of:

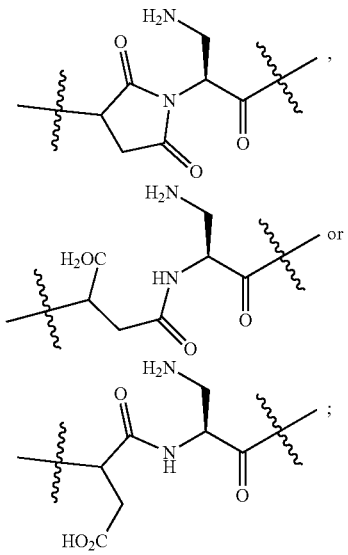

wherein the Connector Unit (A) is absent;
wherein subscript p is an integer ranging from 1 to 8;
wherein the activateable self-immolative moiety (X) has the structure of formula (i)

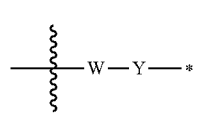
(i)

wherein the way line indicates covalent attachment of W to A, B or Z depending on the presence or absence of A and/or B and the asterisk (*) indicates covalent attachment of Y to the methylene carbamate unit and wherein;
W is an Activation Unit;
Y has the structure:

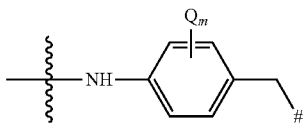

wherein the wavy line indicates covalent attachment to the Activation Unit (W) and the hashtag (#) indicates covalent attachment of the benzylic carbon to the methylene carbamate unit;
wherein Q is $C_1$-$C_6$ alkyl, –O–($C_1$-$C_6$ alkyl), halogen, nitro, or cyano; and
m is an integer ranging from 0 to 4.

52. The Ligand-Drug Conjugate Compound of claim 1,
wherein B is absent and t is 1;
R is a Basic Unit having the structure –$CH_2CH_2N(R^{op})_2$, wherein each $R^{op}$ is independently selected from the group consisting of hydrogen and methyl;

wherein the Stretcher unit (Z) has the structure of:

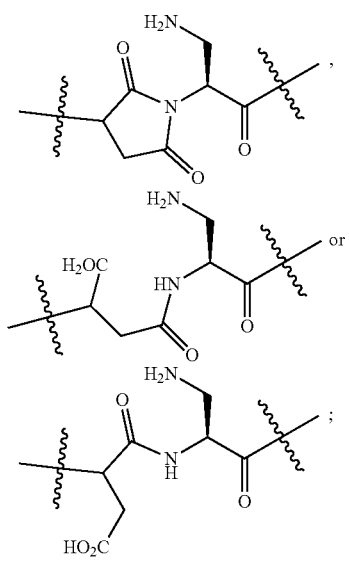

wherein the Connector Unit (A) is present and has the structure of:

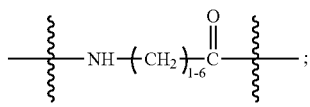

wherein subscript p is an integer ranging from 1 to 8;
wherein the activateable self-immolative moiety (X) has the structure of formula (i)

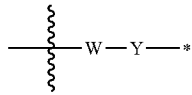

(i)

wherein the way line indicates covalent attachment of W to A; B or Z depending on the presence or absence of A and/or B and the asterisk (*) indicates covalent attachment of Y to the methylene carbamate unit and wherein;
W is an Activation Unit;
Y has the structure:

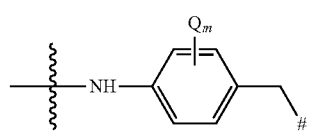

wherein the wavy line indicates covalent attachment to the Activation Unit (W) and the hashtag (#) indicates covalent attachment of the benzylic carbon to the methylene carbamate unit;
wherein Q is $C_1$-$C_6$ alkyl; -O-($C_1$-$C_6$ alkyl); halogen; nitro; or cyano; and
m is an integer ranging from 0 to 4.

53. The Ligand-Drug Conjugate Compound of claim 2;
wherein B is absent and t is 1;
R is a Basic Unit having the structure -$CH_2CH_2N(R^{op})_2$; wherein each $R^{op}$ is independently selected from the group consisting of hydrogen and methyl;
wherein the Stretcher unit (Z) has the structure of:

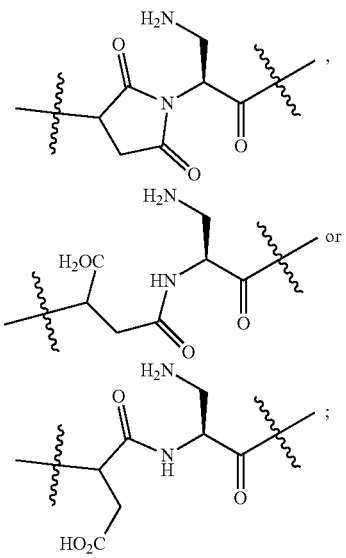

wherein the Connector Unit (A) is absent;
wherein subscript p is an integer ranging from 1 to 8;
wherein the activateable self-immolative moiety (X) has the structure of formula (i)

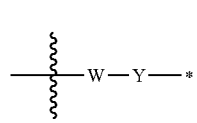

(i)

wherein the way line indicates covalent attachment of W to A; B or Z depending on the presence or absence of A and/or B and the asterisk (*) indicates covalent attachment of Y to the methylene carbamate unit and wherein;
W is an Activation Unit;
Y has the structure:

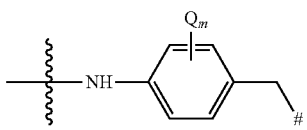

wherein the wavy line indicates covalent attachment to the Activation Unit (W) and the hashtag (#) indicates covalent attachment of the benzylic carbon to the methylene carbamate unit;
wherein Q is $C_1$-$C_6$ alkyl, -O-($C_1$-$C_6$ alkyl), halogen, nitro, or cyano; and
m is an integer ranging from 0 to 4.

* * * * *